US010431748B2

(12) United States Patent
Heo et al.

(10) Patent No.: US 10,431,748 B2
(45) Date of Patent: Oct. 1, 2019

(54) CYCLIC COMPOUND AND ORGANIC LIGHT-EMITTING ELEMENT COMPRISING SAME

(71) Applicant: LG CHEM, LTD., Seoul (KR)

(72) Inventors: Dong Uk Heo, Daejeon (KR); Dong Hoon Lee, Daejeon (KR); Jungoh Huh, Daejeon (KR); Boonjae Jang, Daejeon (KR); Minyoung Kang, Daejeon (KR); Miyeon Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/515,975

(22) PCT Filed: Sep. 11, 2015

(86) PCT No.: PCT/KR2015/009593
§ 371 (c)(1),
(2) Date: Mar. 30, 2017

(87) PCT Pub. No.: WO2016/068478
PCT Pub. Date: May 6, 2016

(65) Prior Publication Data
US 2017/0301866 A1 Oct. 19, 2017

(30) Foreign Application Priority Data
Oct. 30, 2014 (KR) .................. 10-2014-0149355

(51) Int. Cl.
*C07D 403/10* (2006.01)
*C07D 251/12* (2006.01)
*C07D 239/26* (2006.01)
*C09K 11/06* (2006.01)
*H01L 51/50* (2006.01)
*H01L 51/00* (2006.01)
*C07D 251/24* (2006.01)

(52) U.S. Cl.
CPC ........ *H01L 51/0067* (2013.01); *C07D 239/26* (2013.01); *C07D 251/12* (2013.01); *C07D 251/24* (2013.01); *C07D 403/10* (2013.01); *C09K 11/06* (2013.01); *H01L 51/0035* (2013.01); *H01L 51/50* (2013.01)

(58) Field of Classification Search
CPC ...... C07D 403/10; C09K 11/06; H05B 33/14; H01L 51/5032; H01L 51/5064; H01L 51/5296; H01L 51/0032
USPC ............. 544/295; 257/40, E51.019, E51.09; 428/917; 313/501
See application file for complete search history.

(56) References Cited

U.S. PATENT DOCUMENTS

| | | | |
|---|---|---|---|
| 3,412,036 A | 11/1968 | McIntosh | |
| 5,343,050 A | 8/1994 | Egusa et al. | |
| 8,003,227 B2 * | 8/2011 | Vestweber ........... | C07D 239/26 257/40 |
| 2002/0010243 A1 | 1/2002 | Katsube et al. | |
| 2002/0079489 A1 | 6/2002 | Ishikawa et al. | |
| 2003/0168970 A1 | 9/2003 | Tominaga et al. | |
| 2006/0186797 A1 | 8/2006 | Nishiyama et al. | |
| 2007/0051944 A1 | 3/2007 | Vestweber et al. | |
| 2009/0033213 A1 | 2/2009 | Sugita et al. | |
| 2010/0197668 A1 | 8/2010 | Baudoin et al. | |
| 2011/0140043 A1 | 6/2011 | Stoessel et al. | |
| 2015/0357582 A1 | 12/2015 | Hirata et al. | |

FOREIGN PATENT DOCUMENTS

| | | |
|---|---|---|
| CN | 1954446 A | 4/2007 |
| CN | 103305210 A | 9/2013 |
| EP | 0553950 A2 | 4/1993 |
| JP | 1993-326146 A | 12/1993 |
| JP | 2002-198179 A | 7/2002 |
| JP | 2003-206278 A | 7/2003 |
| JP | 2003-261472 A | 9/2003 |
| JP | 2003-282270 A | 10/2003 |
| JP | 2004-146368 A | 5/2004 |
| JP | 2004-342391 A | 12/2004 |
| JP | 2005-032488 A | 2/2005 |
| JP | 2005-093159 A | 4/2005 |
| JP | 2005-158289 A | 6/2005 |
| JP | 2005-213188 A | 8/2005 |
| JP | 2005-220080 A | 8/2005 |
| JP | 2007-049055 A | 2/2007 |
| JP | 2007-223904 A | 9/2007 |
| JP | 2007-254297 A | 10/2007 |
| JP | 2008-074939 A | 4/2008 |
| JP | 2009182088 A * | 8/2009 |
| JP | 2011500563 A | 1/2011 |
| JP | 2011-093825 A | 5/2011 |
| JP | 2011-093854 A | 5/2011 |
| KR | 10-2010-0050485 A | 5/2010 |
| KR | 10-2010-0131745 A | 12/2010 |
| KR | 10-2015-0106668 A | 9/2015 |
| WO | 2002043449 A1 | 5/2002 |

(Continued)

OTHER PUBLICATIONS

JP 2009-182088 A, Aug. 13, 2009—English Machine Translation (EPO).*
Zimmermann et al. European Journal of Organic Chemistry (2000), (19), 3305-3312.*
Atzrodt et al. Angew. Chem. Int. Ed. 2007, 46, 7744-7765.*
Pccompound—Selected Items—76, Create Date Dec. 6, 2007 to Create Date Nov. 30, 2012.*
Pccompound-1-2, Create date Aug. 19, 2012 to Create Dtae Mar. 21, 2013.*

(Continued)

Primary Examiner — Venkataraman Balasubramanian
(74) Attorney, Agent, or Firm — Dentons US LLP

(57) ABSTRACT

The present specification relates to a cyclic compound and an organic light emitting device comprising the same.

9 Claims, 1 Drawing Sheet

(56) References Cited

FOREIGN PATENT DOCUMENTS

| WO | 2006-104118 A1 | 5/2006 |
|---|---|---|
| WO | 2007-020718 A1 | 2/2007 |
| WO | 2009048547 A1 | 4/2009 |
| WO | 2010/126270 A1 | 11/2010 |
| WO | 2014/115743 A1 | 7/2014 |

OTHER PUBLICATIONS

L. Zhao et al., "Stable and efficient deep-blue terfluorenes functionalized with carbazole dendrons for solution-processed organic light-emitting diodes", J. Mater. Chem. C, 2015, 3, pp. 8895-8903.

J. Sukegawa et al., "Large Electronic Coupling in a Homoconjugated Donor-Acceptor System Involving Carbon-bridged Oligo(p-phenylenevinylene) and Triazine", Chemistry Letters, 2014, 43, 5, pp. 699-701.

Hartman et al., Organic Synthesis, 1943, Coll. vol. 2, pp. 232-234.

\* cited by examiner

CYCLIC COMPOUND AND ORGANIC LIGHT-EMITTING ELEMENT COMPRISING SAME

TECHNICAL FIELD

This application is a National Stage Application of International Application No. PCT/KR2015/009593 filed on Sep. 11, 2015, which claims the benefit of Korean Patent Application No. 10-2014-0149355 filed on Oct. 30, 2014, all of which are hereby incorporated by reference in their entirety for all purposes as if fully set forth herein.

The present specification relates to a cyclic compound and an organic light emitting device comprising the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

International Patent Application Laid-Open Publication No. 2003-012890

DISCLOSURE

Technical Problem

The present specification provides a cyclic compound and an organic light emitting device comprising the same.

Technical Solution

The present specification provides a cyclic compound represented by the following Chemical Formula 1.

[Chemical Formula 1]

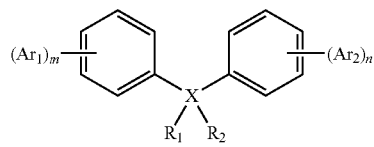

In Chemical Formula 1, $Ar_1$ and $Ar_2$ are the same as or different from each other, and each independently selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group having 2 to 30 carbon atoms, m and n are the same as or different from each other, and each independently an integer of 1 to 5, when m is two or more, $Ar_1$s are the same as or different from each other, when n is two or more, $Ar_2$s are the same as or different from each other, X is a non-conjugated group, $R_1$ and $R_2$ are the same as or different from each other, and each independently selected from the group consisting of hydrogen; deuterium; a nitrile group; a substituted or unsubstituted linear or branched alkyl group having 1 to 30 carbon atoms; a substituted or unsubstituted monocyclic or multicyclic cycloalkyl group having 3 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms, or $R_1$ and $R_2$ may be linked to each other to form a substituted or unsubstituted monocyclic or multicyclic hydrocarbon ring; or a substituted or unsubstituted monocyclic or multicyclic heterocyclic ring.

In addition, one embodiment of the present specification provides an organic light emitting device including a first electrode; a second electrode provided opposite to the first electrode; and one or two or more organic material layers provided between the first electrode and the second electrode, wherein one or more layers of the organic material layers include the cyclic compound represented by Chemical Formula 1.

Advantageous Effects

A cyclic compound according to one embodiment of the present specification can be used as a material of an organic material layer of an organic light emitting device, and by using the compound, efficiency enhancement, a low driving voltage and/or lifespan property enhancement can be obtained in the organic light emitting device.

In addition, the organic light emitting device according to one embodiment of the present specification has a wide band gap, and a deep highest occupied molecular orbital (HOMO) level.

REFERENCE NUMERAL

Figure 1:
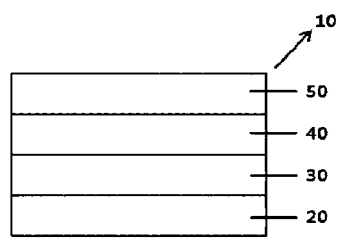
FIG. 1 is a diagram showing an organic light emitting device (10) according to one embodiment of the present specification.
Figure 2:
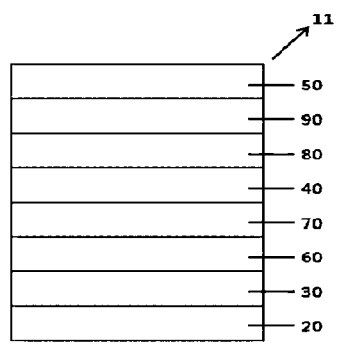
FIG. 2 is a diagram showing an organic light emitting device (11) according to another embodiment of the present specification.

10, 11: Organic Light Emitting Device
20: Substrate
30: First Electrode
40: Light Emitting Layer
50: Second Electrode
60: Hole Injection Layer
70: Hole Transfer Layer 80: Electron Transfer Layer
90: Electron Injection Layer

BEST MODE

Hereinafter, the present specification will be described in more detail.

The present specification provides a cyclic compound represented by Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent may substitute, and when two or more substituents substitute, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably 1 to 30. Specifically, compounds having the following structures may be included, but the compound is not limited thereto.

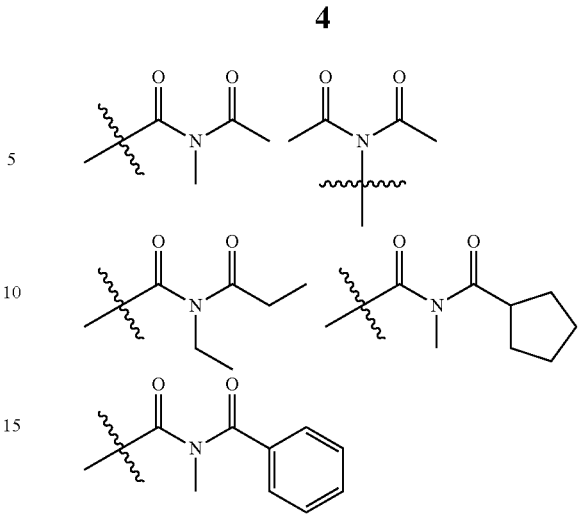

In the present specification, in the amide group, the nitrogen of the amide group may be once or twice substituted with hydrogen, a linear, branched or cyclic alkyl group having 1 to 30 carbon atoms, or an aryl group having 6 to 30 carbon atoms. Specifically, compounds having the following structural formulae may be included, but the compound is not limited thereto.

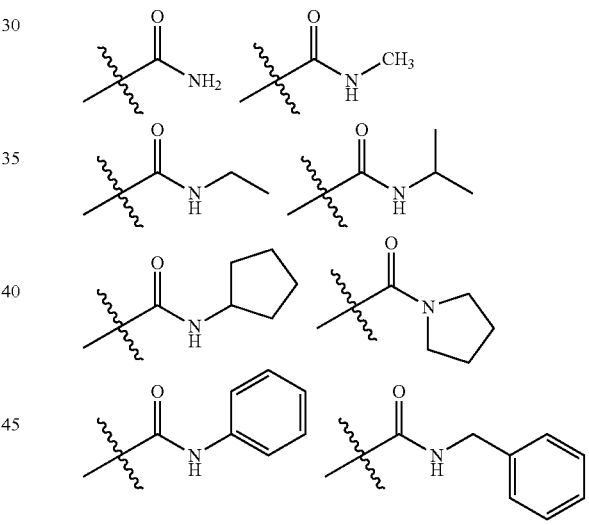

In the present specification, the alkyl group may be linear or branched, and the number of carbon atoms is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the amine group may be selected from the group consisting of $-NH_2$; an alkylamine group; an aralkylamine group; an arylamine group; and a heteroarylamine group, and although not particularly limited thereto, the number of carbon atoms is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

When the aryl group is a monocyclic aryl group, the number of carbon atoms is not particularly limited, but is preferably 6 to 25. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably 10 to 24. Specific example of the multicyclic aryl group may include a naphthyl group, a triphenylenyl group, an anthracenyl group, a phenanthryl group, a pyrenyl group, a perylenyl group, a crycenyl group, a fluorenyl group and the like, but are not limited thereto.

In the present specification, the fluorenyl group may be substituted, and adjacent substituents may bond to each other to form a ring.

When the fluorenyl group is substituted,

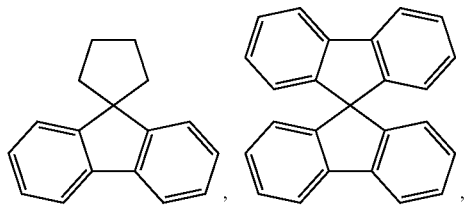

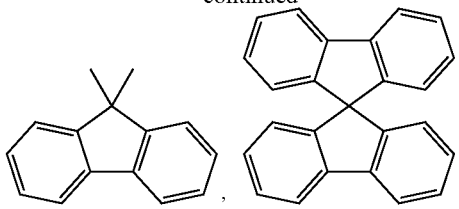

and the like may be included. However, the structure is not limited thereto.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably 2 to 60. Examples of the heteroaryl group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazolyl group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a thiazolyl group, an isoxazolyl group, an oxadiazolyl group, a thiadiazolyl group, a benzothiazolyl group, a thienothiophene group, a phenothiazinyl group, a dibenzofuranyl group and the like, but are not limited thereto.

The heteroaryl group may be monocyclic or multicyclic, and may be aromatic, aliphatic, or a fused ring of aromatic and aliphatic.

In the present specification, an arylene group means an aryl group having two bonding sites, that is, a divalent group. Descriptions on the aryl group made above may be applied except for those that are each a divalent group.

In the present specification, a heteroarylene group means a heteroaryl group having two bonding sites, that is, a divalent group. Descriptions on the heteroaryl group made above may be applied except for those that are each a divalent group.

In the present specification, the hydrocarbon ring include all of a cycloalkyl group; a cycloalkenyl group; an aromatic cyclic group; or an aliphatic cyclic group, may be multicyclic or monocyclic, and includes all rings in which one or two or more of these bond to be fused.

In the present specification, the aromatic ring may be monocyclic or multicyclic, and may be selected from among the examples of the aryl group except for those that are not monovalent.

In the present specification, the heterocyclic ring may be an aliphatic ring or aromatic ring, and means at least one carbon atom of the aliphatic ring or aromatic ring being substituted with an N, O, Se or S atom, and may be multicyclic or monocyclic.

According to one embodiment of the present specification, at least one of $Ar_1$s is $-L_1-(Z_1)_p$ in Chemical Formula 1, $L_1$ is selected from the group consisting of a direct bond; a substituted or unsubstituted monocyclic or multicyclic arylene group having 6 to 30 carbon atoms; and a substituted or unsubstituted monocyclic or multicyclic heteroarylene group having 2 to 30 carbon atoms, $Z_1$ is selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group having 2 to 30 carbon atoms, however, $Z_1$ is not hydrogen when $L_1$ is a direct bond, p is an integer of 1 to 3, and when p is 2 or more, $Z_1$s are the same as or different from each other.

According to another embodiment of the present specification, $L_1$ is selected from the group consisting of a direct bond; a substituted or unsubstituted monocyclic or multicyclic arylene group having 6 to 20 carbon atoms; and a substituted or unsubstituted monocyclic or multicyclic heteroarylene group having 2 to 20 carbon atoms.

According to another embodiment of the present specification, $L_1$ is selected from the group consisting of a direct bond; a substituted or unsubstituted monocyclic or multicyclic arylene group having 6 to 10 carbon atoms; and a substituted or unsubstituted monocyclic or multicyclic heteroarylene group having 2 to 10 carbon atoms.

According to another embodiment of the present specification, $L_1$ is selected from the group consisting of a direct bond; a substituted or unsubstituted phenylene group; a substituted or unsubstituted biphenylylene group; a substituted or unsubstituted naphthylene group; a substituted or unsubstituted pyrimidylene group; a substituted or unsubstituted quinolylene group; a substituted or unsubstituted quinazolylene group; a substituted or unsubstituted pyridylene group; and a substituted or unsubstituted triazinylene group.

According to another embodiment of the present specification, $L_1$ is selected from the group consisting of a direct bond; a phenylene group; a biphenylylene group; a naphthylene group; a pyrimidylene group; a quinolylene group; a quinazolylene group; a pyridylene group; and a triazinylene group.

According to another embodiment of the present specification, $Z_1$ is selected from the group consisting of hydrogen; deuterium; a nitrile group; a substituted or unsubstituted monocyclic or multicyclic aryl group having 6 to 20 carbon atoms; and a substituted or unsubstituted monocyclic or multicyclic heteroaryl group having 2 to 20 carbon atoms.

According to another embodiment of the present specification, $Z_1$ is selected from the group consisting of hydrogen; deuterium; a nitrile group; a substituted or unsubstituted monocyclic or multicyclic aryl group having 6 to 10 carbon atoms; and a substituted or unsubstituted monocyclic or multicyclic heteroaryl group having 2 to 10 carbon atoms.

According to another embodiment of the present specification, $Z_1$ is selected from the group consisting of hydrogen; deuterium; a nitrile group; a substituted or unsubstituted phenyl group; a substituted or unsubstituted biphenyl group; a substituted or unsubstituted naphthyl group; a substituted or unsubstituted thiophene group; a substituted or unsubstituted quinolyl group; and a substituted or unsubstituted pyridyl group.

According to another embodiment of the present specification, $Z_1$ is selected from the group consisting of hydrogen; deuterium; a nitrile group; a phenyl group; a biphenyl group; a naphthyl group; a thiophene group; a quinolyl group; a pyridyl group; a quinolyl group substituted with a phenyl group; a quinolyl group substituted with a pyridyl group; and a quinolyl group substituted with a pyridyl group and a phenyl group.

According to one embodiment of the present specification, at least one of Ar$_2$s is -L$_2$-(Z$_2$)$_q$ in Chemical Formula 1, $L_2$ is selected from the group consisting of a direct bond; a substituted or unsubstituted monocyclic or multicyclic arylene group having 6 to 30 carbon atoms; and a substituted or unsubstituted monocyclic or multicyclic heteroarylene group having 2 to 30 carbon atoms, $Z_2$ is selected from the group consisting of hydrogen; deuterium; a nitrile group; a substituted or unsubstituted monocyclic or multicyclic aryl group having 6 to 30 carbon atoms; and a substituted or unsubstituted monocyclic or multicyclic heteroaryl group having 2 to 30 carbon atoms, however, $Z_2$ is not hydrogen when $L_2$ is a direct bond, q is an integer of 1 to 3, and when q is two or more, $Z_2$s are the same as or different from each other.

According to another embodiment of the present specification, $L_2$ is selected from the group consisting of a direct bond; a substituted or unsubstituted monocyclic or multicyclic arylene group having 6 to 20 carbon atoms; and a substituted or unsubstituted monocyclic or multicyclic heteroarylene group having 2 to 20 carbon atoms.

According to another embodiment of the present specification, $L_2$ is selected from the group consisting of a direct bond; a substituted or unsubstituted monocyclic or multicyclic arylene group having 6 to 10 carbon atoms; and a substituted or unsubstituted monocyclic or multicyclic heteroarylene group having 2 to 10 carbon atoms.

According to another embodiment of the present specification, $L_2$ is selected from the group consisting of a direct bond; a substituted or unsubstituted phenylene group; a substituted or unsubstituted biphenylylene group; a substituted or unsubstituted naphthylene group; a substituted or unsubstituted pyrimidylene group; a substituted or unsubstituted quinolylene group; a substituted or unsubstituted quinazolylene group; a substituted or unsubstituted pyridylene group; and a substituted or unsubstituted triazinylene group.

According to another embodiment of the present specification, $L_2$ is selected from the group consisting of a direct bond; a phenylene group; a biphenylylene group; a naphthylene group; a pyrimidylene group; a quinolylene group; a quinazolylene group; a pyridylene group; and a triazinylene group.

According to another embodiment of the present specification, $Z_2$ is selected from the group consisting of hydrogen; deuterium; a nitrile group; a substituted or unsubstituted monocyclic or multicyclic aryl group having 6 to 20 carbon atoms; and a substituted or unsubstituted monocyclic or multicyclic heteroaryl group having 2 to 20 carbon atoms.

According to another embodiment of the present specification, $Z_2$ is selected from the group consisting of hydrogen; deuterium; a nitrile group; a substituted or unsubstituted monocyclic or multicyclic aryl group having 6 to 10 carbon atoms; and a substituted or unsubstituted monocyclic or multicyclic heteroaryl group having 2 to 10 carbon atoms.

According to another embodiment of the present specification, $Z_2$ is selected from the group consisting of hydrogen; deuterium; a nitrile group; a substituted or unsubstituted phenyl group; a substituted or unsubstituted biphenyl group; a substituted or unsubstituted naphthyl group; a substituted or unsubstituted thiophene group; a substituted or unsubstituted quinolyl group; and a substituted or unsubstituted pyridyl group.

According to another embodiment of the present specification, $Z_2$ is selected from the group consisting of hydrogen; deuterium; a nitrile group; a phenyl group; a biphenyl group; a naphthyl group; a thiophene group; a quinolyl group; a pyridyl group; a quinolyl group substituted with a phenyl group; a quinolyl group substituted with a pyridyl group; and a quinolyl group substituted with a pyridyl group and a phenyl group.

According to one embodiment of the present specification, X is a non-conjugated group in Chemical Formula 1.

According to one embodiment of the present specification, X may be carbon.

The cyclic compound represented by Chemical Formula 1 according to one embodiment of the present specification has wider band gap than organic materials used in existing organic light emitting devices by introducing a structure suppressing conjugation between $Ar_1$ and $Ar_2$, and as a result, is capable of having a deep HOMO level.

According to one embodiment of the present specification, in Chemical Formula 1, $R_1$ and $R_2$ are the same as or different from each other, and each independently selected from the group consisting of hydrogen; deuterium; a nitrile group; a substituted or unsubstituted linear or branched alkyl group having 1 to 20 carbon atoms; a substituted or unsubstituted monocyclic or multicyclic cycloalkyl group having 3 to 20 carbon atoms; a substituted or unsubstituted monocyclic or multicyclic aryl group having 6 to 20 carbon atoms; and a substituted or unsubstituted heteroaryl group having 2 to 20 carbon atoms.

According to another embodiment of the present specification, $R_1$ and $R_2$ are the same as or different from each other, and each independently selected from the group consisting of hydrogen; deuterium; a nitrile group; a substituted or unsubstituted linear or branched alkyl group having 1 to 10 carbon atoms; a substituted or unsubstituted monocyclic or multicyclic cycloalkyl group having 3 to 10 carbon atoms; a substituted or unsubstituted monocyclic or multicyclic aryl group having 6 to 10 carbon atoms; and a substituted or unsubstituted heteroaryl group having 2 to 10 carbon atoms.

According to another embodiment of the present specification, $R_1$ and $R_2$ are the same as or different from each other, and each independently selected from the group consisting of hydrogen; a substituted or unsubstituted phenyl group; and a substituted or unsubstituted naphthyl group.

According to another embodiment of the present specification, $R_1$ and $R_2$ are the same as or different from each other, and each independently selected from the group consisting of hydrogen; a phenyl group; and a naphthyl group.

According to another embodiment of the present specification, $R_1$ and $R_2$ are the same as or different from each other, and each independently selected from the group consisting of a substituted or unsubstituted methyl group; and a substituted or unsubstituted ethyl group.

According to another embodiment of the present specification, $R_1$ and $R_2$ may be linked to each other to form a substituted or unsubstituted hydrocarbon ring.

According to another embodiment of the present specification, $R_1$ and $R_2$ may be linked to each other to form a substituted or unsubstituted cyclohexyl ring.

According to another embodiment of the present specification, $R_1$ and $R_2$ may be linked to each other to form a cyclohexyl ring.

According to another embodiment of the present specification, $Ar_1$ and $Ar_2$ are the same as or different from each other, and each independently a monocyclic or multicyclic heteroaryl group including a substituted or unsubstituted 6-membered heterocyclic ring.

According to another embodiment of the present specification, $Ar_1$ and $Ar_2$ are the same as or different from each other, and each independently a substituted or unsubstituted 6-membered heteroaryl group.

According to another embodiment of the present specification, $Ar_1$ and $Ar_2$ are the same as or different from each other, and each independently a multicyclic heteroaryl group including a substituted or unsubstituted 6-membered heterocyclic ring.

According to another embodiment of the present specification, $Ar_1$ and $Ar_2$ are the same as or different from each other, and each independently a monocyclic or multicyclic heteroaryl group including a substituted or unsubstituted pyridyl group; a substituted or unsubstituted pyrimidyl group; or a substituted or unsubstituted triazinyl group.

According to another embodiment of the present specification, $Ar_1$ and $Ar_2$ are the same as or different from each other, and each independently a substituted or unsubstituted pyridyl group; a substituted or unsubstituted pyrimidyl group; a substituted or unsubstituted triazinyl group; a substituted or unsubstituted quinolyl group; a substituted or unsubstituted quinazolinyl group; or a substituted or unsubstituted quinoxalinyl group.

According to another embodiment of the present specification, $Ar_1$ and $Ar_2$ are the same as or different from each other, and each independently a pyridyl group; a pyrimidyl group; a triazinyl group; a quinolyl group; or a quinazolinyl group.

$Ar_1$ and $Ar_2$ may be unsubstituted or substituted with one or more selected from the group consisting of a nitrile group; a phenyl group; a biphenyl group; a naphthyl group; a thiophene group; a quinolyl group substituted with a phenyl group, a quinolyl group substituted with a pyridyl group, and a pyridyl group.

According to another embodiment of the present specification, $R_1$ and $R_2$ are the same as or different from each other and each independently selected from the group consisting of a substituted or unsubstituted methyl group; and a substituted or unsubstituted ethyl group, and $Ar_1$ and $Ar_2$ are the same as or different from each other and each independently a monocyclic heteroaryl group including a substituted or unsubstituted 6-membered heterocyclic ring. The cyclic compound represented by Chemical Formula 1 including the above-illustrated $R_1$, $R_2$, $Ar_1$ and $Ar_2$ as a substituent induces a wide band gap in the molecule due to $sp^3$ bonding and a steric effect of $Ar_1$ and $Ar_2$, forms a high triplet, and has a small π-π overlap in an intermolecular influence since, among the $sp^3$ bonding four directional substituents, only two directions excluding $R_1$ and $R_2$ are conjugation groups, and therefore exhibits excellent hole mobility and/or electron mobility in an organic light emitting device, and as a result, efficiency of the organic light emitting device may be enhanced.

According to another embodiment of the present specification, $R_1$ and $R_2$ are the same as or different from each other and each independently selected from the group consisting of a substituted or unsubstituted methyl group; and a substituted or unsubstituted ethyl group, and $Ar_1$ and $Ar_2$ are the same as or different from each other and each independently a substituted or unsubstituted pyridyl group, a substituted or unsubstituted pyrimidyl group, or a substituted or unsubstituted triazinyl group.

According to another embodiment of the present specification, $R_1$ and $R_2$ are the same as or different from each other and each independently selected from the group consisting of a methyl group; and an ethyl group, and $Ar_1$ and $Ar_2$ are the same as or different from each other and each independently a pyridyl group, a pyrimidyl group, or a triazinyl group.

$Ar_1$ and $Ar_2$ may be unsubstituted or substituted with one or more selected from the group consisting of a nitrile group; a phenyl group; a biphenyl group; a naphthyl group; a thiophene group; a quinolyl group substituted with a phenyl group, a quinolyl group substituted with a pyridyl group, and a pyridyl group.

According to another embodiment of the present specification, $R_1$ and $R_2$ are linked to each other to form a substituted or unsubstituted hydrocarbon ring, and $Ar_1$ and $Ar_2$ are the same as or different from each other and each independently a monocyclic heteroaryl group including a substituted or unsubstituted 6-membered heterocyclic ring.

According to another embodiment of the present specification, $R_1$ and $R_2$ are linked to each other to form a substituted or unsubstituted cyclohexyl ring, and $Ar_1$ and $Ar_2$ are the same as or different from each other and each independently a monocyclic heteroaryl group including a substituted or unsubstituted 6-membered heterocyclic ring. The cyclic compound represented by Chemical Formula 1 including the above-illustrated $R_1$, $R_2$, $Ar_1$ and $Ar_2$ as a substituent induces a wide band gap in the molecule due to $sp^3$ bonding and a steric effect of $Ar_1$ and $Ar_2$, forms a high triplet, and has a small π-π overlap in an intermolecular influence since, among the $sp^3$ bonding four directional substituents, only two directions excluding $R_1$ and $R_2$ are conjugation groups, and therefore exhibits excellent hole mobility and/or electron mobility in an organic light emitting device, and as a result, efficiency of the organic light emitting device may be enhanced.

According to another embodiment of the present specification, $R_1$ and $R_2$ are linked to each other to form a substituted or unsubstituted cyclohexyl ring, and $Ar_1$ and $Ar_2$ are the same as or different from each other and each independently a substituted or unsubstituted pyridyl group, a substituted or unsubstituted pyrimidyl group, or a substituted or unsubstituted triazinyl group.

According to another embodiment of the present specification, $R_1$ and $R_2$ are linked to each other to form a substituted or unsubstituted cyclohexyl ring, and $Ar_1$ and $Ar_2$ are the same as or different from each other and each independently a pyridyl group, a pyrimidyl group, or a triazinyl group.

$Ar_1$ and $Ar_2$ may be unsubstituted or substituted with one or more selected from the group consisting of a nitrile group; a phenyl group; a biphenyl group; a naphthyl group; a thiophene group; a quinolyl group substituted with a phenyl group, a quinolyl group substituted with a pyridyl group, and a pyridyl group.

According to another embodiment of the present specification, $R_1$ and $R_2$ are linked to each other to form a substituted or unsubstituted cyclohexyl ring, and $Ar_1$ and $Ar_2$ are the same as or different from each other and each independently a substituted or unsubstituted quinolyl group; or a substituted or unsubstituted quinazolinyl group.

According to another embodiment of the present specification, $R_1$ and $R_2$ are linked to each other to form a cyclohexyl ring, and $Ar_1$ and $Ar_2$ are the same as or different from each other, and each independently a quinolyl group; or a quinazolinyl group.

$Ar_1$ and $Ar_2$ may be unsubstituted or substituted with one or more selected from the group consisting of a nitrile group; a phenyl group; a biphenyl group; a naphthyl group; a thiophene group; a quinolyl group substituted with a phenyl group, a quinolyl group substituted with a pyridyl group, and a pyridyl group.

According to one embodiment of the present specification, the cyclic compound represented by Chemical Formula 1 may be selected from among the following compounds.

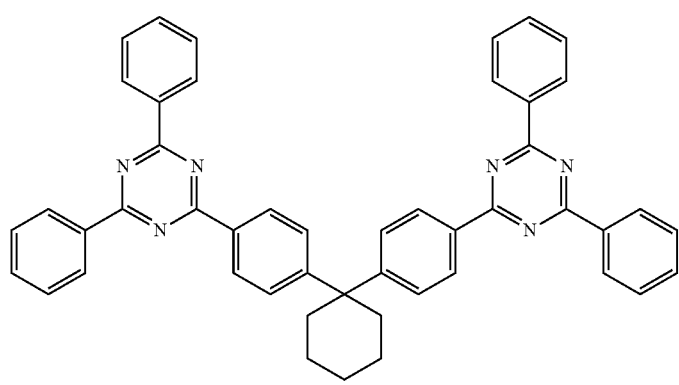
Compound 1
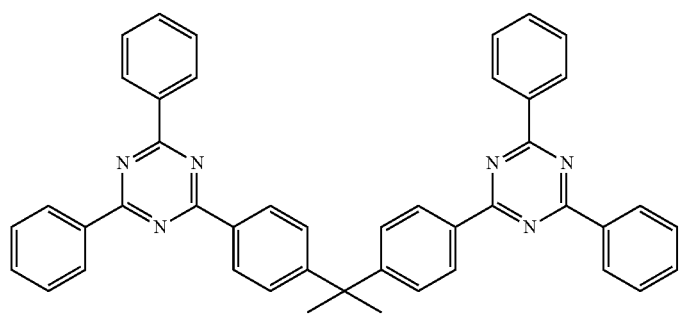
Compound 2
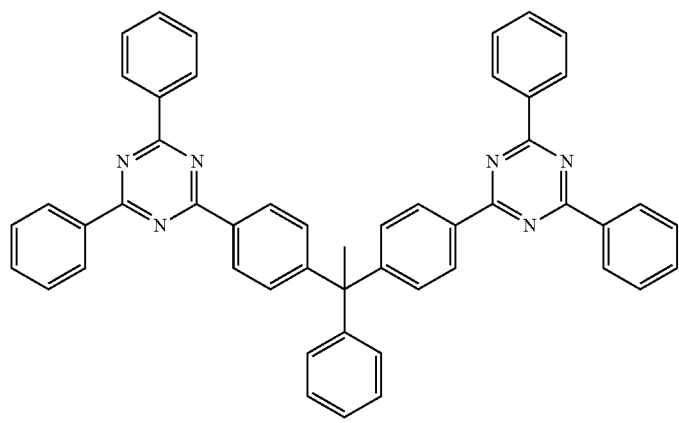
Compound 3
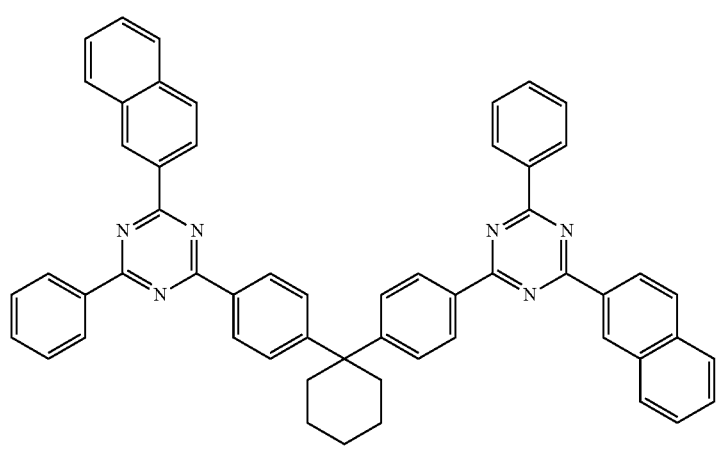
Compound 4

Compound 5
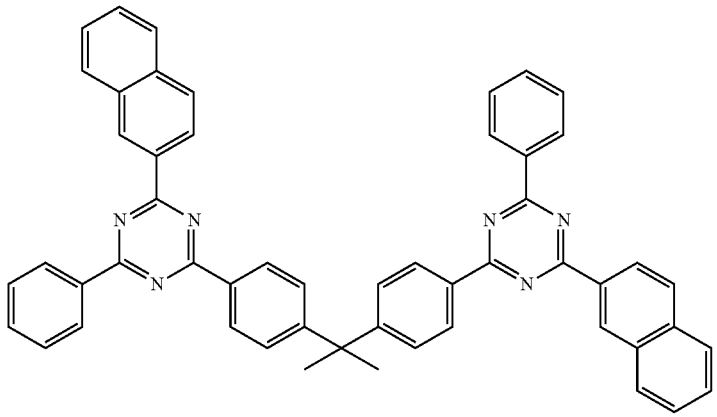
Compound 6
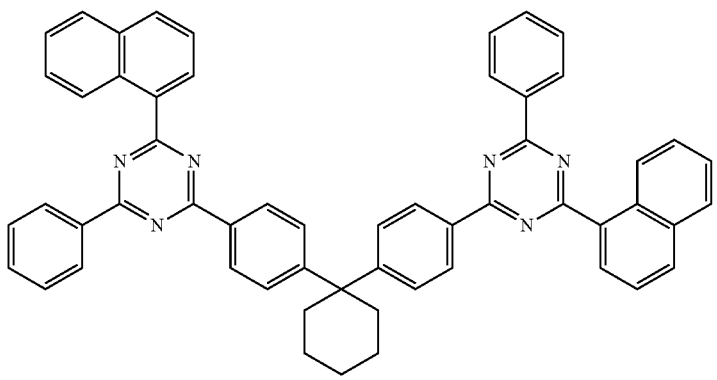
Compound 7
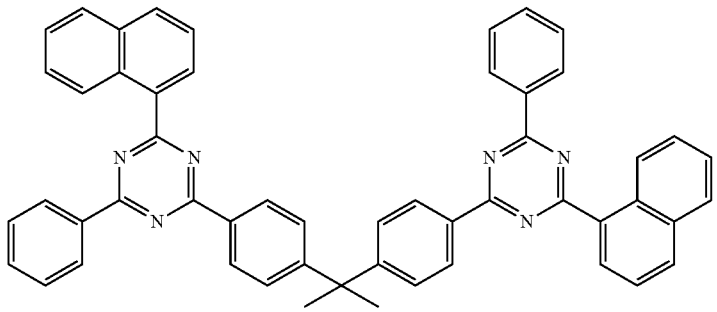
Compound 8
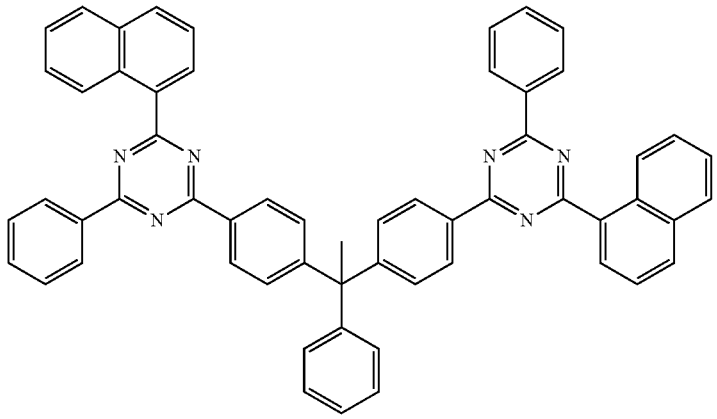

Compound 9
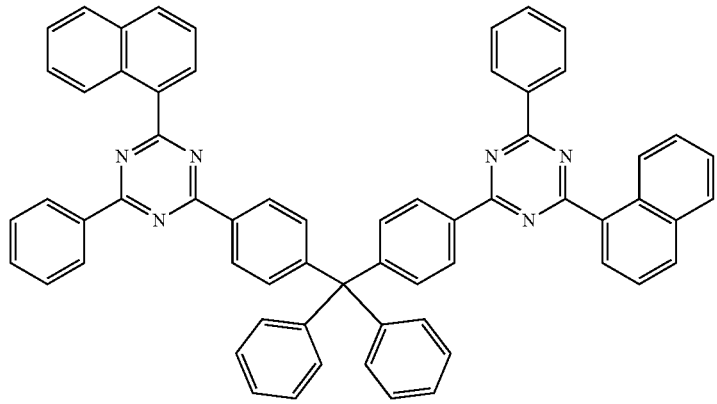
Compound 10
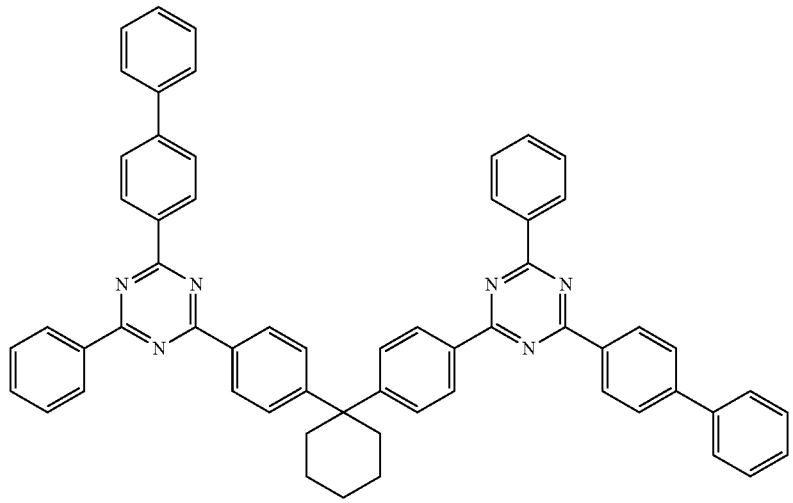
Compound 11
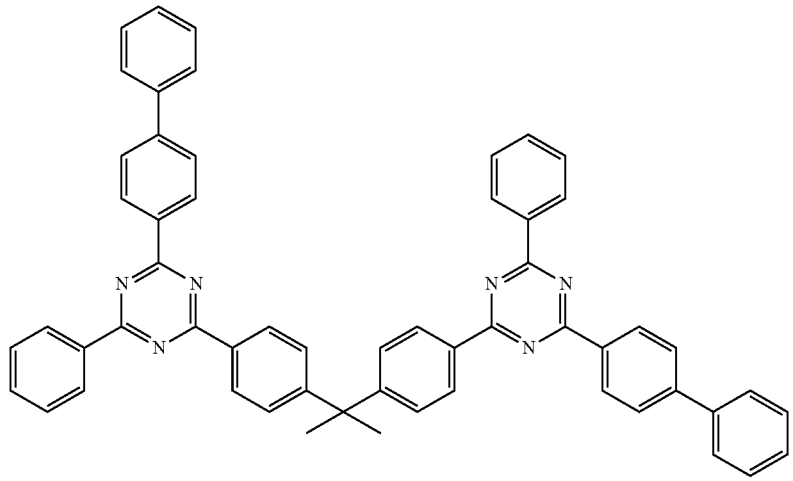

Compound 12
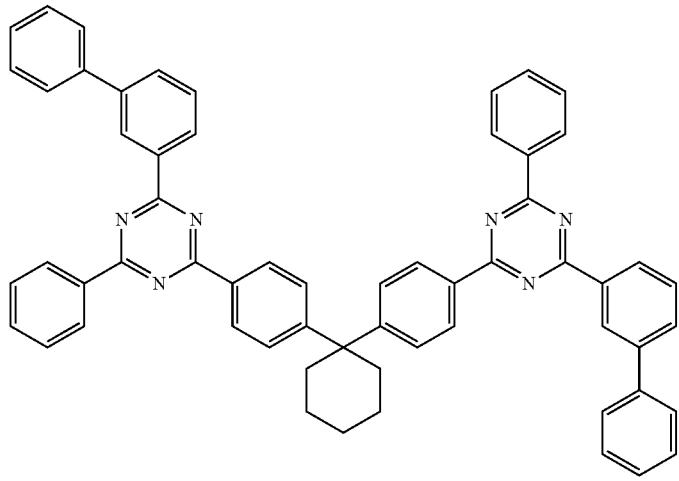
Compound 13
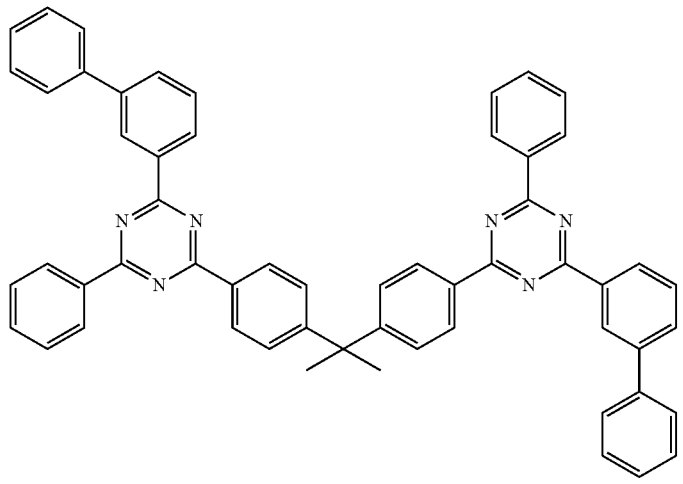
Compound 14
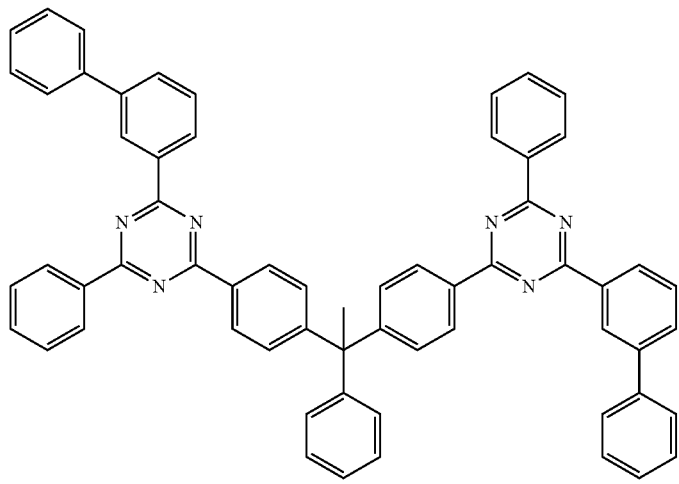

-continued
Compound 15
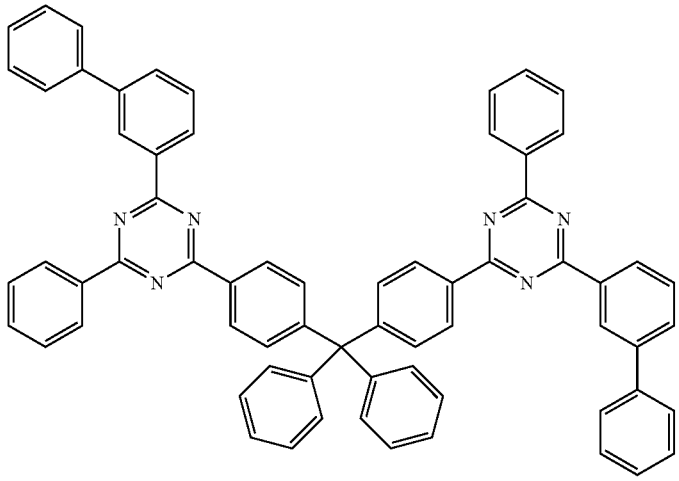
Compound 16
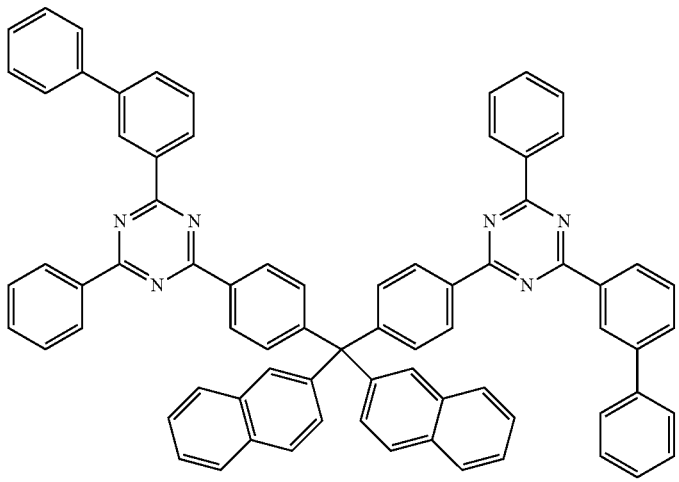
Compound 17
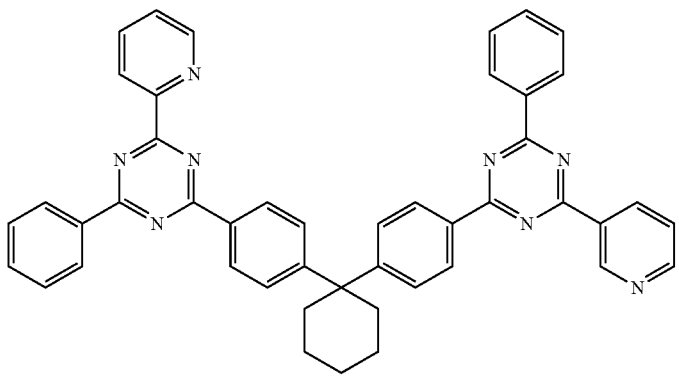
Compound 18
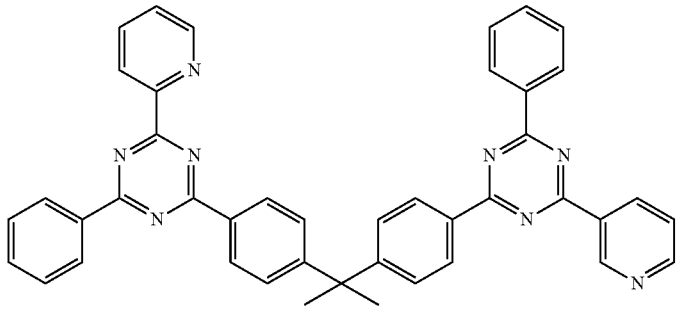

Compound 19
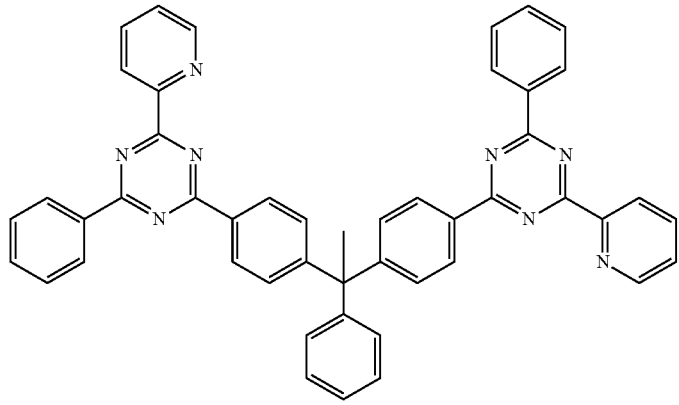
Compound 20
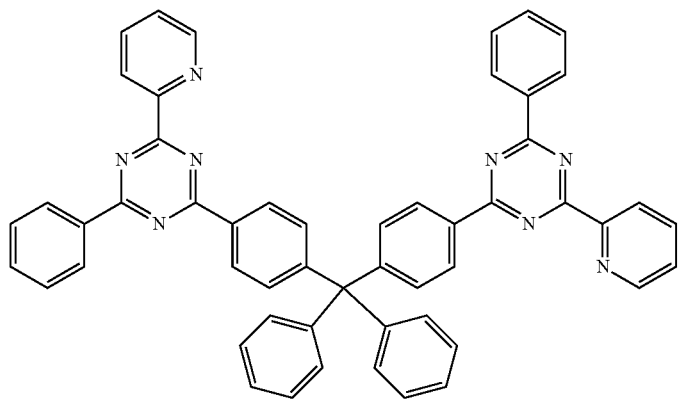
Compound 21
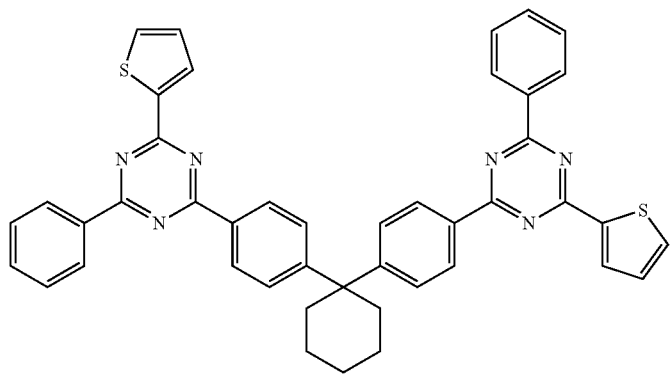
Compound 22
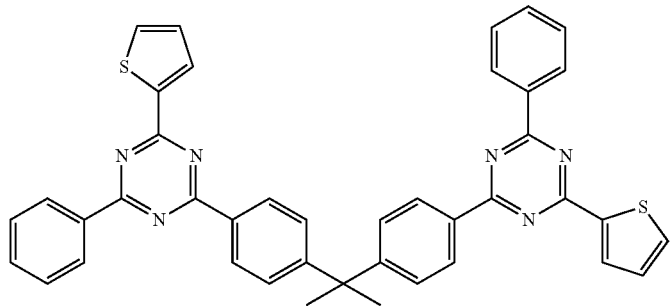

-continued
Compound 23
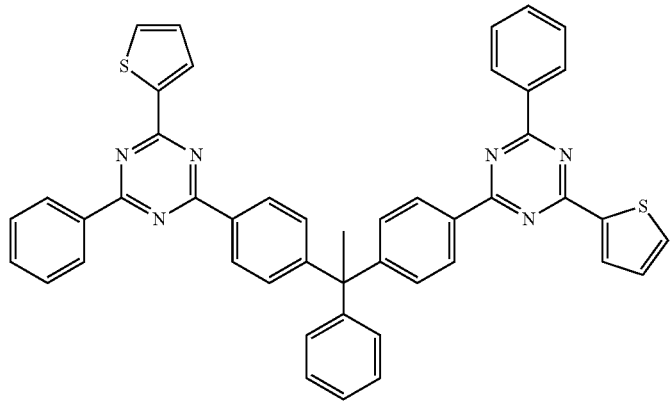
Compound 24
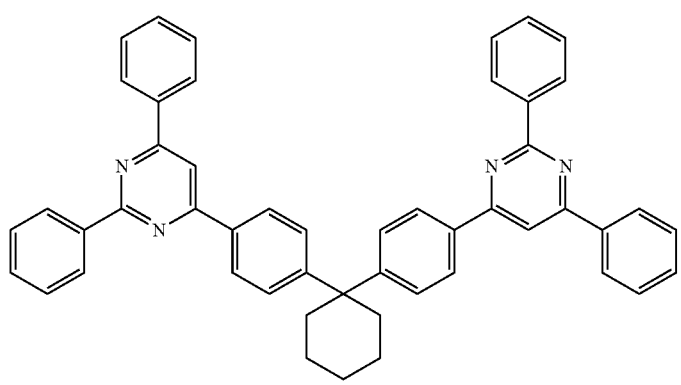
Compound 25
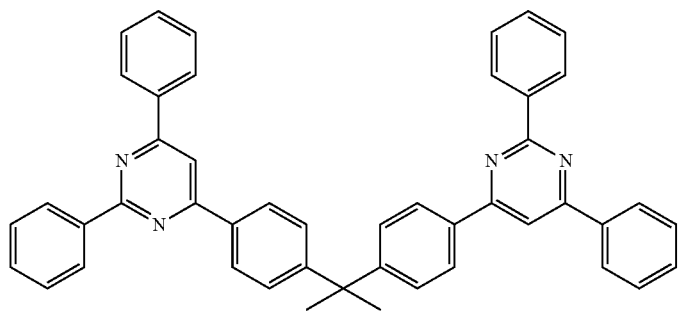
Compound 26
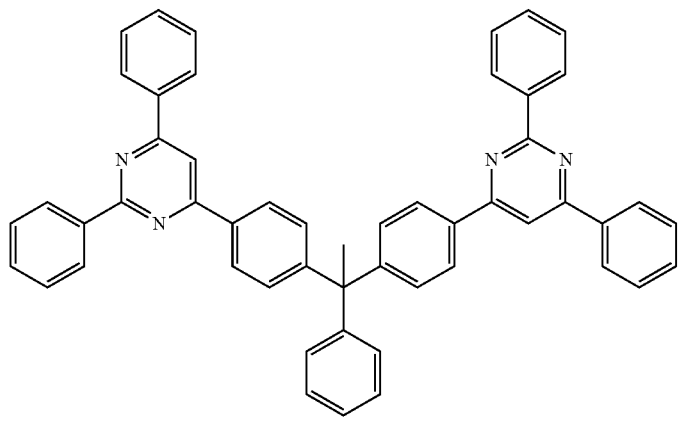

Compound 27
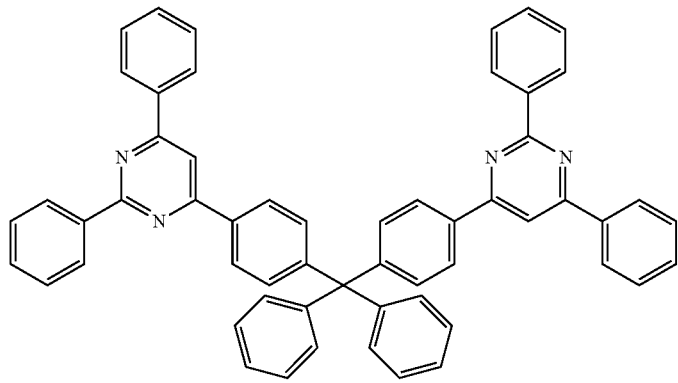
Compound 28
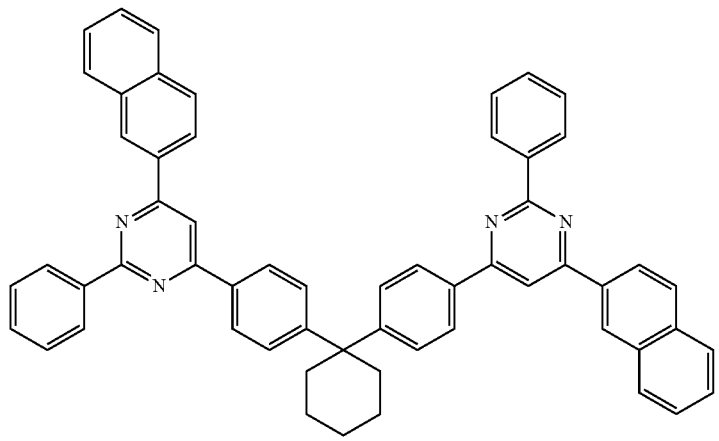
Compound 29
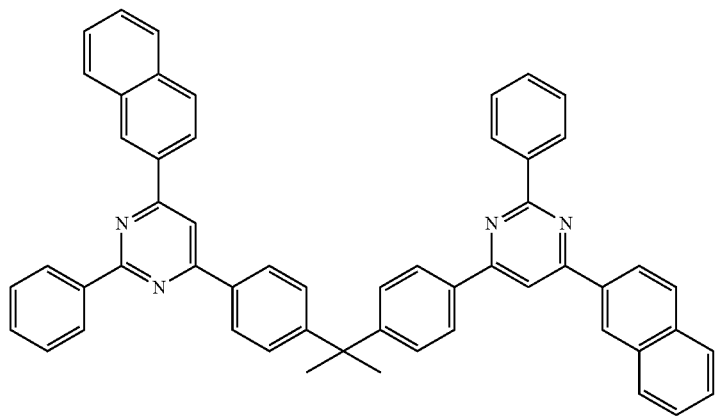

Compound 30
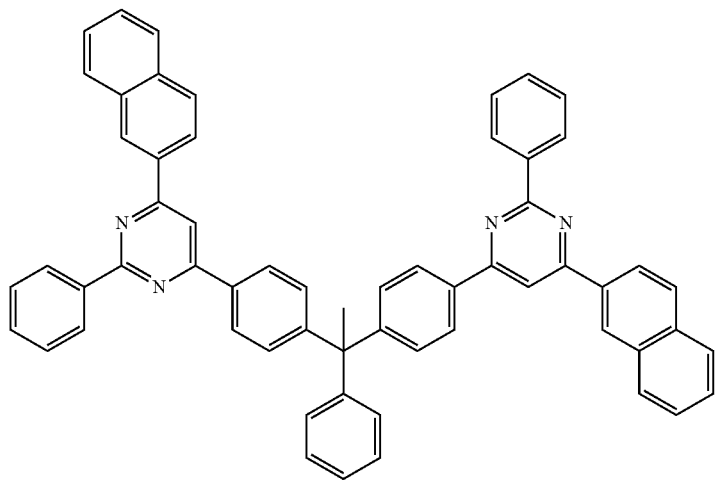
Compound 31
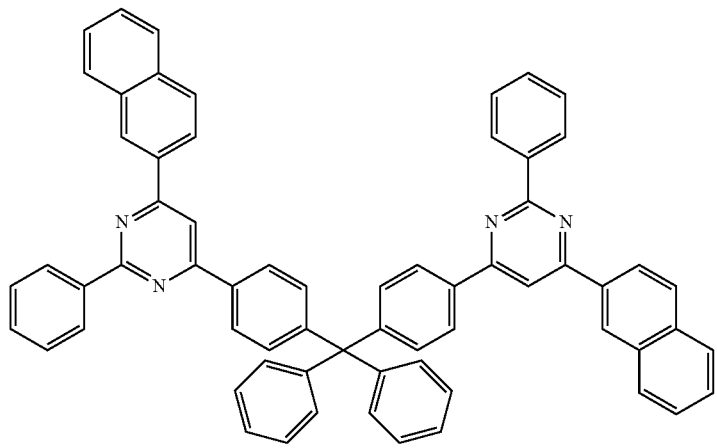
Compound 32
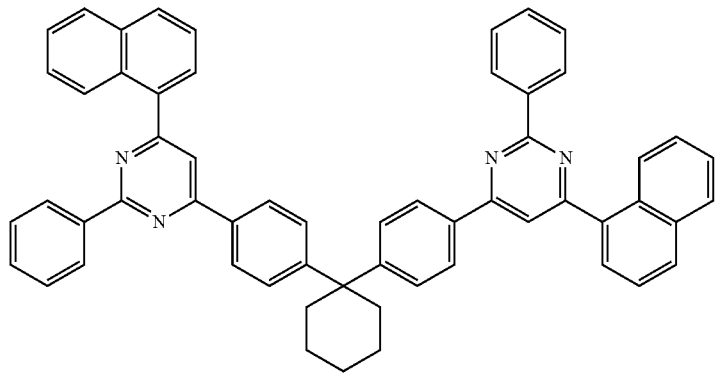
Compound 33
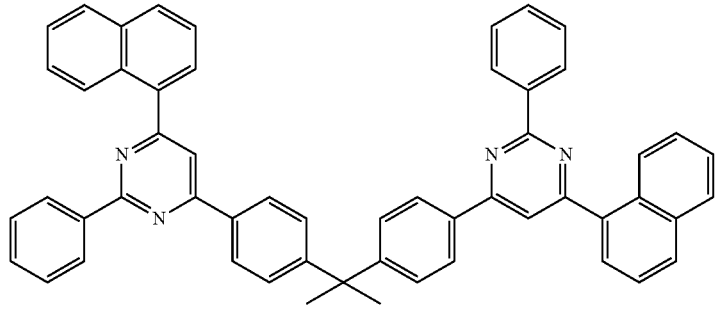

Compound 34
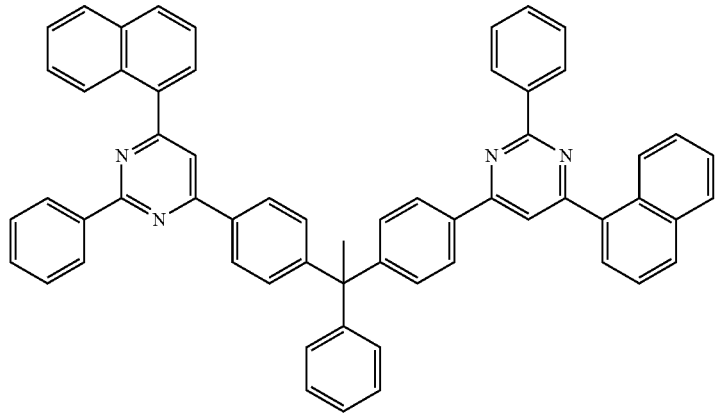
Compound 35
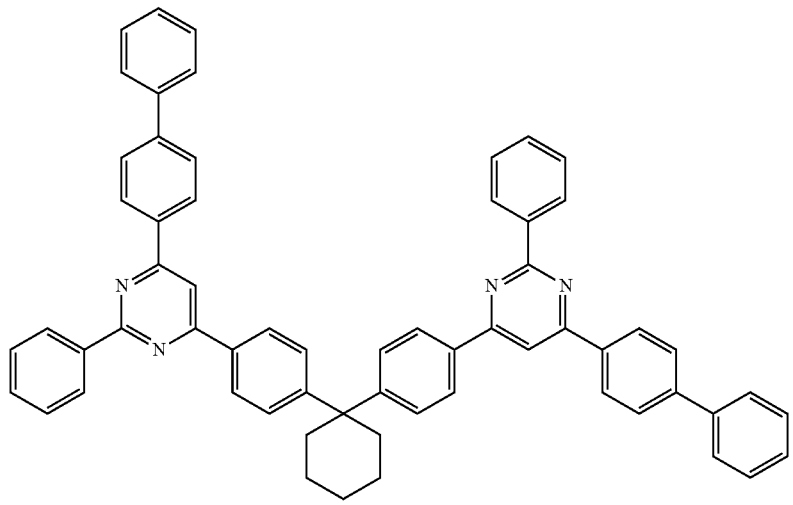
Compound 36
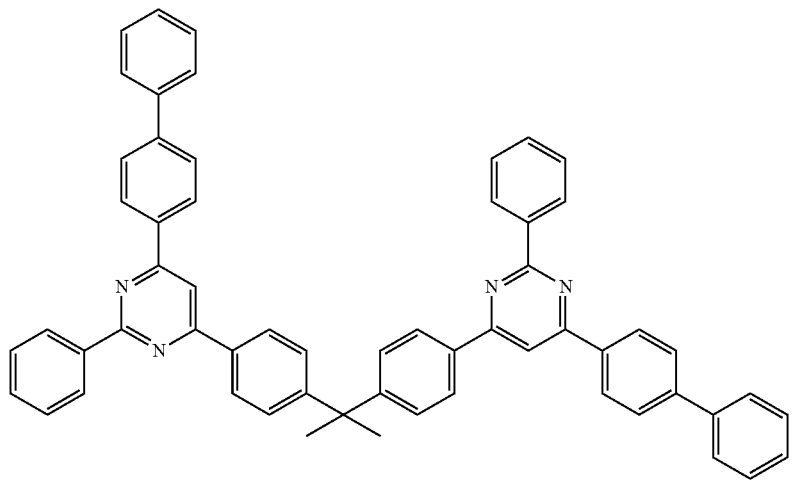

-continued
Compound 37
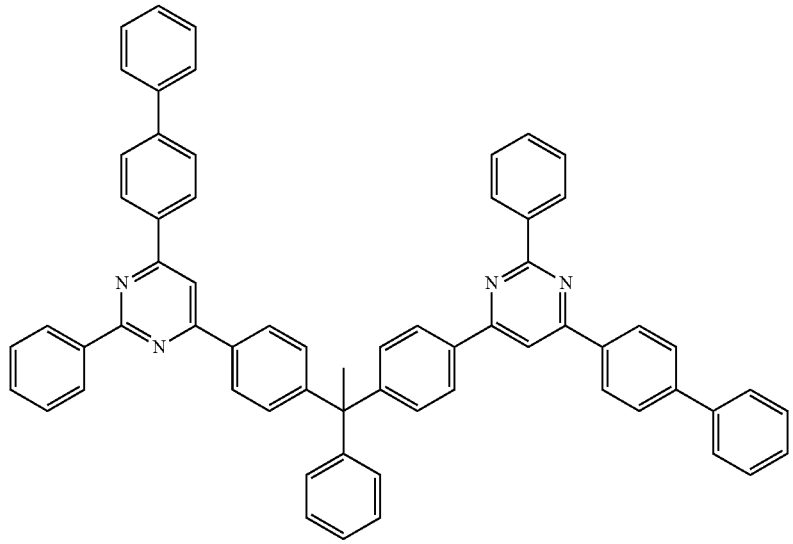
Compound 36
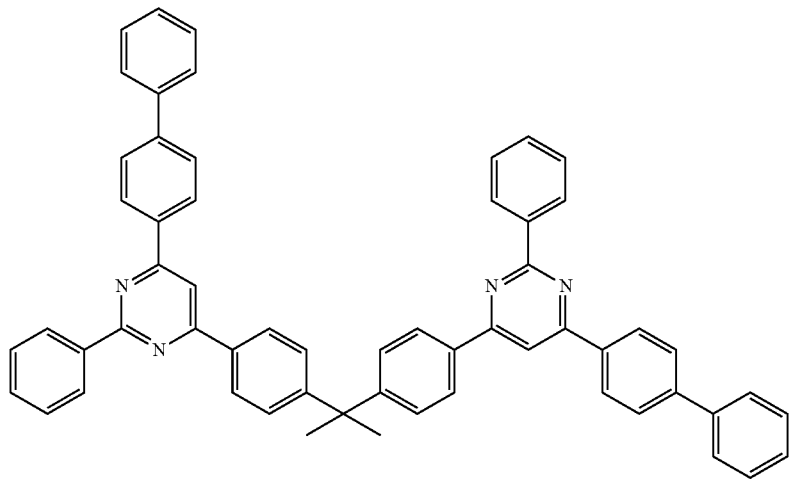
Compound 37
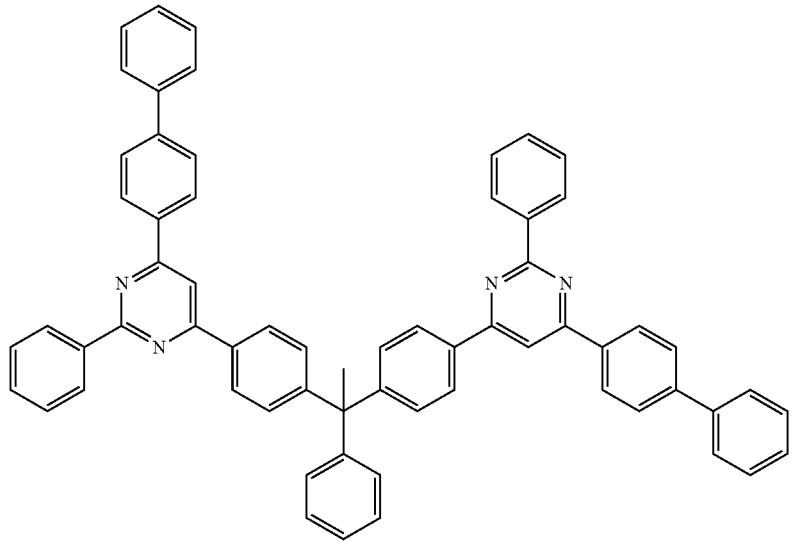

-continued
Compound 38
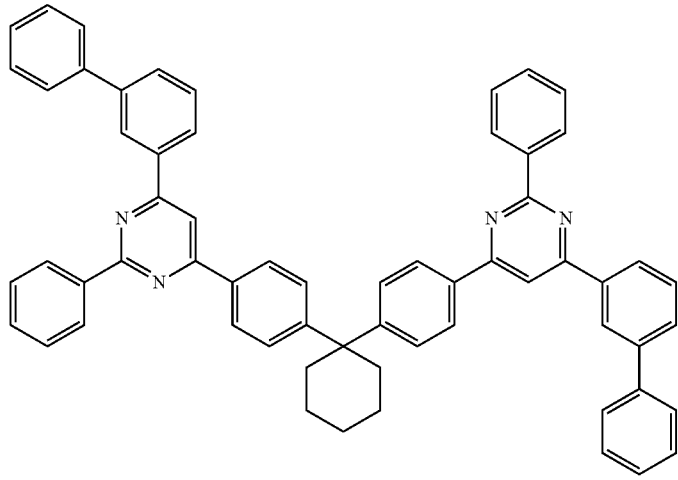
Compound 39
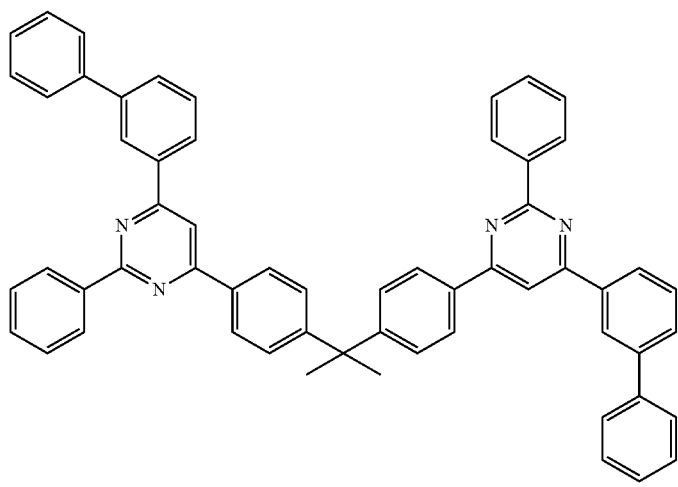
Compound 40
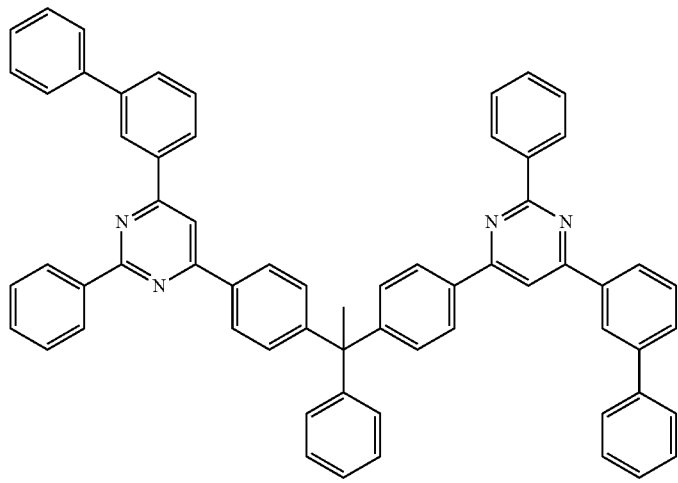

-continued
Compound 41
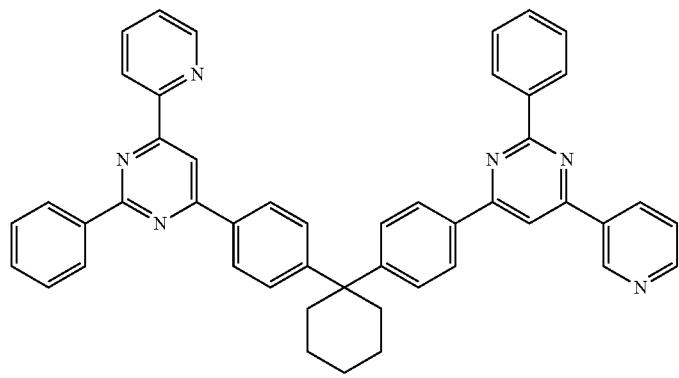
Compound 42
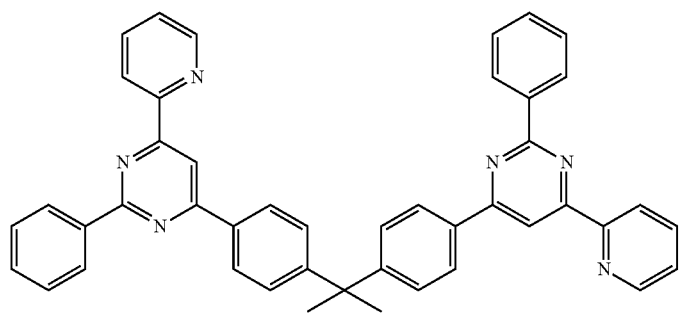
Compound 43
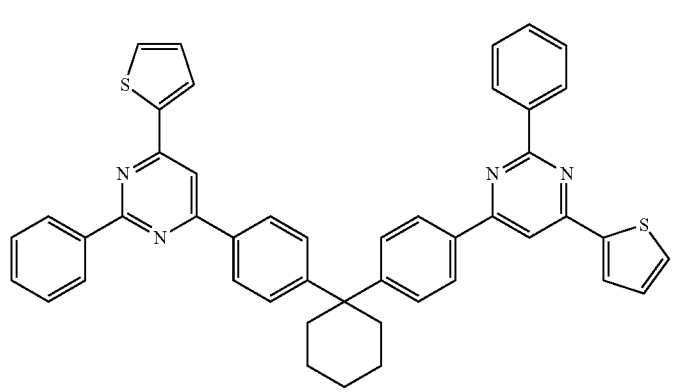
Compound 44
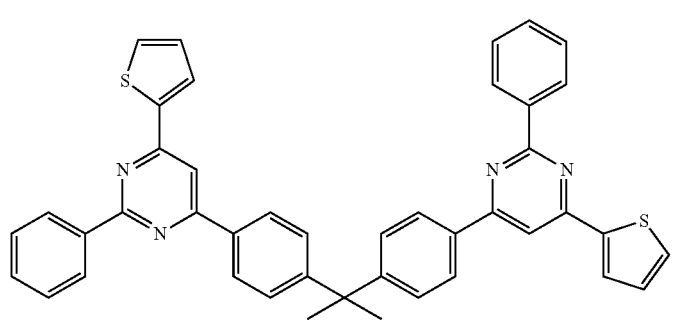

-continued
Compound 45
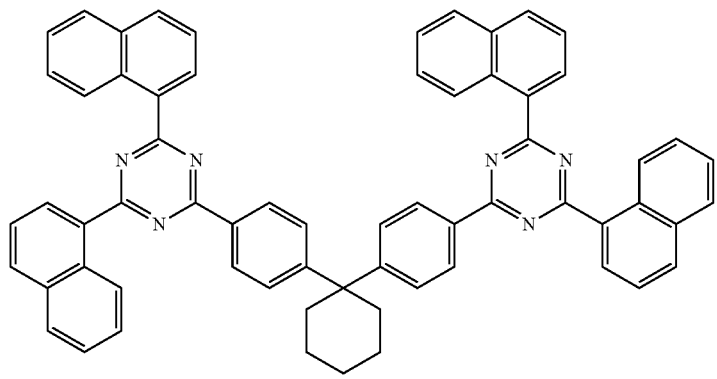
Compound 46
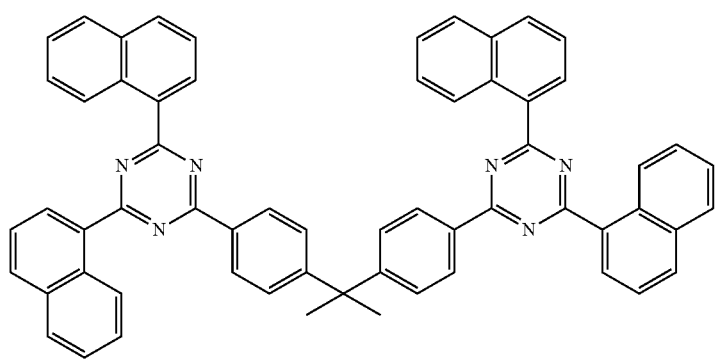
Compound 47
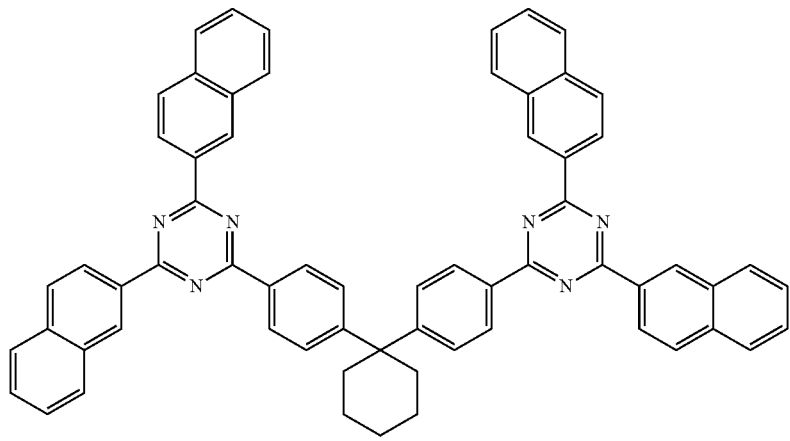
Compound 48
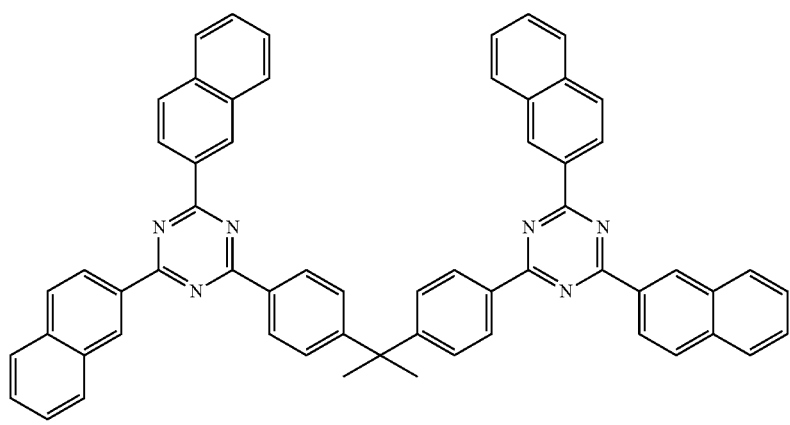

-continued
Compound 49
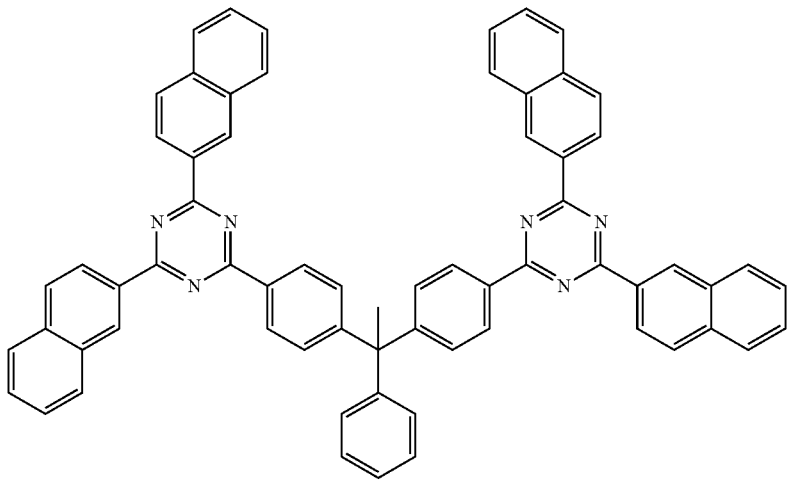
Compound 50
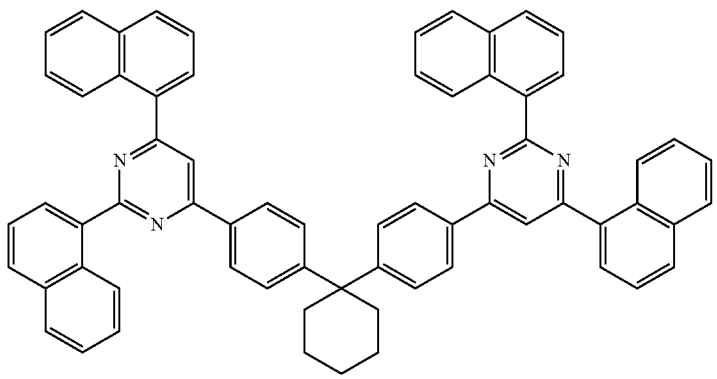
Compound 51
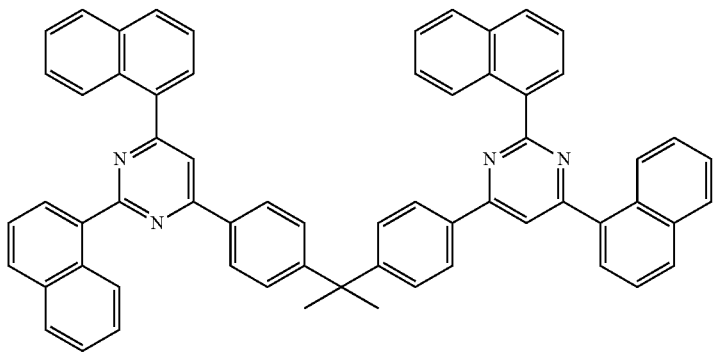
Compound 52
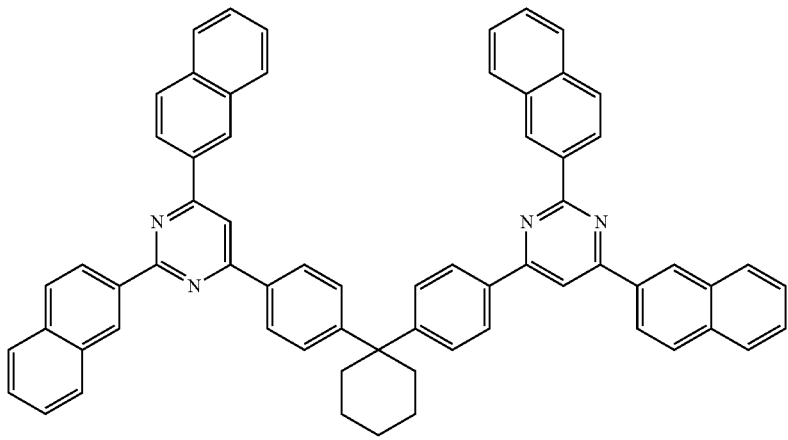

-continued
Compound 53
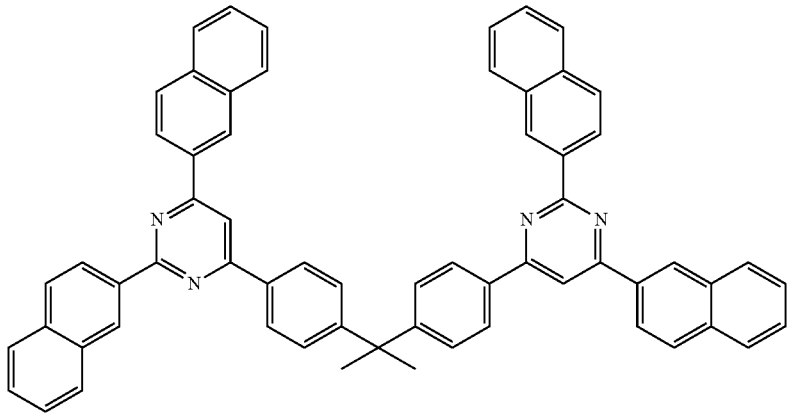
Compound 54
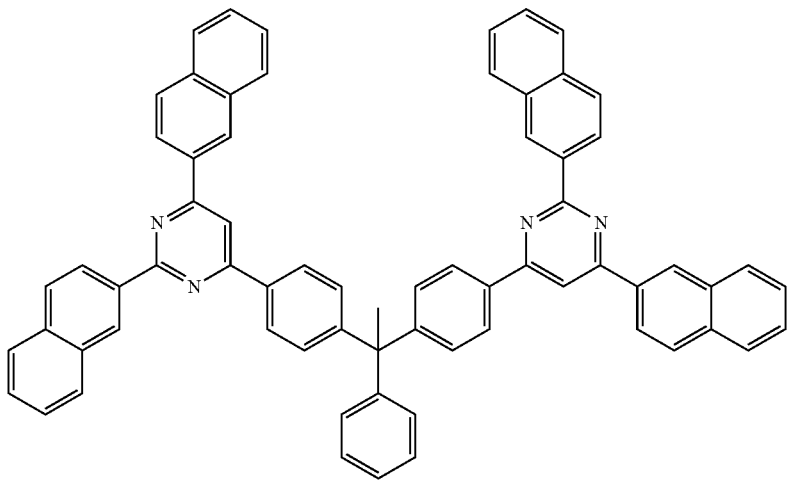
Compound 55
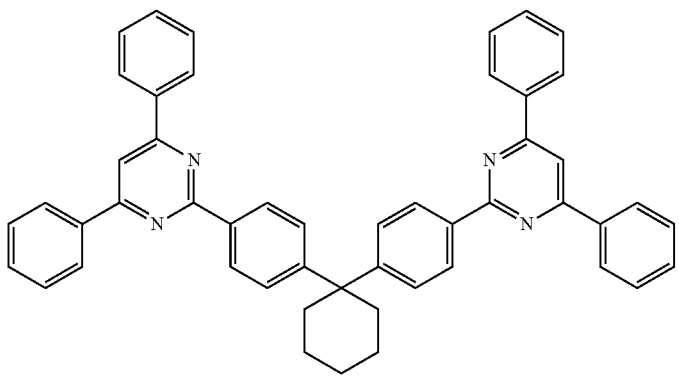
Compound 56
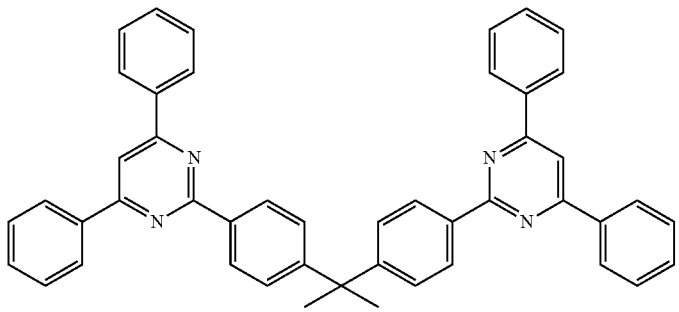

-continued
Compound 57
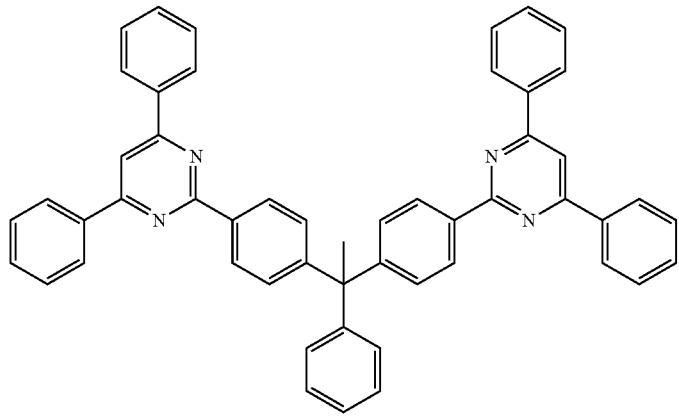
Compound 58
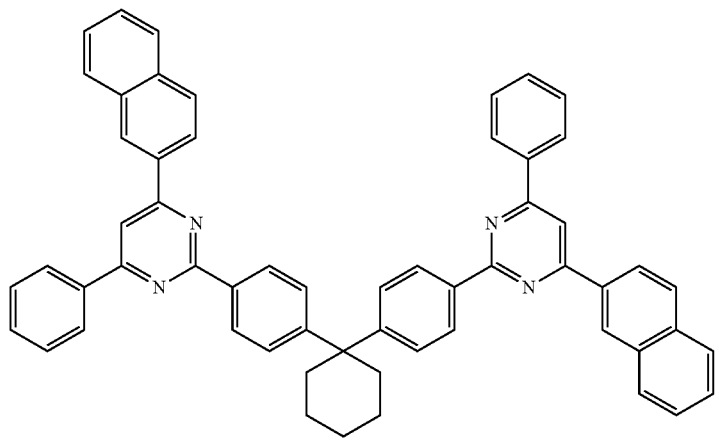
Compound 59
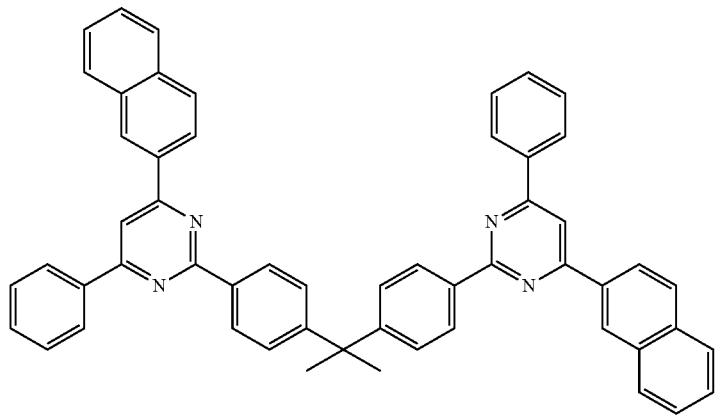
Compound 60
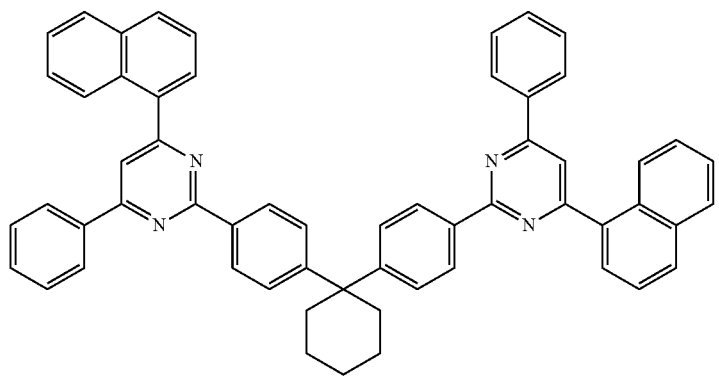

-continued
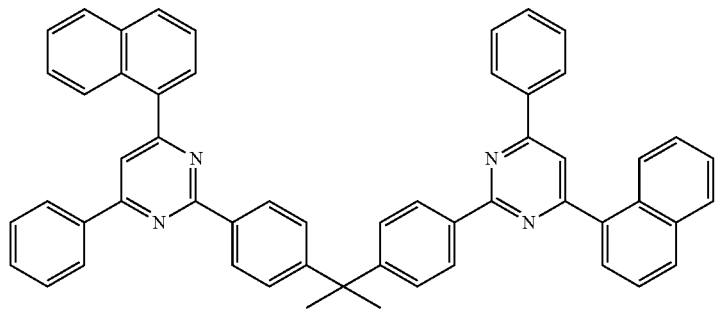
Compound 61
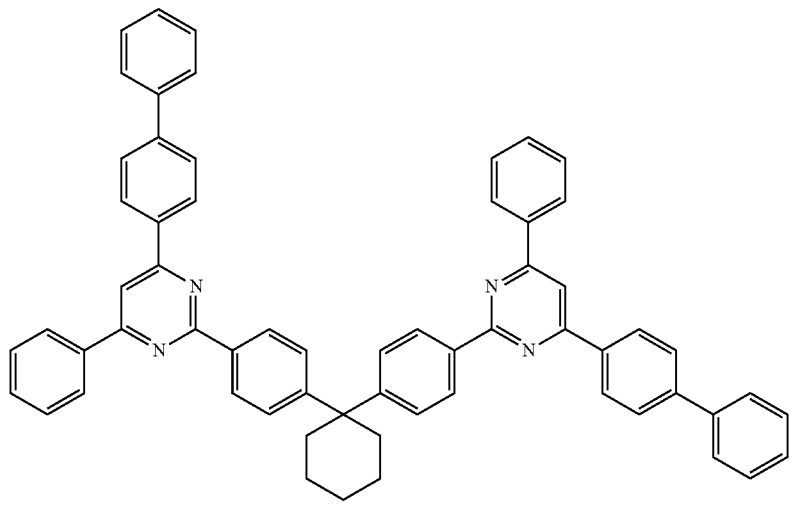
Compound 62
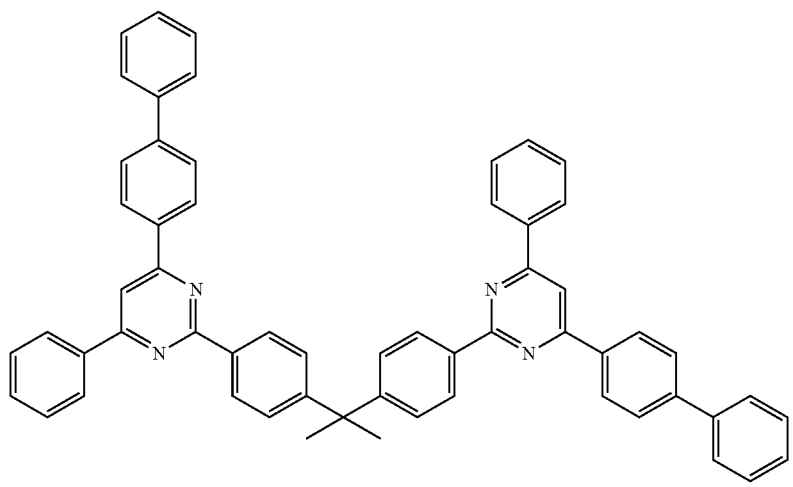
Compound 63

-continued
Compound 64
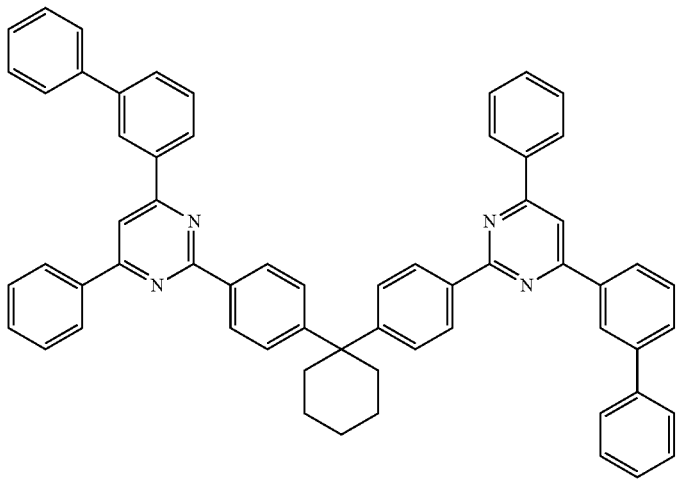
Compound 65
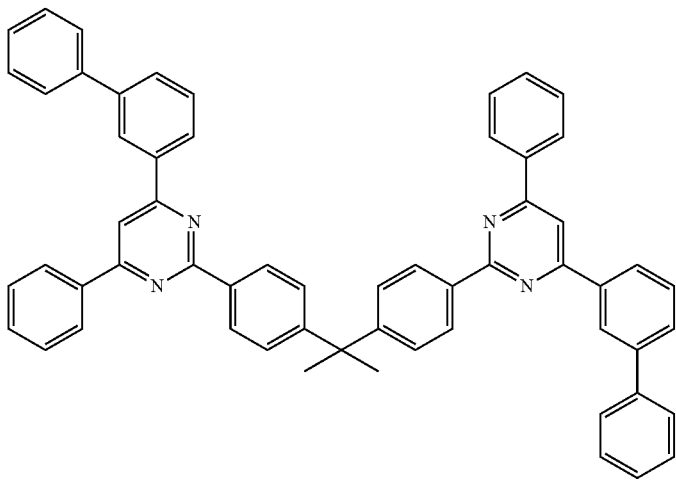
Compound 66
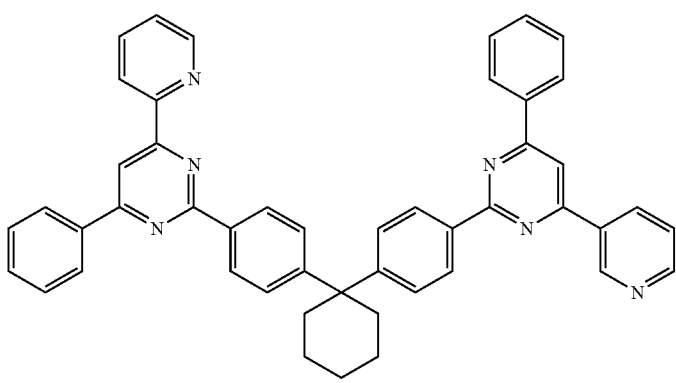
Compound 67
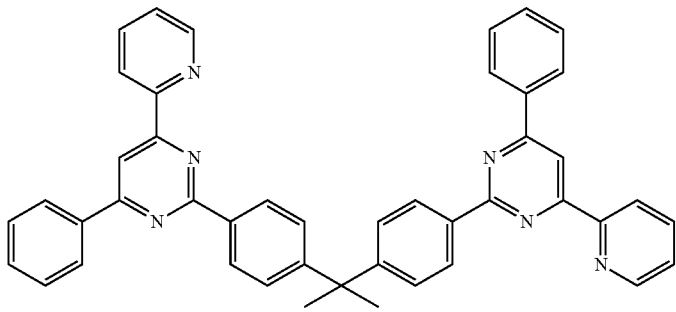

-continued
Compound 68
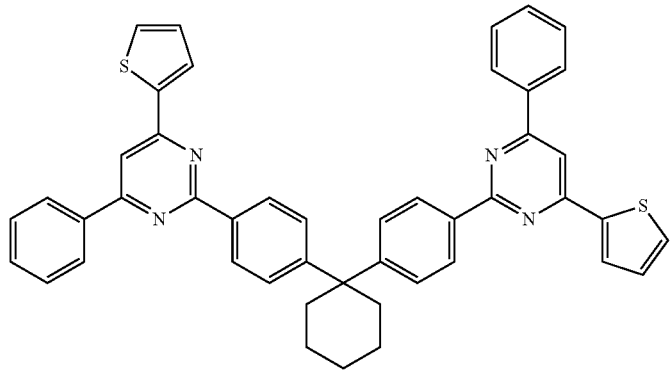
Compound 69
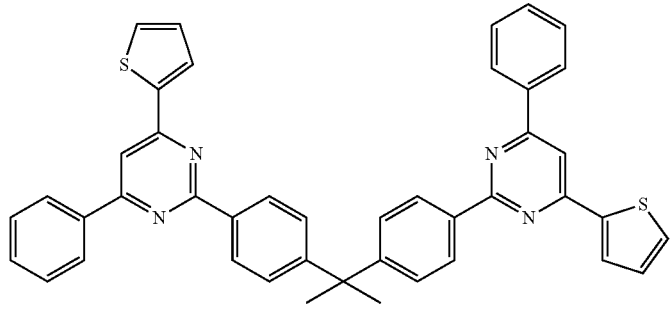
Compound 70
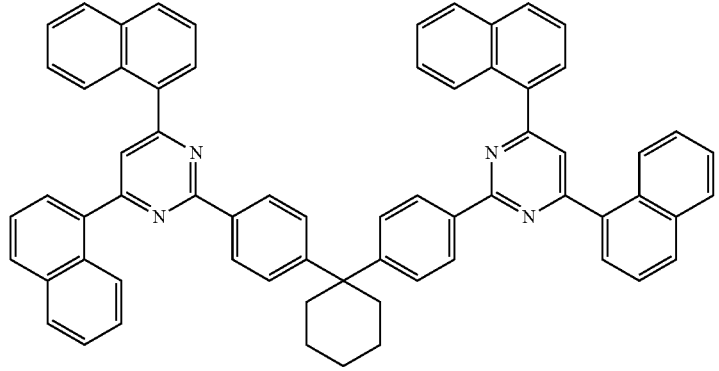
Compound 71
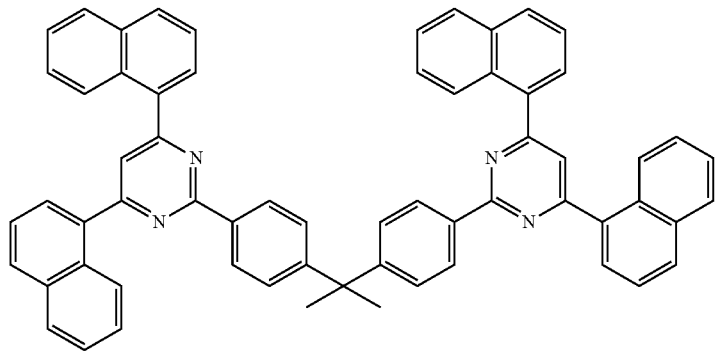

Compound 72
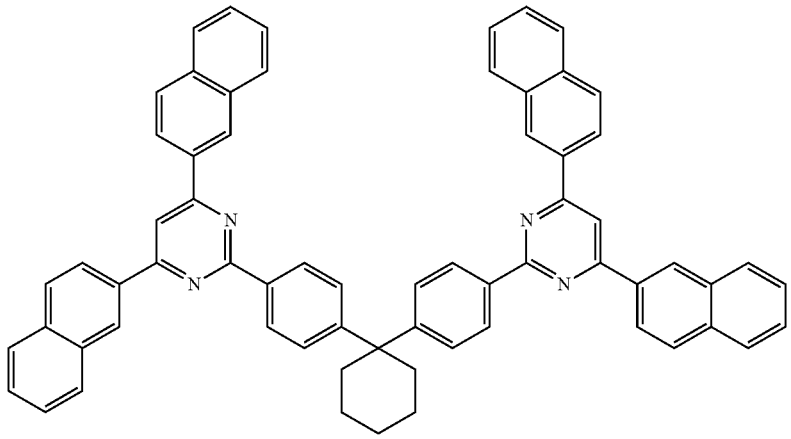
Compound 73
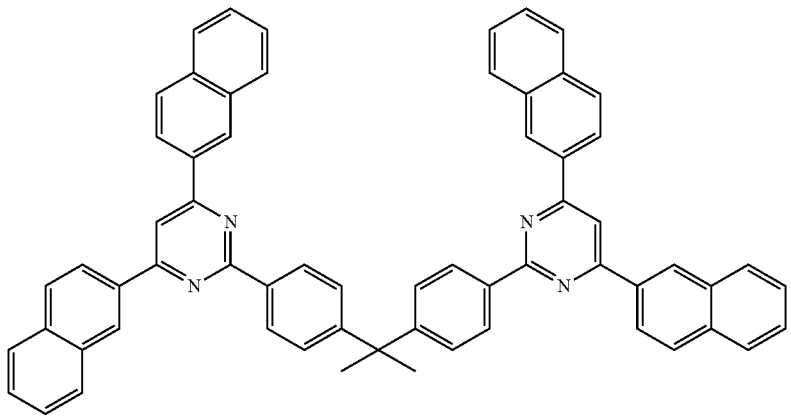
Compound 74
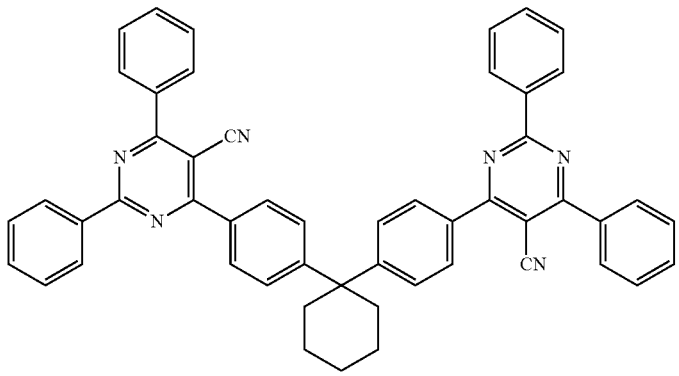
Compound 75
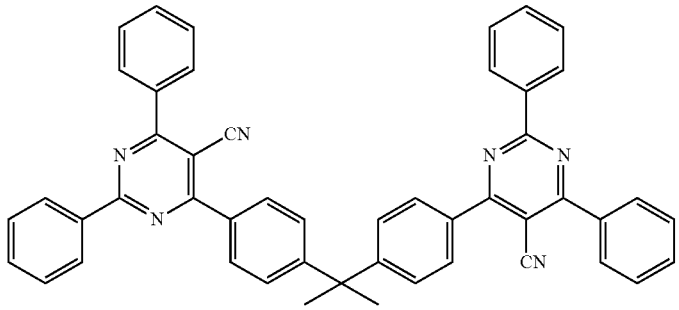

Compound 76
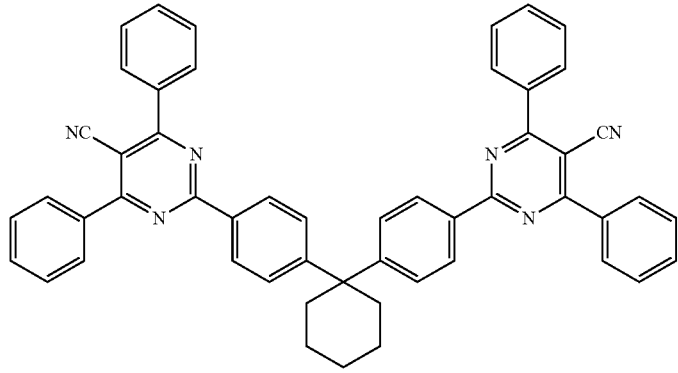
Compound 77
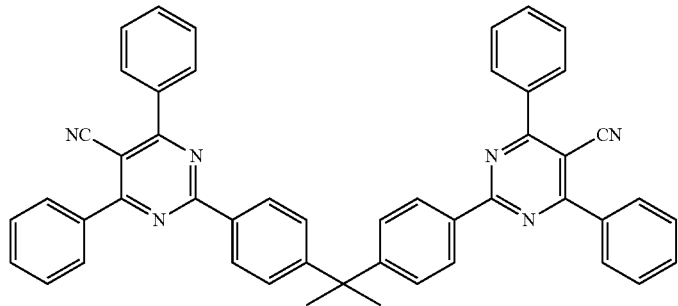
Compound 78
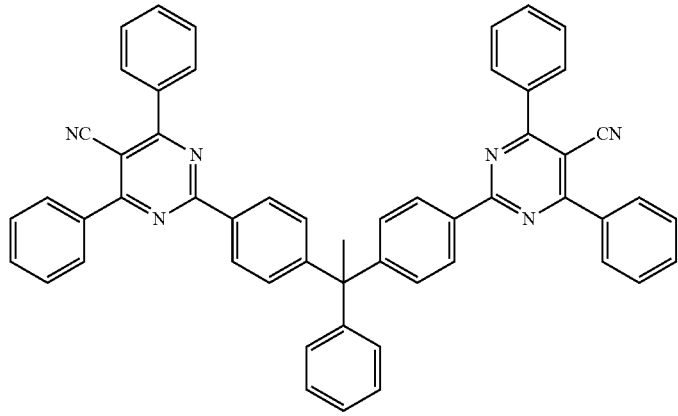
Compound 79
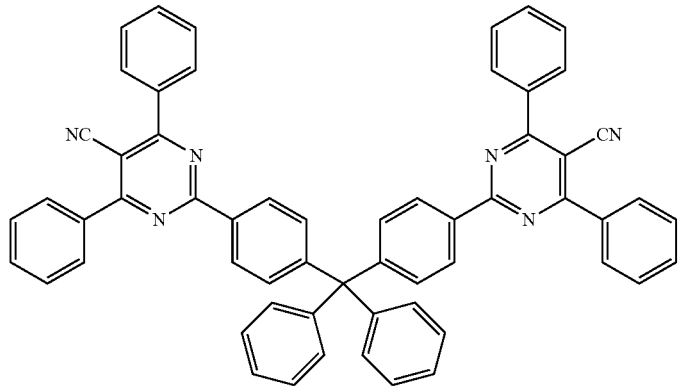

-continued
Compound 80
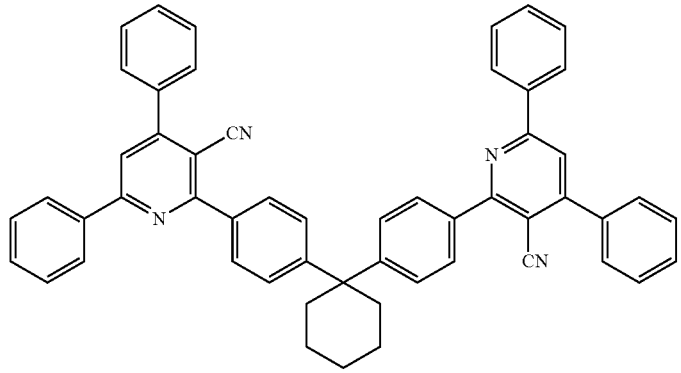
Compound 81
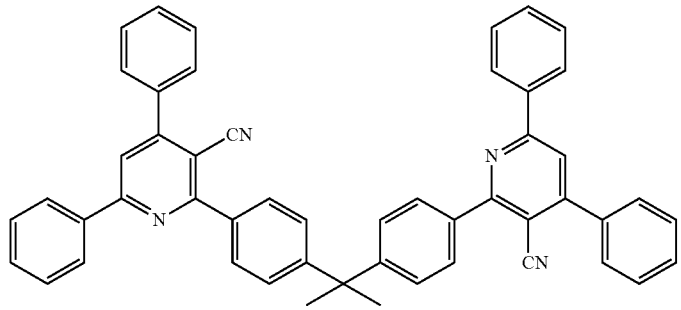
Compound 82
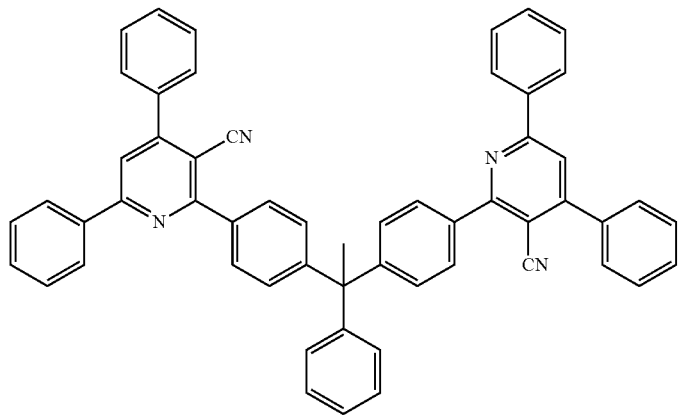
Compound 83
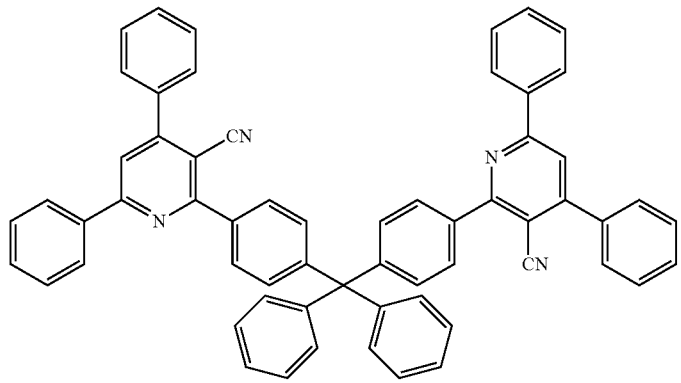

-continued
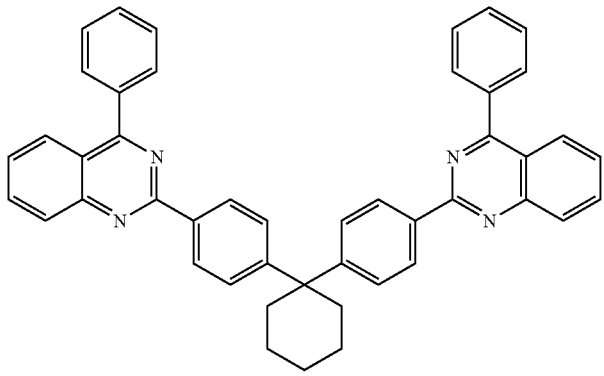
Compound 84
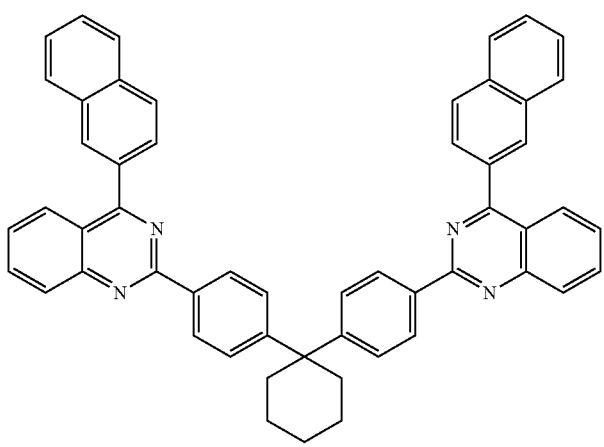
Compound 85
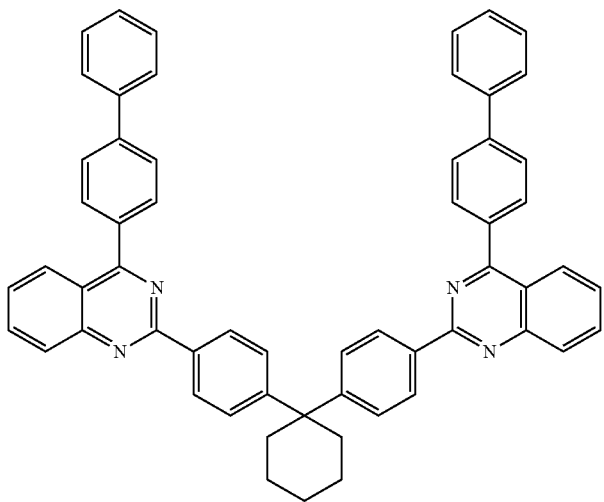
Compound 86

-continued
Compound 87
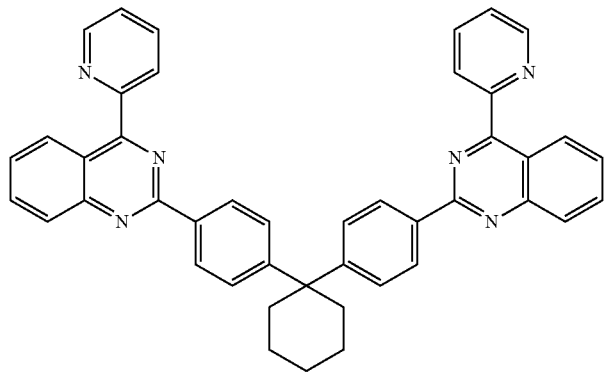
Compound 88
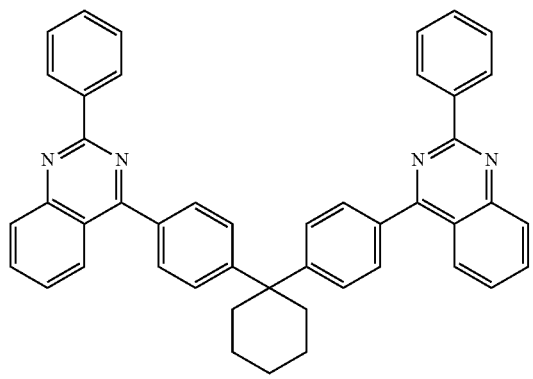
Compound 89
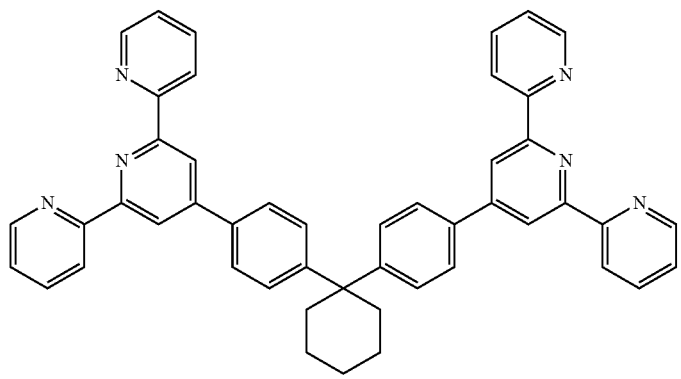
Compound 90
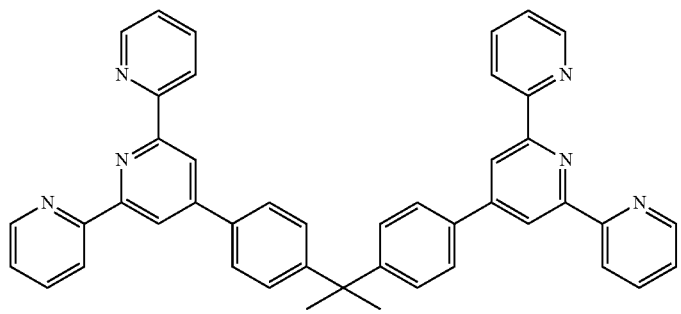

Compound 91
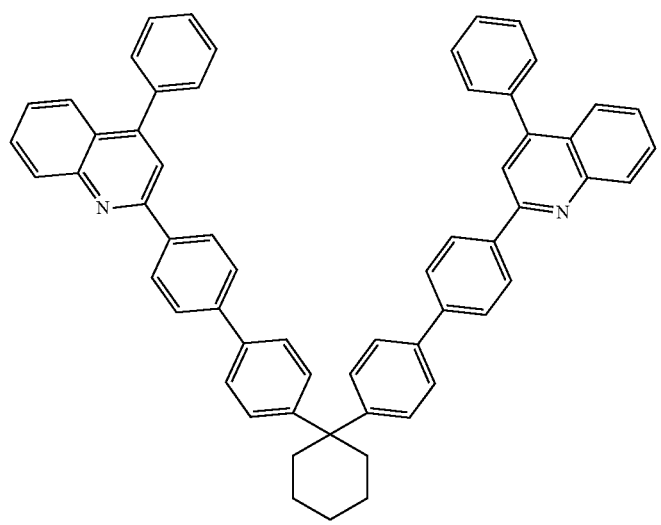
Compound 92
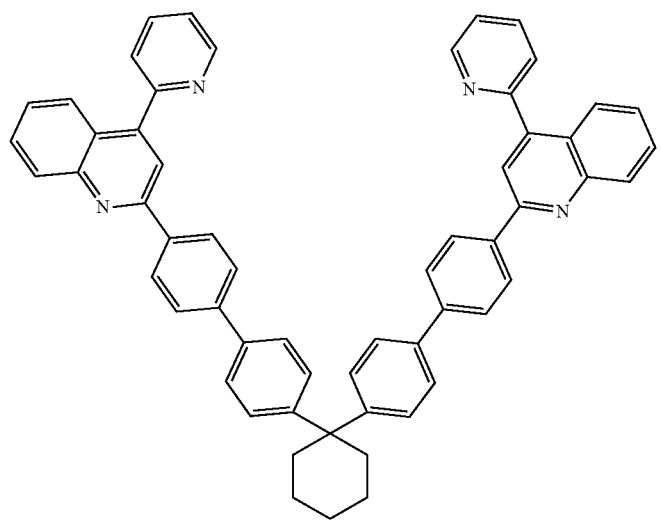
Compound 93
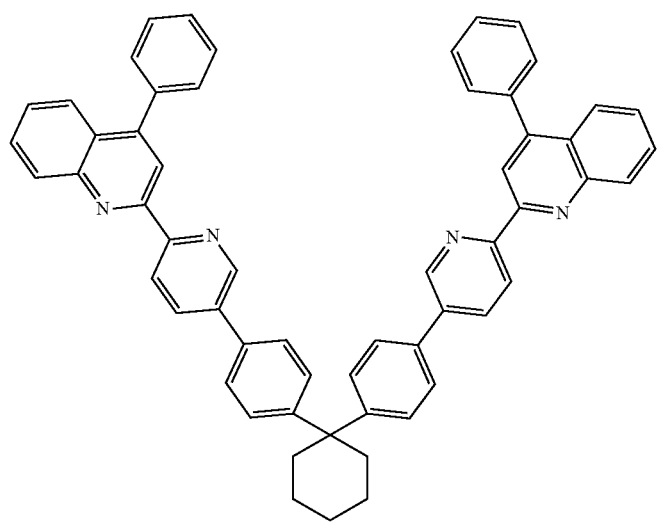

-continued
Compound 94
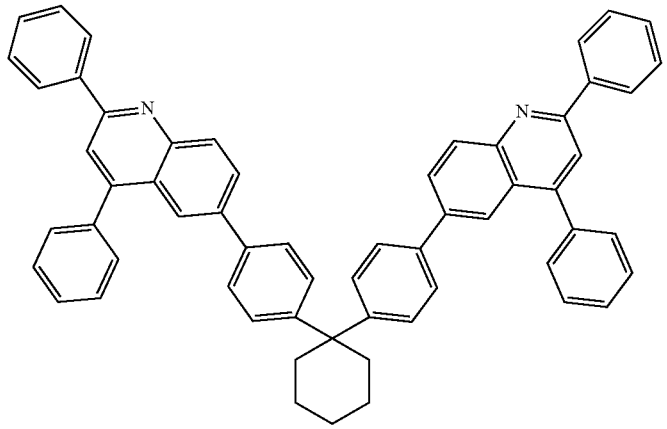
Compound 95
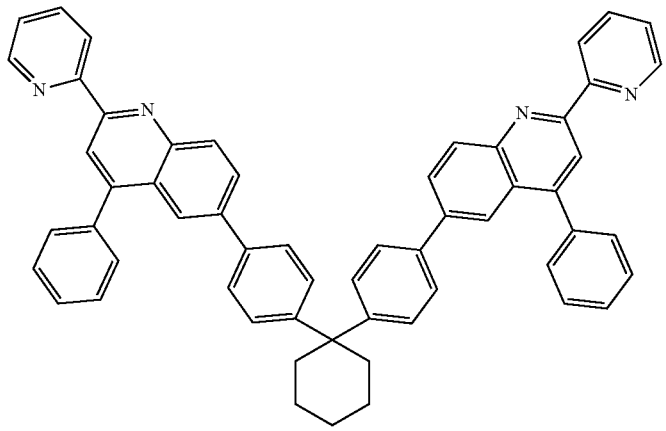
Compound 96
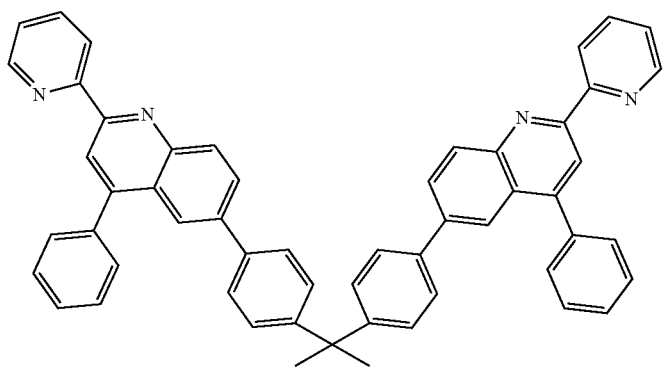
Compound 97
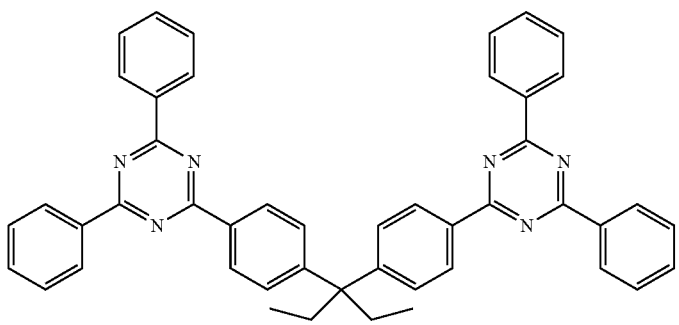

-continued
Compound 98
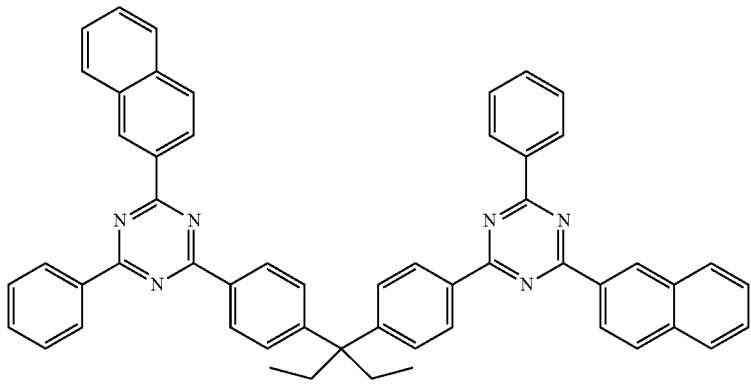
Compound 99
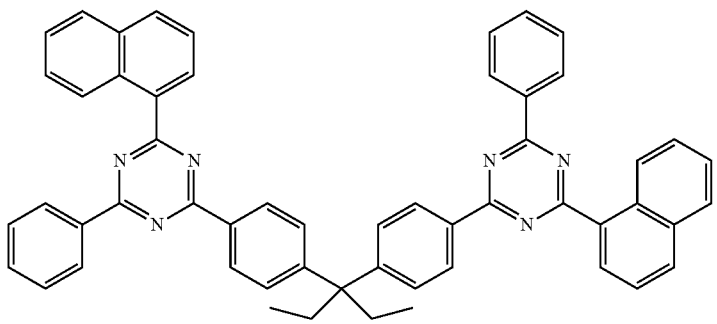
Compound 100
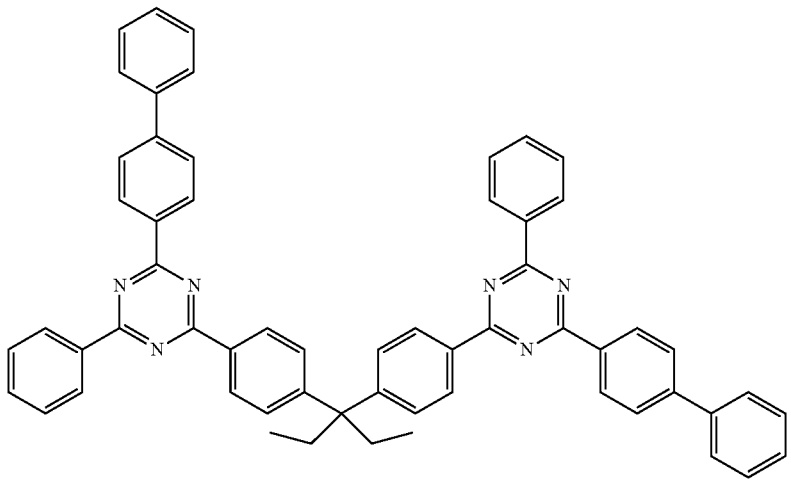
Compound 101
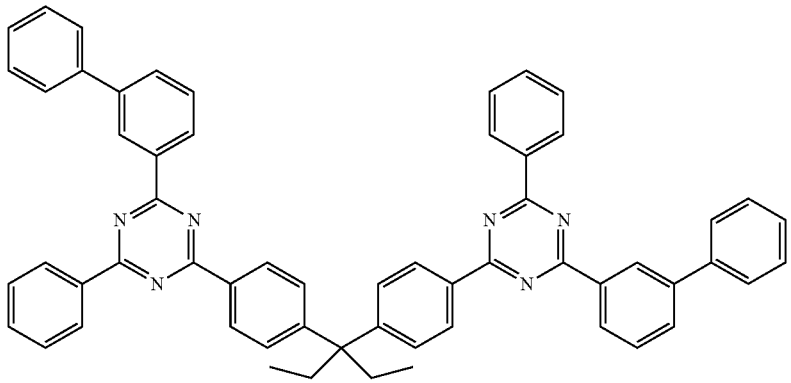

Compound 102
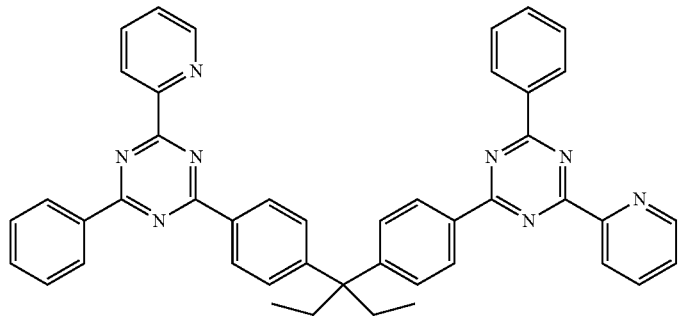
Compound 103
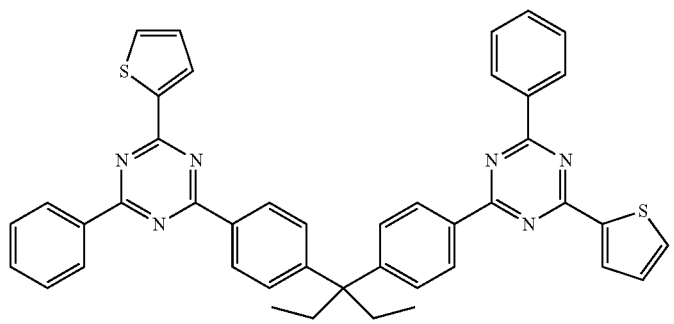
Compound 104
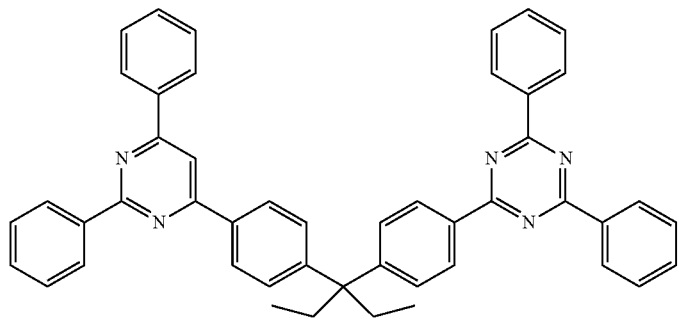
Compound 105
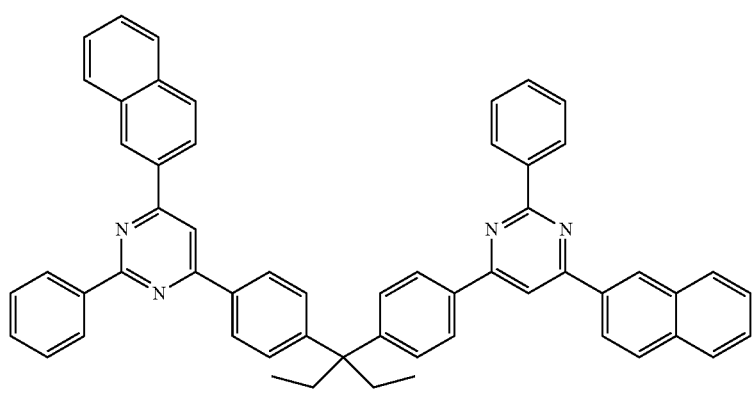

Compound 106
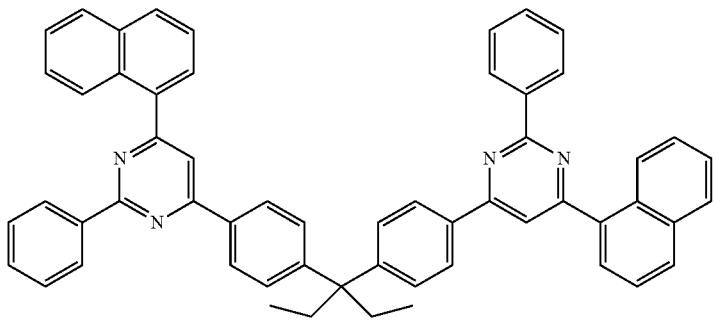
Compound 107
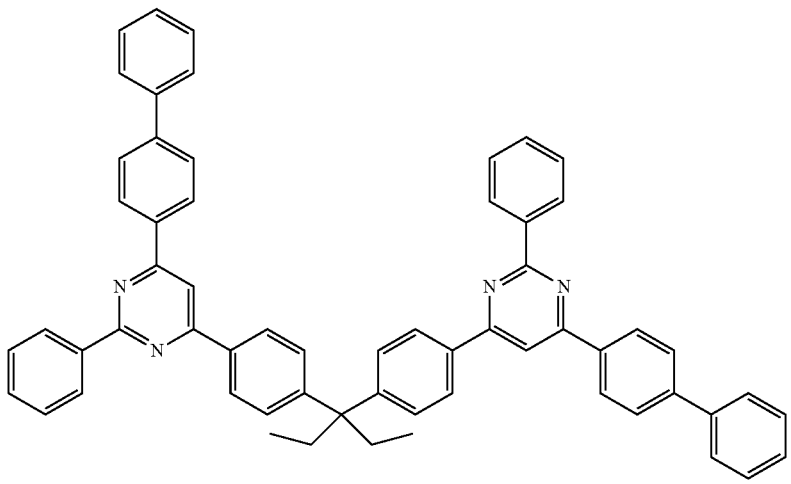
Compound 108
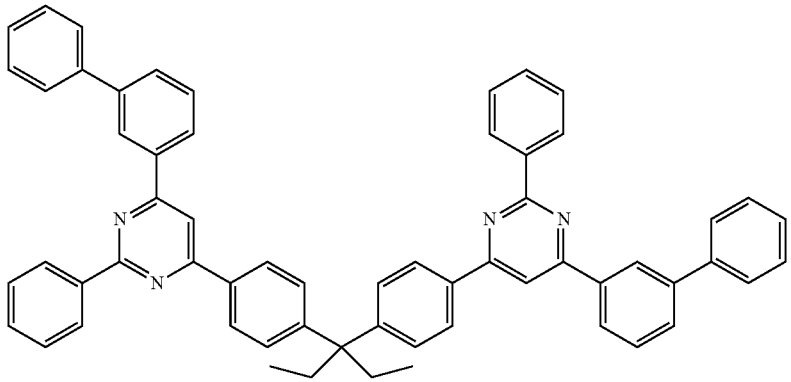
Compound 109
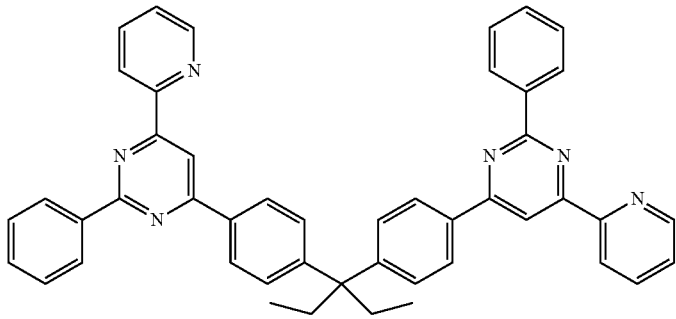

Compound 110
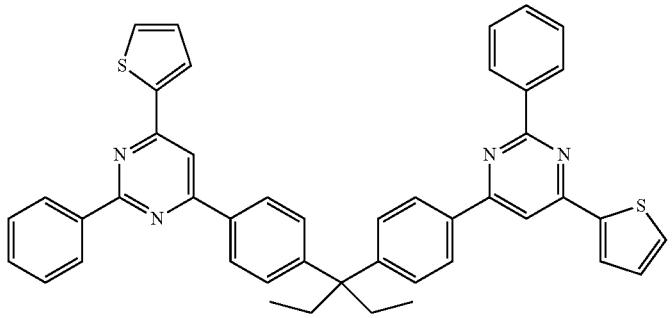
Compound 111
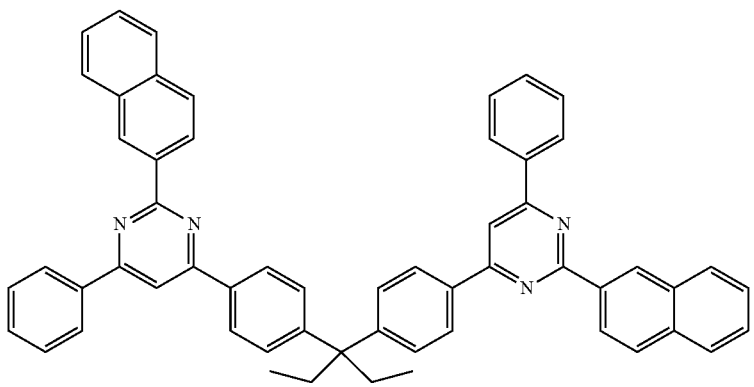
Compound 112
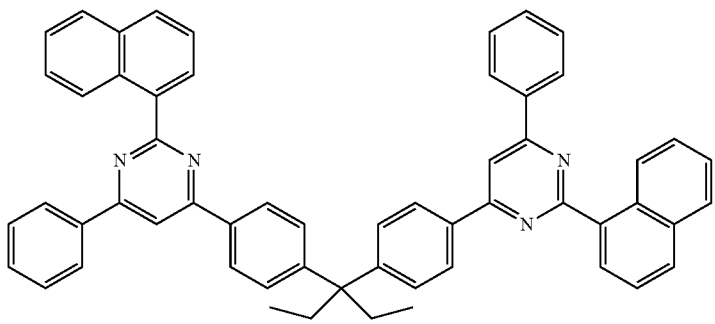
Compound 113
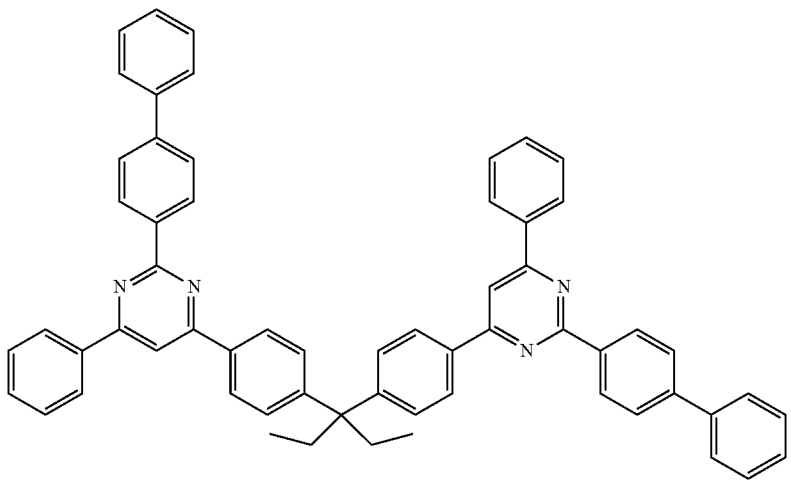

-continued
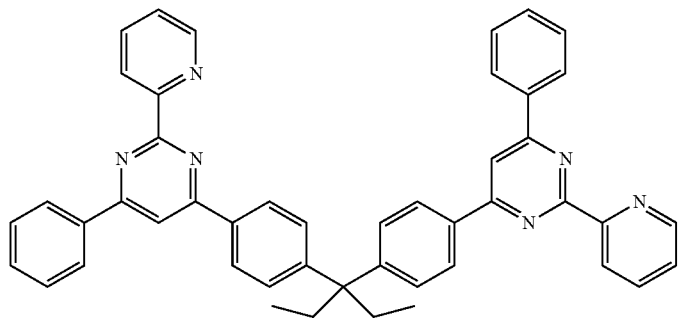
Compound 114
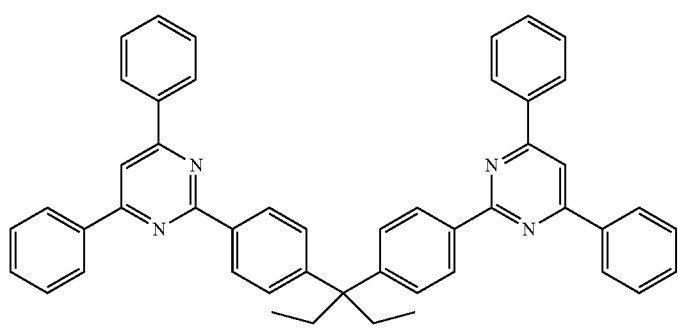
Compound 115
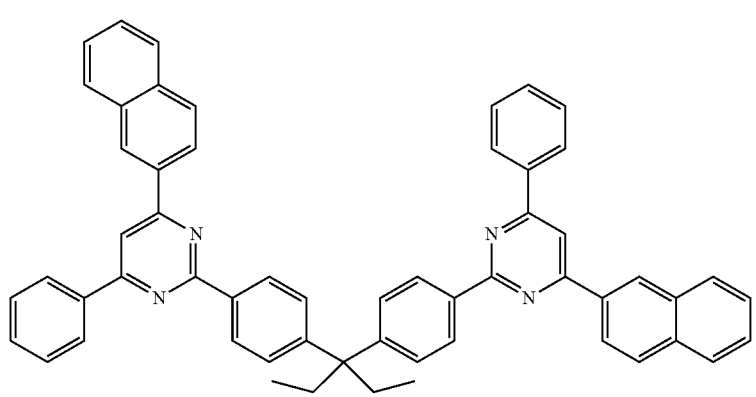
Compound 116
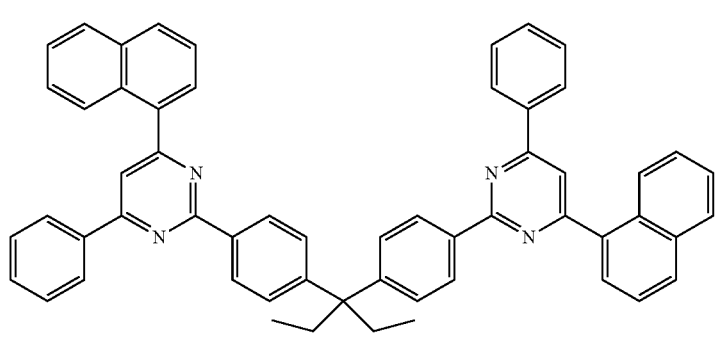
Compound 117

Compound 118
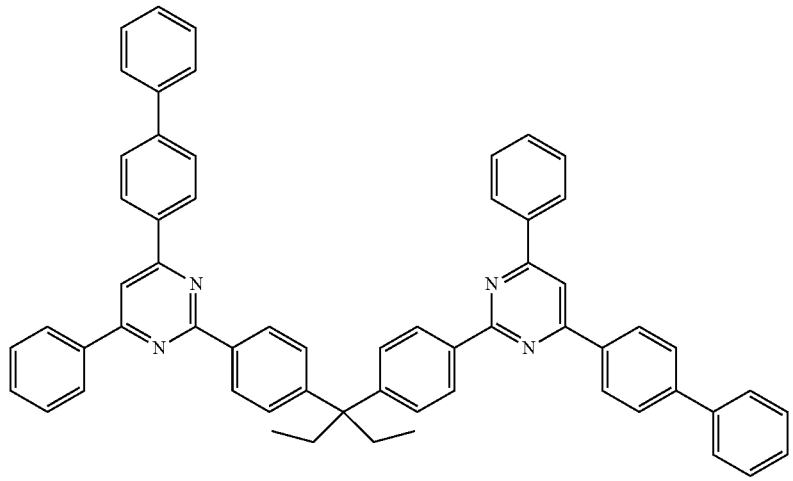
Compound 119
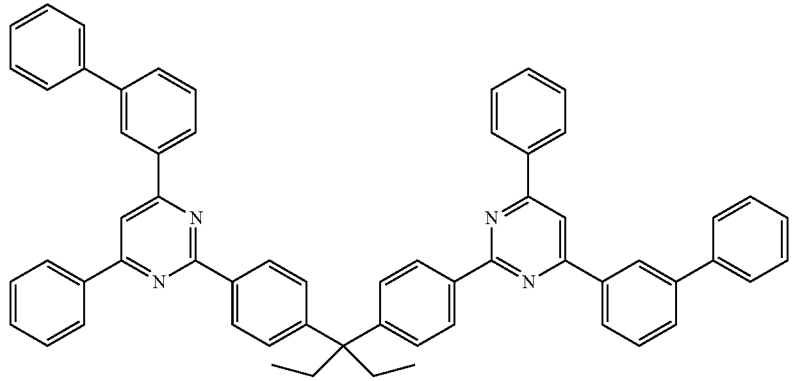
Compound 120
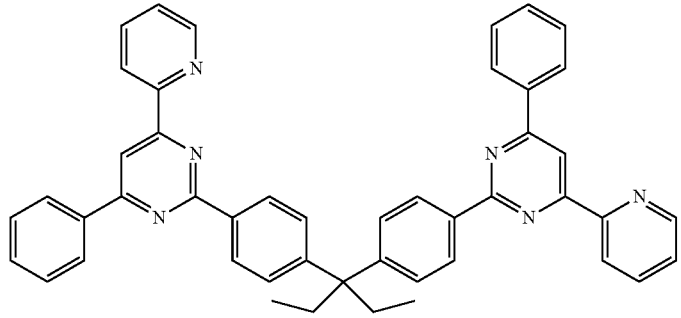
Compound 121
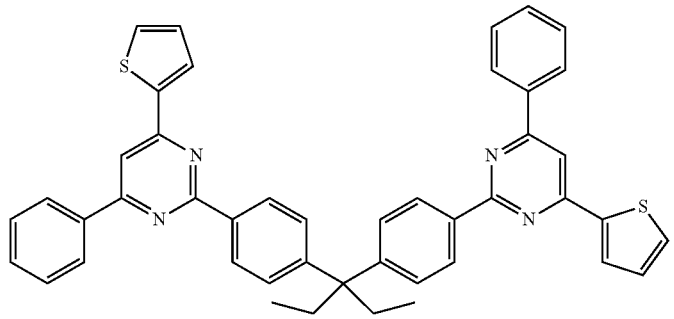

Compound 122
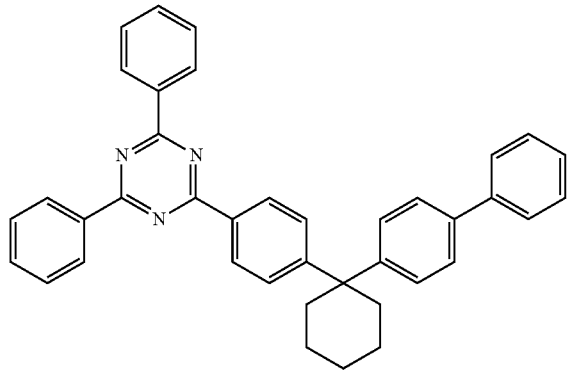
Compound 123
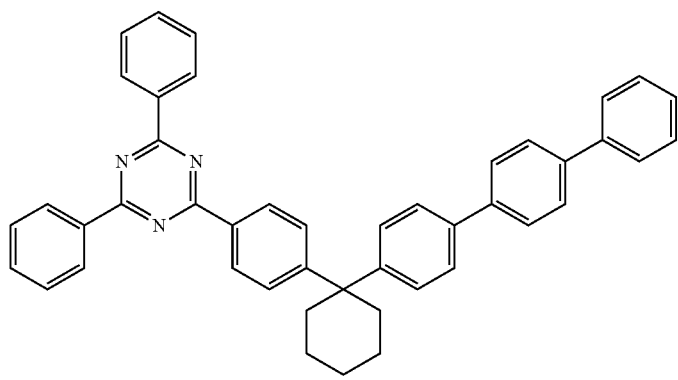
Compound 124
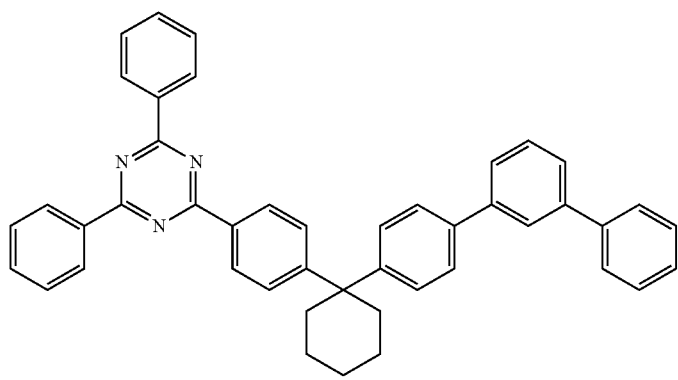
Compound 125
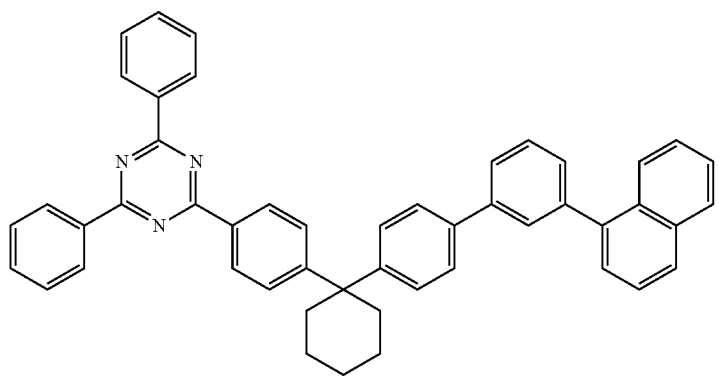

Compound 126
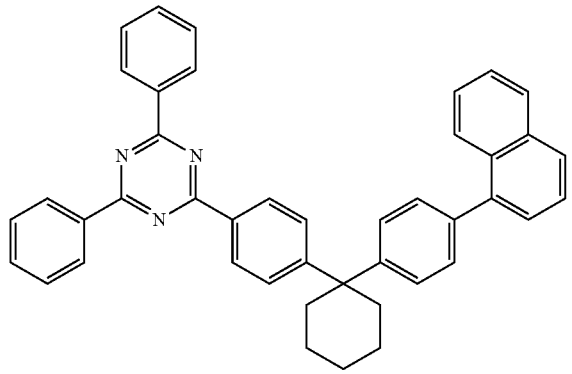
Compound 127
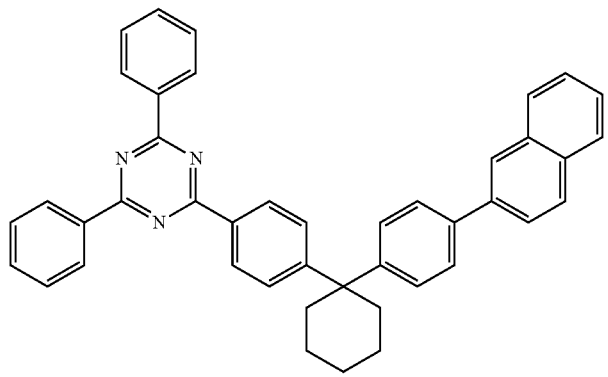
Compound 128
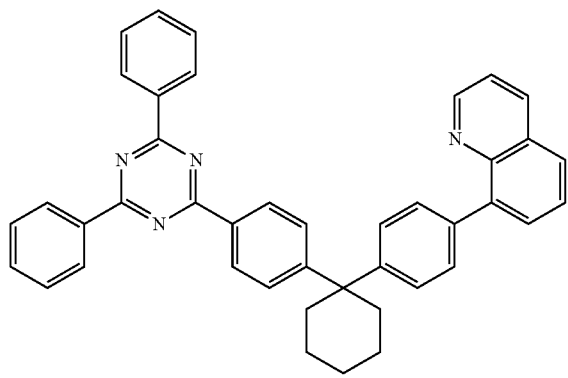
Compound 129
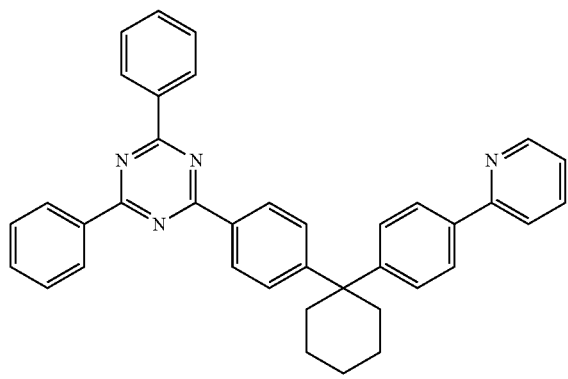

-continued
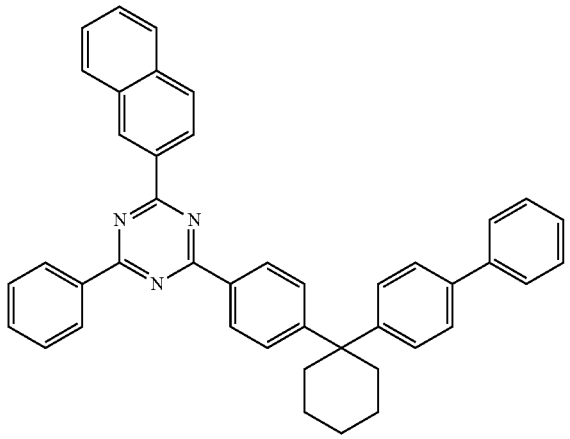
Compound 130
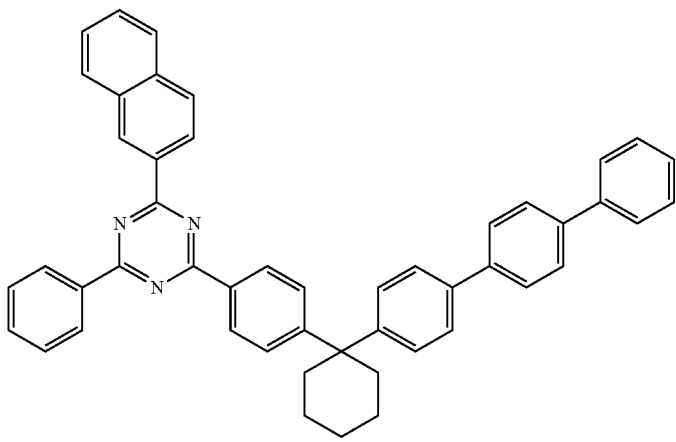
Compound 131
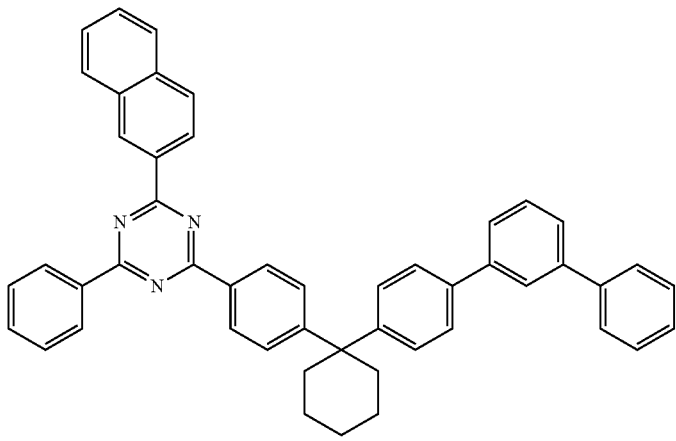
Compound 132

Compound 133
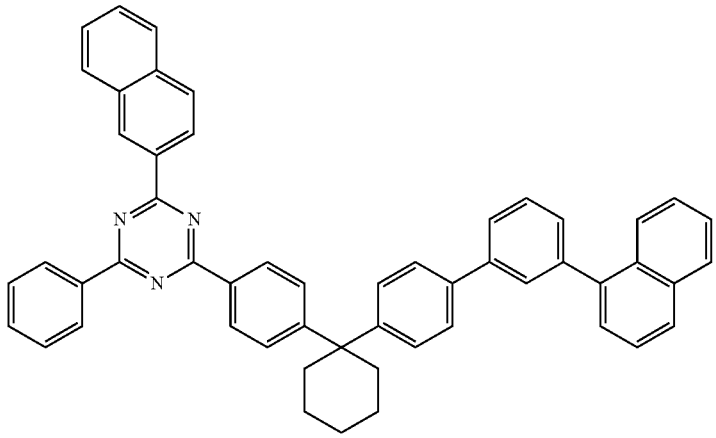
Compound 134
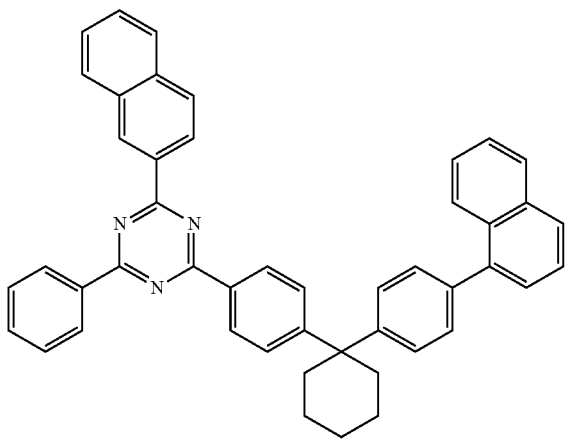
Compound 135
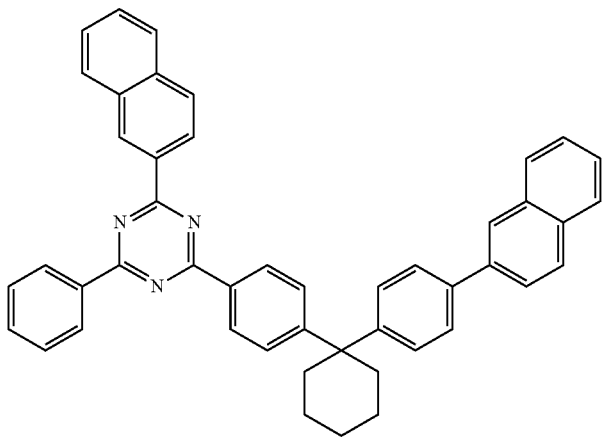

-continued
Compound 136
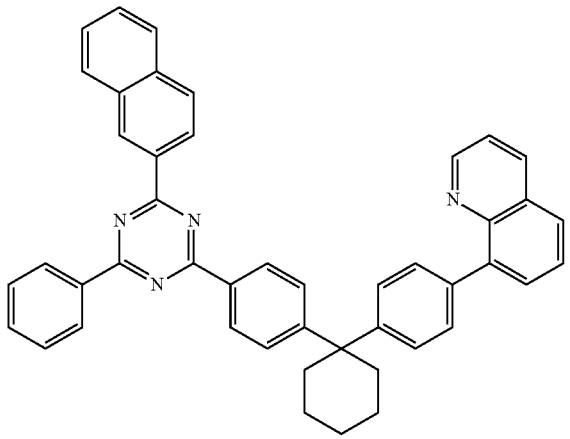
Compound 137
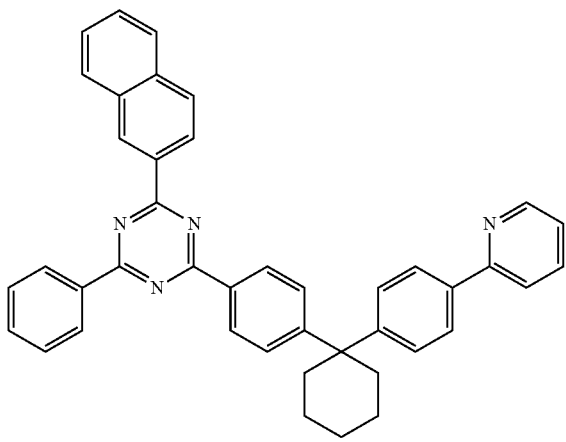
Compound 138
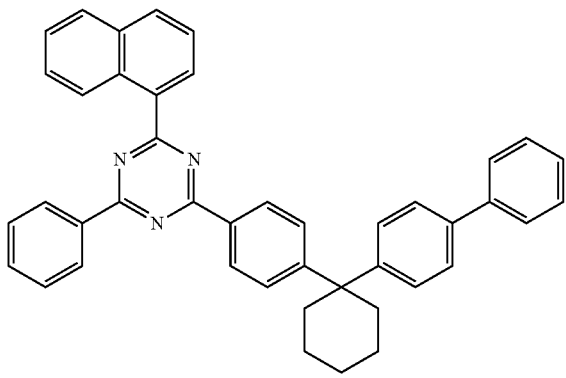
Compound 139
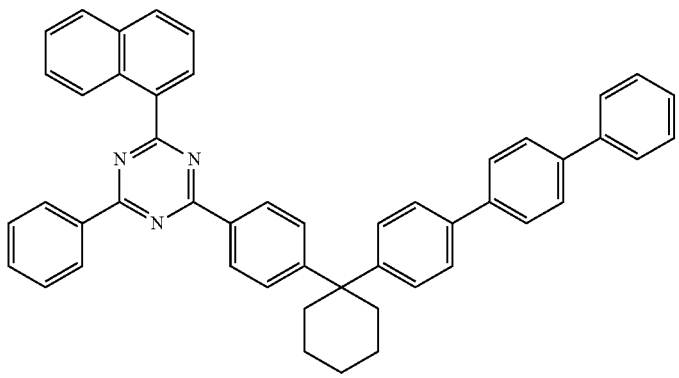

Compound 140
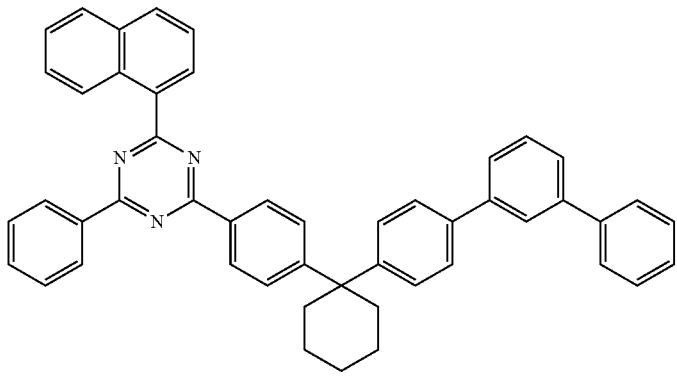
Compound 141
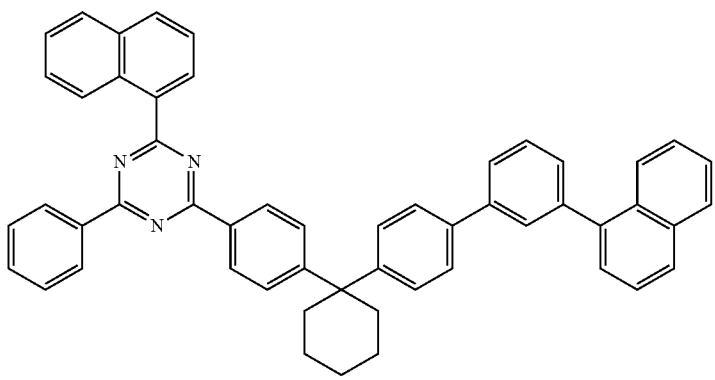
Compound 142
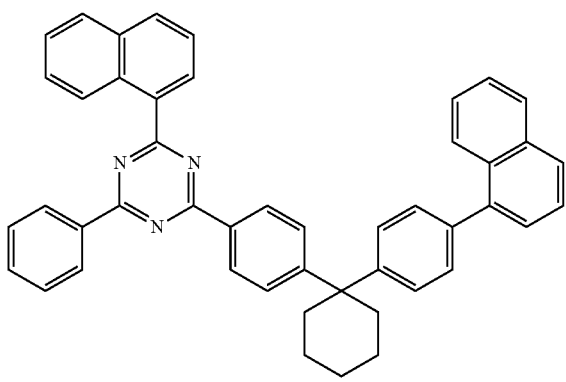
Compound 143
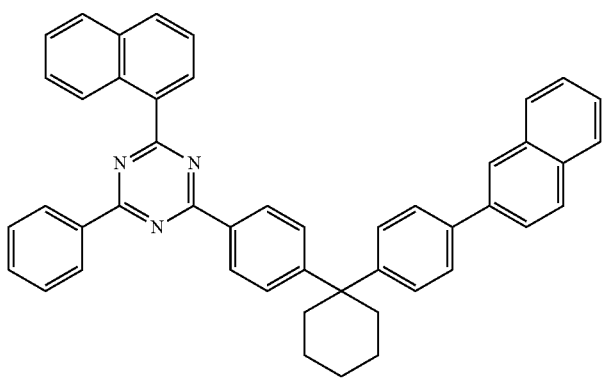

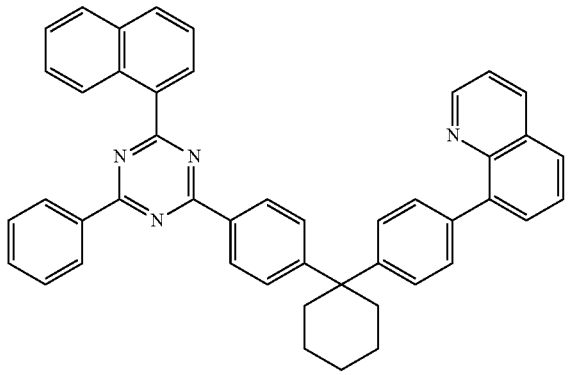
Compound 144
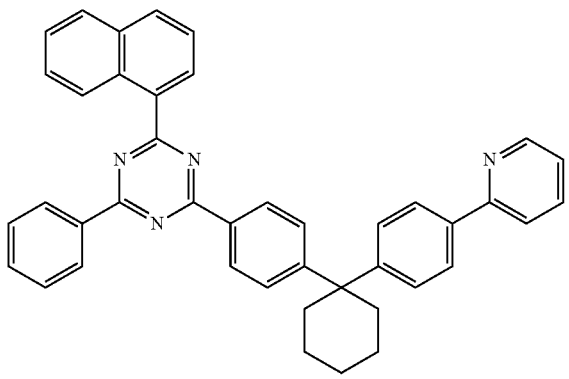
Compound 145
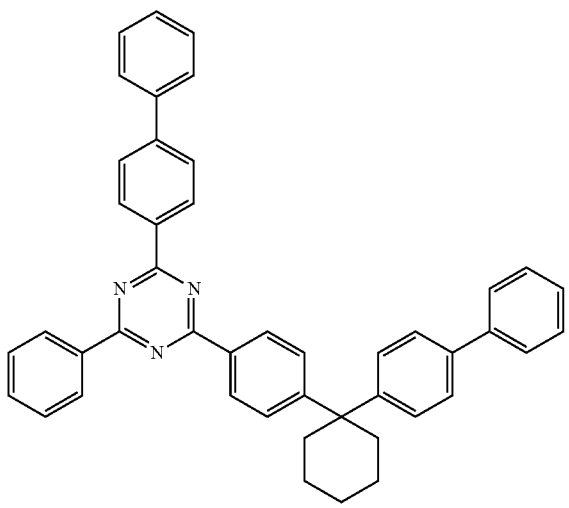
Compound 146

Compound 147
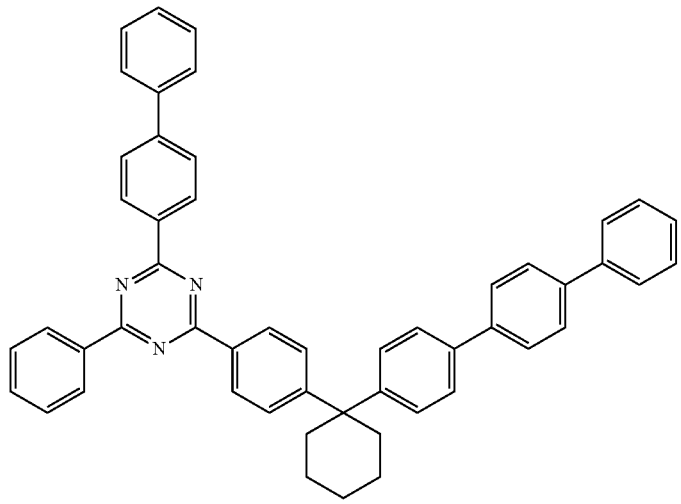
Compound 148
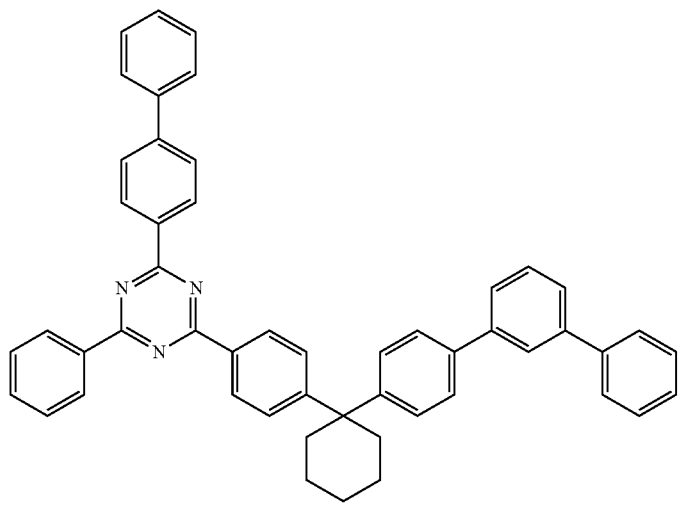
Compound 149
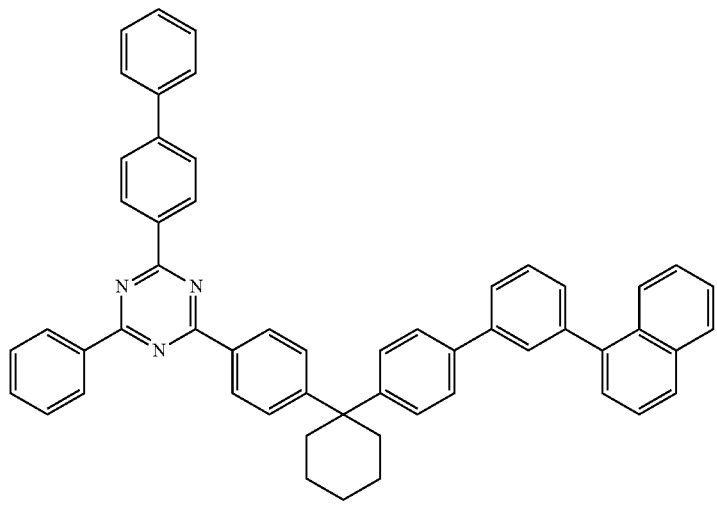

-continued
Compound 150
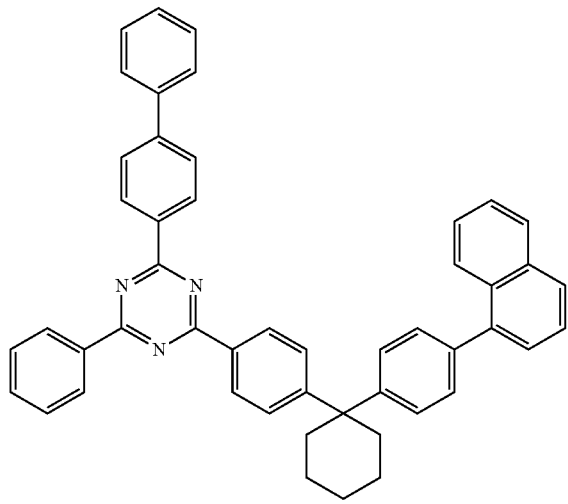
Compound 151
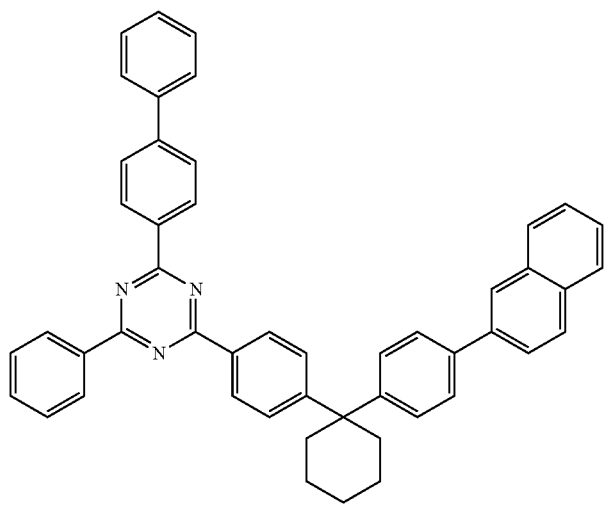
Compound 152
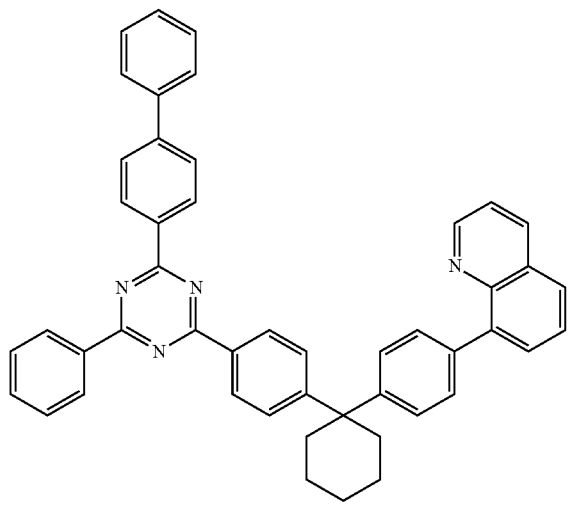

Compound 153
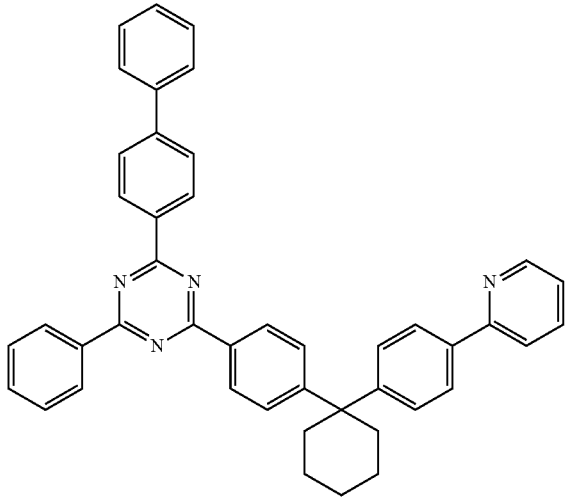
Compound 154
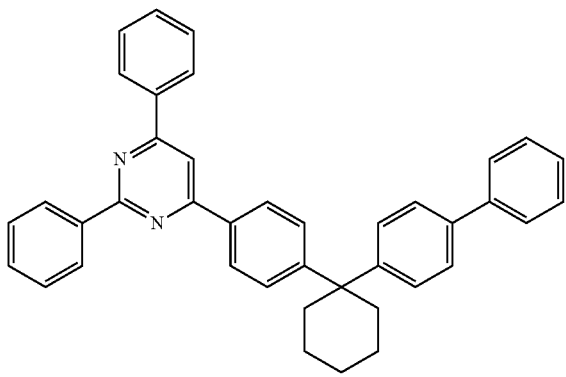
Compound 155
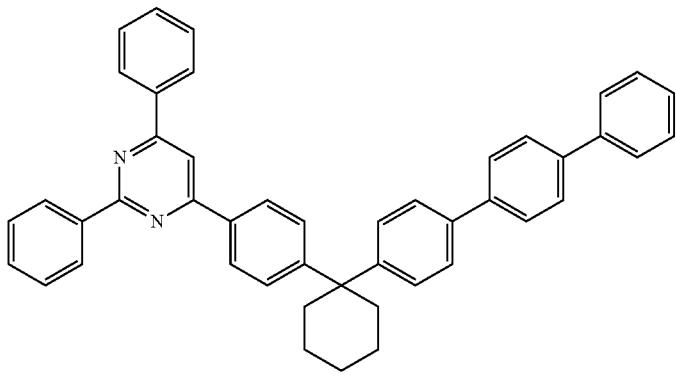
Compound 156
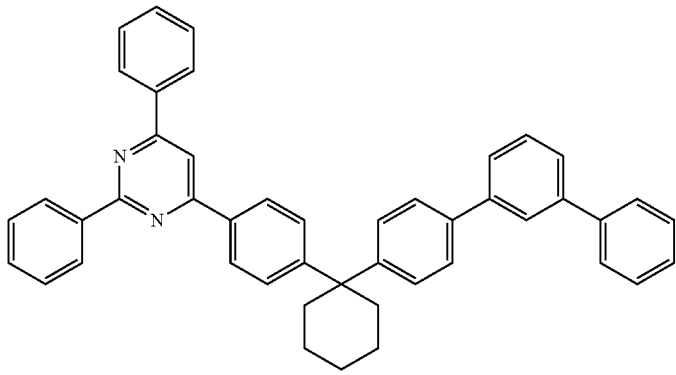

Compound 157
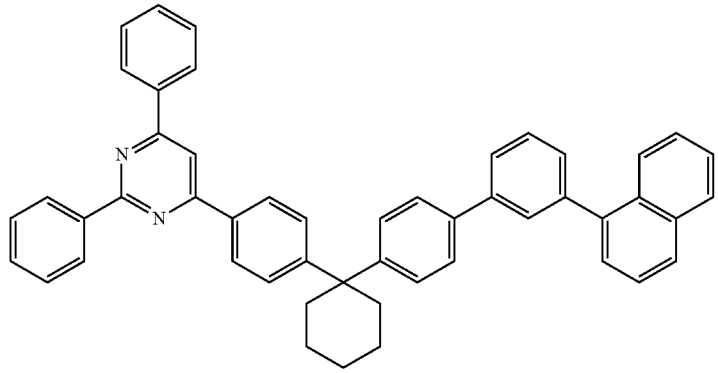
Compound 158
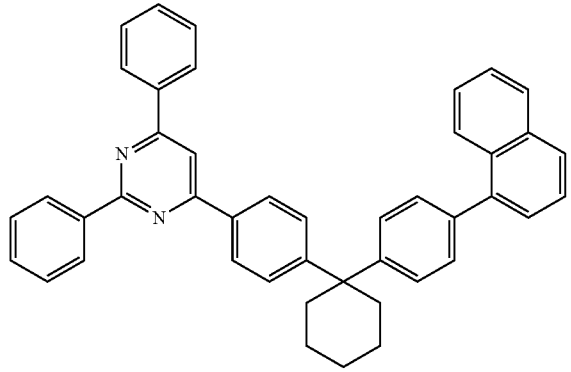
Compound 159
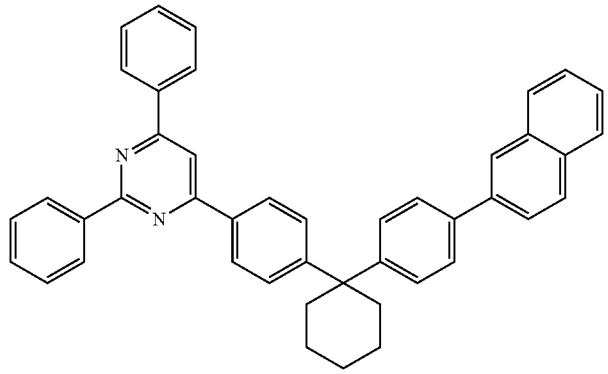
Compound 160
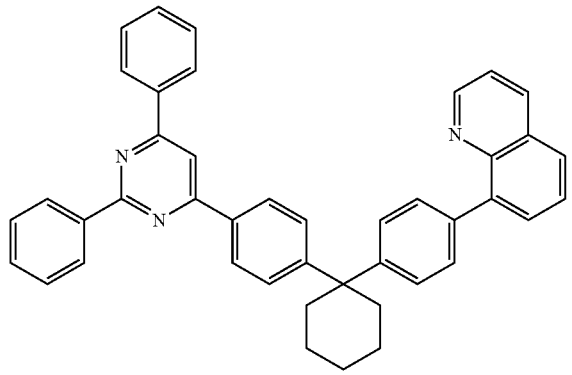

-continued
Compound 161
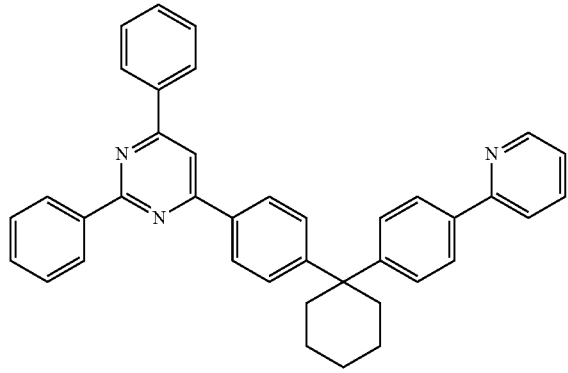
Compound 162
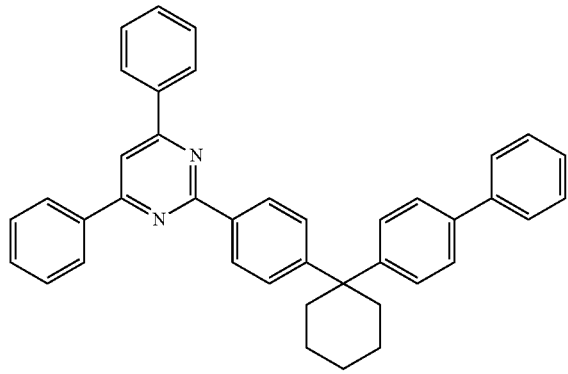
Compound 163
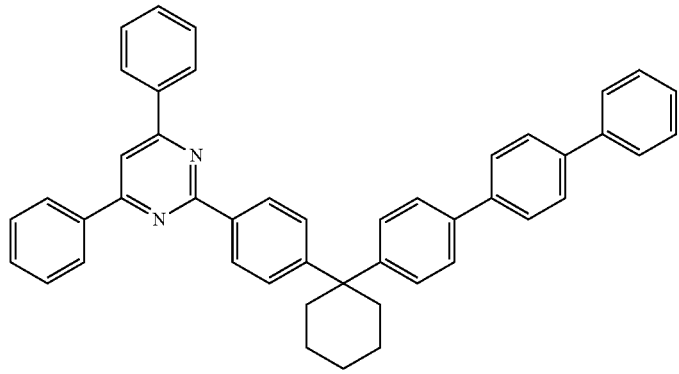
Compound 164
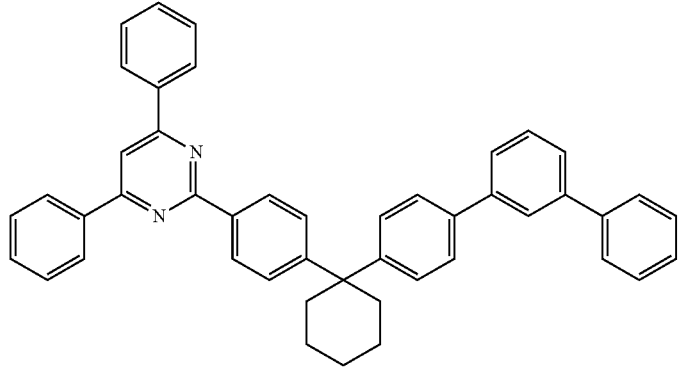

Compound 165
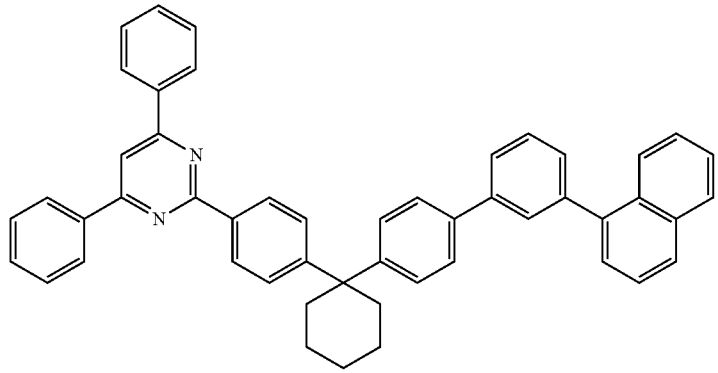
Compound 166
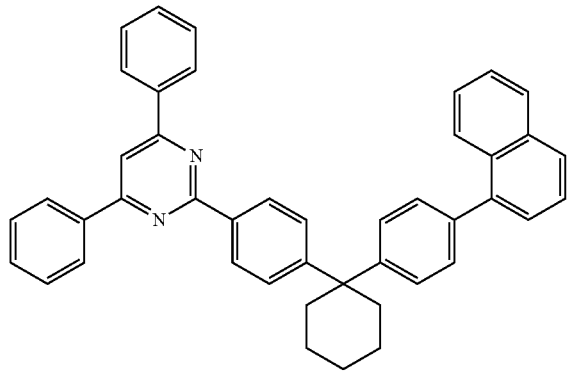
Compound 167
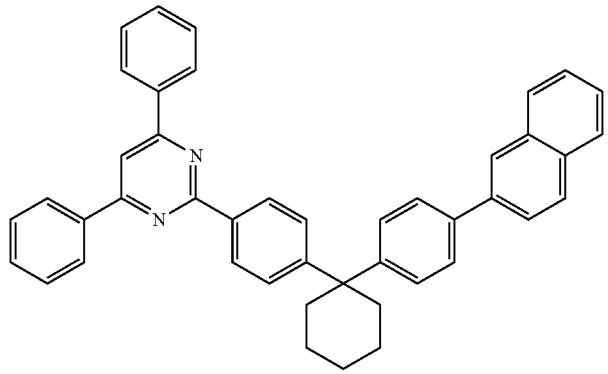
Compound 168
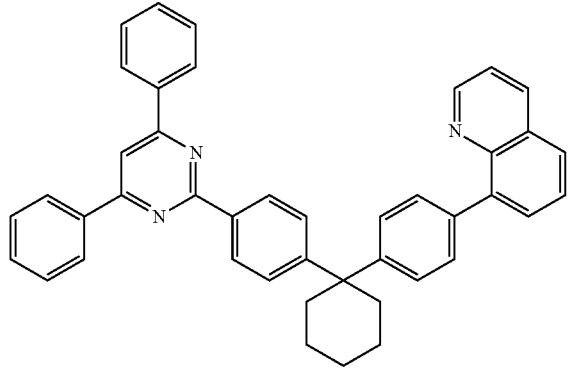

Compound 169
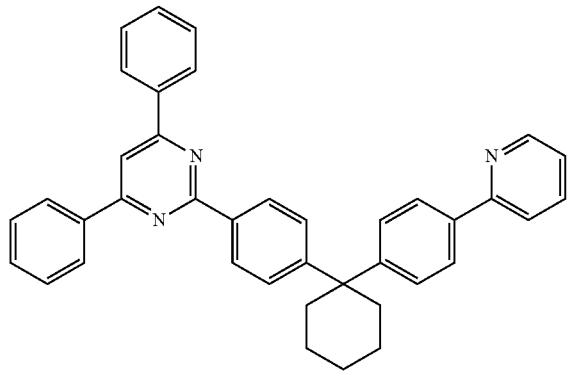
Compound 170
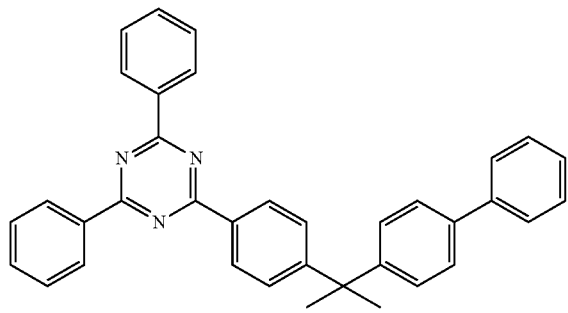
Compound 171
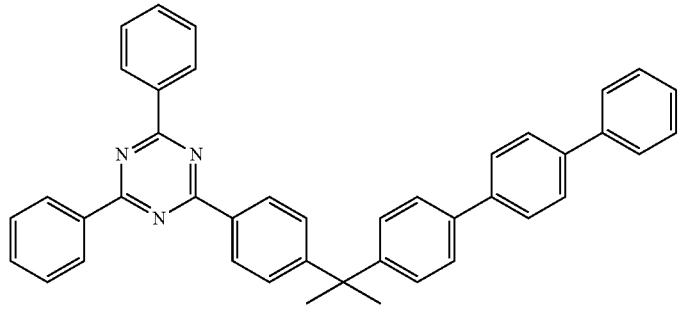
Compound 172
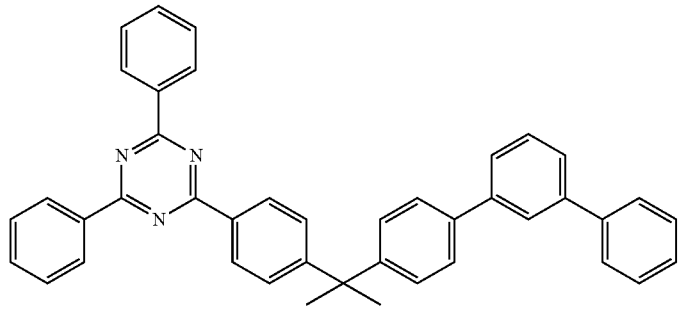
Compound 173
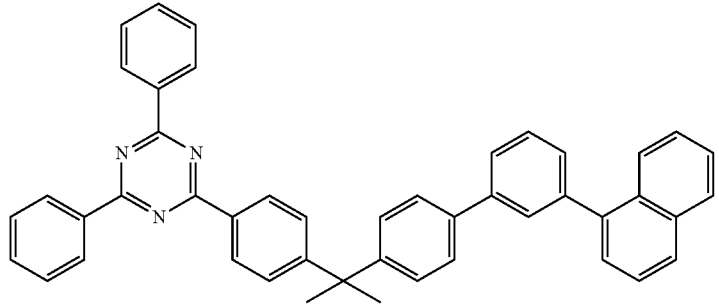

Compound 174
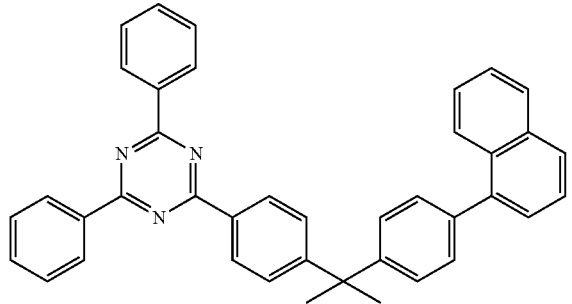
Compound 175
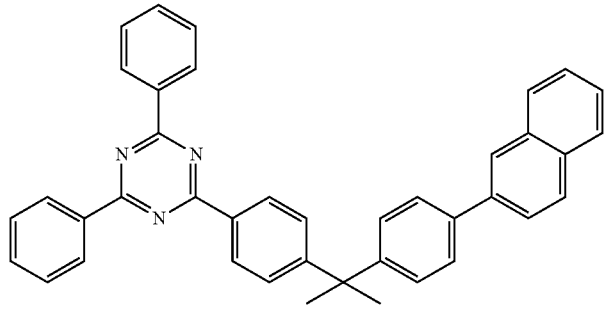
Compound 176
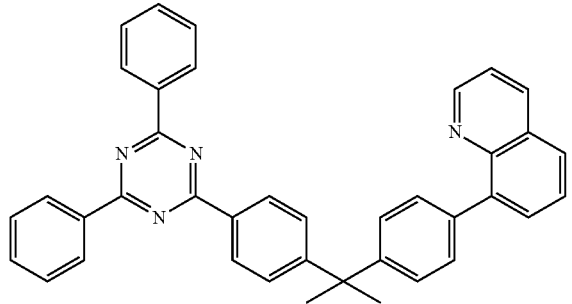
Compound 177
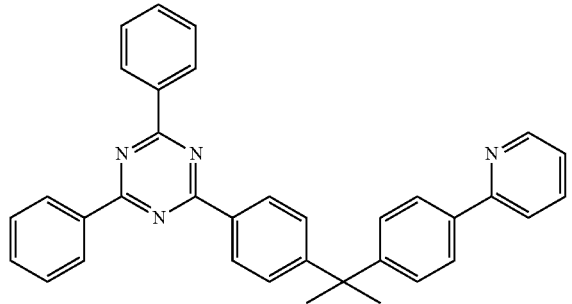
Compound 178
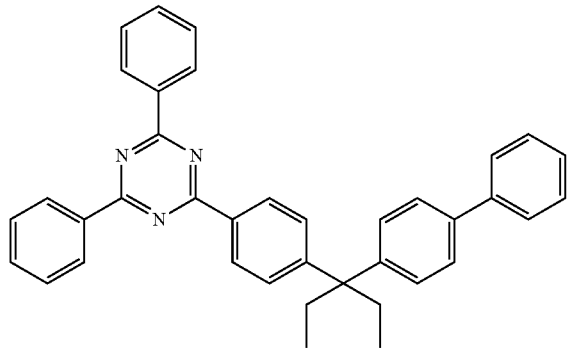

-continued
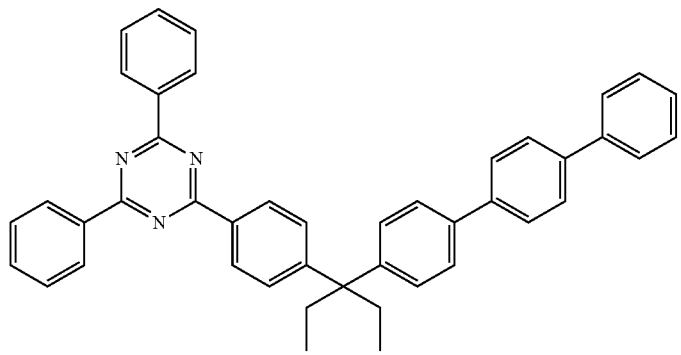
Compound 179
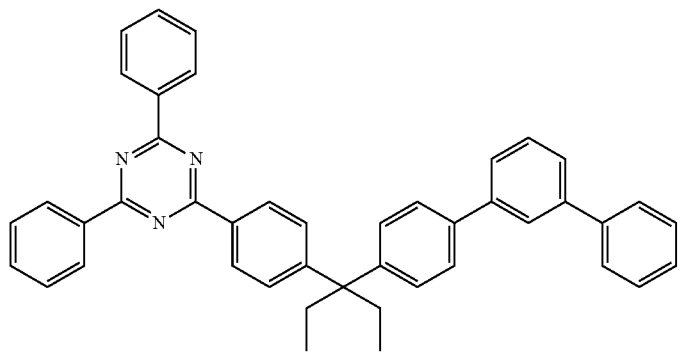
Compound 180
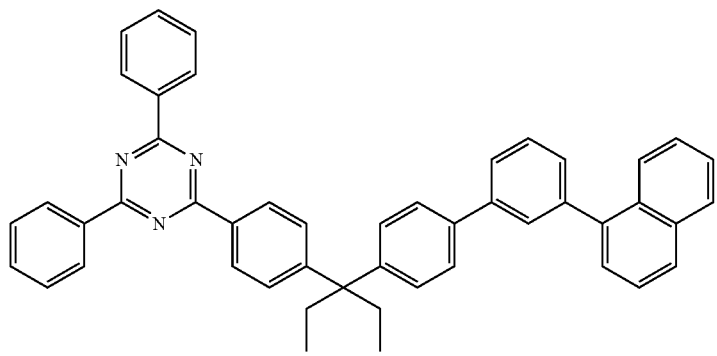
Compound 181
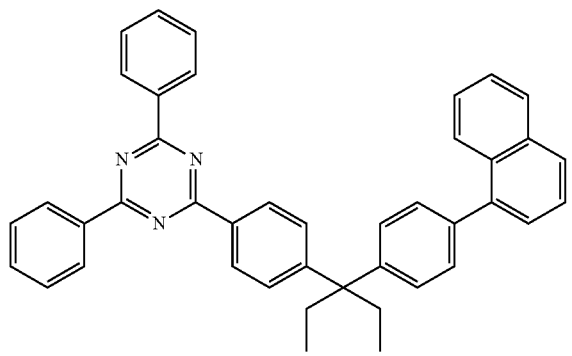
Compound 182

-continued
Compound 183
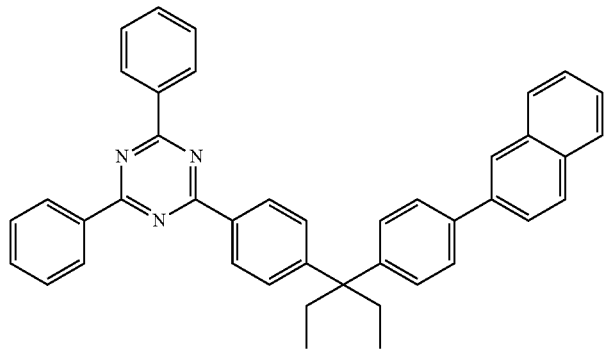
Compound 184
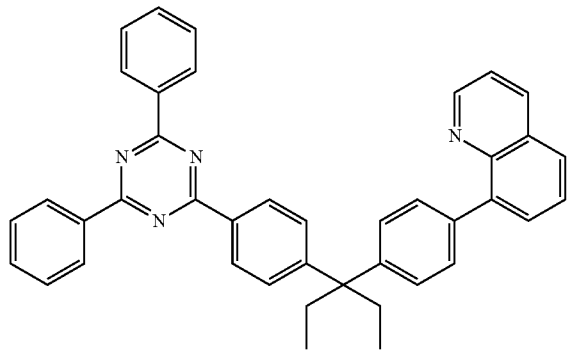
Compound 185
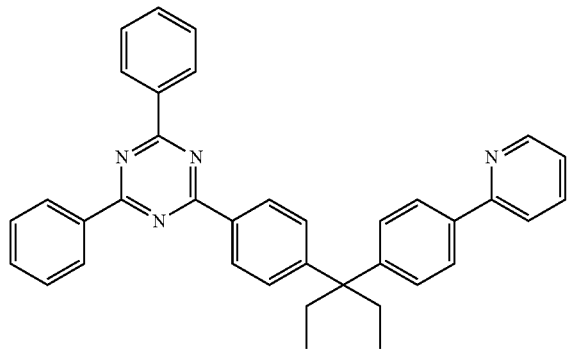
Compound 186
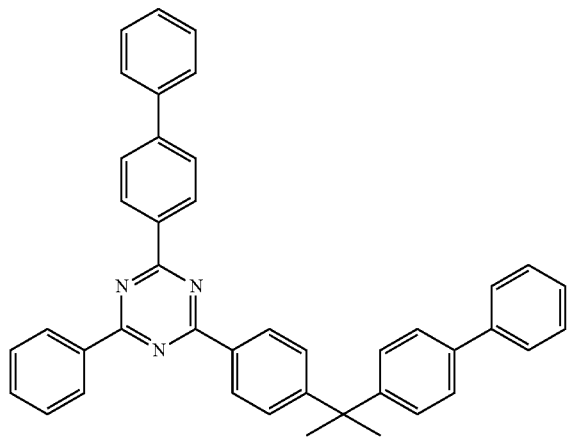

-continued
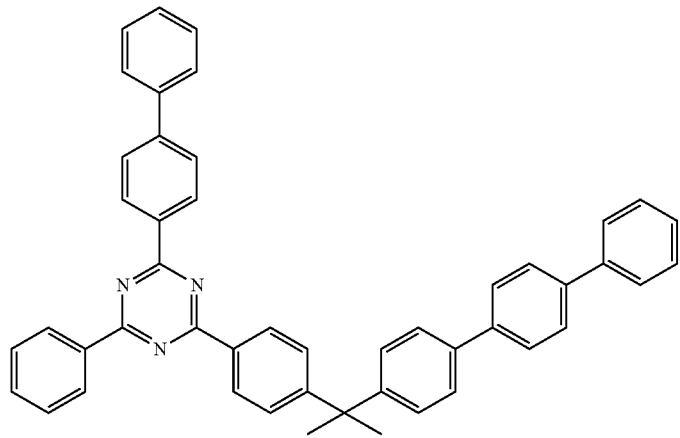
Compound 187
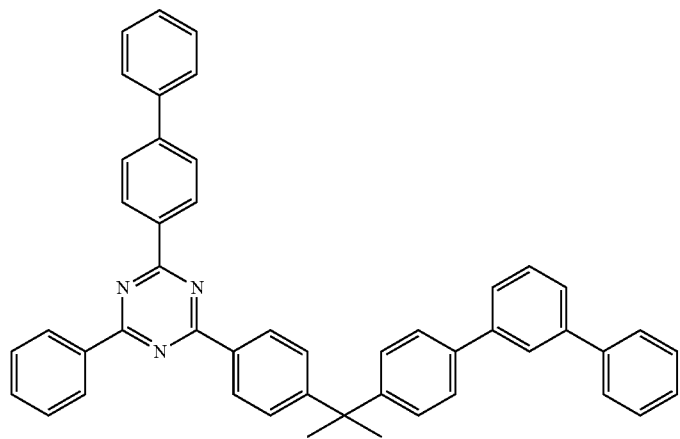
Compound 188
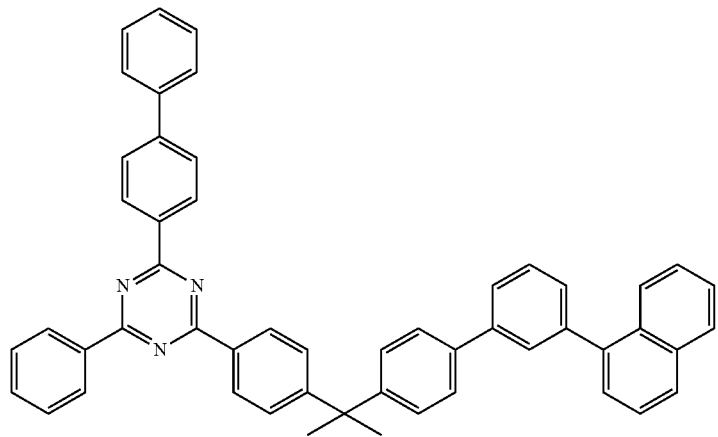
Compound 189

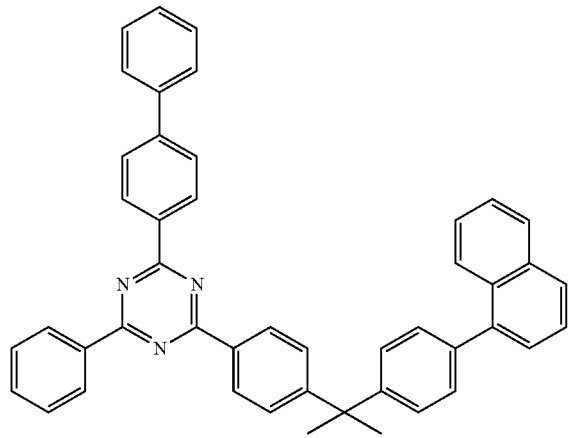
Compound 190
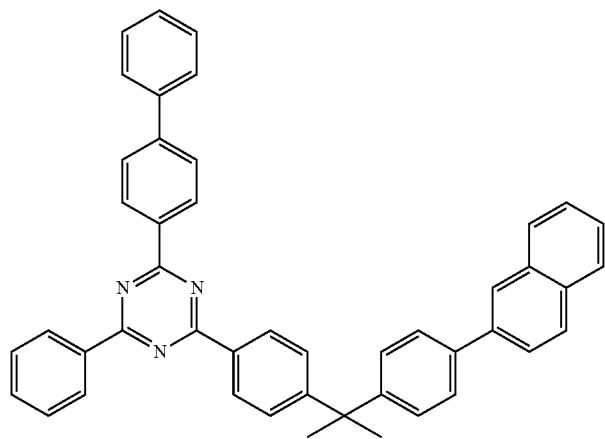
Compound 191
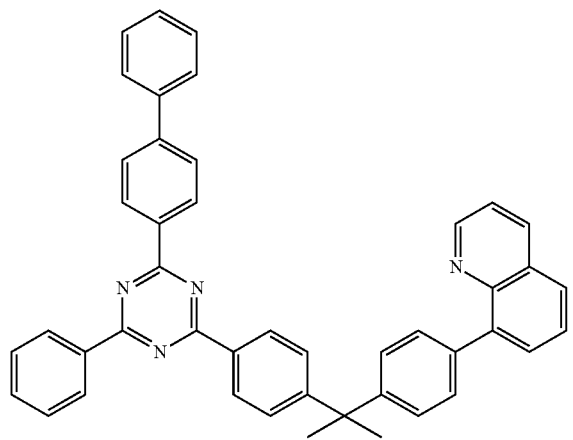
Compound 192

-continued
Compound 193
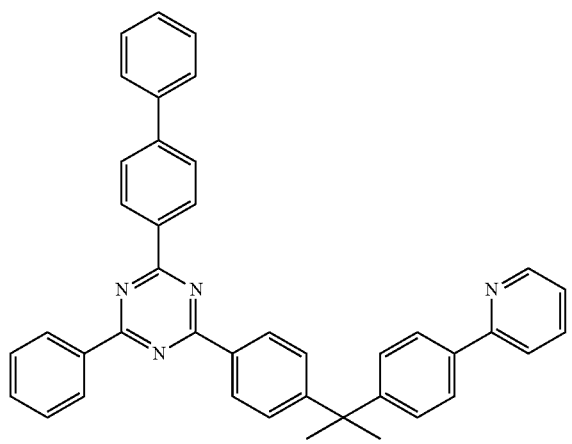
Compound 194
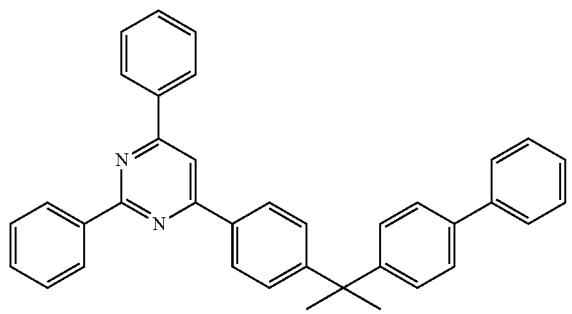
Compound 195
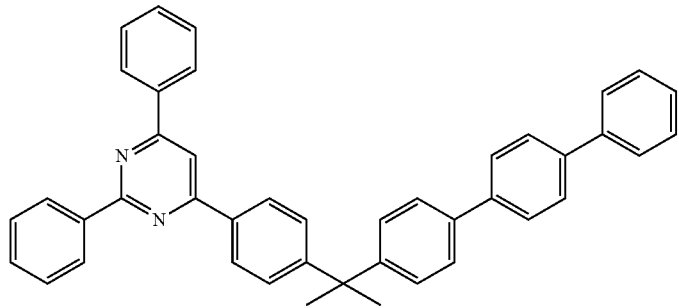
Compound 196
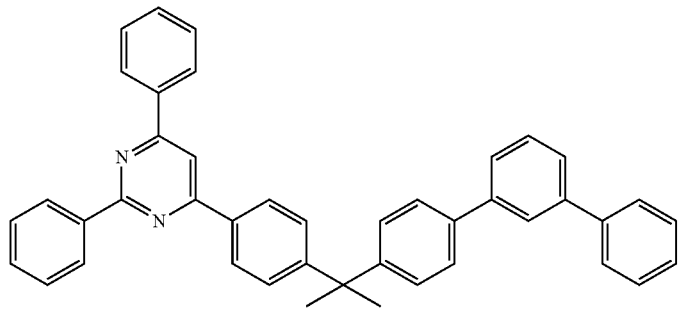

Compound 197
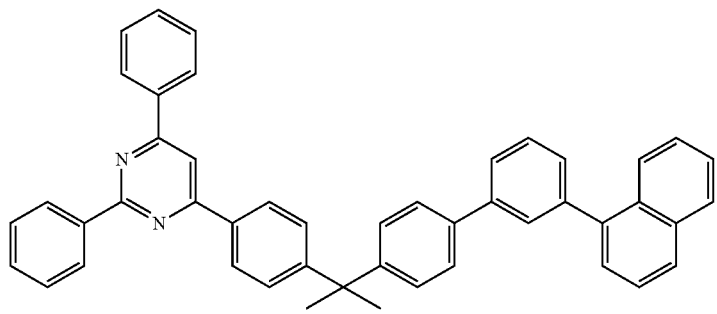
Compound 198
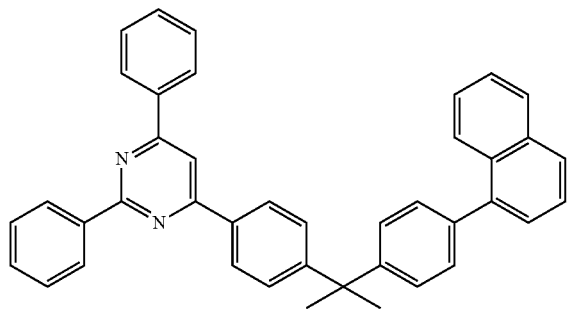
Compound 199
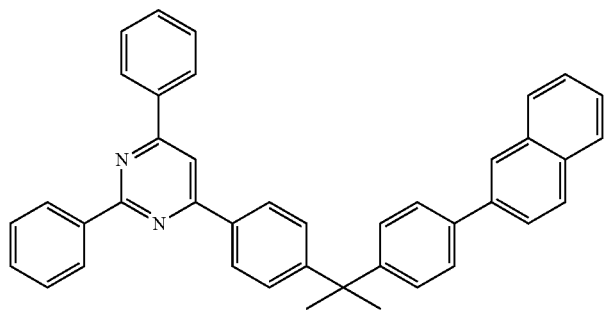
Compound 200
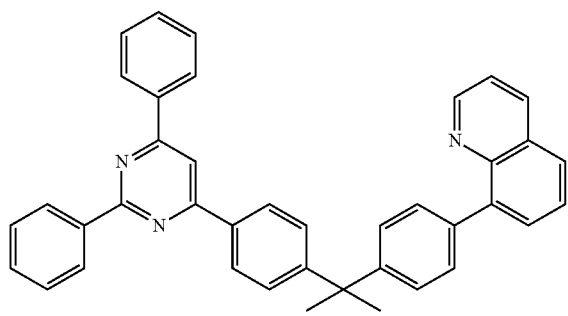
Compound 201
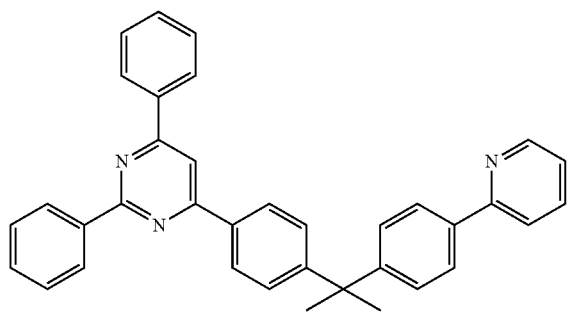

Compound 202
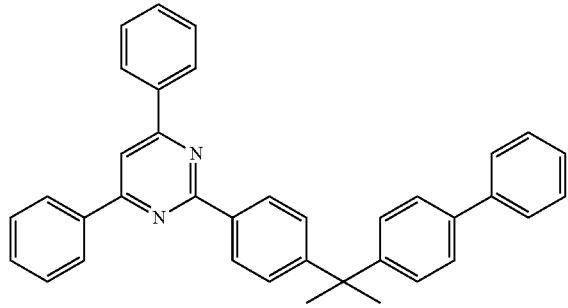
Compound 203
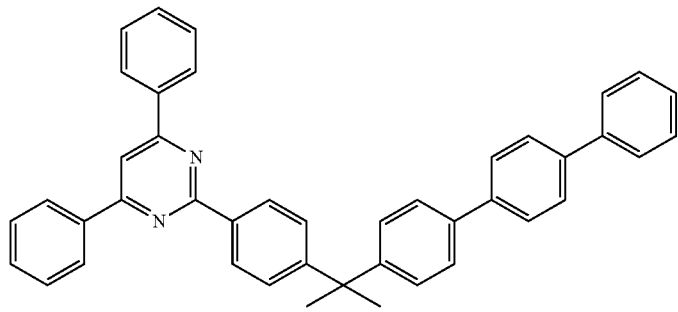
Compound 204
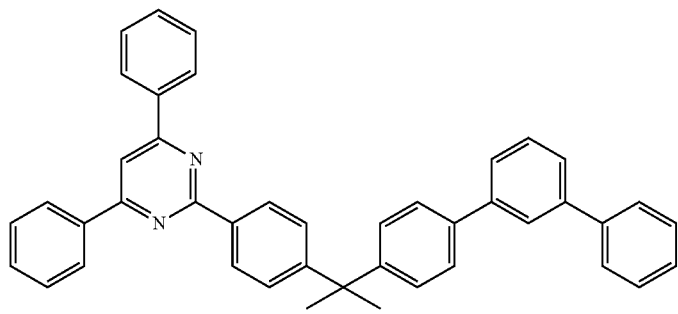
Compound 205
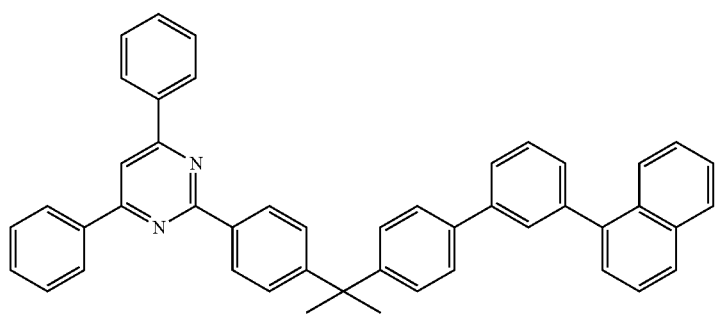
Compound 206
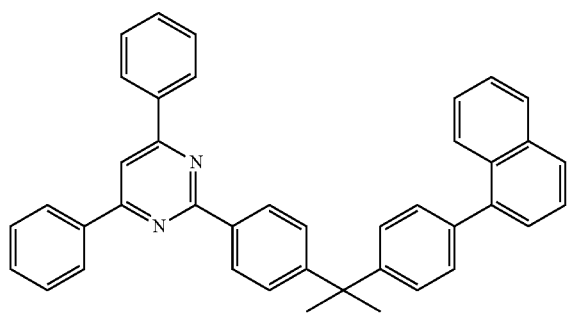

-continued

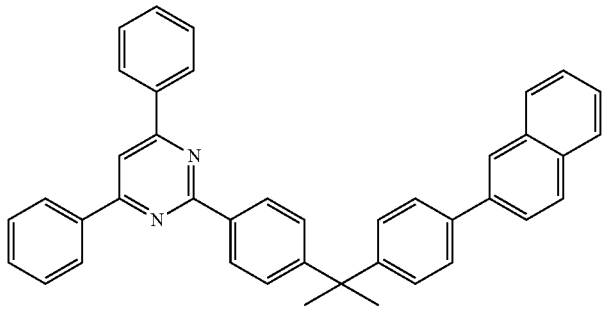
Compound 207

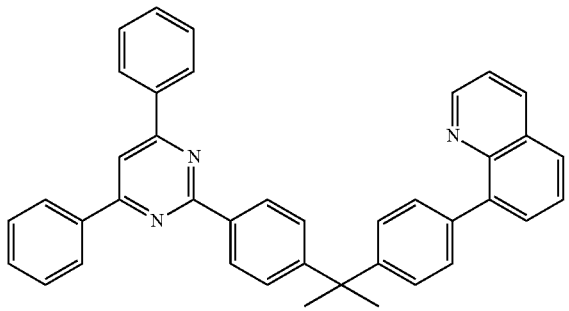
Compound 208

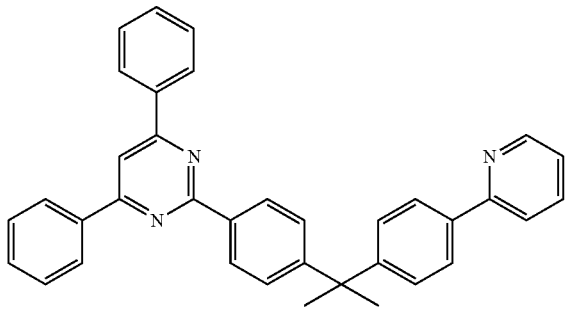
Compound 209

One embodiment of the present specification provides an organic light emitting device including the cyclic compound represented by Chemical Formula 1.

One embodiment of the present specification provides an organic light emitting device including a first electrode; a second electrode provided opposite to the first electrode; and one or two or more organic material layers provided between the first electrode and the second electrode, wherein one or more layers of the organic material layers includes the cyclic compound represented by Chemical Formula 1.

The organic material layer of the organic light emitting device of the present specification may be formed in a monolayer structure, but may also be formed in a multilayer structure in which two or more organic material layers are laminated. For example, the organic light emitting device of the present invention may have a structure including a hole injection layer, a hole transfer layer, a light emitting layer, a hole blocking layer, an electron transfer layer, an electron injection layer and the like as the organic material layer. However, the structure of the organic light emitting device is not limited thereto, and may include less numbers of organic material layers.

According to one embodiment of the present specification, the organic material layer includes a hole injection layer or a hole transfer layer, and the hole injection layer or the hole transfer layer includes the cyclic compound represented by Chemical Formula 1.

According to one embodiment of the present specification, the organic material layer includes a light emitting layer, and the light emitting layer includes the cyclic compound represented by Chemical Formula 1.

According to another embodiment of the present specification, the organic material layer includes a light emitting layer, and the light emitting layer includes the cyclic compound represented by Chemical Formula 1 as a host of the light emitting layer.

According to one embodiment of the present specification, the organic material layer includes an electron transfer layer or an electron injection layer, and the electron transfer layer or the electron injection layer includes the cyclic compound represented by Chemical Formula 1.

According to one embodiment of the present specification, the organic material layer includes an electron transfer layer, an electron injection layer or a layer carrying out electron transfer and electron injection at the same time, and the electron transfer layer, the electron injection layer or the layer carrying out electron transfer and electron injection at the same time includes the cyclic compound represented by Chemical Formula 1.

According to one embodiment of the present specification, the organic material layer includes a hole blocking layer, and the hole blocking layer includes the cyclic compound represented by Chemical Formula 1.

According to one embodiment of the present specification, the organic material layer further includes a hole injection layer or a hole transfer layer including a compound including an arylamino group, a carbazole group or a benzocarbazole group in addition to the organic material layer including the cyclic compound represented by Chemical Formula 1.

According to one embodiment of the present specification, the organic material layer including the cyclic compound represented by Chemical Formula 1 includes the cyclic compound represented by Chemical Formula 1 as a host, and includes other organic compounds, metals or metal compounds as a dopant.

Another embodiment of the present specification provides an organic light emitting device including a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the cyclic compound represented by Chemical Formula 1. In another embodiment, two or more from the group consisting of an electron transfer layer, an electron injection layer, a layer carrying out electron transfer and electron injection at the same time, and a hole blocking layer may be selected as the two or more organic material layers.

According to another embodiment of the present specification, the organic material layer includes two or more electron transfer layers, and at least one of the two or more electron transfer layers includes the cyclic compound represented by Chemical Formula 1. Specifically, in one embodiment of the present specification, the cyclic compound represented by Chemical Formula 1 may be either included in one of the two or more electron transfer layers, or included in each of the two or more electron transfer layers.

In addition, according to one embodiment of the present specification, when the cyclic compound represented by Chemical Formula 1 is included in each of the two or more electron transfer layers, materials other than the cyclic compound represented by Chemical Formula 1 may be the same as or different from each other.

The organic light emitting device of the present specification may be manufactured using materials and methods known in the art, except that one of more layers of the organic material layers include the cyclic compound of the present specification, that is, the cyclic compound represented by Chemical Formula 1.

When the organic light emitting device includes a plurality of organic material layers, the organic material layers may be formed with the same material or with different materials.

For example, the organic light emitting device of the present specification may be manufactured by consecutively laminating a first electrode, an organic material layer and a second electrode on a substrate. Herein, the organic light emitting device may be manufactured by forming the first electrode on the substrate by depositing a metal, a metal oxide having conductivity, or an alloy thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material capable of being used as the second electrode thereon. In addition to this method, the organic light emitting device may be manufactured by consecutively depositing a second electrode material, an organic material layer and a first electrode material on a substrate. In addition, the cyclic compound represented by Chemical Formula 1 may be formed as the organic material layer using a solution coating method as well as a vacuum deposition method when manufacturing the organic light emitting device. Herein, the solution coating method means spin coating, dip coating, doctor blading, ink jet printing, screen printing, a spray method, roll coating and the like, but is not limited thereto.

In addition to this method, the organic light emitting device may also be manufactured by consecutively depositing the second electrode material, an organic material layer and the first electrode material on a substrate (International Patent Application Laid-Open Publication No. 2003/012890). However, the manufacturing method is not limited thereto.

According to one embodiment of the present specification, the first electrode is an anode, and the second electrode is a cathode.

According to another embodiment of the present specification, the first electrode is a cathode, and the second electrode is an anode.

As the anode material, a material having large work function is normally preferable so that hole injection to the organic material layer is smooth. Specific examples of the anode material capable of being used in the present invention include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylen-1,2-dioxy)thiophene] (PEDOT), polypyrrole and polyaniline, and the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamine-based organic material, a hexanitrile hexazatriphenylene-based organic material, a quinacridone-based organic material, a perylene-based organic material, anthraquinone, and a polyaniline- and a polythiophene-based conductive polymer, and the like, but are not limited thereto.

The hole transfer layer is a layer that receives holes from a hole injection layer and transfers the holes to a light emitting layer, and as the hole transfer material, a material capable of receiving holes from an anode or a hole injection layer, moving the holes to a light emitting layer, and having high mobility for the holes, is suitable. Specific examples thereof include an arylamine-based organic material, a conductive polymer, a block copolymer having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly (p-phenylenevinylene) (PPV)-based polymer; a Spiro compound; polyfluorene, rubrene, and the like, but are not limited thereto.

The light emitting layer may include a host material and a dopant material. The host material includes a fused aromatic ring derivative, a heterocyclic ring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heterocyclic ring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex and the like. Specifically, the aromatic amine derivative is a fused aromatic ring derivative having a substituted or unsubstituted arylamino group and includes arylamino group-including pyrene, anthracene, crycene, peryflanthene and the like, and the styrylamine compound is a compound in which substituted or unsubstituted arylamine is substituted with at least one arylvinyl group, and one or two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including $Alq_3$; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer that blocks holes from reaching a cathode, and may generally be formed under the same condition as the hole injection layer. Specific examples thereof include an oxadiazole derivative or a triazole derivative, a phenanthroline derivative, BCP, an aluminum complex and the like, but are not limited thereto.

The organic light emitting device according to the present specification may be a top-emission type, a bottom-emission type or a dual-emission type depending on the materials used.

In one embodiment of the present specification, the compound of Chemical Formula 1 may be included in an organic solar cell or an organic transistor in addition to an organic light emitting device.

Hereinafter, the present specification will be described in detail with reference to examples. However, the examples according to the present specification may be modified to various other forms, and the scope of the present specification is not interpreted to be limited to the examples described below. The examples of the present specification are provided in order to more completely describe the present specification for those having average knowledge in the art.

Synthesis Example 1. Synthesis of Compound A-2

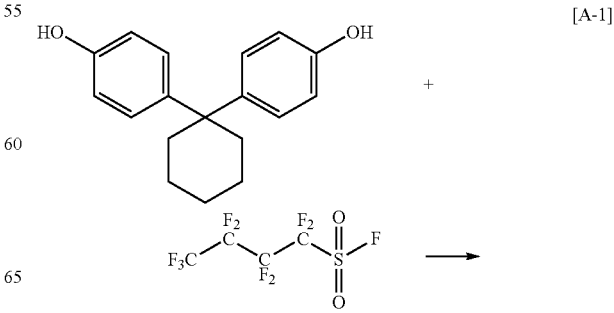

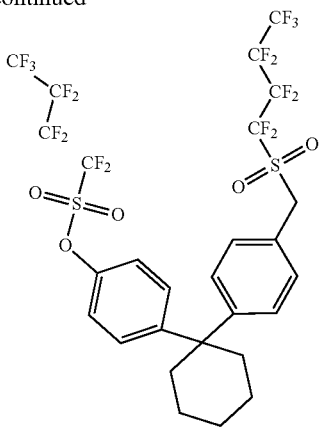

[A-2]

and added to 1000 ml of dioxane, and the result was heated while stirring. Bis(dibenzylideneacetone)palladium (6.0 g, 0.0104 mmol) and tricyclohexylphosphine (5.8 g, 0.0208 mmol) were added thereto while being refluxed, and the result was heated and stirred for 10 hours. After the reaction was complete, the result was cooled to room temperature and then filtered. The filtrate was poured into water, extracted with chloroform, and the organic layer was dried with anhydrous magnesium sulfate. The result was vacuum distilled, recrystallized with ethanol to prepare Compound A-2 (50.7 g, yield: 60%).

MS $[M+H]^+=489$

Synthesis Example 2. Synthesis of Compound B-2

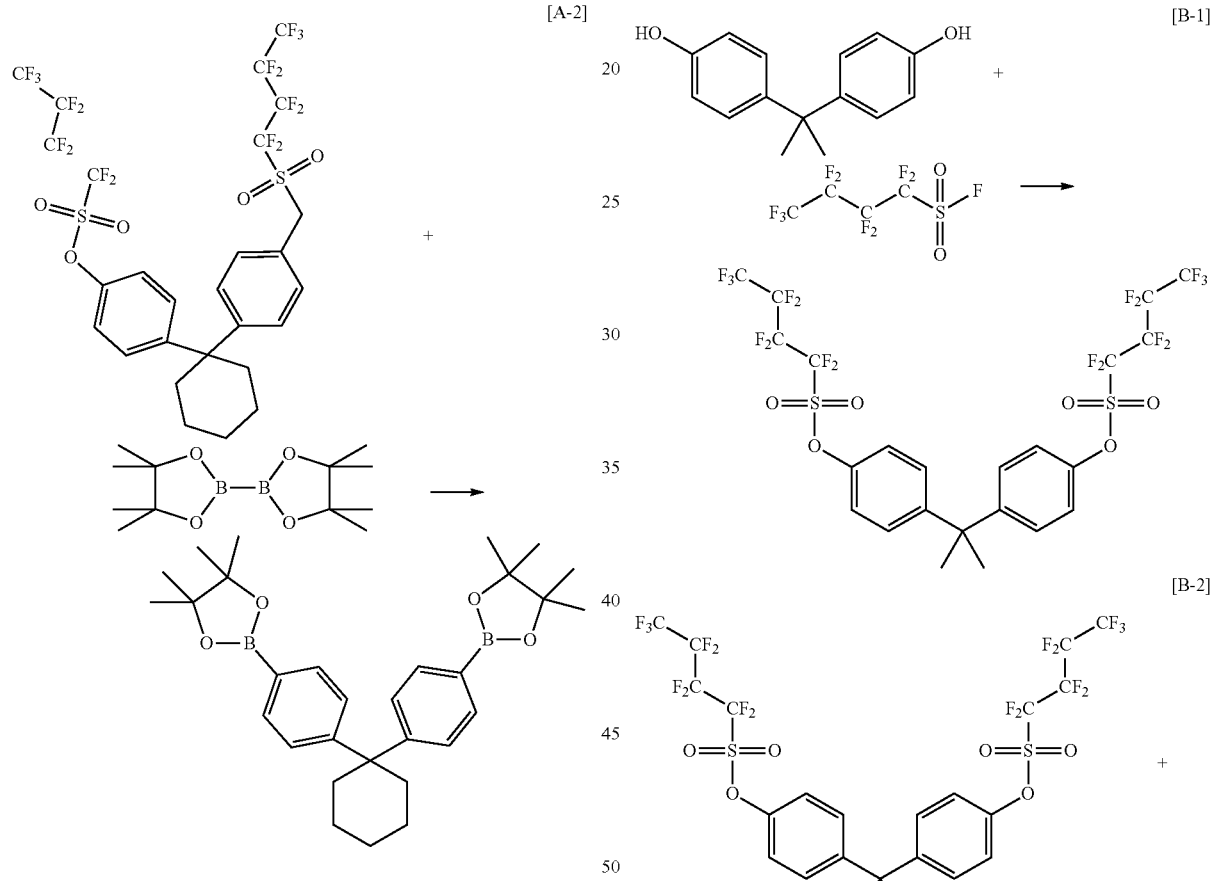

1) Synthesis of Compound A-1

Under nitrogen atmosphere, after the compound 4,4'-(cyclohexane-1,1-diyl)diphenol (100 g, 0.372 mol) was dissolved in 1000 ml of acetonitrile, potassium carbonate (154.5 g, 1.117 mol) dissolved in 300 ml of water was added thereto, then 1,1,2,2,3,3,4,4,4-nonafluorobutane-1-sulfonyl fluoride (270 g, 0.894 mmol) was slowly added dropwise thereto, and the result was stirred for 1 hour. The water layer was removed, then the result was dried with anhydrous magnesium sulfate, and vacuum concentrated to prepare Compound A-1 (279 g, yield: 90%).

MS $[M+H]^+=833$

2) Synthesis of Compound A-2

Under nitrogen atmosphere, Compound A-1 (144.1 g, 0.173 mol), bis(pinacolato)diboron (105.5 g, 0.415 mmol) and potassium acetate (101.9 g, 1.084 mmol) were mixed 1) Synthesis of Compound B-1

Under nitrogen atmosphere, after the compound bisphenol A (85 g, 0.372 mol) was dissolved in 900 ml of acetonitrile, potassium carbonate (154.5 g, 1.117 mol) dissolved in 300 ml of water was added thereto, then 1,1,2,2,3,3,4,4,4-nonafluorobutane-1-sulfonyl fluoride (270 g, 0.894 mmol) was slowly added dropwise thereto, and the result was stirred for 1 hour. The water layer was removed, and the result was dried with anhydrous magnesium sulfate and vacuum concentrated to prepare Compound B-1 (265 g, yield: 90%).

MS $[M+H]^+=792$

2) Synthesis of Compound B-2

Under nitrogen atmosphere, Compound B-1 (137.1 g, 0.173 mol), bis(pinacolato)diboron (105.5 g, 0.415 mmol) and potassium acetate (101.9 g, 1.084 mmol) were mixed and added to 1000 ml of dioxane, and the result was heated while stirring. Bis(dibenzylideneacetone)palladium (6.0 g, 0.0104 mmol) and tricyclohexylphosphine (5.8 g, 0.0208 mmol) were added thereto while being refluxed, and the result was heated and stirred for 10 hours. After the reaction was complete, the result was cooled to room temperature and then filtered. The filtrate was poured into water, extracted with chloroform, and the organic layer was dried with anhydrous magnesium sulfate. The result was vacuum distilled, recrystallized with ethanol to prepare Compound B-2 (45 g, yield: 58%).

MS $[M+H]^+=449$

Synthesis Example 3. Synthesis of Compound C-2

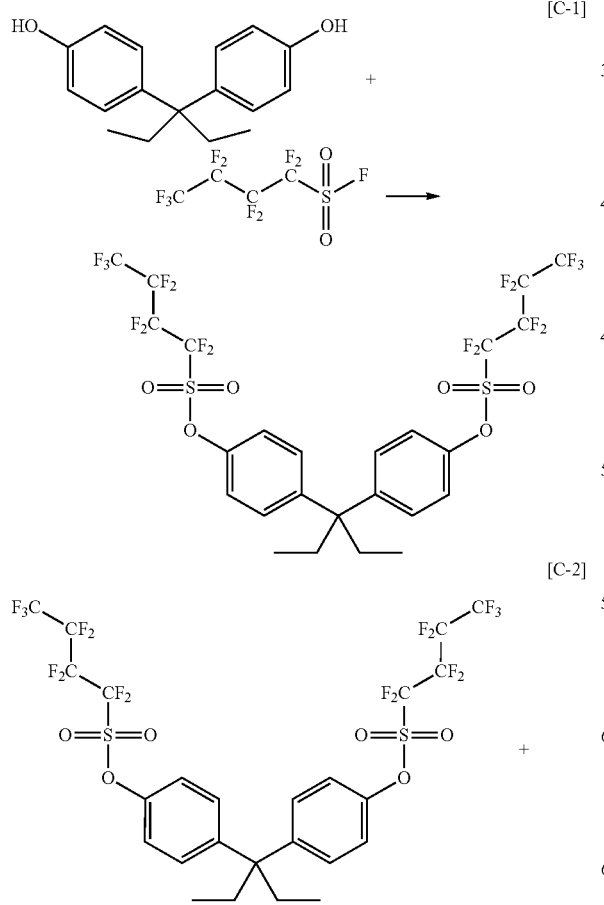

1) Synthesis of Compound C-1

Under nitrogen atmosphere, after the compound 4,4'-(pentane-3,3-diyl)diphenol (95 g, 0.372 mol) was dissolved in acetonitrile 1000 ml, potassium carbonate (154.5 g, 1.117 mol) dissolved in 300 ml of water was added thereto, then 1,1,2,2,3,3,4,4,4-nonafluorobutane-1-sulfonyl fluoride (270 g, 0.894 mmol) was slowly added dropwise thereto, and the result was stirred for 1 hour. The water layer was removed, and the result was dried with anhydrous magnesium sulfate and vacuum concentrated to prepare Compound C-1 (271 g, yield: 89%).

MS $[M+H]^+=821$

2) Synthesis of Compound C-2

Under nitrogen atmosphere, Compound C-1 (142 g, 0.173 mol), bis(pinacolato)diboron (105.5 g, 0.415 mmol) and potassium acetate (101.9 g, 1.084 mmol) were mixed and added to 1000 ml of dioxane, and the result was heated while stirring. Bis(dibenzylideneacetone)palladium (6.0 g, 0.0104 mmol) and tricyclohexylphosphine (5.8 g, 0.0208 mmol) were added thereto while being refluxed, and the result was heated and stirred for 10 hours. After the reaction was complete, the result was cooled to room temperature and then filtered. The filtrate was poured into water, extracted with chloroform, and the organic layer was dried with anhydrous magnesium sulfate. The result was vacuum distilled, recrystallized with ethanol to prepare Compound C-2 (48.6 g, yield: 59%).

MS $[M+H]^+=477$

Preparation Example 1. Preparation of Compound 1

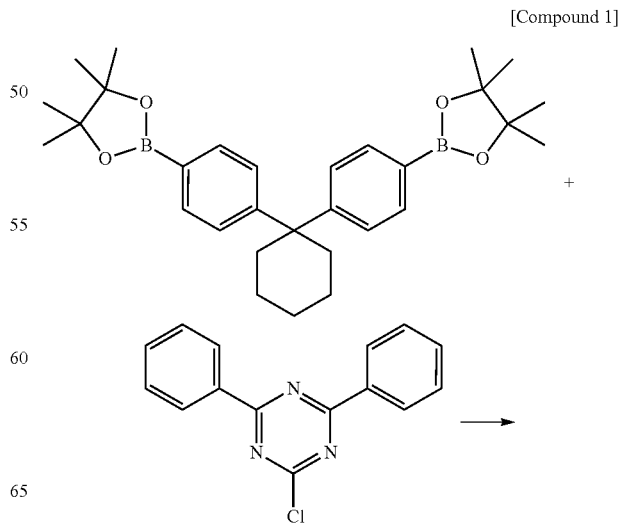

-continued

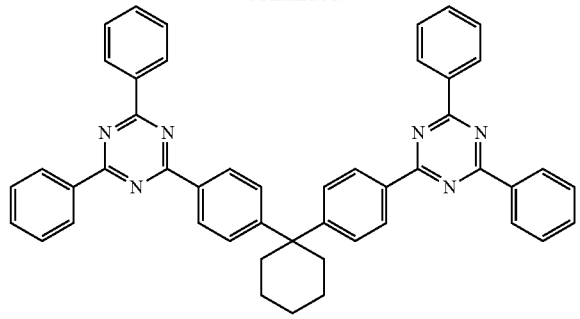

Under nitrogen atmosphere, after Compound A-2 (30 g, 0.0614 mol) and 2-chloro-4,6-diphenyl-1,3,5-triazine (32.9 g, 0.123 mol) were completely dissolved in tetrahydrofuran (600 ml), potassium carbonate (25.5 g, 0.184 mol) dissolved in 200 ml of water was added thereto, then tetrakistriphenylphosphino palladium (2.1 g, 0.00184 mmol) was added thereto, and the result was heated and stirred for 4 hours. After lowering the temperature to room temperature and completing the reaction, the aqueous potassium carbonate solution was removed and white solids were filtered. The filtered white solids were washed twice with tetrahydrofuran and ethyl acetate each to prepare Compound 1 (31.7 g, yield 74%).

MS $[M+H]^+=699$

Preparation Example 2. Preparation of Compound 2

[Compound 2]

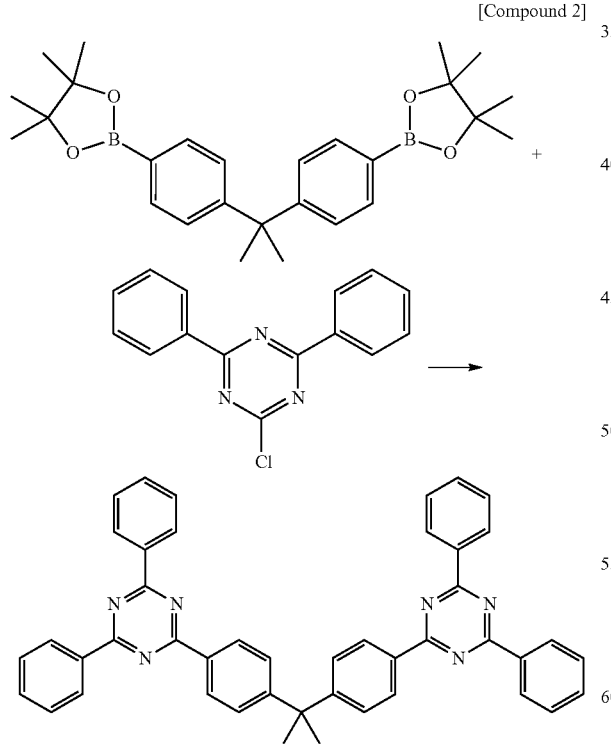

Compound 2 was prepared in the same manner as in Preparation Example 1 except that Compound B-2 was used instead of Compound A-2 in Preparation Example 1.

MS $[M+H]^+=659$

Preparation Example 3. Preparation of Compound 6

[Compound 6]

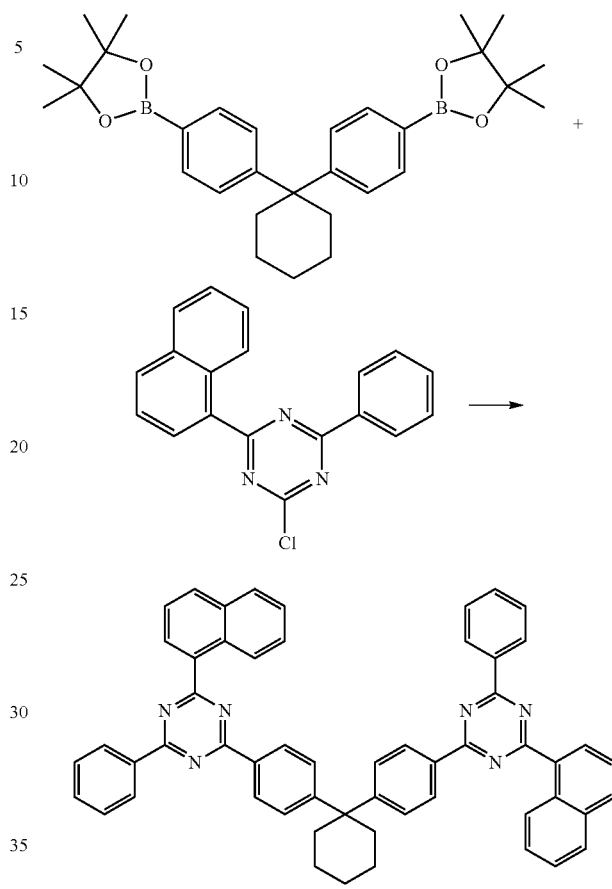

Compound 6 was prepared in the same manner as in Preparation Example 1 except that 2-chloro-4-(naphthalen-1-yl)-6-phenyl-1,3,5-triazine was used instead of 2-chloro-4,6-diphenyl-1,3,5-triazine in Preparation Example 1.

MS $[M+H]^+=799$

Preparation Example 4. Preparation of Compound 10

[Compound 10]

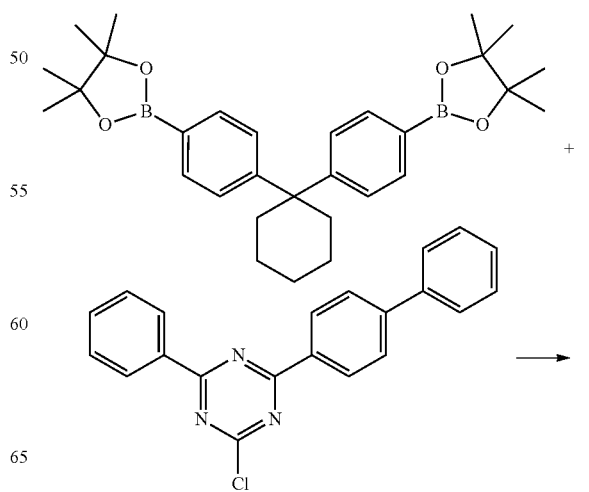

-continued

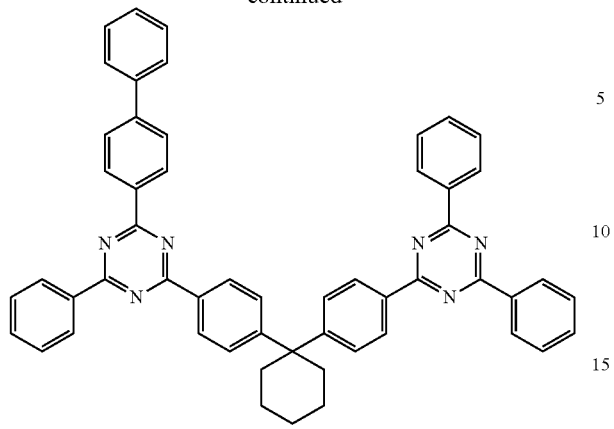

Compound 10 was prepared in the same manner as in Preparation Example 1 except that 2-([1,1'-biphenyl]-4-yl)-4-chloro-6-phenyl-1,3,5-triazine was used instead of 2-chloro-4,6-diphenyl-1,3,5-triazine in Preparation Example 1.

MS [M+H]$^+$=851

Preparation Example 5. Preparation of Compound 11

Compound 11 was prepared in the same manner as in Preparation Example 2 except that 2-([1,1'-biphenyl]-4-yl)-4-chloro-6-phenyl-1,3,5-triazine was used instead of 2-chloro-4,6-diphenyl-1,3,5-triazine in Preparation Example 2.

MS [M+H]$^+$=811

Preparation Example 6. Preparation of Compound 15

[Comound 15]

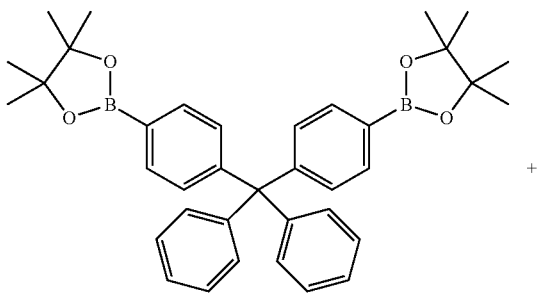

+

[Compound 11]

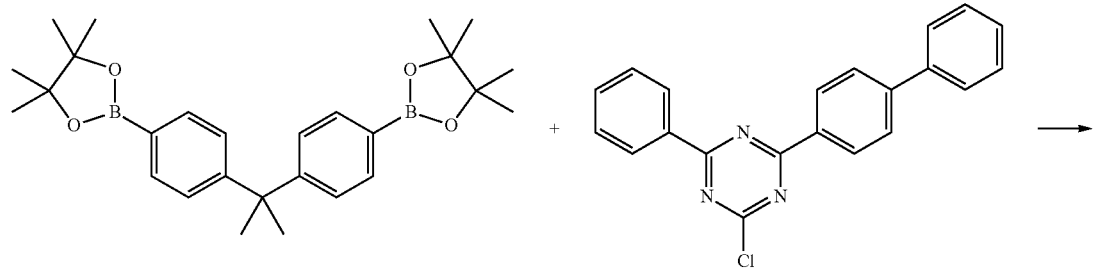

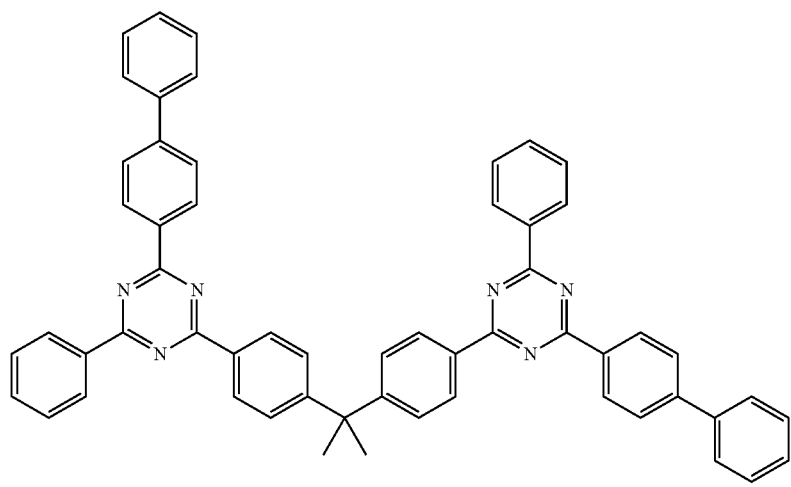

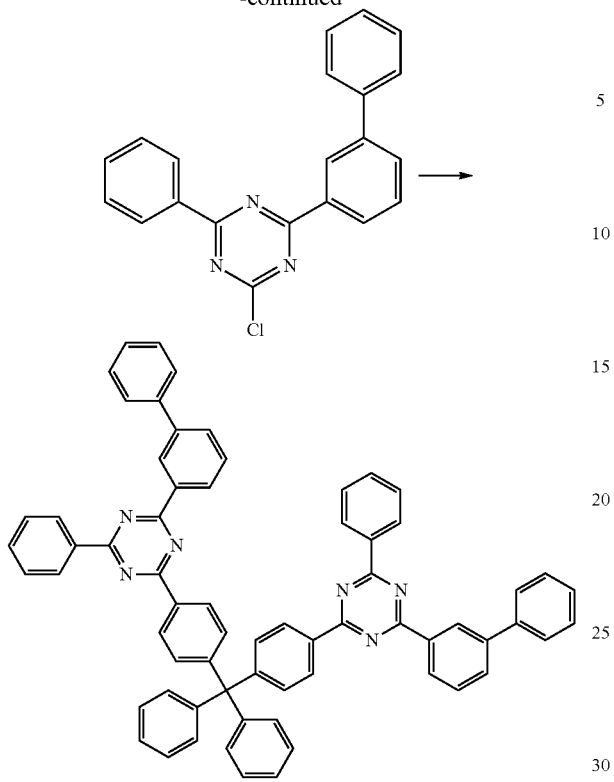

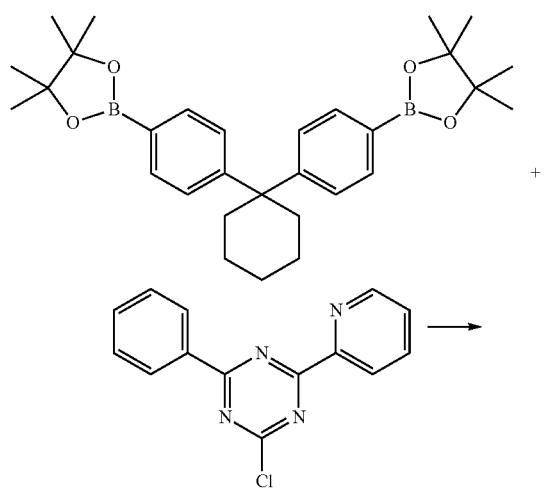

Compound 15 was prepared in the same manner as in Preparation Example 1 except that diphenylbis(4-(4,4,5,5-tetramethyl-1,3,2-dioxaborolan-2-yl)phenyl)methane was used instead of Compound A-2, and 2-([1,1'-biphenyl]-4-yl)-4-chloro-6-phenyl-1,3,5-triazine was used instead of 2-chloro-4,6-diphenyl-1,3,5-triazine in Preparation Example 1.

MS [M+H]$^+$=935

Preparation Example 7. Preparation of Compound 17

[Comound 17]

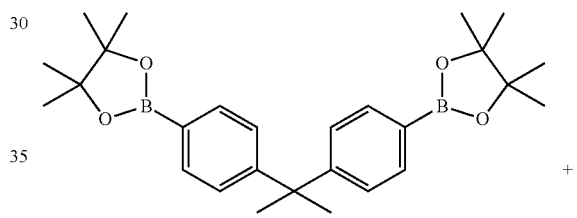

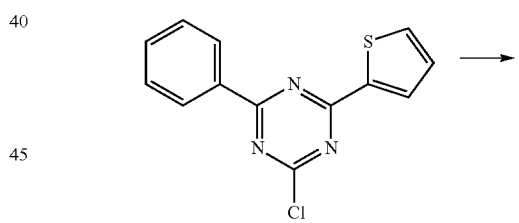

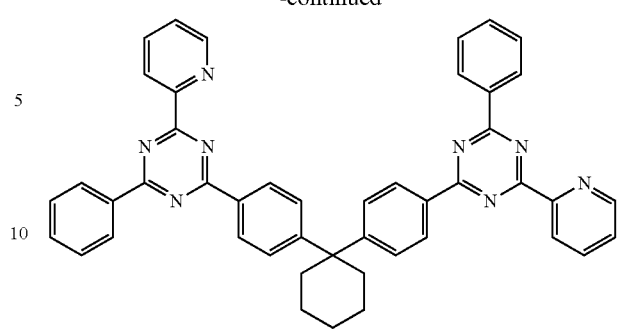

Compound 17 was prepared in the same manner as in Preparation Example 1 except that 2-chloro-4-phenyl-6-(pyridin-2-yl)-1,3,5-triazine was used instead of 2-chloro-4,6-diphenyl-1,3,5-triazine in Preparation Example 1.

MS [M+H]$^+$=701

Preparation Example 8. Preparation of Compound 22

[Compound 22]

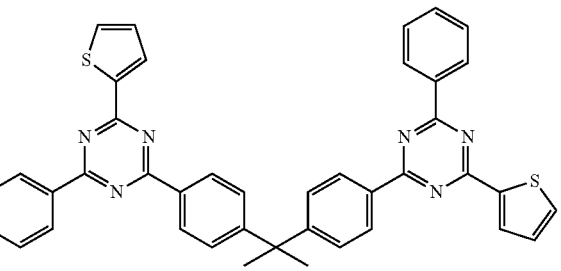

Compound 22 was prepared in the same manner as in Preparation Example 2 except that 2-chloro-4-phenyl-6-(thiophen-2-yl)-1,3,5-triazine was used instead of 2-chloro-4,6-diphenyl-1,3,5-triazine in Preparation Example 2.

MS [M+H]$^+$=671

Preparation Example 9. Preparation of Compound 24

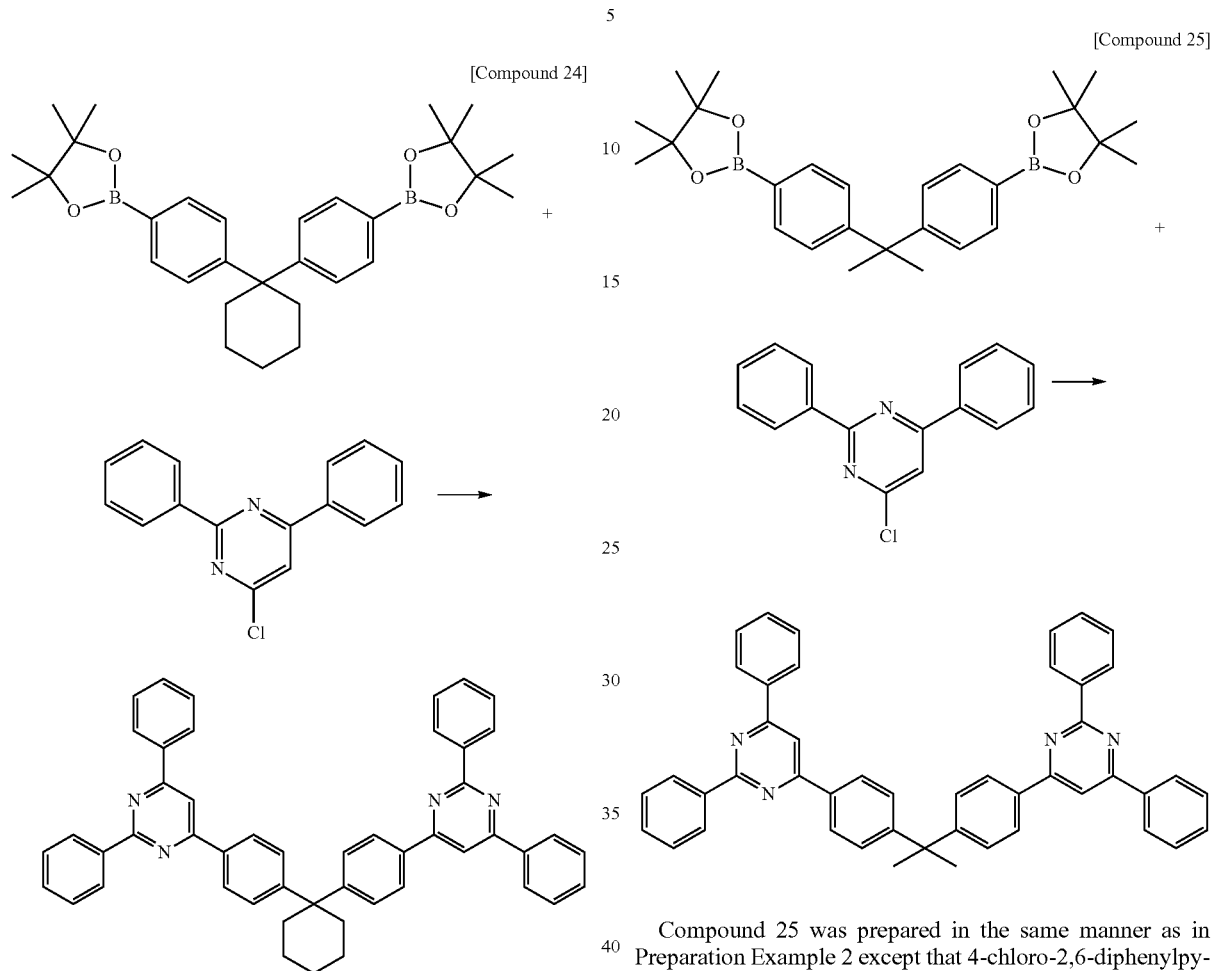

Compound 24 was prepared in the same manner as in Preparation Example 1 except that 4-chloro-2,6-diphenylpyrimidine was used instead of 2-chloro-4,6-diphenyl-1,3,5-triazine in Preparation Example 1.
MS [M+H]$^+$=697

Preparation Example 10. Preparation of Compound 25

Compound 25 was prepared in the same manner as in Preparation Example 2 except that 4-chloro-2,6-diphenylpyrimidine was used instead of 2-chloro-4,6-diphenyl-1,3,5-triazine in Preparation Example 2.
MS [M+H]$^+$=657

Preparation Example 11. Preparation of Compound 35

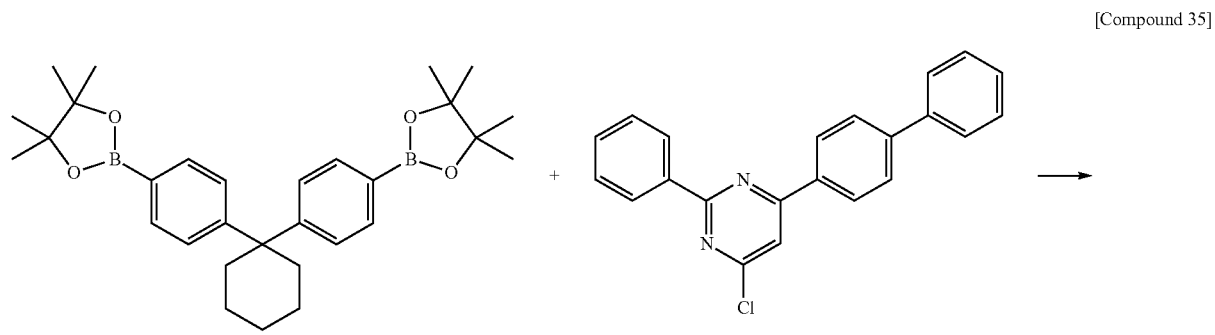

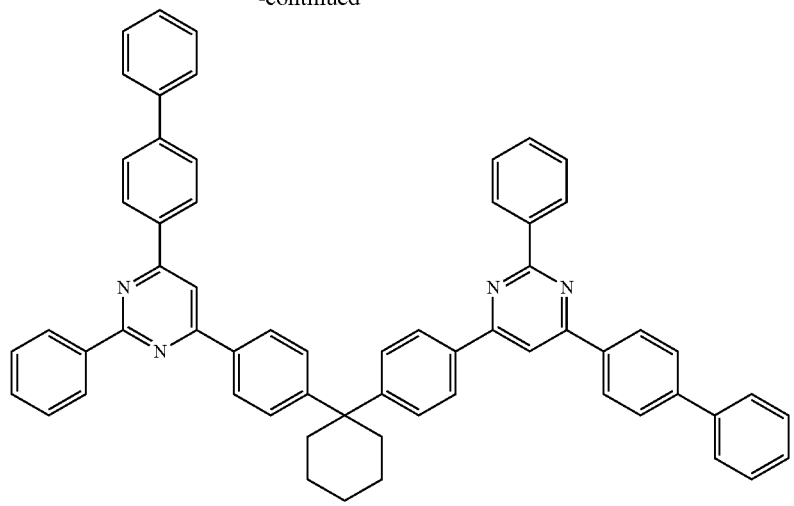

Compound 35 was prepared in the same manner as in Preparation Example 1 except that 4-([1,1'-biphenyl]-4-yl)-6-chloro-2-phenylpyrimidine was used instead of 2-chloro-4,6-diphenyl-1,3,5-triazine in Preparation Example 1.

MS [M+H]⁺=849

Preparation Example 12. Preparation of Compound 55

Compound 55 was prepared in the same manner as in Preparation Example 1 except that 2-chloro-4,6-diphenylpyrimidine was used instead of 2-chloro-4,6-diphenyl-1,3,5-triazine in Preparation Example 1.

MS [M+H]⁺=697

Preparation Example 13. Preparation of Compound 56

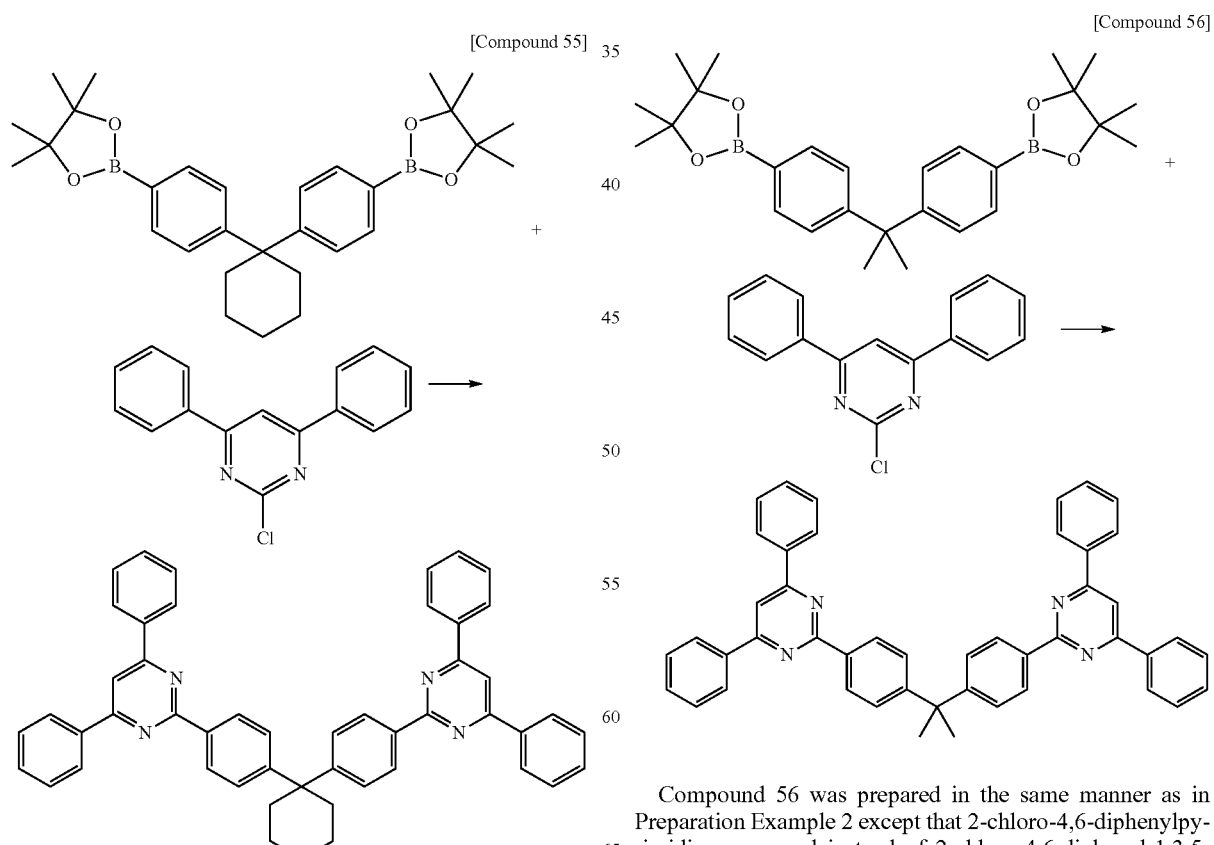

Compound 56 was prepared in the same manner as in Preparation Example 2 except that 2-chloro-4,6-diphenylpyrimidine was used instead of 2-chloro-4,6-diphenyl-1,3,5-triazine in Preparation Example 2.

MS [M+H]⁺=657

Preparation Example 14. Preparation of Compound 72

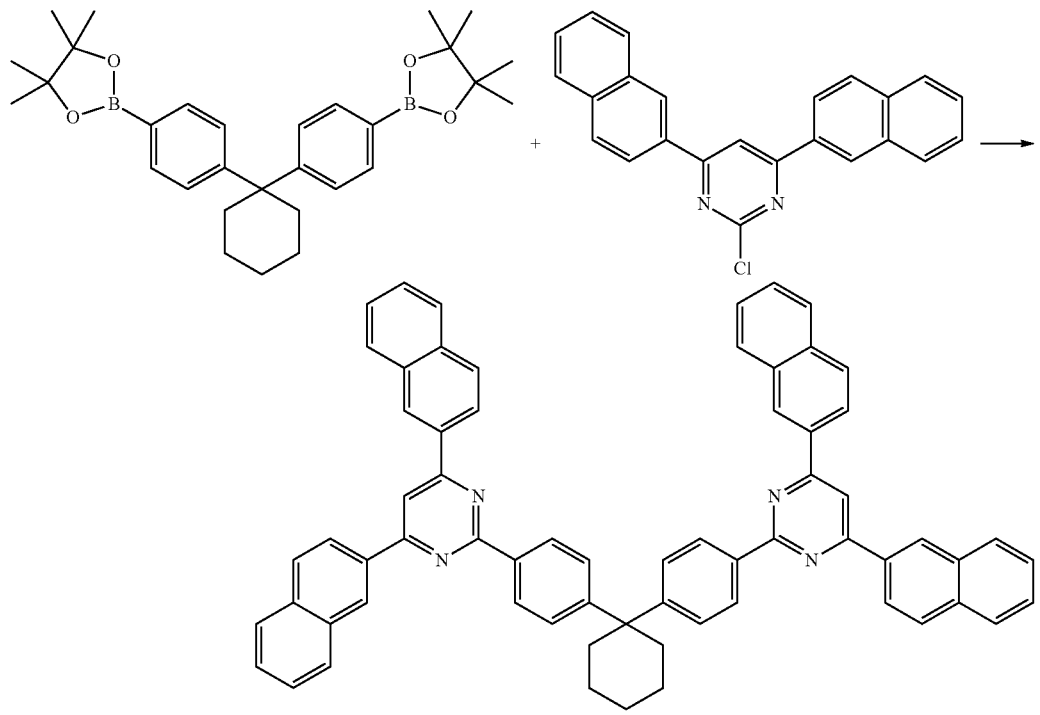

[Compound 72]

Compound 72 was prepared in the same manner as in Preparation Example 1 except that 2-chloro-4,6-di(naphthalen-2-yl)pyrimidine was used instead of 2-chloro-4,6-diphenyl-1,3,5-triazine in Preparation Example 1.

MS [M+H]$^+$=897

Preparation Example 15. Preparation of Compound 74

[Compound 74]

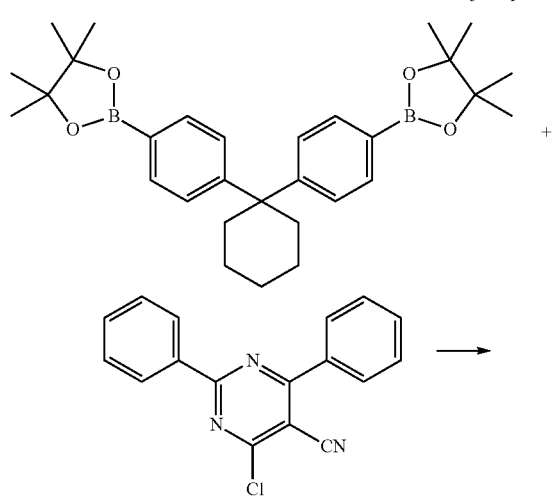

-continued

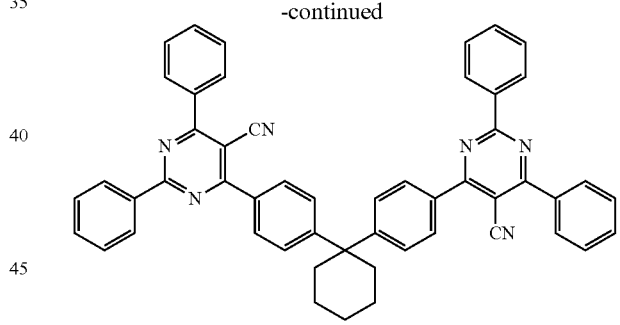

Compound 74 was prepared in the same manner as in Preparation Example 1 except that 4-chloro-2,6-diphenylpyrimidine-5-carbonitrile was used instead of 2-chloro-4,6-diphenyl-1,3,5-triazine in Preparation Example 1.

MS [M+H]$^+$=747

Preparation Example 16. Preparation of Compound 75

[Compound 75]

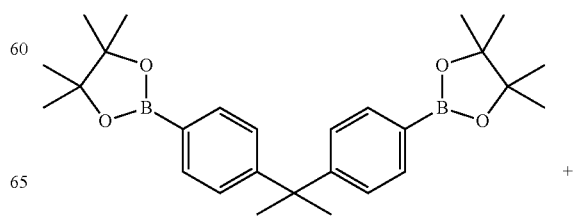

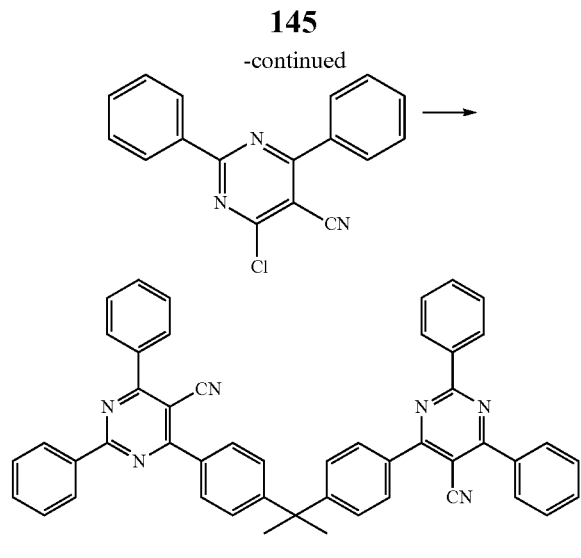

Compound 75 was prepared in the same manner as in Preparation Example 2 except that 4-chloro-2,6-diphenylpyrimidine-5-carbonitrile was used instead of 2-chloro-4,6-diphenyl-1,3,5-triazine in Preparation Example 2.

MS [M+H]$^+$=707

Preparation Example 17. Preparation of Compound 85

[Compound 85]

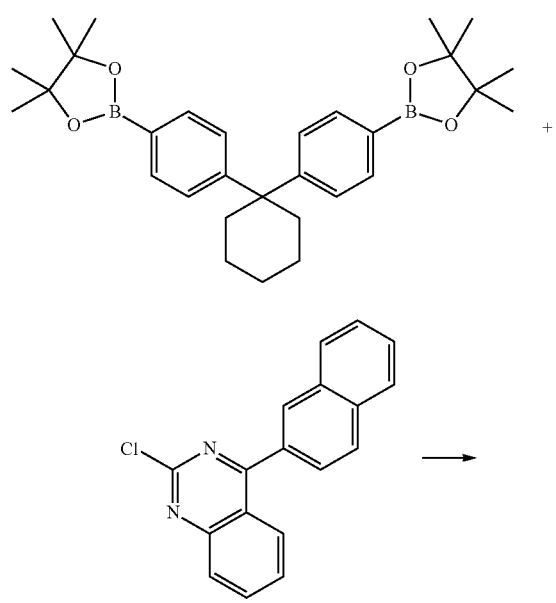

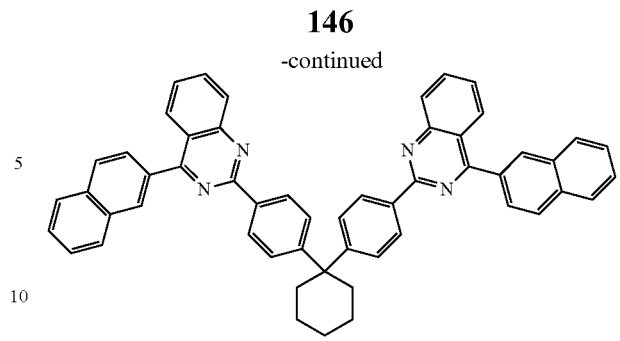

Compound 85 was prepared in the same manner as in Preparation Example 1 except that 2-chloro-4-(naphthalen-2-yl)quinazoline was used instead of 2-chloro-4,6-diphenyl-1,3,5-triazine in Preparation Example 1.

MS [M+H]$^+$=745

Preparation Example 18. Preparation of Compound 90

[Compound 90]

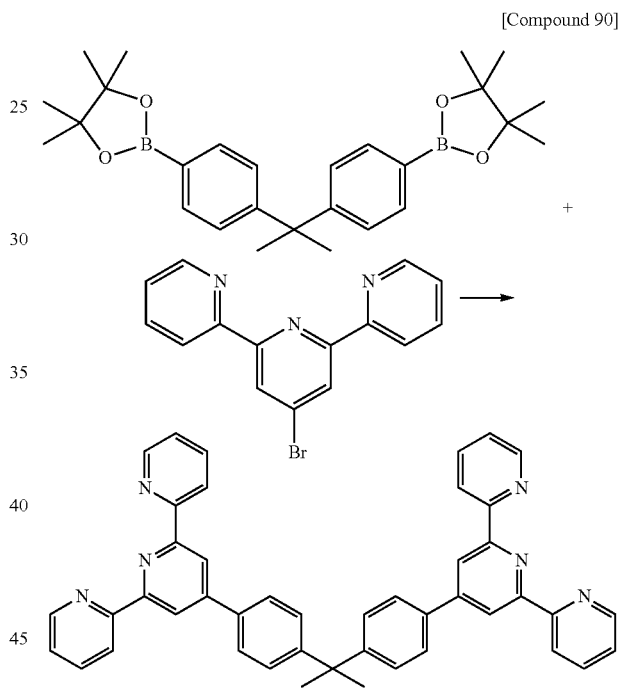

Compound 90 was prepared in the same manner as in Preparation Example 2 except that 4'-bromo-2,2':6'2"-terpyridine was used instead of 2-chloro-4,6-diphenyl-1,3,5-triazine in Preparation Example 2.

MS [M+H]$^+$=659

Preparation Example 19. Preparation of Compound 92

[Compound 92]

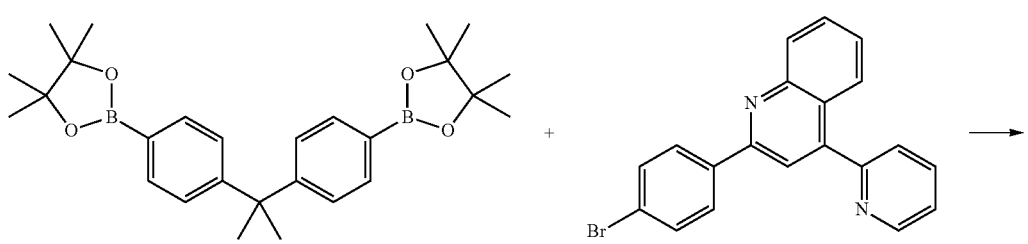

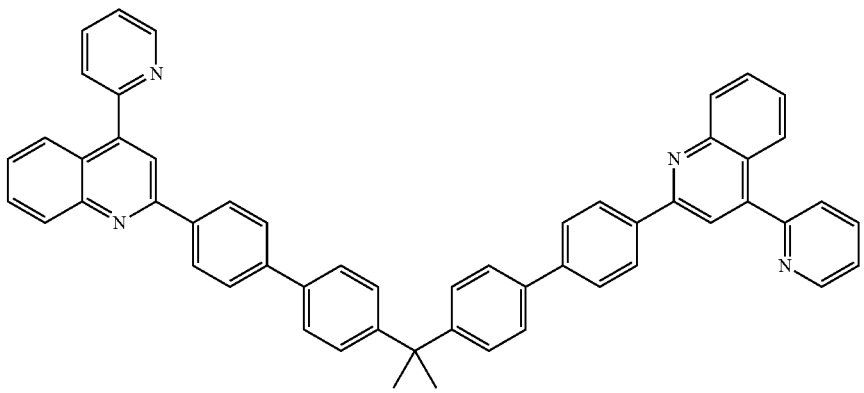

Compound 92 was prepared in the same manner as in Preparation Example 2 except that 2-(4-bromophenyl)-4-(pyridin-2-yl)quinoline was used instead of 2-chloro-4,6-diphenyl-1,3,5-triazine in Preparation Example 2.

MS [M+H]$^+$=659

Preparation Example 20. Preparation of Compound 97

[Compound 97]

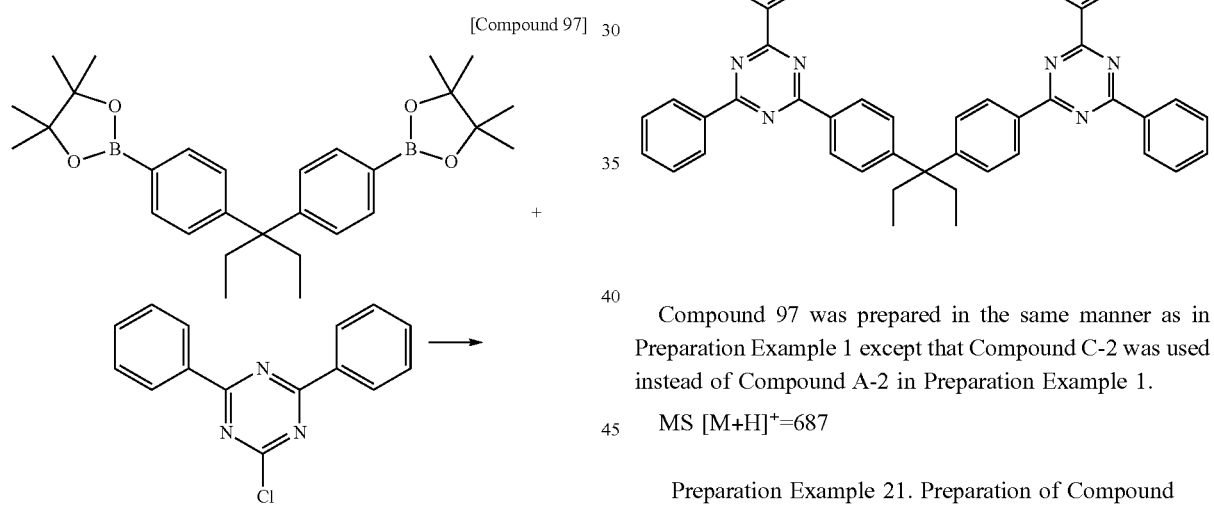

Compound 97 was prepared in the same manner as in Preparation Example 1 except that Compound C-2 was used instead of Compound A-2 in Preparation Example 1.

MS [M+H]$^+$=687

Preparation Example 21. Preparation of Compound 100

[Compound 100]

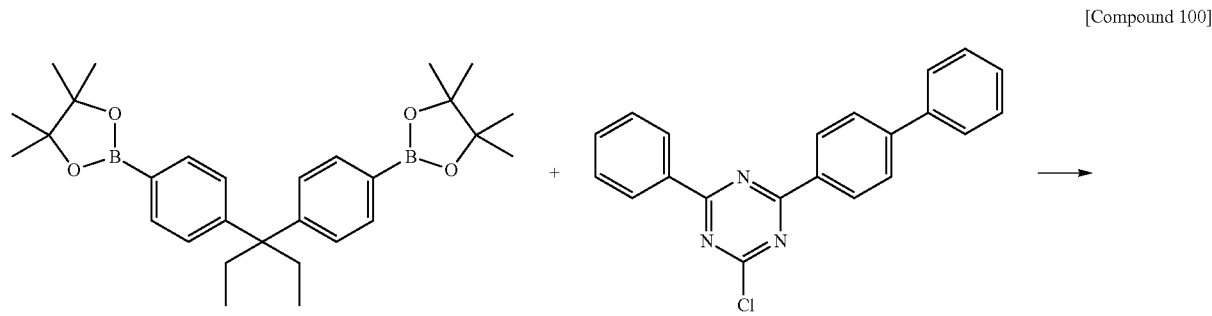

-continued

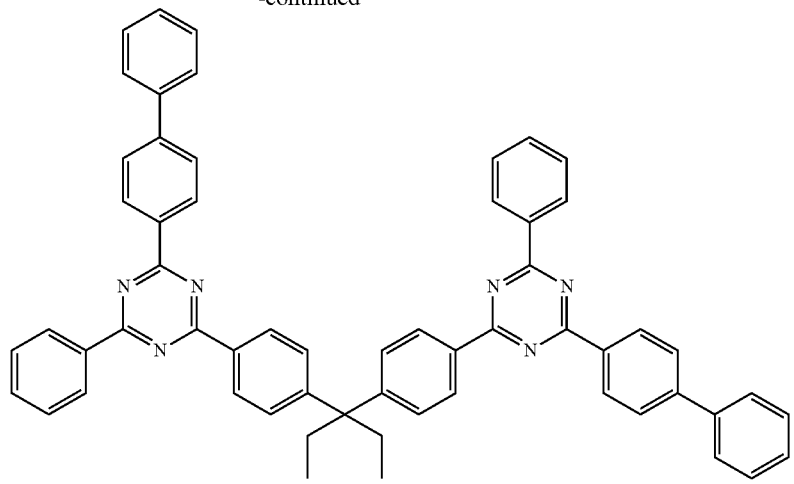

Compound 100 was prepared in the same manner as in Preparation Example 5 except that Compound C-2 was used instead of Compound A-2 in Preparation Example 5.

MS [M+H]$^+$=839

Preparation Example 22. Preparation of Compound 124

[Compound 124]

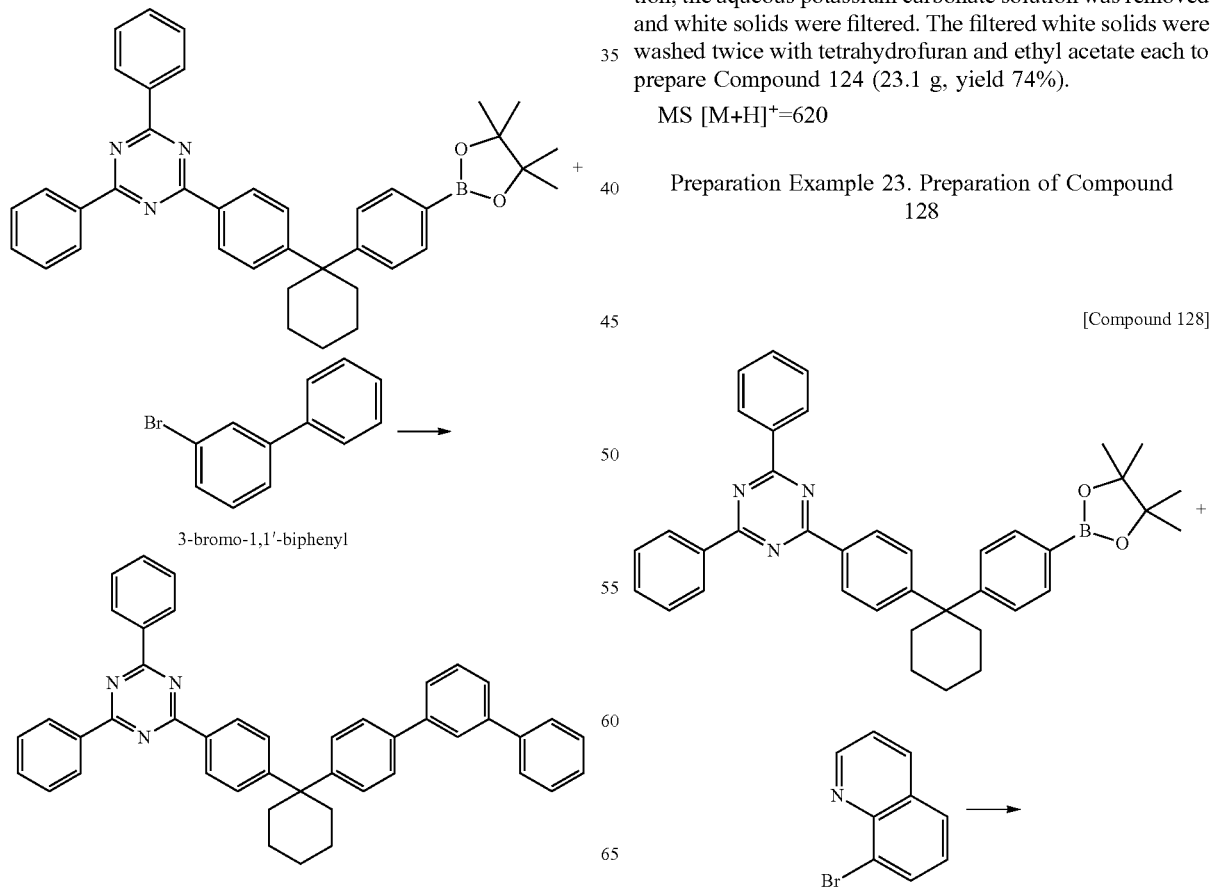

Under nitrogen atmosphere, after the compound 2,4-diphenyl-6-(4-(4,4,5,5-tetramethyl-1,3,2-dioxaborolan-2-yl)phenyl)cyclohexyl)phenyl)1,3,5-triazine (30 g, 0.0505 mol) and 3-bromo-1,1'-biphenyl (11.8 g, 0.0505 mol) were completely dissolved in tetrahydrofuran (600 ml), potassium carbonate (21 g, 0.152 mol) dissolved in 200 ml of water was added thereto, then tetrakistriphenyl-phosphino palladium (1.8 g, 0.00152 mmol) was added thereto, and the result was heated and stirred for 4 hours. After lowering the temperature to room temperature and completing the reaction, the aqueous potassium carbonate solution was removed and white solids were filtered. The filtered white solids were washed twice with tetrahydrofuran and ethyl acetate each to prepare Compound 124 (23.1 g, yield 74%).

MS [M+H]$^+$=620

Preparation Example 23. Preparation of Compound 128

[Compound 128]

-continued

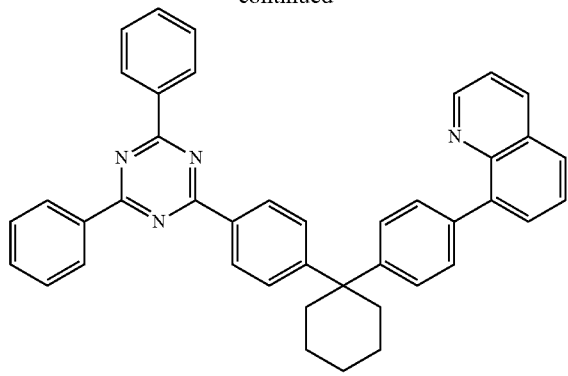

Compound 128 was prepared in the same manner as in Preparation Example 22 except that 8-bromoquinoline was used instead of 3-bromo-1,1'-biphenyl in Preparation Example 22.
MS [M+H]$^+$=595

Preparation Example 24. Preparation of Compound 155

[Compound 155]

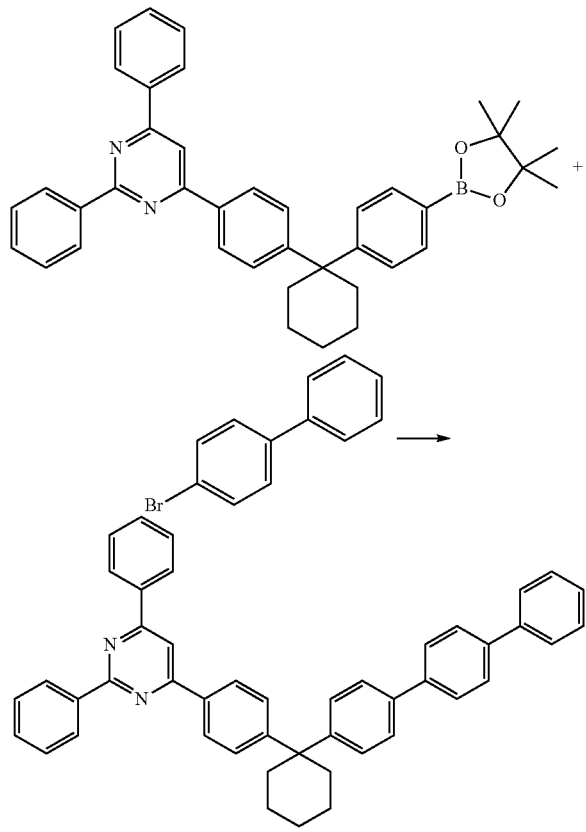

Under nitrogen atmosphere, after the compound 2,4-diphenyl-6-(4-(4,4,5,5-tetramethyl-1,3,2-dioxaborolan-2-yl)phenyl)cyclohexyl)phenyl)pyrimidine (29.9 g, 0.0505 mol) and 4-bromo-1,1'-biphenyl (11.8 g, 0.0505 mol) were completely dissolved in tetrahydrofuran (600 ml), potassium carbonate (21 g, 0.152 mol) dissolved in 200 ml of water was added thereto, then tetrakistriphenyl-phosphino palladium (1.8 g, 0.00152 mmol) was added thereto, and the result was heated and stirred for 4 hours. After lowering the temperature to room temperature and completing the reaction, the aqueous potassium carbonate solution was removed and white solids were filtered. The filtered white solids were washed twice with tetrahydrofuran and ethyl acetate each to prepare Compound 155 (22.1 g, yield 71%).
MS [M+H]$^+$=619

Preparation Example 25. Preparation of Compound 177

[Compound 177]

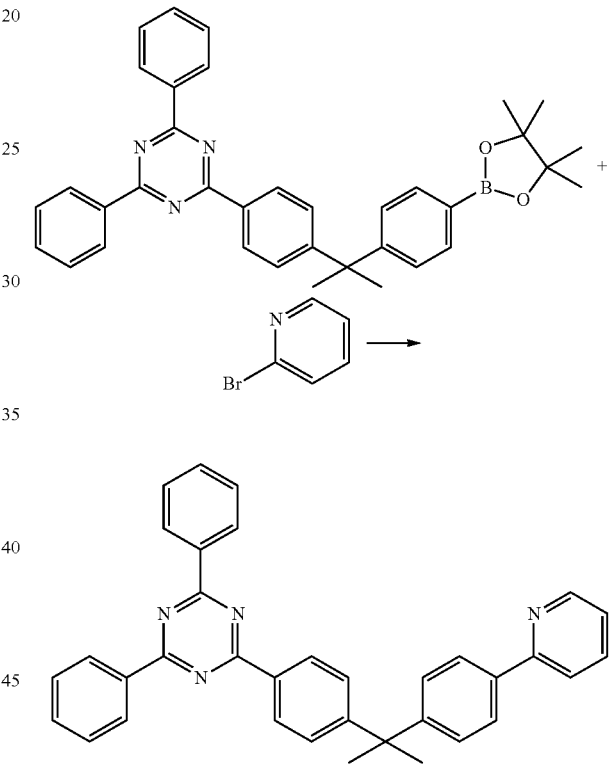

Under nitrogen atmosphere, after the compound 2,4-diphenyl-6-(4-(2-(4-(4,4,5,5-tetramethyl-1,3,2-dioxaborolan-2-yl)phenyl)propan-2-yl)phenyl)-1,3,5-triazine (28.0 g, 0.0505 mol) and 2-bromopyridine (8.0 g, 0.0505 mol) were completely dissolved in tetrahydrofuran (600 ml), potassium carbonate (21 g, 0.152 mol) dissolved in 200 ml of water was added thereto, then tetrakistriphenyl-phosphino palladium (1.8 g, 0.00152 mmol) was added thereto, and the result was heated and stirred for 4 hours. After lowering the temperature to room temperature and completing the reaction, the aqueous potassium carbonate solution was removed and white solids were filtered.

The filtered white solids were washed twice with tetrahydrofuran and ethyl acetate each to prepare Compound 177 (17 g, yield 69%).
MS [M+H]$^+$=504

Preparation Example 26. Preparation of Compound 182

[Compound 182]

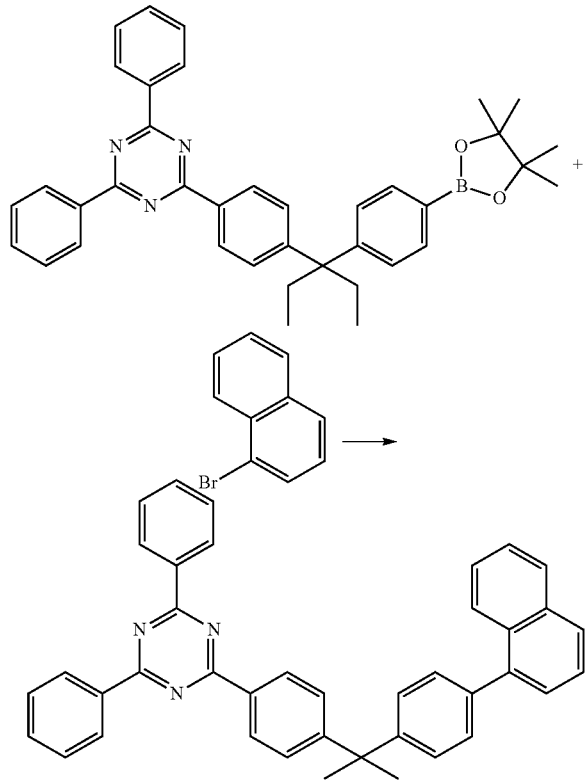

Under nitrogen atmosphere, after the compound 2,4-diphenyl-6-(4-(3-(4-(4,4,5,5-tetramethyl-1,3,2-dioxaborolan-2-yl)phenyl)pentan-3-yl)phenyl)-1,3,5-triazine (29.4 g, 0.0505 mol) and 1-bromonaphthalene (10.5 g, 0.0505 mol) were completely dissolved in tetrahydrofuran (600 ml), potassium carbonate (21 g, 0.152 mol) dissolved in 200 ml of water was added thereto, then tetrakistriphenyl-phosphino palladium (1.8 g, 0.00152 mmol) was added thereto, and the result was heated and stirred for 4 hours. After lowering the temperature to room temperature and completing the reaction, the aqueous potassium carbonate solution was removed and white solids were filtered. The filtered white solids were washed twice with tetrahydrofuran and ethyl acetate each to prepare Compound 182 (19 g, yield 68%).

MS [M+H]$^+$=554

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following Compound [HI-A] to a thickness of 600 Å. A hole transfer layer was formed on the hole injection layer by consecutively vacuum depositing hexanitrile hexaazatriphenylene (HAT) of the following chemical formula to a thickness of 50 Å and the following Compound [HT-A] (600 Å).

Subsequently, a light emitting layer was formed on the hole transfer layer to a film thickness of 200 Å by vacuum depositing the following compounds [BH] and [BD] in a weight ratio of 25:1.

An electron injection and transfer layer was formed on the light emitting layer to a thickness of 350 Å by vacuum depositing Compound 1 and the following compound lithium quinolate [LiQ] in a weight ratio of 1:1. A cathode was formed on the electron injection and transfer layer by depositing lithium fluoride (LiF) to a thickness of 10 Å and aluminum to a thickness of 1,000 Å in consecutive order.

The organic light emitting device was manufactured by maintaining the deposition rates of the organic materials at 0.4 to 0.9 Å/sec, the deposition rates of the lithium fluoride and the aluminum of the cathode at 0.3 Å/sec and 2 Å/sec, respectively, and the degree of vacuum when being deposited at 1×10$^{-7}$ to 5×10$^{-8}$ torr in the above-mentioned process.

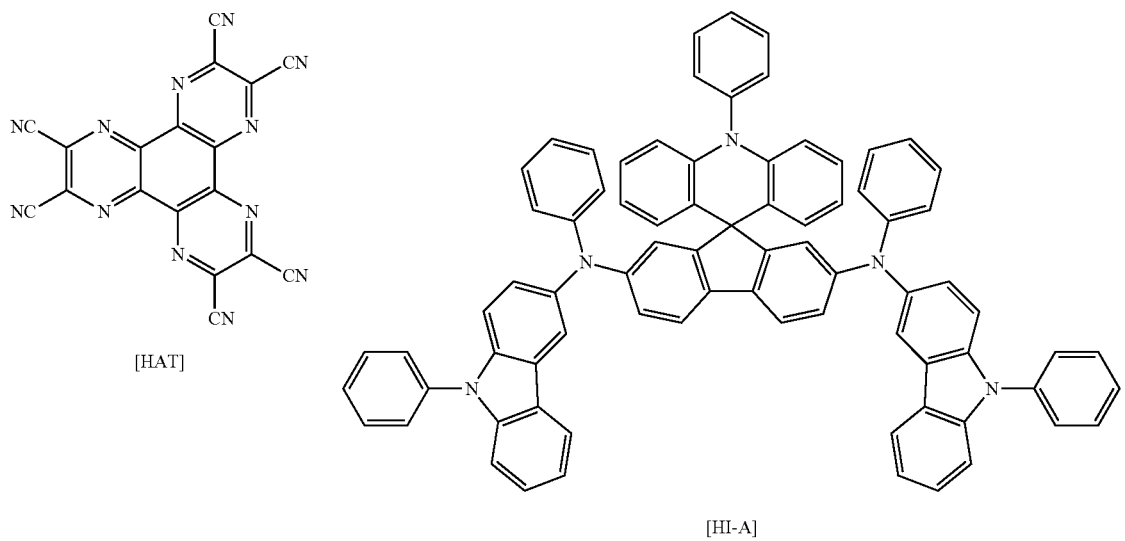

[HAT]

[HI-A]

-continued
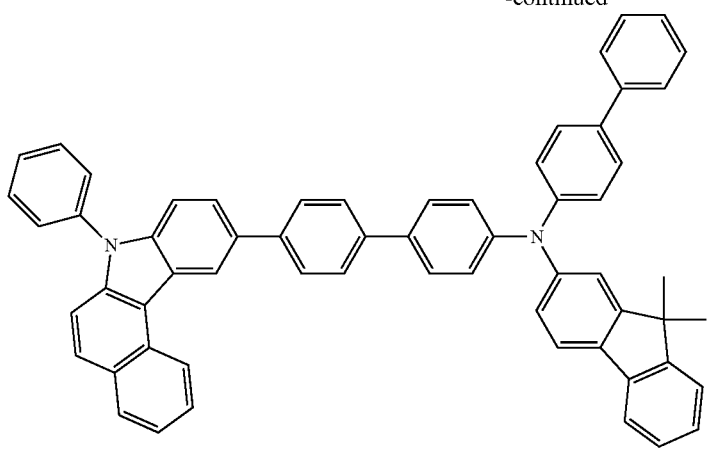
[HT-A]
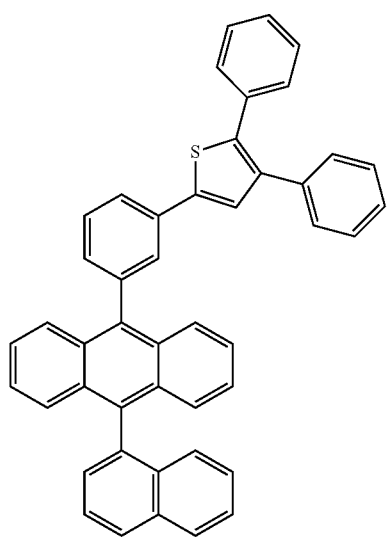
[BH]
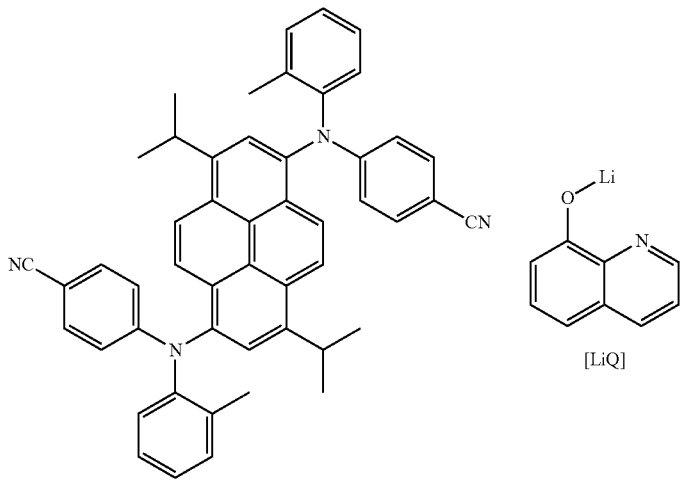
[BD]
[LiQ]
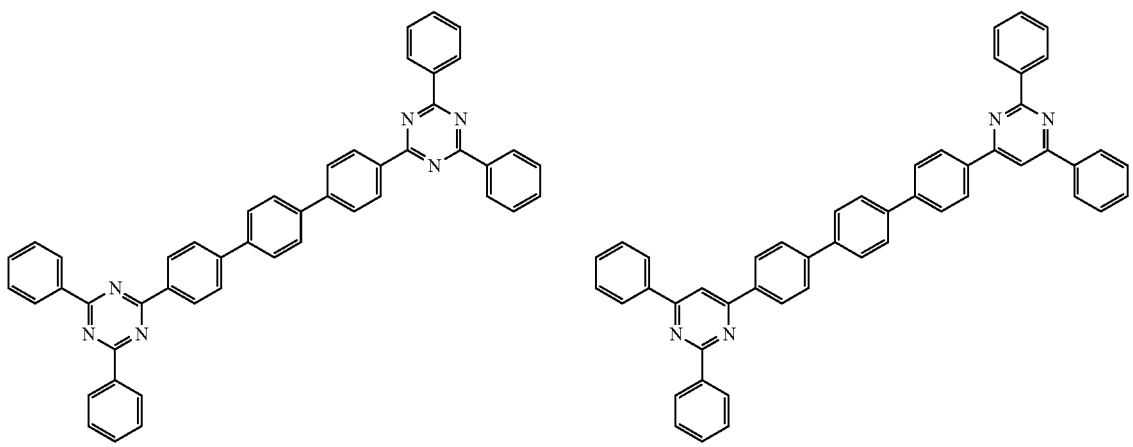
[ET-1-A]              [ET-1-B]

-continued
[ET-1-C]
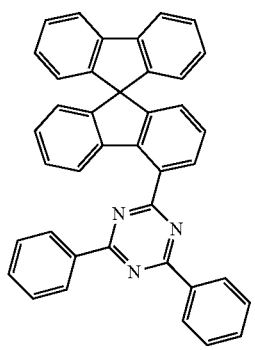
[ET-1-D]
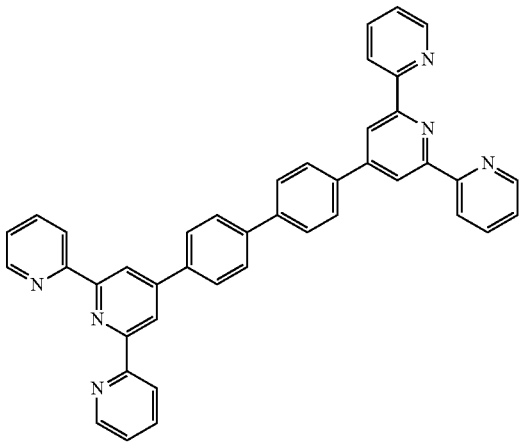
[ET-1-E]
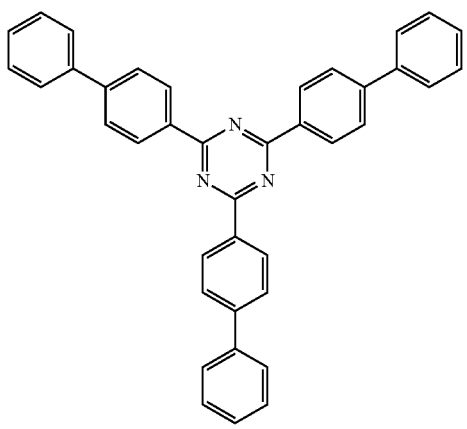
[ET-1-F]
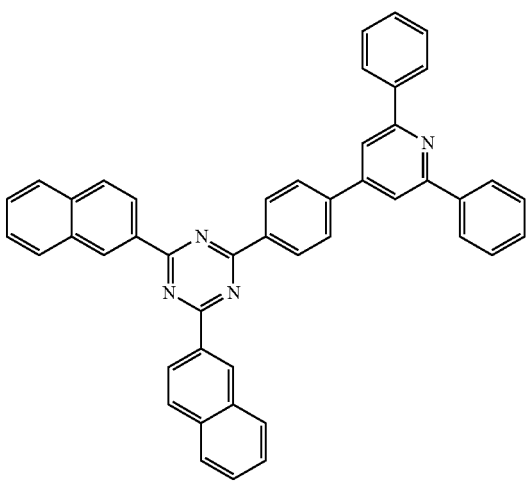
[ET-1-G]
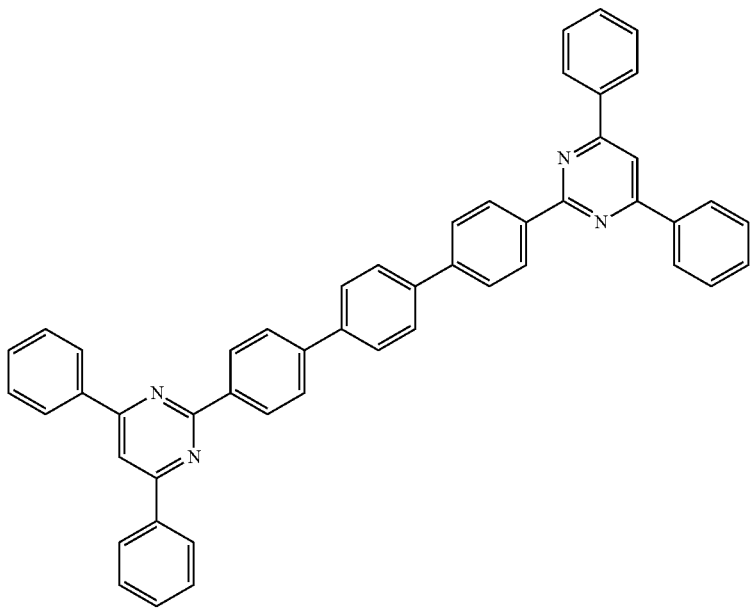

Example 1-2

An organic light emitting device was prepared in the same manner as in Example 1-1 except that Compound 2 was used instead of the compound of Compound 1 in Example 1-1.

Example 1-3

An organic light emitting device was prepared in the same manner as in Example 1-1 except that Compound 6 was used instead of the compound of Compound 1 in Example 1-1.

Example 1-4

An organic light emitting device was prepared in the same manner as in Example 1-1 except that Compound 10 was used instead of the compound of Compound 1 in Example 1-1.

Example 1-5

An organic light emitting device was prepared in the same manner as in Example 1-1 except that Compound 11 was used instead of the compound of Compound 1 in Example 1-1.

Example 1-6

An organic light emitting device was prepared in the same manner as in Example 1-1 except that Compound 15 was used instead of the compound of Compound 1 in Example 1-1.

Example 1-7

An organic light emitting device was prepared in the same manner as in Example 1-1 except that Compound 17 was used instead of the compound of Compound 1 in Example 1-1.

Example 1-8

An organic light emitting device was prepared in the same manner as in Example 1-1 except that Compound 22 was used instead of the compound of Compound 1 in Example 1-1.

Example 1-9

An organic light emitting device was prepared in the same manner as in Example 1-1 except that Compound 24 was used instead of the compound of Compound 1 in Example 1-1.

Example 1-10

An organic light emitting device was prepared in the same manner as in Example 1-1 except that Compound 25 was used instead of the compound of Compound 1 in Example 1-1.

Example 1-11

An organic light emitting device was prepared in the same manner as in Example 1-1 except that Compound 35 was used instead of the compound of Compound 1 in Example 1-1.

Example 1-12

An organic light emitting device was prepared in the same manner as in Example 1-1 except that Compound 55 was used instead of the compound of Compound 1 in Example 1-1.

Example 1-13

An organic light emitting device was prepared in the same manner as in Example 1-1 except that Compound 56 was used instead of the compound of Compound 1 in Example 1-1.

Example 1-14

An organic light emitting device was prepared in the same manner as in Example 1-1 except that Compound 72 was used instead of the compound of Compound 1 in Example 1-1.

Example 1-15

An organic light emitting device was prepared in the same manner as in Example 1-1 except that Compound 74 was used instead of the compound of Compound 1 in Example 1-1.

Example 1-16

An organic light emitting device was prepared in the same manner as in Example 1-1 except that Compound 75 was used instead of the compound of Compound 1 in Example 1-1.

Example 1-17

An organic light emitting device was prepared in the same manner as in Example 1-1 except that Compound 85 was used instead of the compound of Compound 1 in Example 1-1.

Example 1-18

An organic light emitting device was prepared in the same manner as in Example 1-1 except that Compound 90 was used instead of the compound of Compound 1 in Example 1-1.

Example 1-19

An organic light emitting device was prepared in the same manner as in Example 1-1 except that Compound 92 was used instead of the compound of Compound 1 in Example 1-1.

Example 1-20

An organic light emitting device was prepared in the same manner as in Example 1-1 except that Compound 97 was used instead of the compound of Compound 1 in Example 1-1.

Example 1-21

An organic light emitting device was prepared in the same manner as in Example 1-1 except that Compound 100 was used instead of the compound of Compound 1 in Example 1-1.

Example 1-22

An organic light emitting device was prepared in the same manner as in Example 1-1 except that Compound 124 was used instead of the compound of Compound 1 in Example 1-1.

Example 1-23

An organic light emitting device was prepared in the same manner as in Example 1-1 except that Compound 128 was used instead of the compound of Compound 1 in Example 1-1.

Example 1-24

An organic light emitting device was prepared in the same manner as in Example 1-1 except that Compound 155 was used instead of the compound of Compound 1 in Example 1-1.

Example 1-25

An organic light emitting device was prepared in the same manner as in Example 1-1 except that Compound 177 was used instead of the compound of Compound 1 in Example 1-1.

Example 1-26

An organic light emitting device was prepared in the same manner as in Example 1-1 except that Compound 182 was used instead of the compound of Compound 1 in Example 1-1.

Comparative Example 1-1

An organic light emitting device was prepared in the same manner as in Example 1-1 except that Compound ET-1-A was used instead of the compound of Compound 1 in Example 1-1.

Comparative Example 1-2

An organic light emitting device was prepared in the same manner as in Example 1-1 except that Compound ET-1-B was used instead of the compound of Compound 1 in Example 1-1.

Comparative Example 1-3

An organic light emitting device was prepared in the same manner as in Example 1-1 except that Compound ET-1-C was used instead of the compound of Compound 1 in Example 1-1.

Comparative Example 1-4

An organic light emitting device was prepared in the same manner as in Example 1-1 except that Compound ET-1-D was used instead of the compound of Compound 1 in Example 1-1.

Comparative Example 1-5

An organic light emitting device was prepared in the same manner as in Example 1-1 except that Compound ET-1-E was used instead of the compound of Compound 1 in Example 1-1.

Comparative Example 1-6

An organic light emitting device was prepared in the same manner as in Example 1-1 except that Compound ET-1-F was used instead of the compound of Compound 1 in Example 1-1.

Comparative Example 1-7

An organic light emitting device was prepared in the same manner as in Example 1-1 except that Compound ET-1-G was used instead of the compound of Compound 1 in Example 1-1.

For the organic light emitting devices manufactured using the above-mentioned methods, a driving voltage and light emission efficiency at current density of 10 mA/cm$^2$ were measured, and a time at which brightness becomes 90% of its initial brightness ($T_{90}$) at current density of 20 mA/cm$^2$ was measured. The results are shown in the following Table 1.

TABLE 1

| | Compound | Voltage (V@10 mA/cm$^2$) | Efficiency (cd/A@10 mA/cm$^2$) | Color Coordinates (x, y) | Lifespan (h) $T_{90}$ at 20 mA/cm$^2$ |
|---|---|---|---|---|---|
| Example 1-1 | 1 | 3.3 | 7.27 | (0.142, 0.097) | 140 |
| Example 1-2 | 2 | 3.2 | 7.32 | (0.142, 0.096) | 139 |
| Example 1-3 | 6 | 3.4 | 7.02 | (0.142, 0.096) | 151 |
| Example 1-4 | 10 | 3.35 | 7.17 | (0.142, 0.096) | 164 |
| Example 1-5 | 11 | 3.31 | 7.20 | (0.142, 0.096) | 153 |
| Example 1-6 | 15 | 3.74 | 6.24 | (0.142, 0.097) | 128 |
| Example 1-7 | 17 | 3.47 | 6.87 | (0.142, 0.096) | 187 |
| Example 1-8 | 22 | 3.58 | 6.76 | (0.142, 0.099) | 201 |
| Example 1-9 | 24 | 3.34 | 7.34 | (0.142, 0.096) | 138 |
| Example 1-10 | 25 | 3.32 | 7.37 | (0.142, 0.098) | 137 |
| Example 1-11 | 35 | 3.37 | 7.10 | (0.142, 0.096) | 154 |
| Example 1-12 | 55 | 3.62 | 6.85 | (0.142, 0.097) | 184 |
| Example 1-13 | 56 | 3.61 | 6.94 | (0.142, 0.096) | 181 |
| Example 1-14 | 72 | 3.67 | 6.88 | (0.142, 0.097) | 179 |
| Example 1-15 | 74 | 3.78 | 6.21 | (0.142, 0.098) | 211 |
| Example 1-16 | 75 | 3.79 | 6.24 | (0.142, 0.097) | 207 |

TABLE 1-continued

| | Compound | Voltage (V@10 mA/cm$^2$) | Efficiency (cd/A@10 mA/cm$^2$) | Color Coordinates (x, y) | Lifespan (h) T$_{90}$ at 20 mA/cm$^2$ |
|---|---|---|---|---|---|
| Example 1-17 | 85 | 3.57 | 6.91 | (0.142, 0.097) | 141 |
| Example 1-18 | 90 | 3.40 | 7.00 | (0.142, 0.096) | 185 |
| Example 1-19 | 92 | 3.24 | 7.07 | (0.142, 0.096) | 151 |
| Example 1-20 | 97 | 3.28 | 7.26 | (0.142, 0.096) | 137 |
| Example 1-21 | 100 | 3.40 | 7.11 | (0.142, 0.096) | 144 |
| Example 1-22 | 124 | 3.14 | 7.34 | (0.142, 0.096) | 127 |
| Example 1-23 | 128 | 3.34 | 7.16 | (0.142, 0.096) | 138 |
| Example 1-24 | 155 | 3.37 | 7.15 | (0.142, 0.096) | 140 |
| Example 1-25 | 177 | 3.31 | 7.23 | (0.142, 0.096) | 137 |
| Example 1-26 | 182 | 3.27 | 7.19 | (0.142, 0.096) | 142 |
| Comparative Example 1-1 | ET-1-A | 4.5 | 3.91 | (0.142, 0.098) | 114 |
| Comparative Example 1-2 | ET-1-B | 4.6 | 3.81 | (0.142, 0.102) | 75 |
| Comparative Example 1-3 | ET-1-C | 3.9 | 5.87 | (0.142, 0.096) | 81 |
| Comparative Example 1-4 | ET-1-D | 4.42 | 4.01 | (0.142, 0.096) | 110 |
| Comparative Example 1-5 | ET-1-E | 3.95 | 5.65 | (0.142, 0.096) | 90 |
| Comparative Example 1-6 | ET-1-F | 4.01 | 5.10 | (0.142, 0.096) | 115 |
| Comparative Example 1-7 | ET-1-G | 4.51 | 5.01 | (0.142, 0.096) | 102 |

From the results of Table 1, it was identified that the compound represented by Chemical Formula 1 according to one embodiment of the present specification may be used in an organic material layer capable of carrying out electron injection and electron transfer at the same time of an organic light emitting device.

In addition, through Examples 1-1 to 1-26 and Comparative Examples 1-1 to 1-7, it was identified that the compound represented by Chemical Formula 1 including a non-conjugation group according to one embodiment of the present specification is capable of providing an organic light emitting device having high efficiency, a low driving voltage and a long lifespan.

Specifically, when comparing Examples 1-1 and 1-2 with Comparative Example 1-1, Examples 1-9 and 1-10 with Comparative Example 1-2, Examples 1-12 and 1-13 with Comparative Example 1-7, and Example 1-18 with Comparative Example 1-4, it was identified that the compound represented by Chemical Formula 1 including a non-conjugation group exhibited excellent properties in terms of a driving voltage, efficiency and a lifespan in an organic light emitting device compared to the compounds including a complete conjugation group with other structures. Such results are obtained since triplet energy increases due to smaller orbital overlap, and a wide optical band gap is capable of being formed.

In addition, when comparing Examples 1-22, 1-24 and 1-26 with Comparative Example 1-5, and Examples 1-23 and 1-25 with Comparative Example 1-6, it was identified that the compound represented by Chemical Formula 1 including a non-conjugation group exhibited excellent properties in terms of a driving voltage, efficiency and a lifespan in an organic light emitting device compared to the compounds including a complete conjugation group with other structures. Such results are obtained since triplet energy increases due to smaller orbital overlap, and a wide optical band gap is capable of being formed.

The compound represented by Chemical Formula 1 according to one embodiment of the present specification has excellent thermal stability, a deep HOMO level of 6.0 eV or more, high triplet energy (ET), and hole stability, and therefore, is capable of exhibiting excellent properties.

In one embodiment of the present specification, when the compound represented by Chemical Formula 1 is used in an organic material layer capable of carrying out electron injection and electron transfer at the same time, an n-type dopant may be mixed thereto and used. As a result, the compound represented by Chemical Formula 1 has a low driving voltage and high efficiency, and is capable of enhancing device stability by hole stability of the compound.

The invention claimed is:

1. A cyclic compound represented by the following Chemical Formula 1:

[Chemical Formula 1]

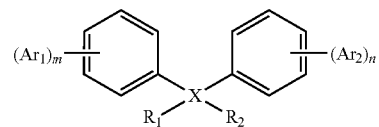

wherein in Chemical Formula 1,
at least one of Ar$_1$ and Ar$_2$ is a substituted or unsubstituted pyrimidyl group, or a substituted or unsubstituted triazinyl group, and wherein when the at least one of Ar$_1$ and Ar$_2$ is a substituted pyrimidyl group or a substituted triazinyl group, the pyrimidyl group or the triazinyl group has 2 or 3 substituents selected from the group consisting of a phenyl group, a naphthyl group, a biphenyl group, a nitrile group, a pyridinyl group, and a thiophenyl group;
when one of the Ar$_1$ and Ar$_2$ is a substituted or unsubstituted pyrimidyl group, or a substituted or unsubstituted triazinyl group, the other one of Ar$_1$ and Ar$_2$ is -L$_1$-(Z$_1$)$_p$;
L$_1$ is selected from the group consisting of a direct bond; a phenylene group, a biphenylylene group, a naphthylene group, a quinolinylene group, a quinazolinylene group, a pyridinylene group, a pyrimidinylene group, and a triazinylene group;

$Z_1$ is selected from the group consisting of hydrogen; a nitrile group; a phenyl group, a naphthyl group, a biphenyl group, a pyridine group, a pyrimidinyl group, a triazinyl group, a quinolinyl group, a quinazolinyl group, and a thiophenyl group; however, $Z_1$ is not hydrogen when $L_1$ is a direct bond;

p is an integer of 1 to 3, and when p is two or more, $Z_1$s are the same as or different from each other;

m and n are 1;

X is C; and $R_1$ and $R_2$ are the same as or different from each other, and each independently selected from the group consisting of a methyl group, an ethyl group, a phenyl group and a naphthyl group, or $R_1$ and $R_2$ are linked to each other to form a cyclohexyl group, with the proviso that when one of $R_1$ and $R_2$ is a phenyl group the other one of $R_1$ and $R_2$ is a methyl group.

2. The cyclic compound of claim 1, wherein $R_1$ and $R_2$ are the same as or different from each other, and each independently selected from the group consisting of a phenyl group; and a naphthyl group.

3. The cyclic compound of claim 1, wherein $R_1$ and $R_2$ are the same as or different from each other, and each independently selected from the group consisting of a substituted or unsubstituted methyl group; and a substituted or unsubstituted ethyl group.

4. The cyclic compound of claim 1, wherein $R_1$ and $R_2$ are linked to each other to form a substituted or unsubstituted cyclohexyl ring.

5. A cyclic compound represented by any one of the following compounds:

Compound 1

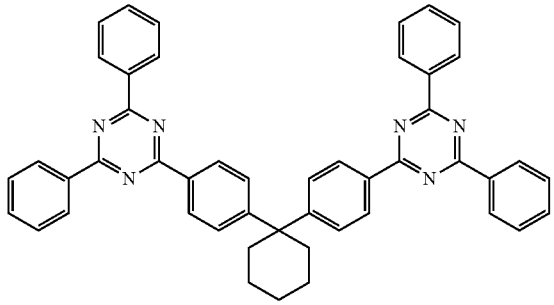

Compound 2

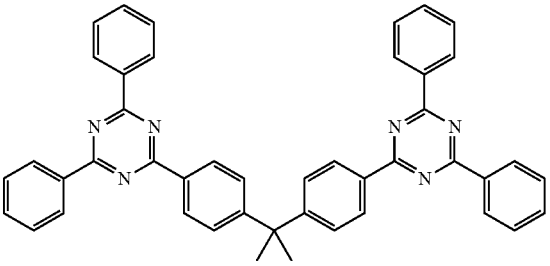

Compound 3

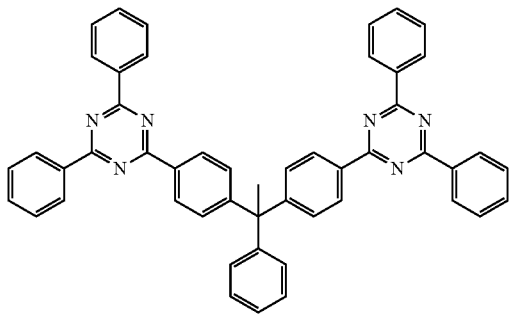

Compound 4

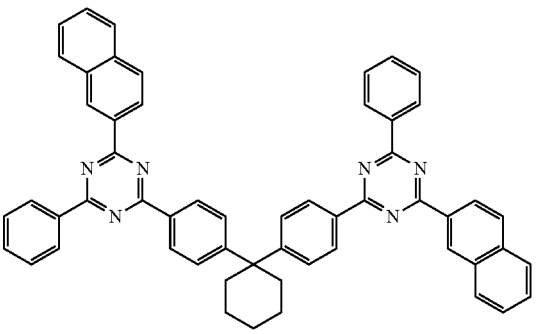

Compound 5

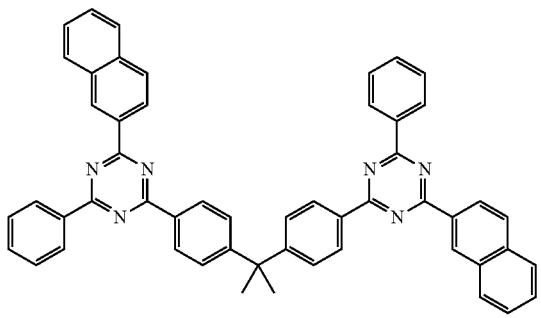

Compound 6

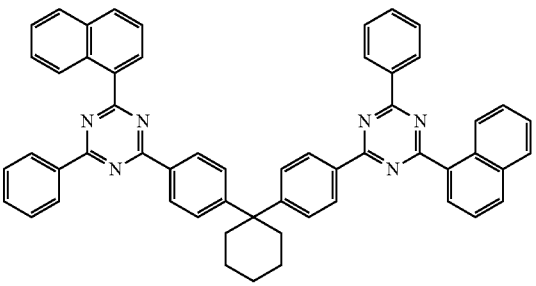

Compound 7
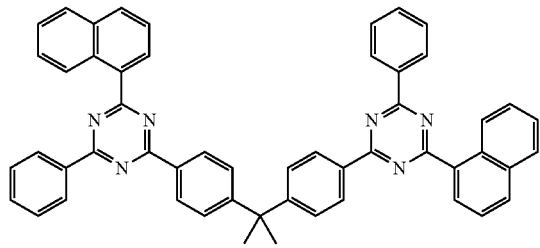
Compound 8
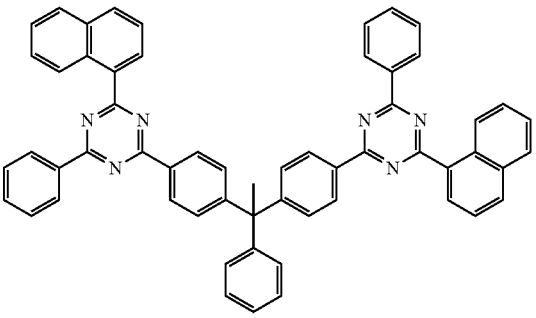
Compound 10
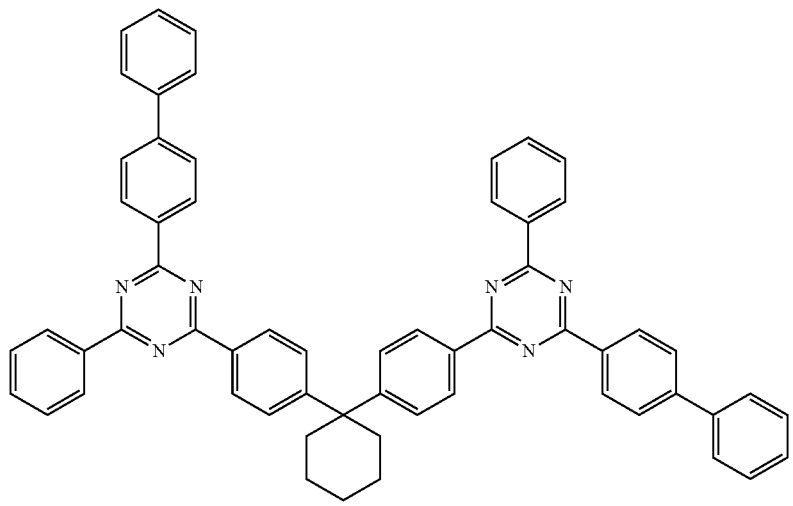
Compound 11
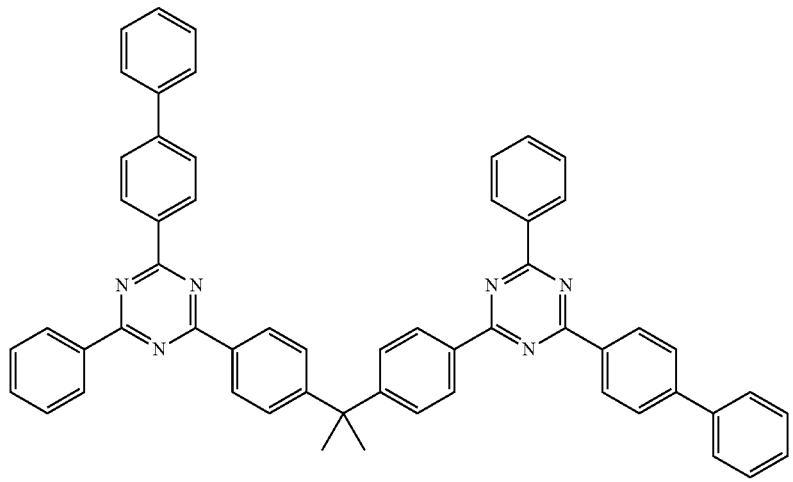

-continued
Compound 12
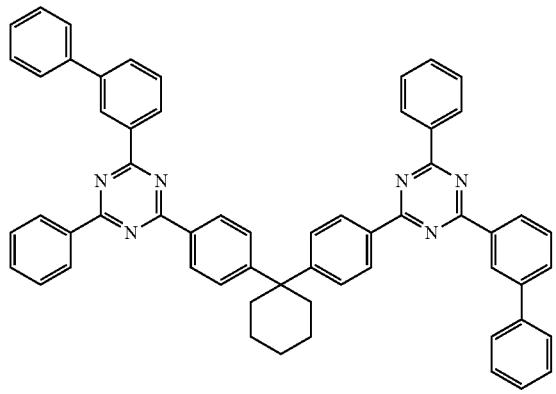
Compound 13
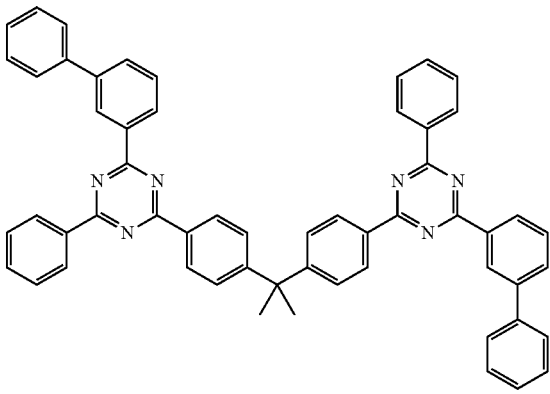
Compound 14
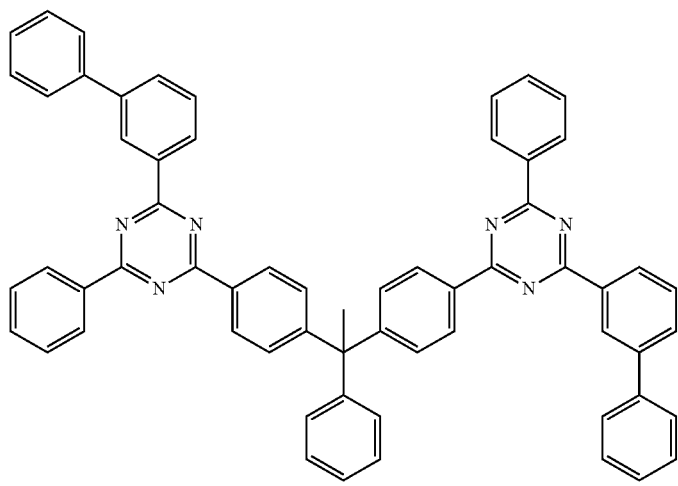
Compound 16
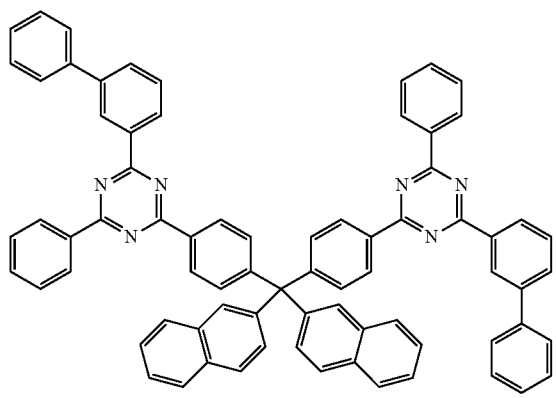
Compound 17
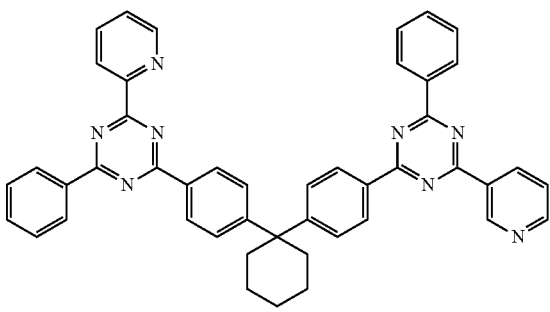

Compound 18
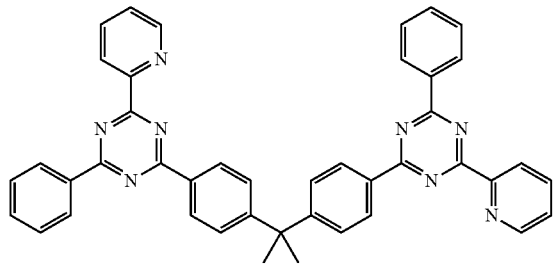
Compound 19
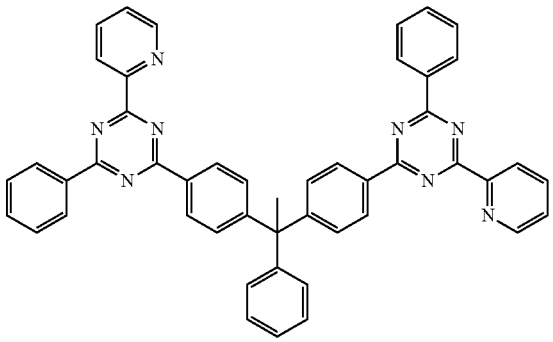
Compound 21
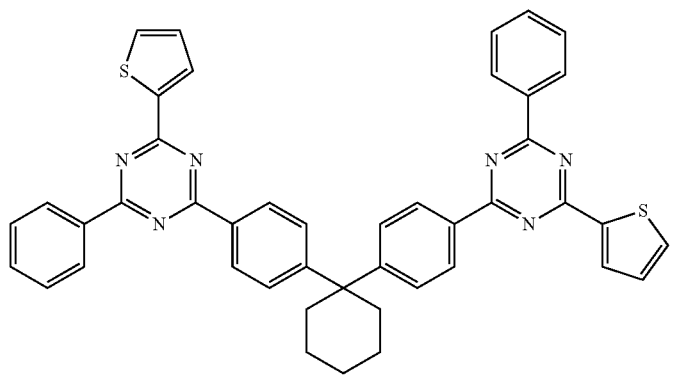
Compound 22
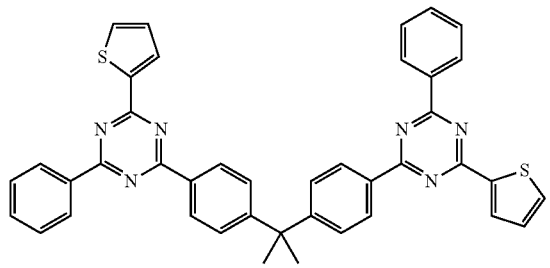
Compound 23
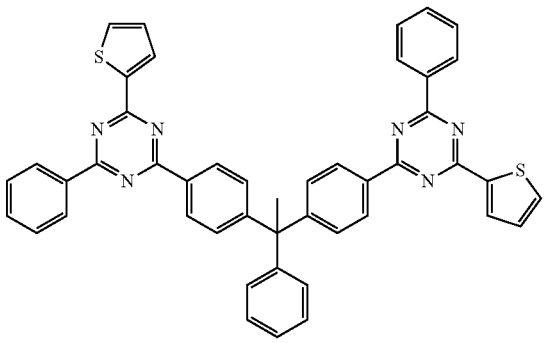
Compound 24
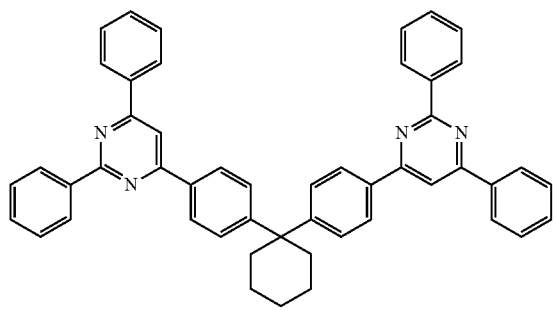
Compound 25
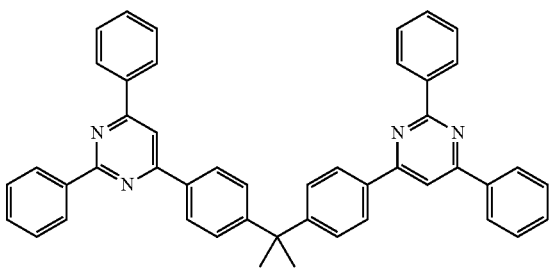

-continued
Compound 26
Compound 27
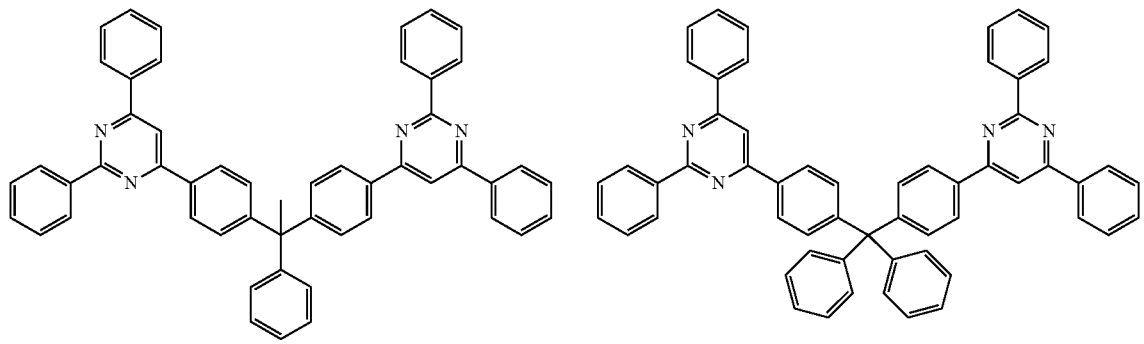
Compound 28
Compound 29
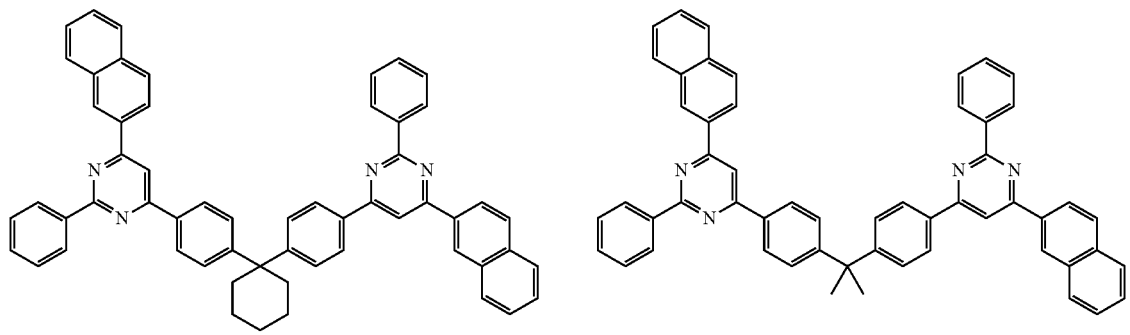
Compound 30
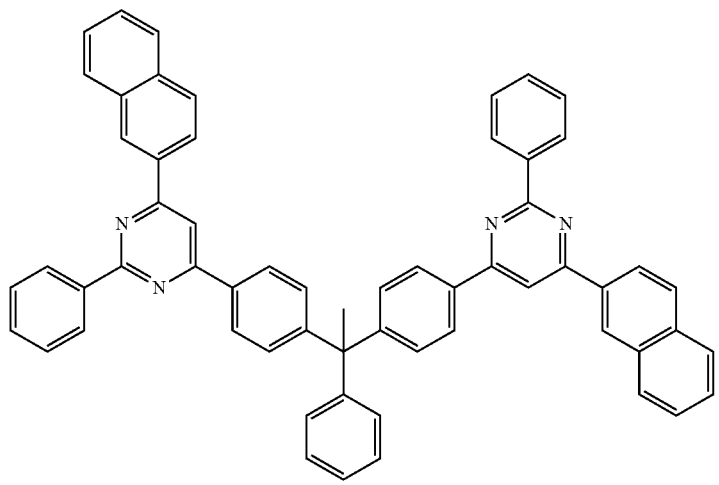
Compound 32
Compound 33
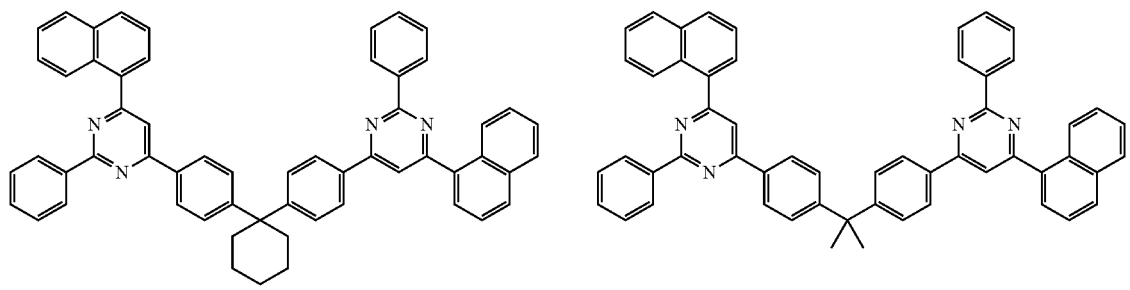

-continued
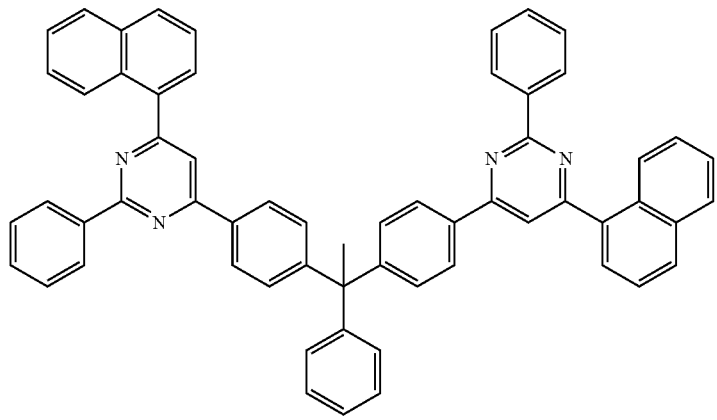
Compound 34
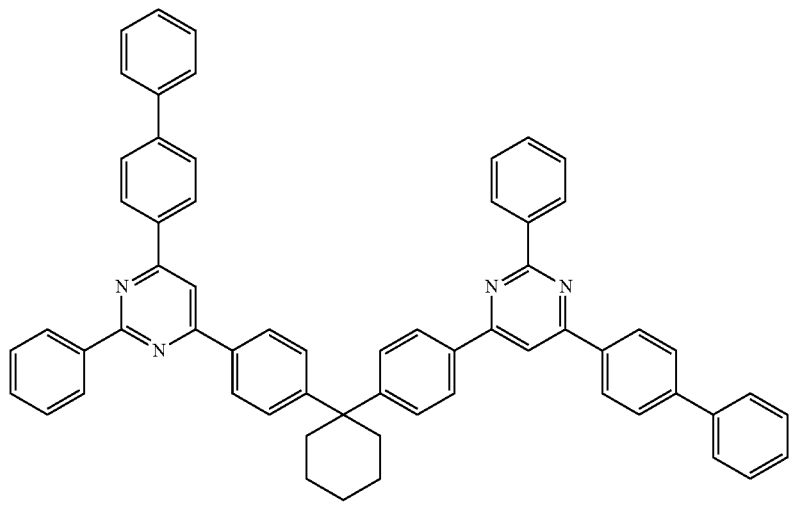
Compound 35
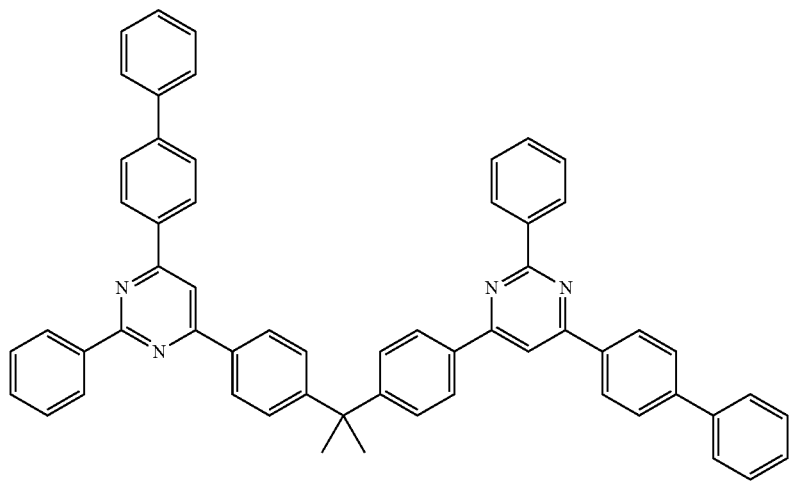
Compound 36

-continued
Compound 37
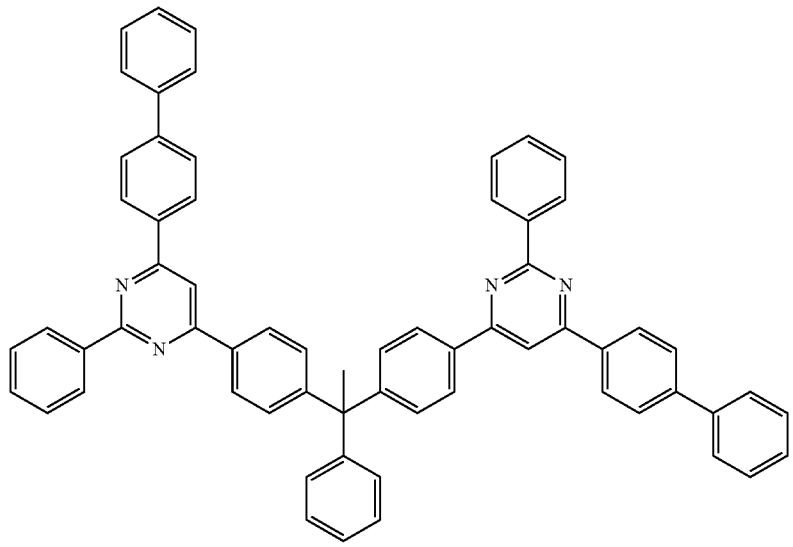
Compound 38
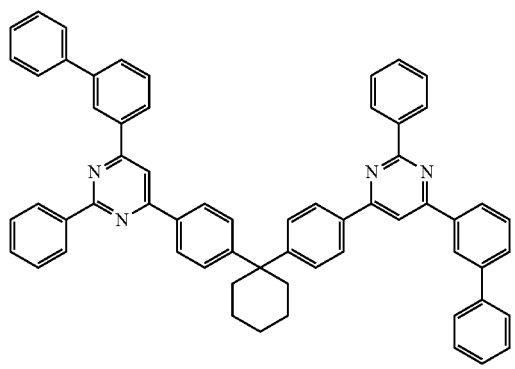
Compound 39
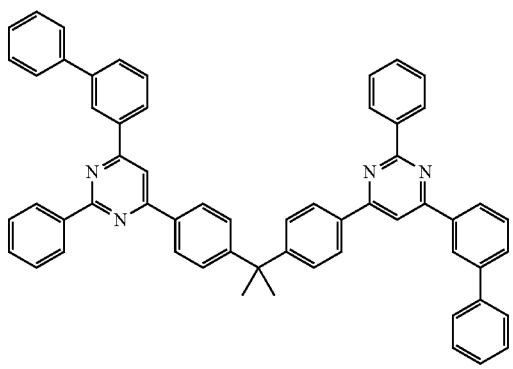
Compound 40
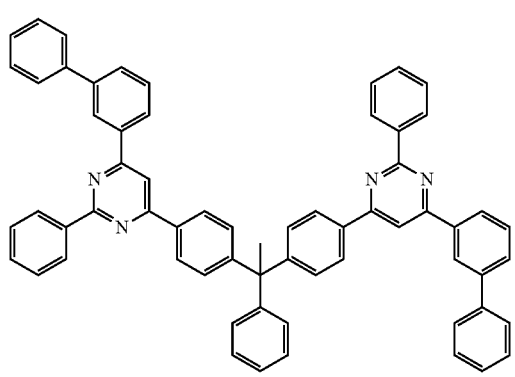
Compound 41
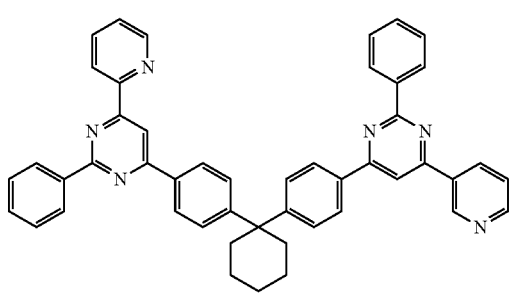
Compound 42
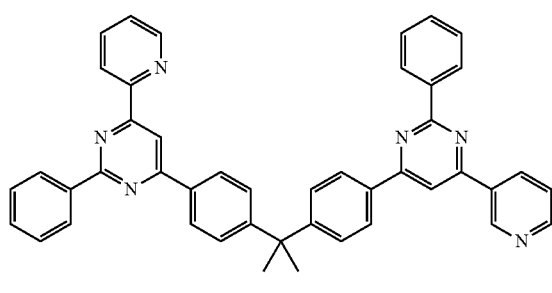
Compound 43
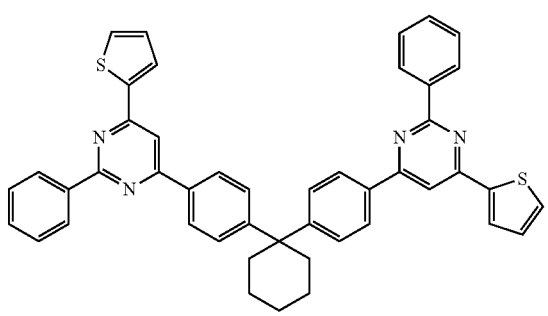

-continued
Compound 44
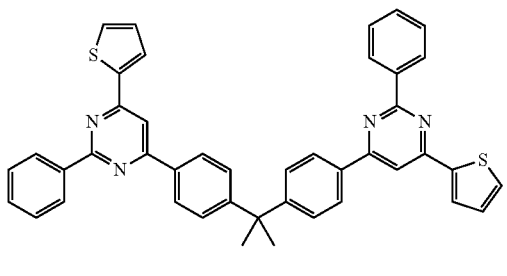
Compound 45
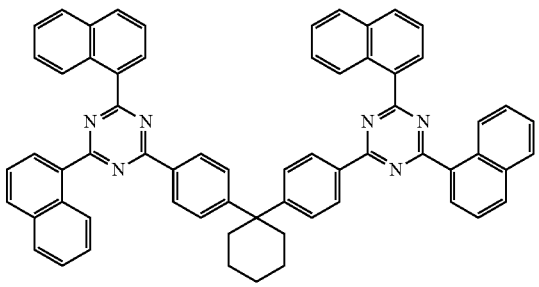
Compound 46
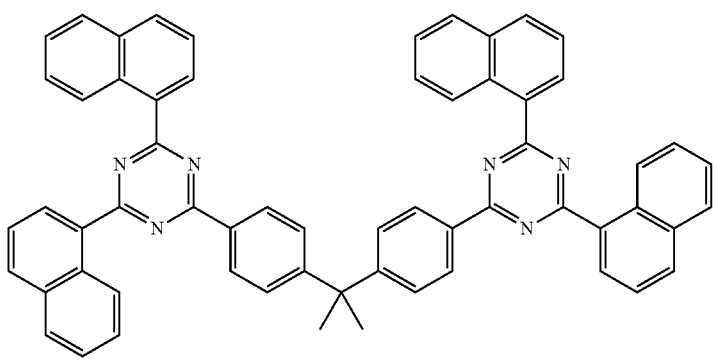
Compound 47
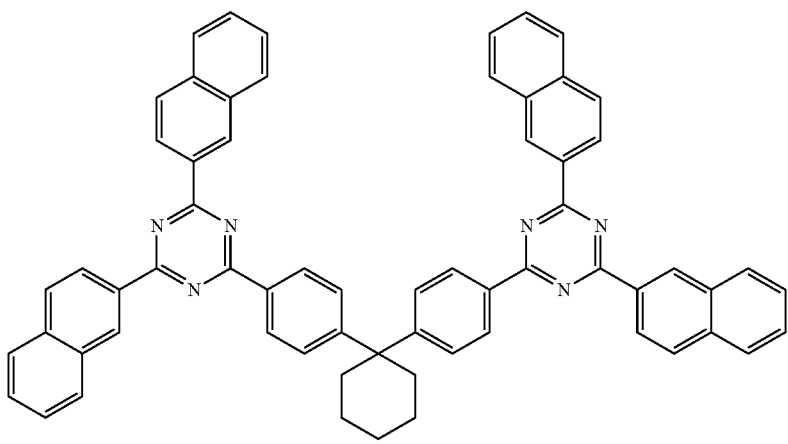
Compound 48
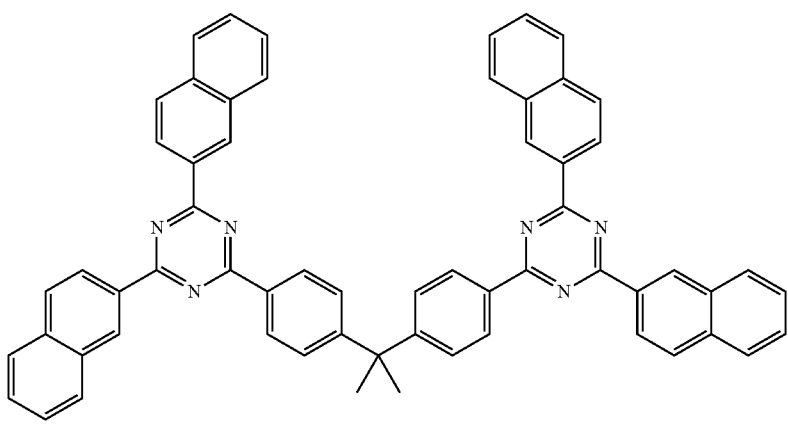

Compound 49
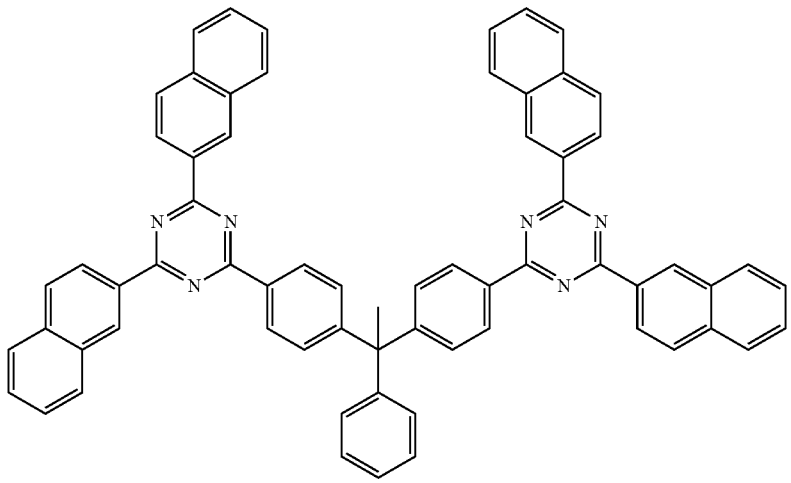
Compound 50
Compound 51
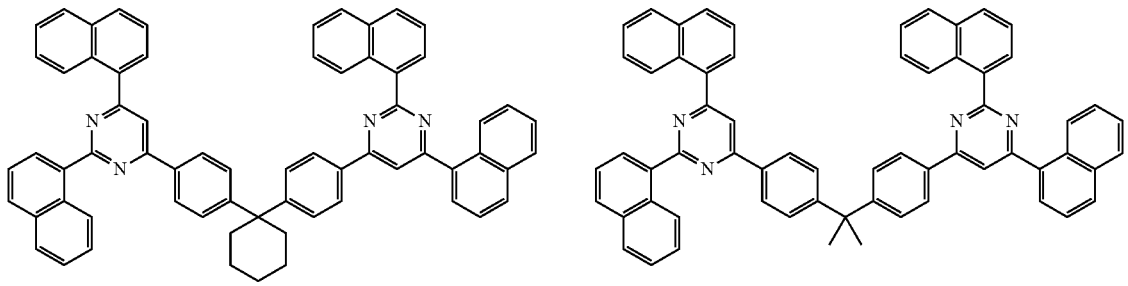
Compound 52
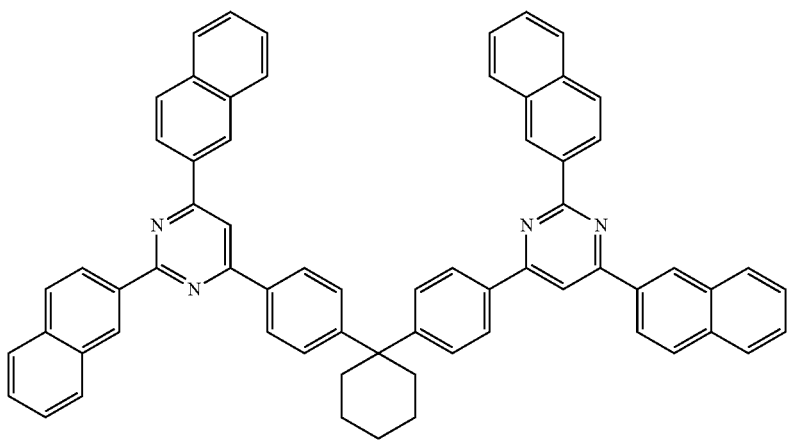
Compound 53
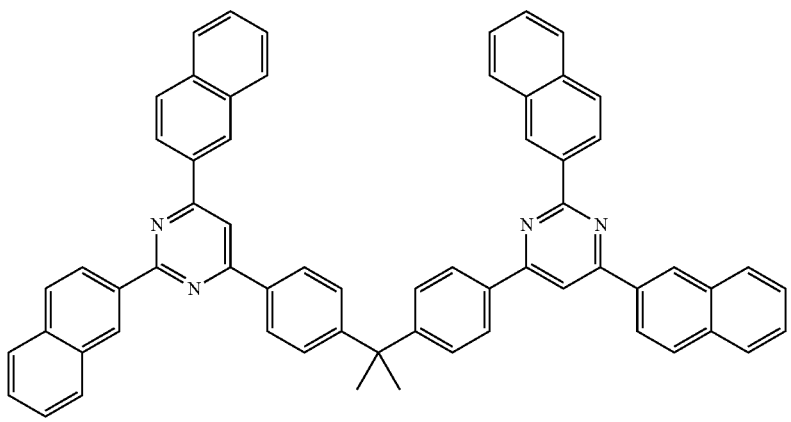

-continued
Compound 54
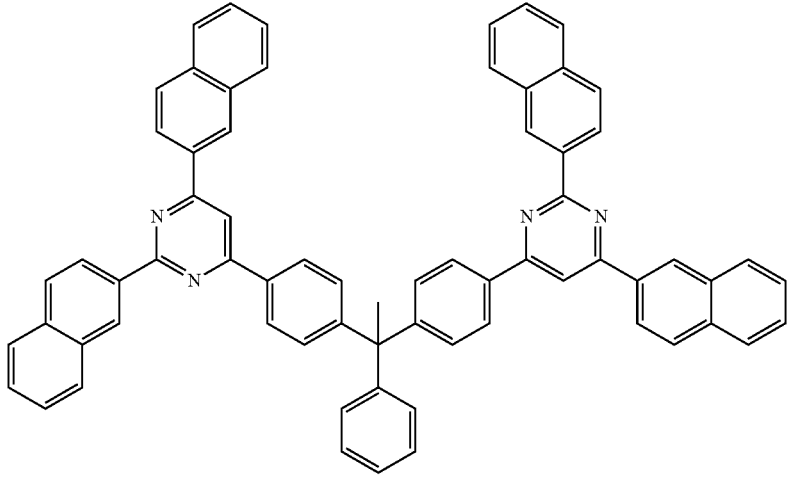
Compound 55 | Compound 56
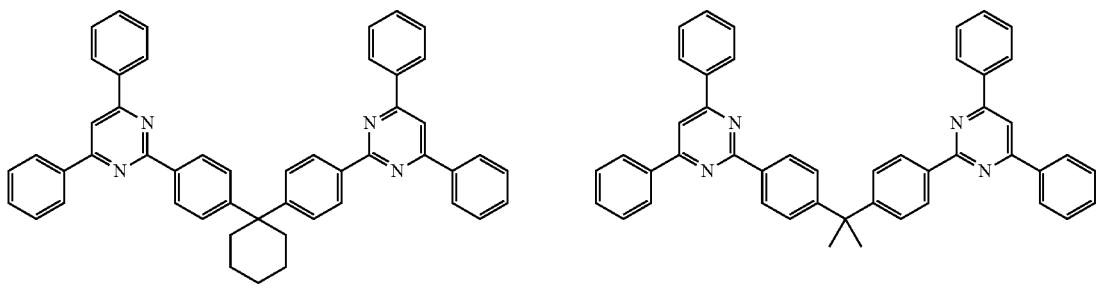
Compound 57 | Compound 58
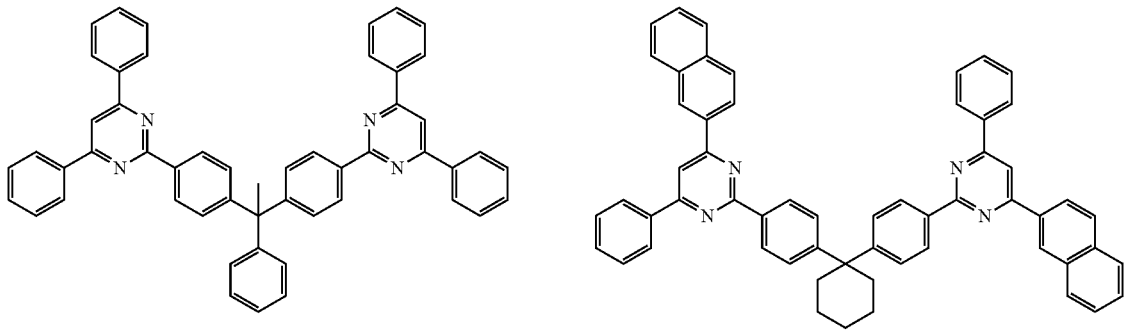
Compound 59 | Compound 60
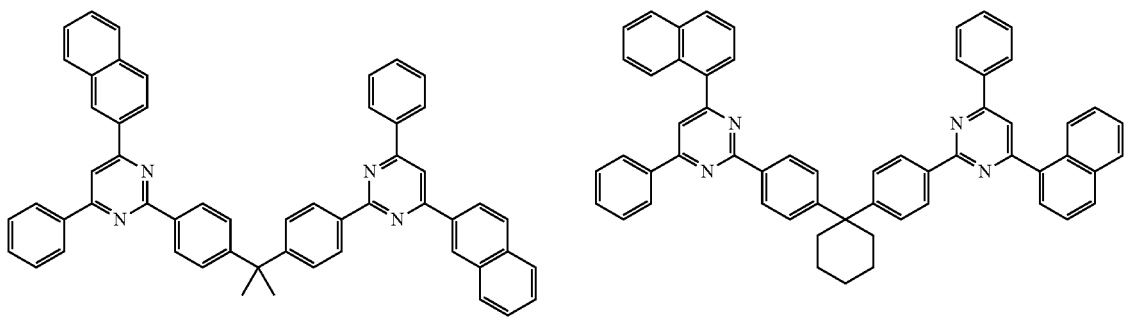

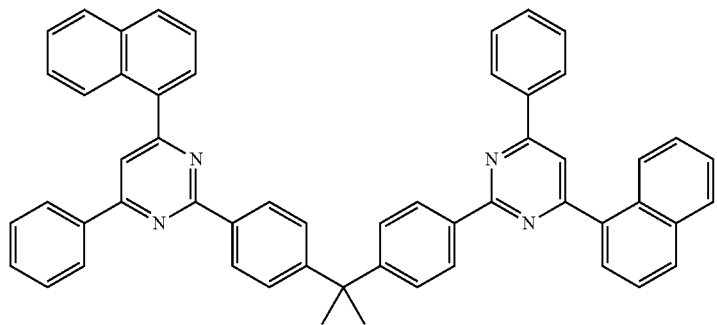
Compound 61
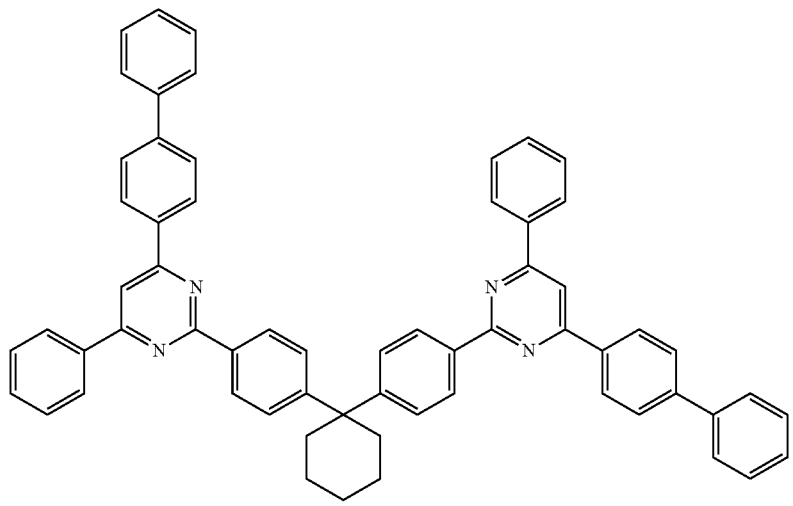
Compound 62
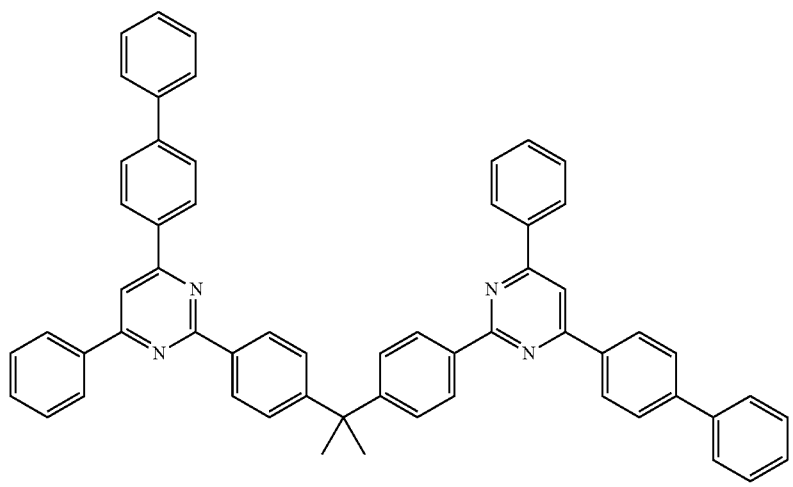
Compound 63

-continued
Compound 64
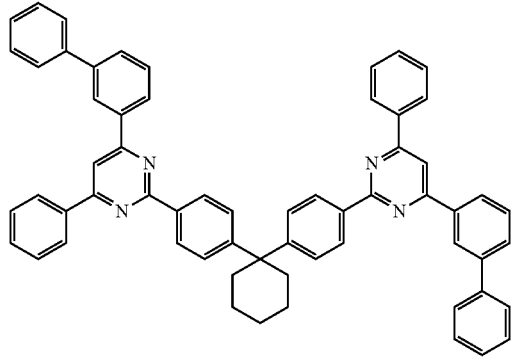
Compound 65
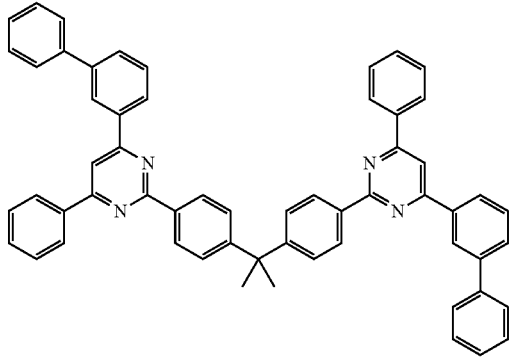
Compound 66
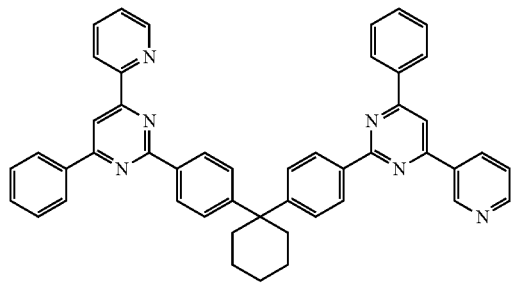
Compound 67
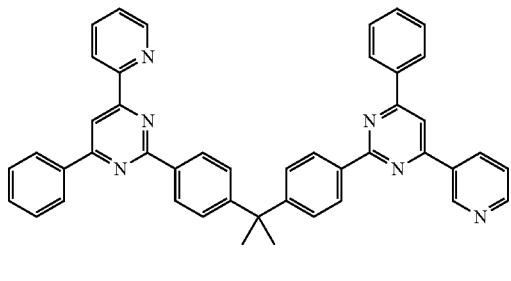
Compound 68
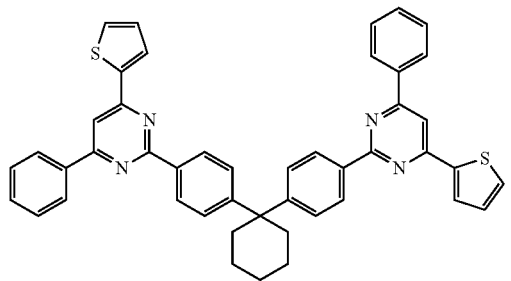
Compound 69
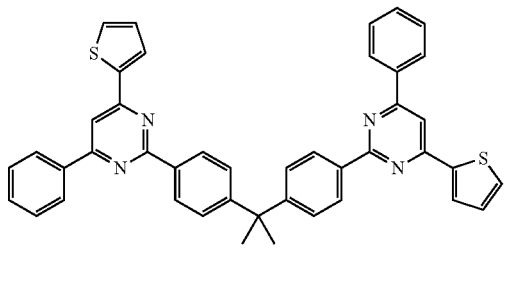
Compound 70
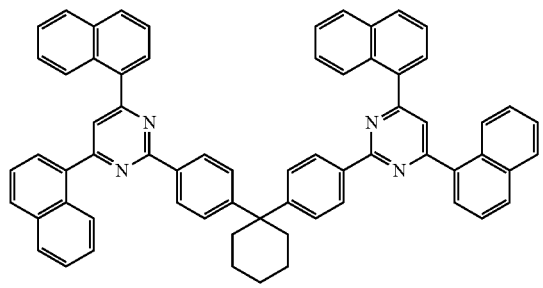
Compound 71
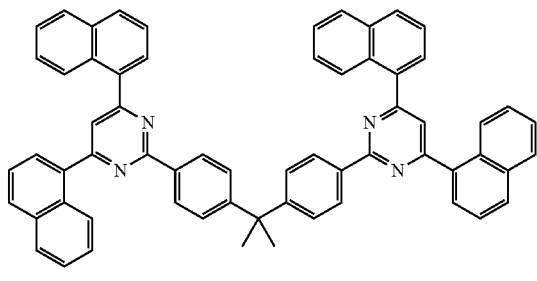

Compound 72
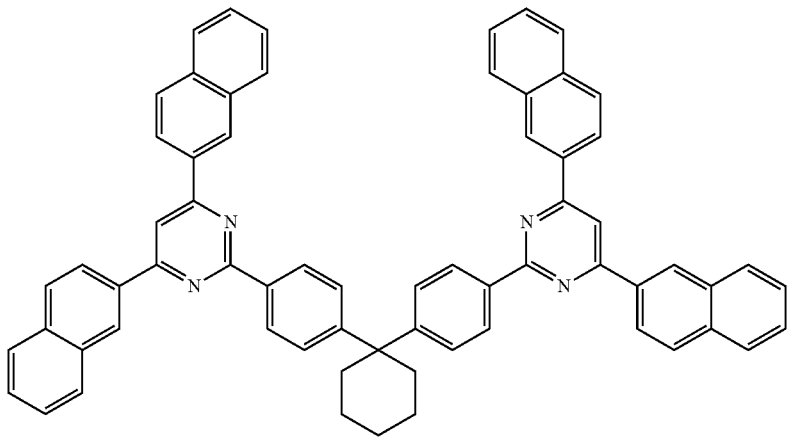
Compound 73
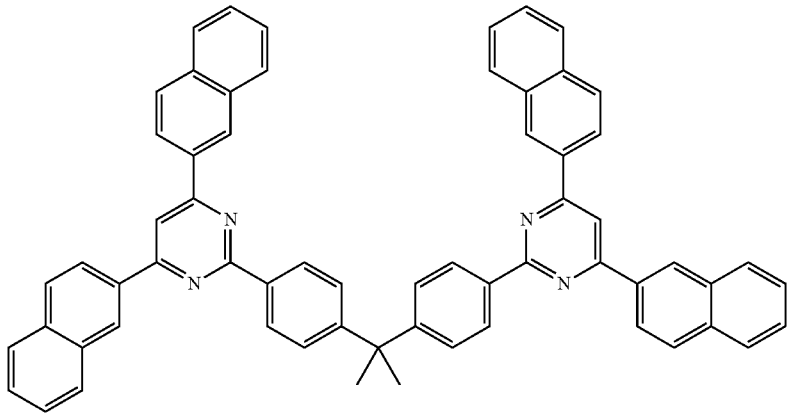
Compound 74
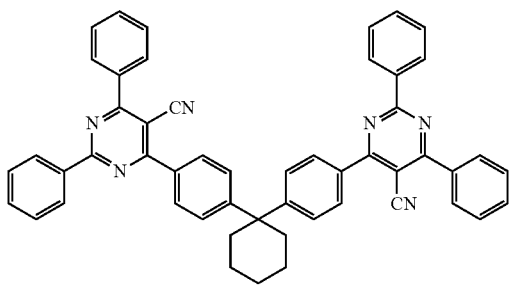
Compound 75
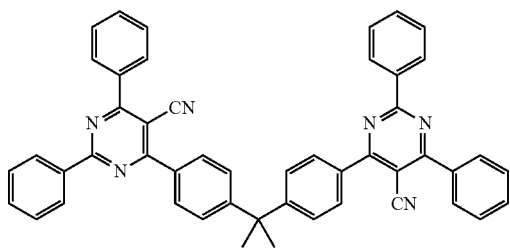
Compound 76
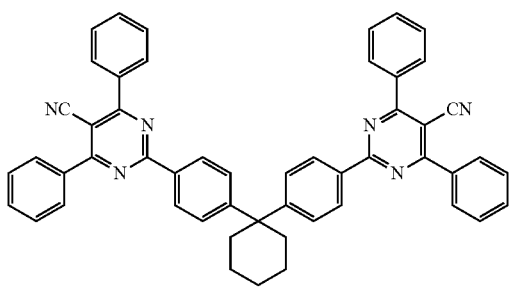
Compound 77
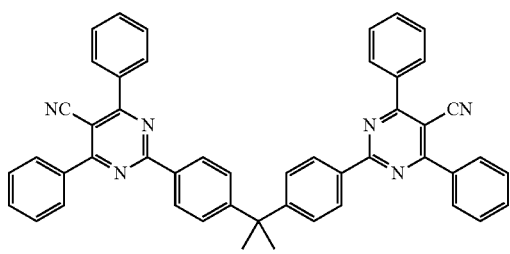

-continued
Compound 78
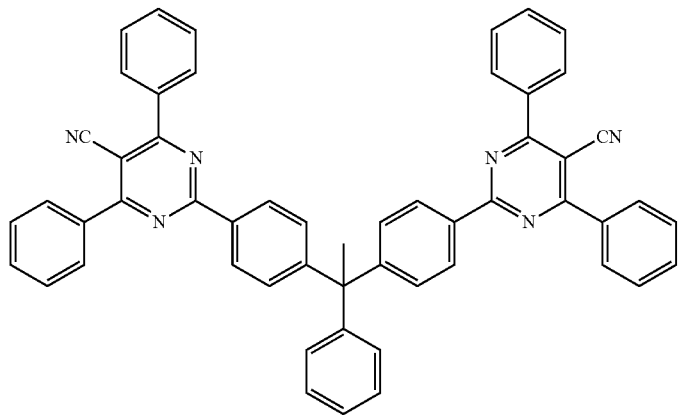
Compound 97
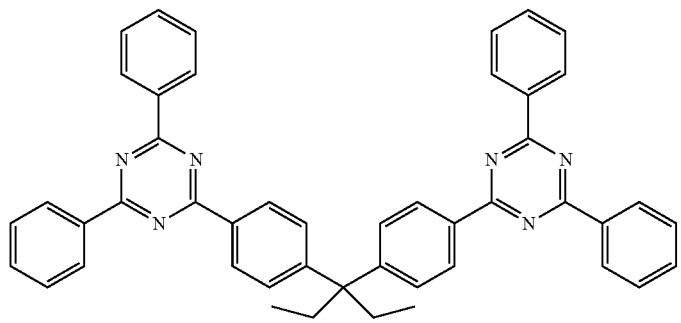
Compound 98
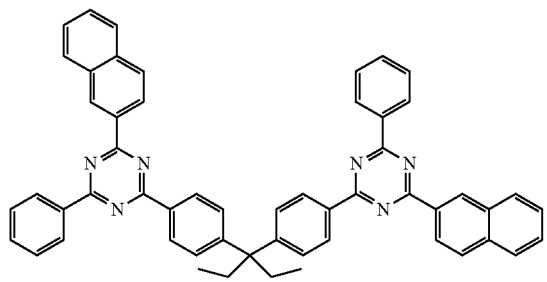
Compound 99
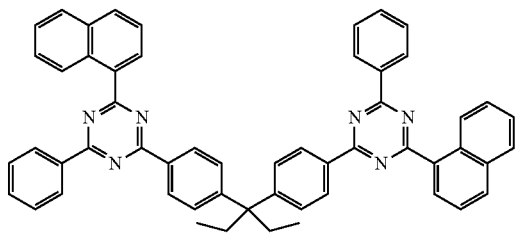
Compound 100
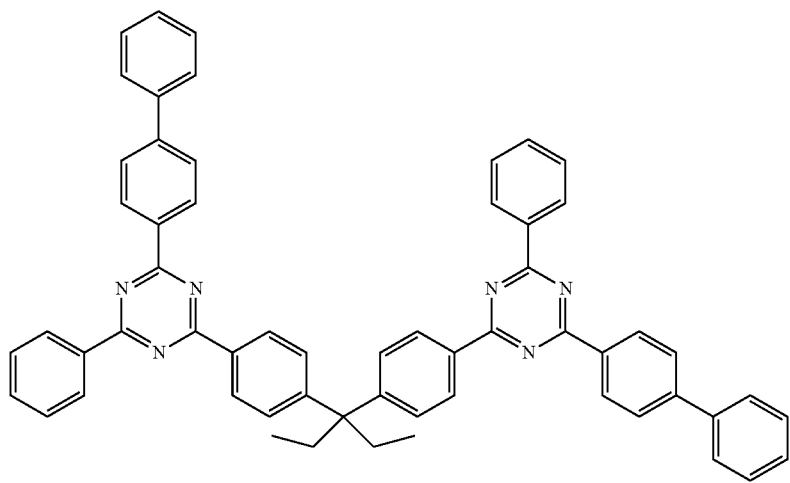

Compound 101
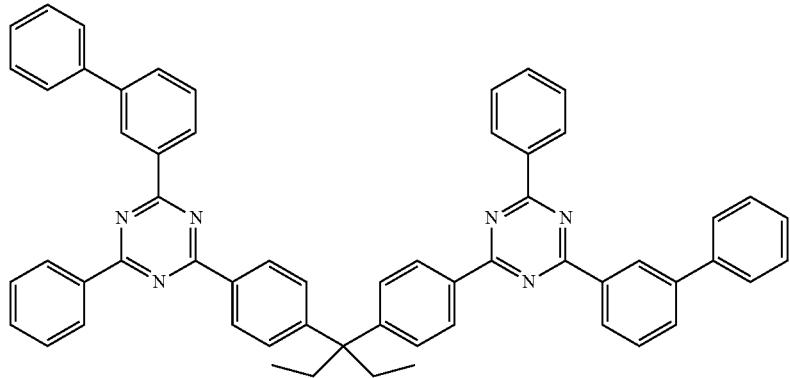
Compound 102
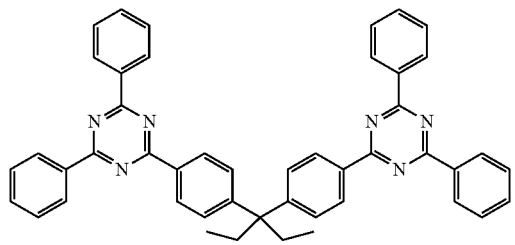
Compound 103
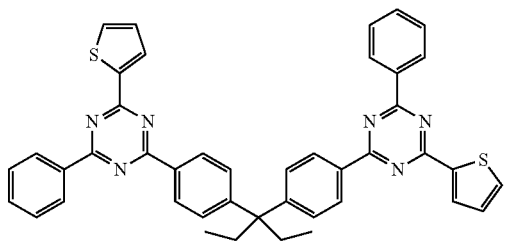
Compound 104
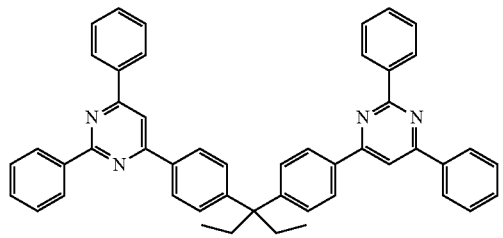
Compound 105
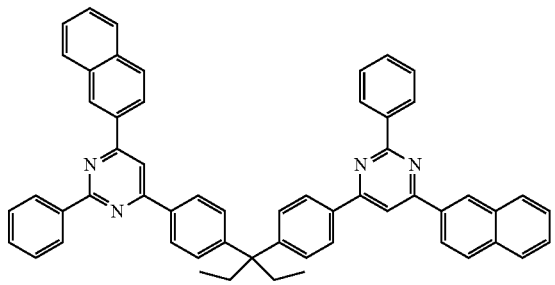
Compound 106
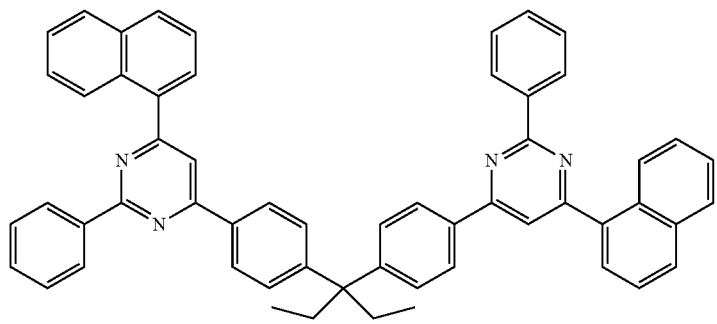

-continued
Compound 107
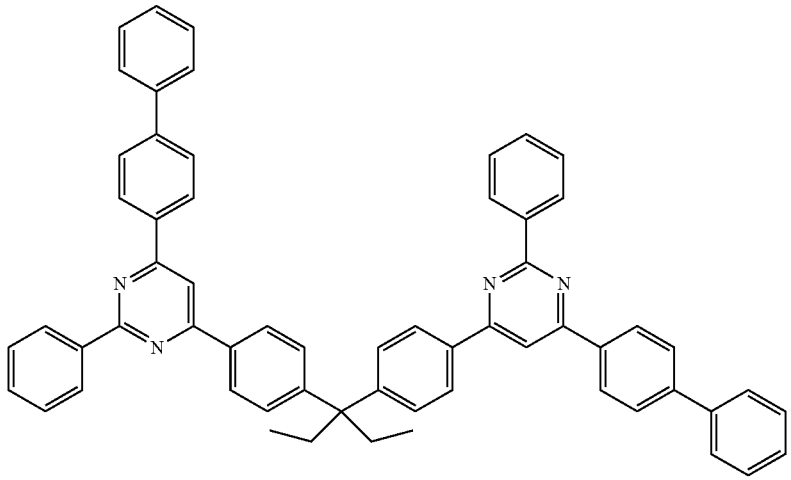
Compound 108
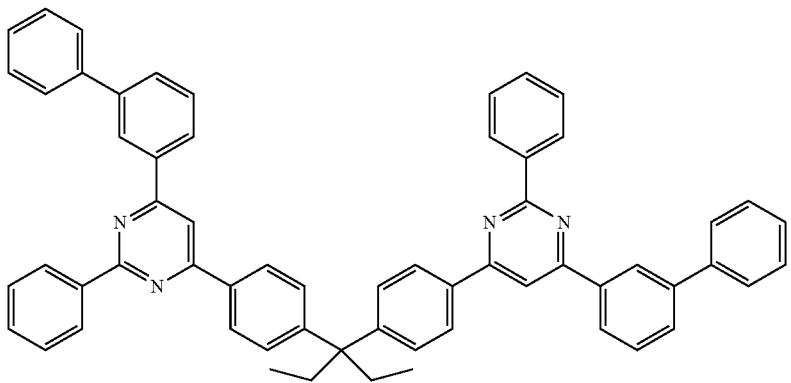
Compound 109
Compound 110
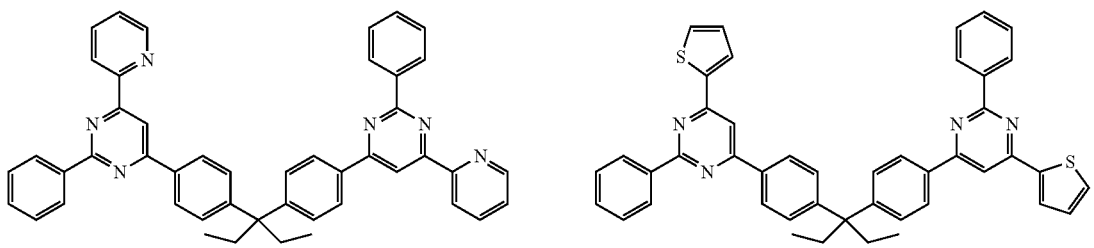
Compound 111
Compound 112
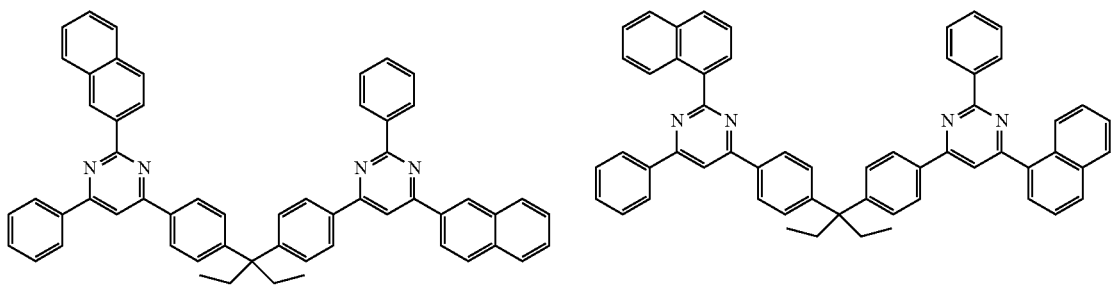

Compound 113
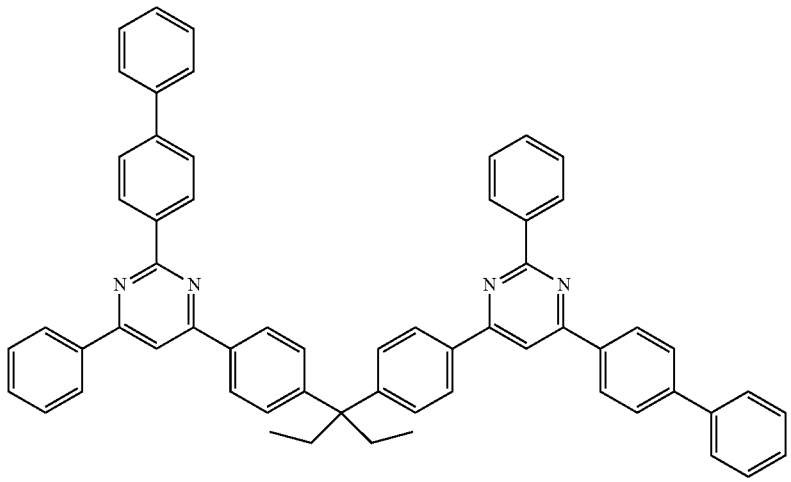
Compound 114
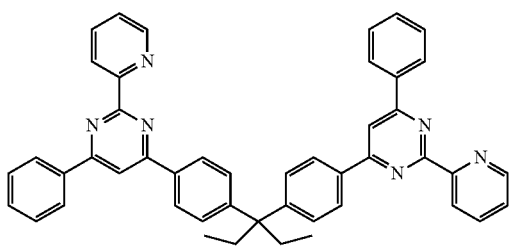
Compound 115
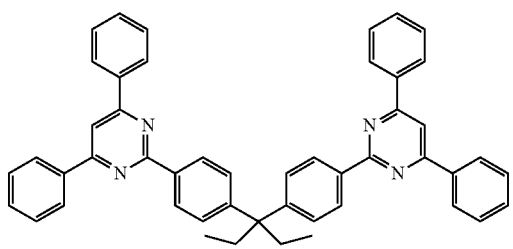
Compound 116
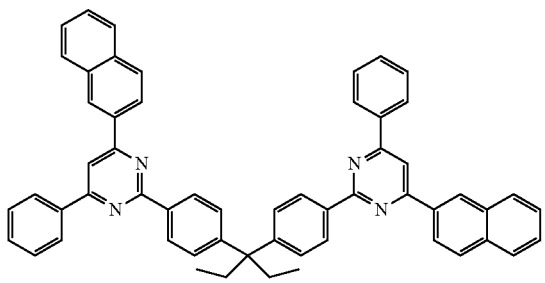
Compound 117
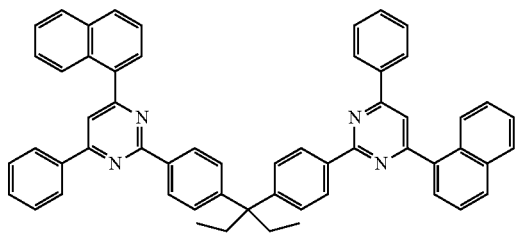
Compound 118
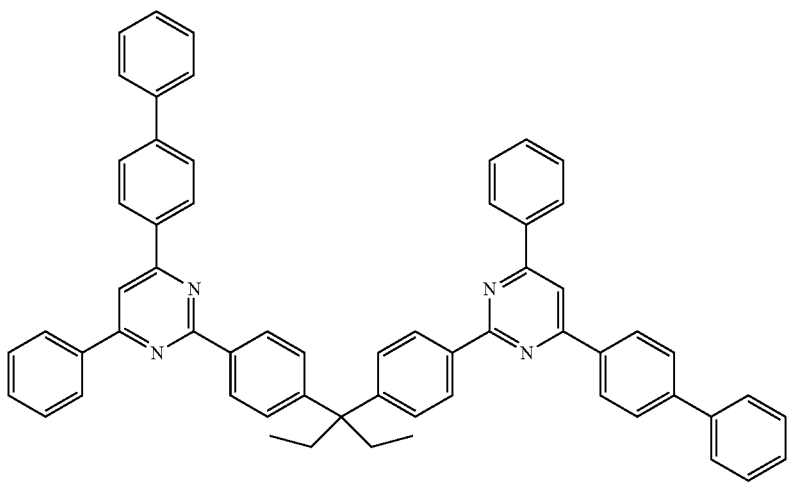

Compound 119
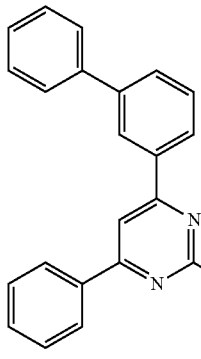 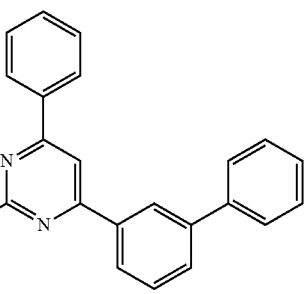
Compound 120
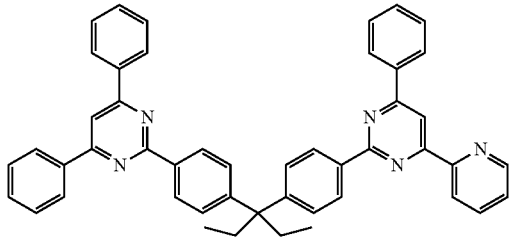
Compound 121
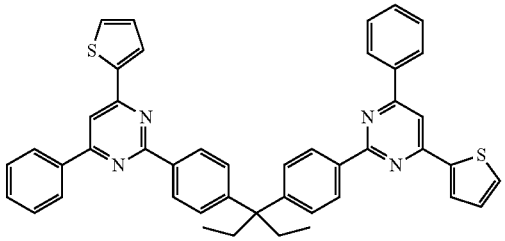
Compound 122
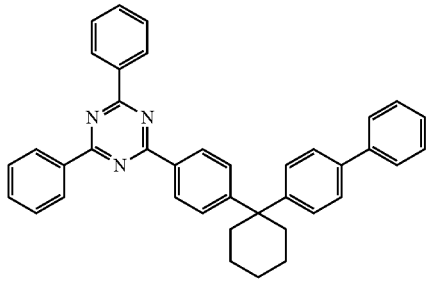
Compound 123
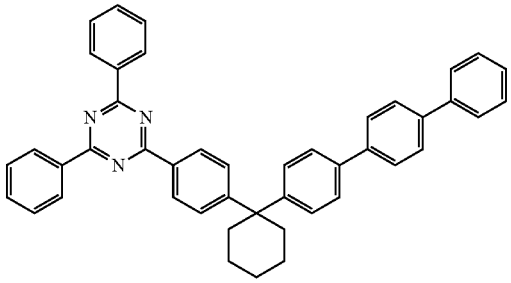
Compound 124
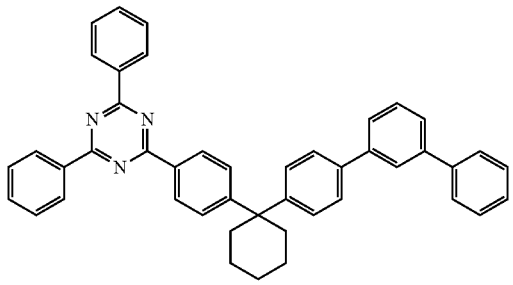
Compound 125
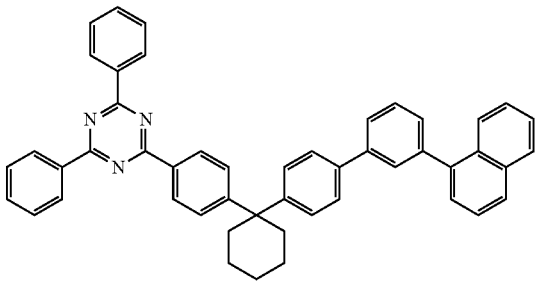
Compound 126
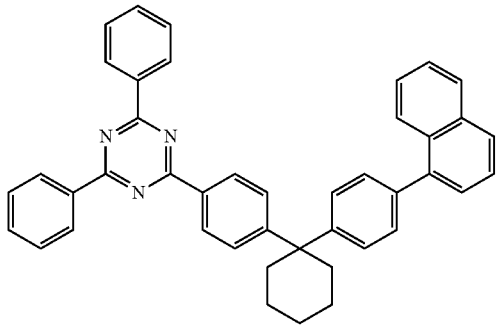
Compound 127
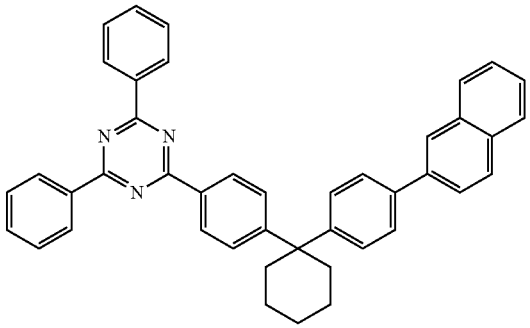

Compound 128
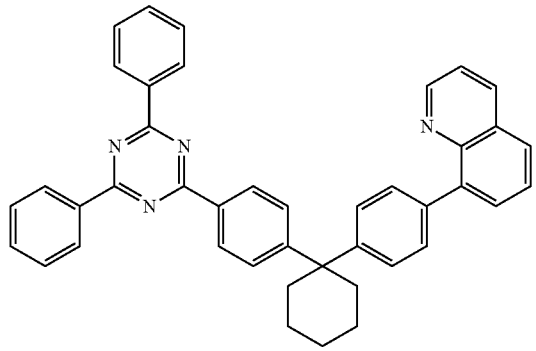
Compound 129
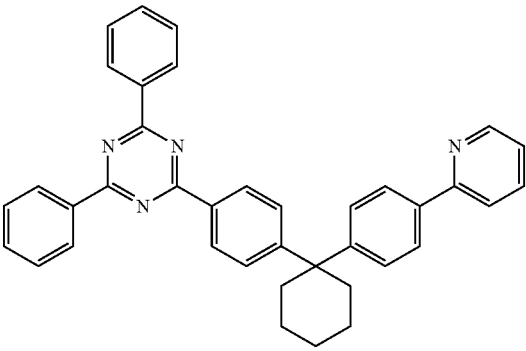
Compound 130
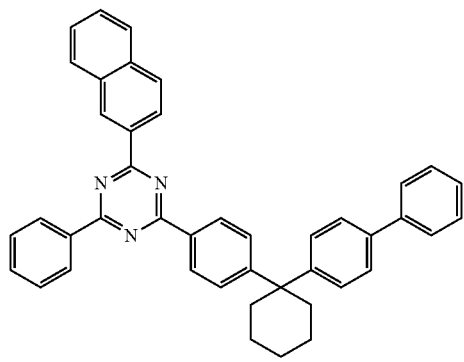
Compound 131
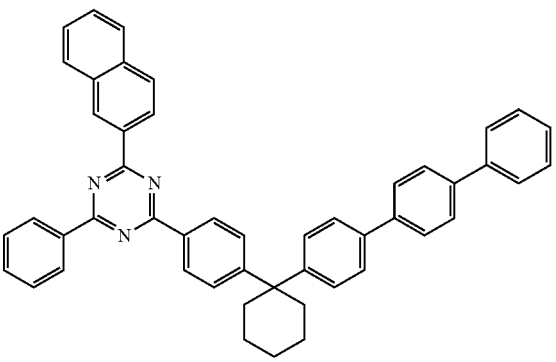
Compound 132
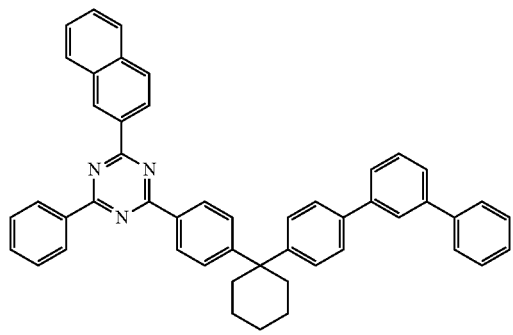
Compound 133
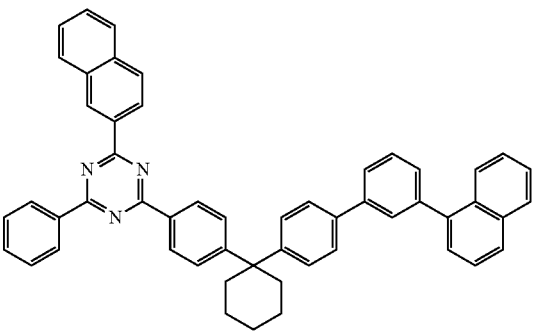
Compound 134
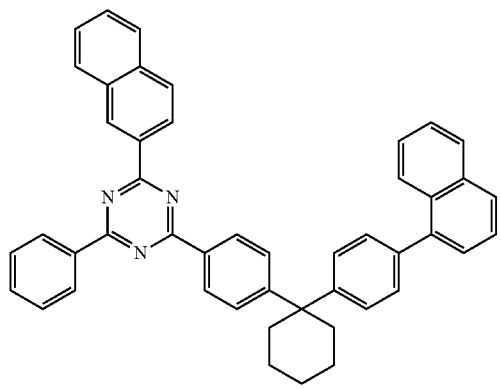
Compound 135
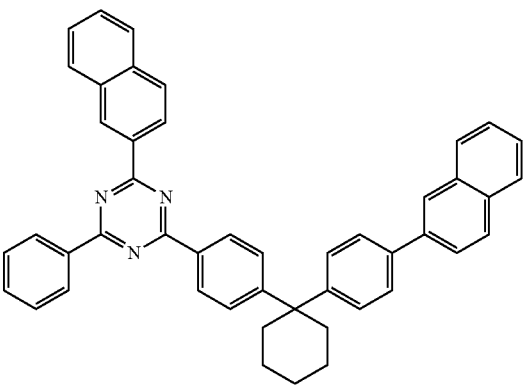

-continued
Compound 136
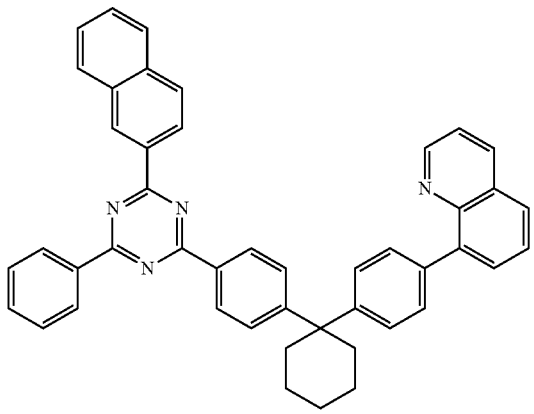
Compound 137
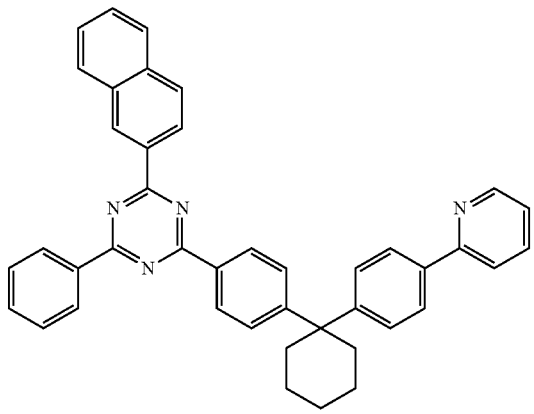
Compound 138
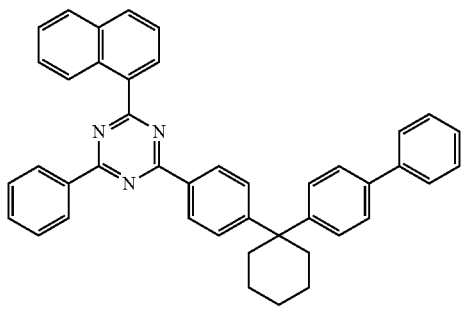
Compound 139
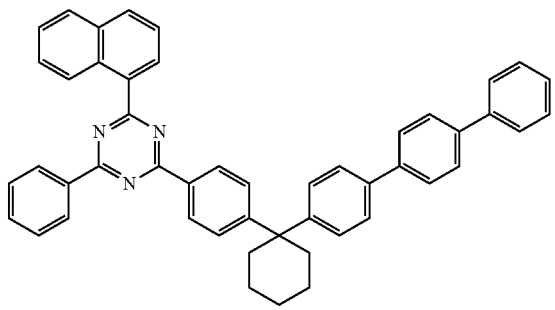
Compound 140
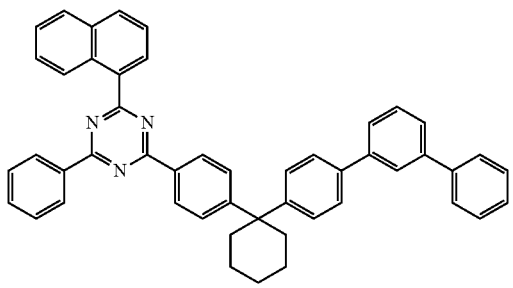
Compound 141
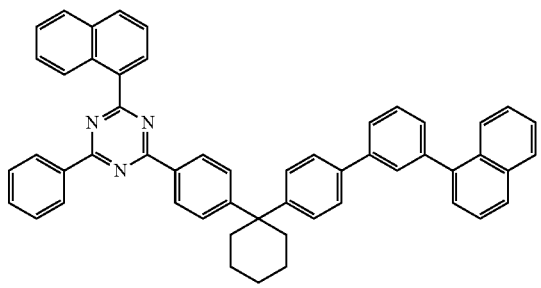
Compound 142
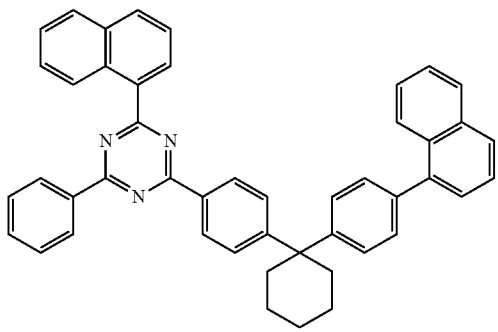
Compound 143
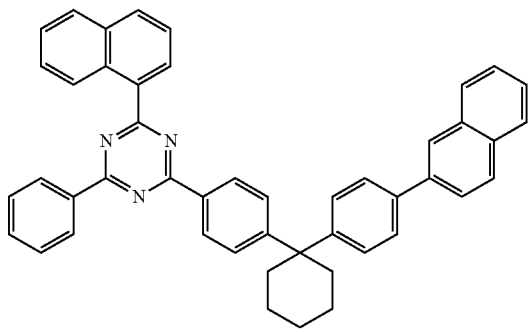

-continued
Compound 144
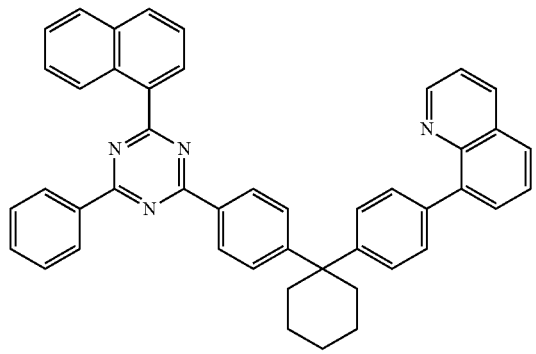
Compound 145
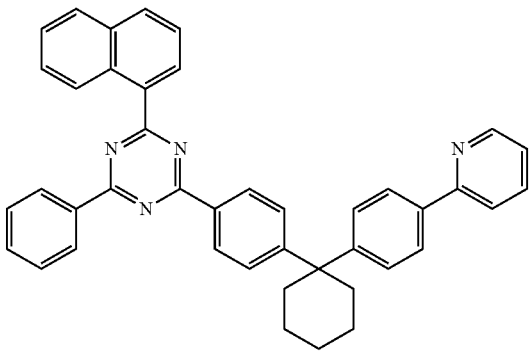
Compound 146
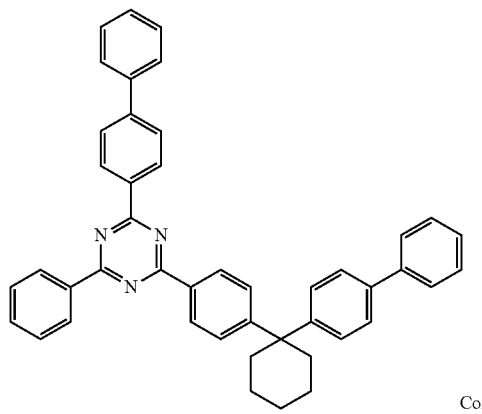
Compound 147
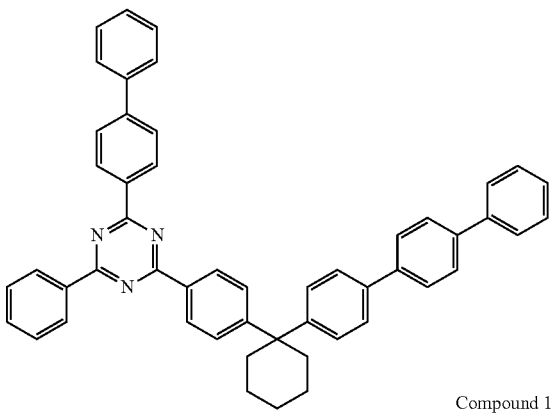
Compound 148
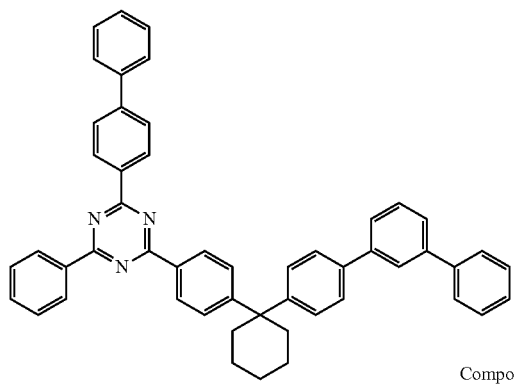
Compound 149
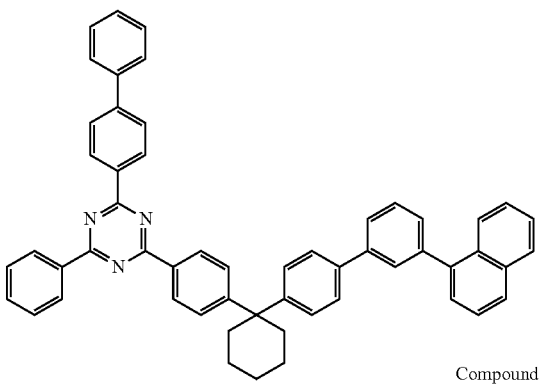
Compound 150
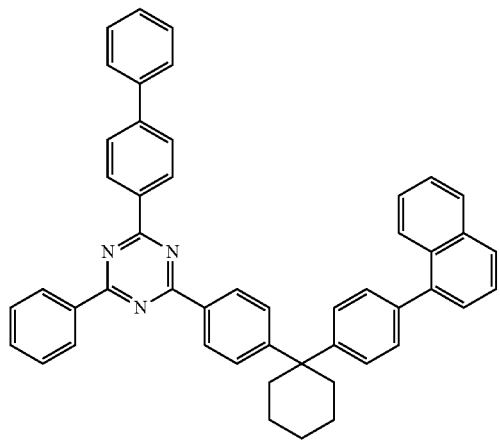
Compound 151
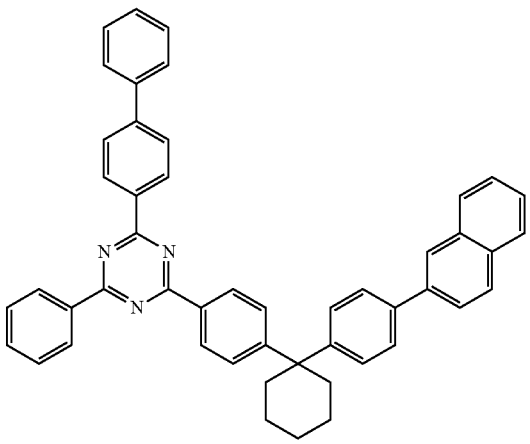

-continued
Compound 152
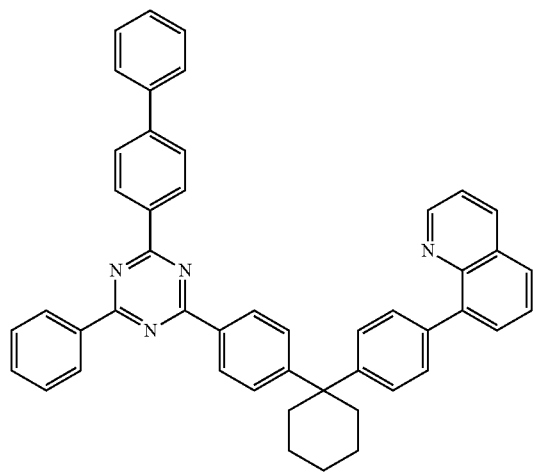
Compound 153
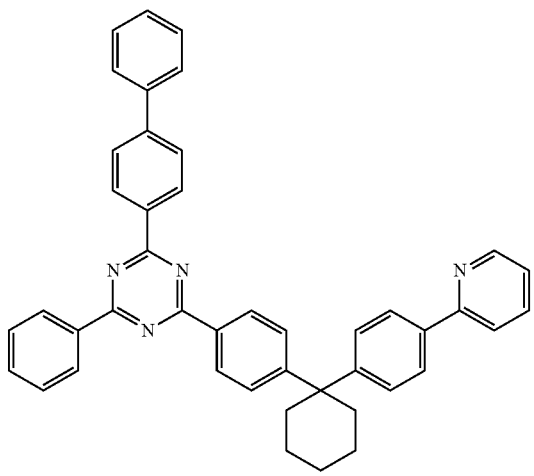
Compound 154
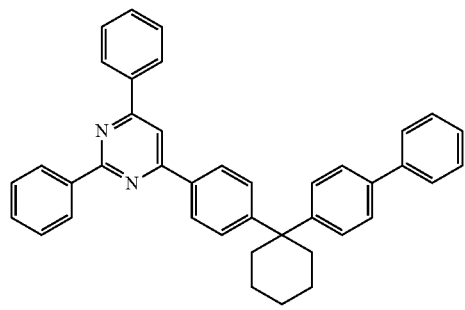
Compound 155
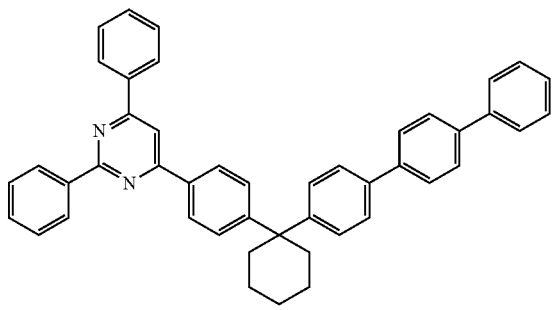
Compound 156
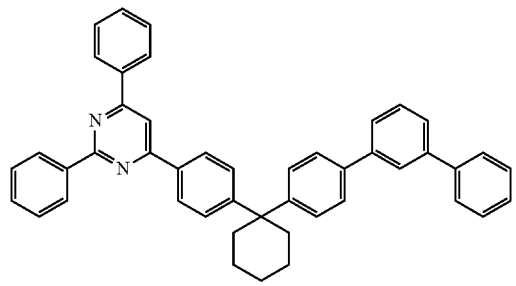
Compound 157
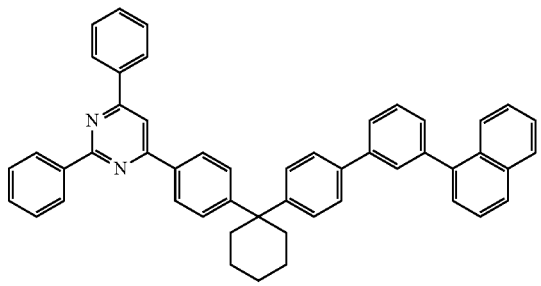
Compound 158
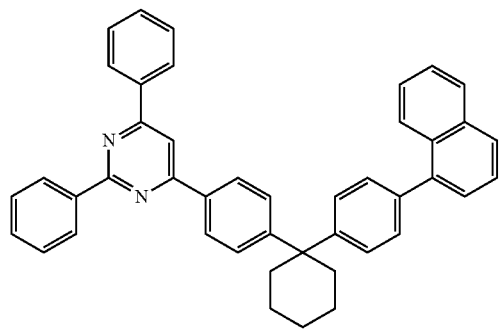
Compound 159
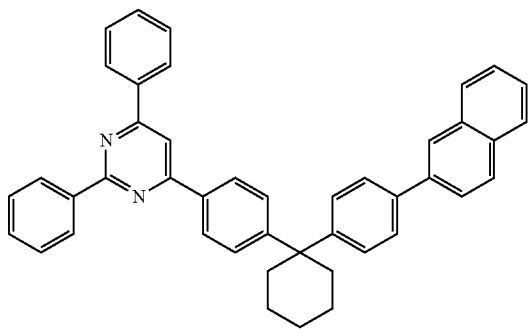

-continued
Compound 160
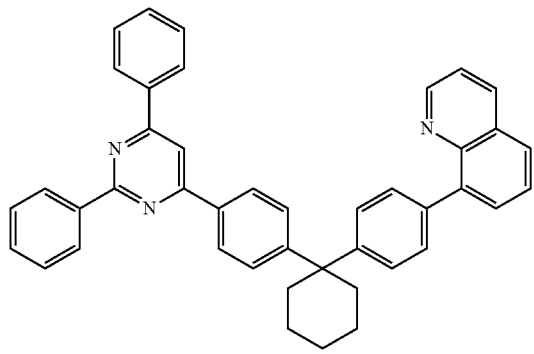
Compound 161
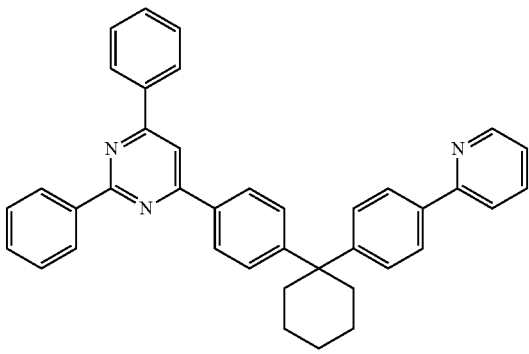
Compound 162
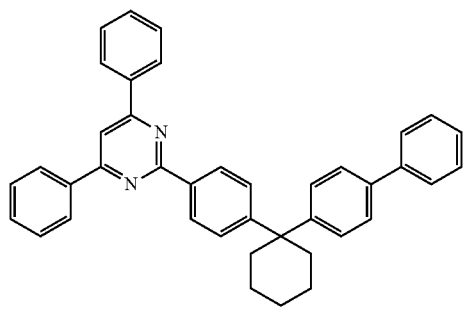
Compound 163
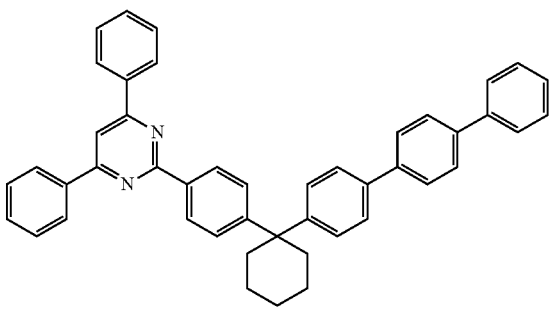
Compound 164
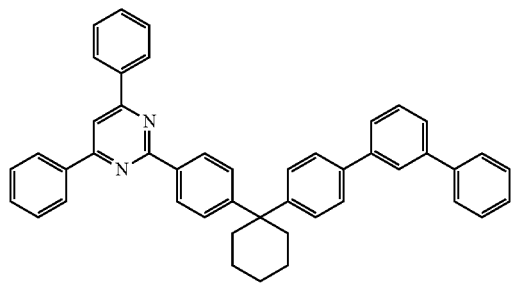
Compound 165
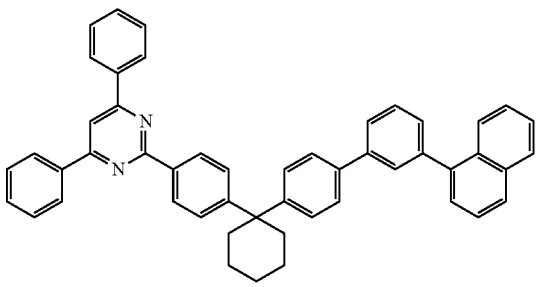
Compound 166
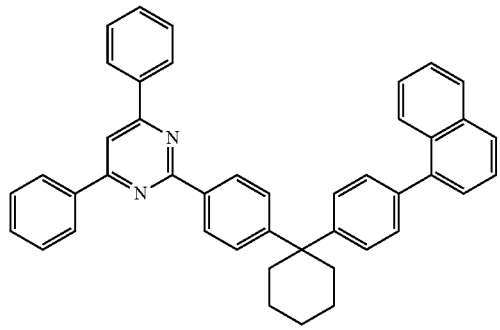
Compound 167
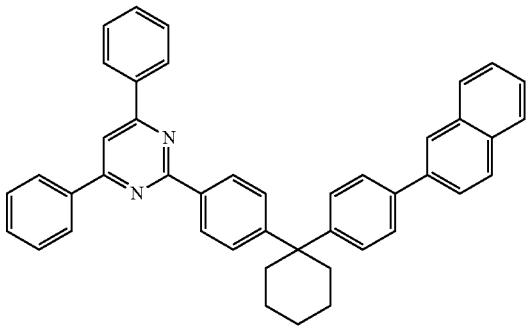

-continued
Compound 168
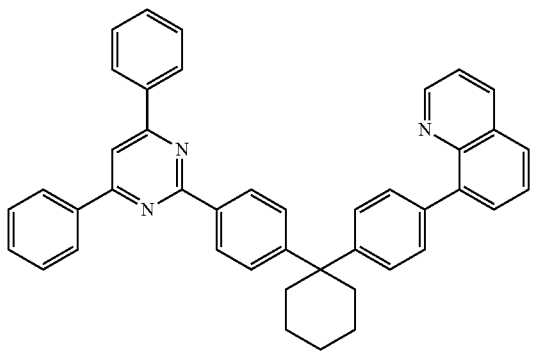
Compound 169
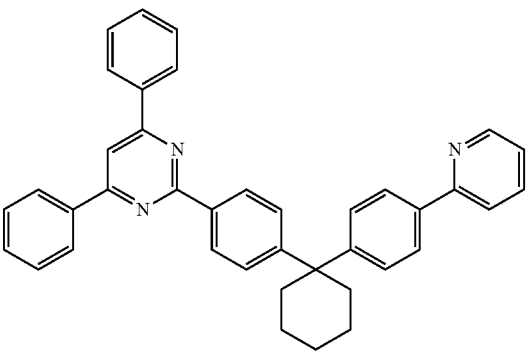
Compound 170
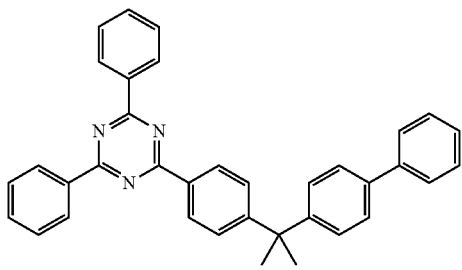
Compound 171
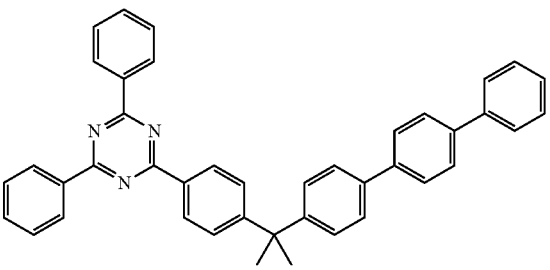
Compound 172
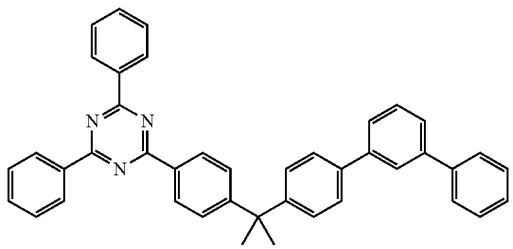
Compound 173
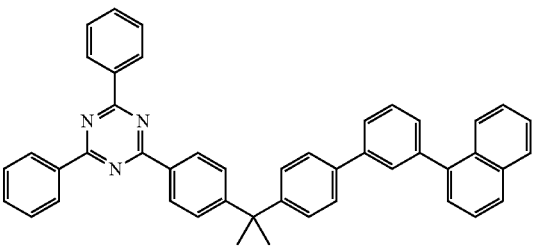
Compound 174
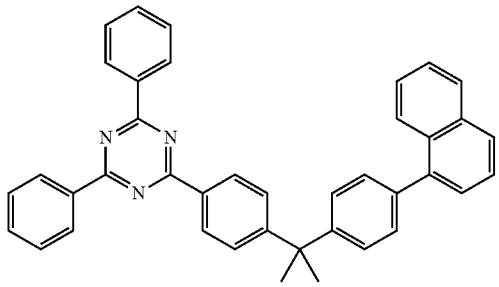
Compound 175
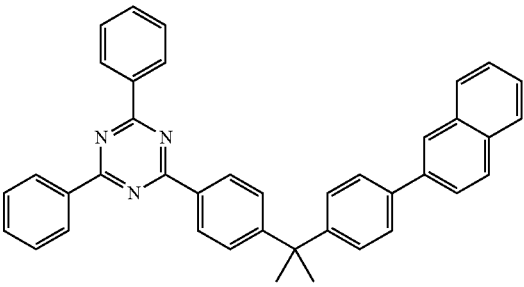
Compound 176
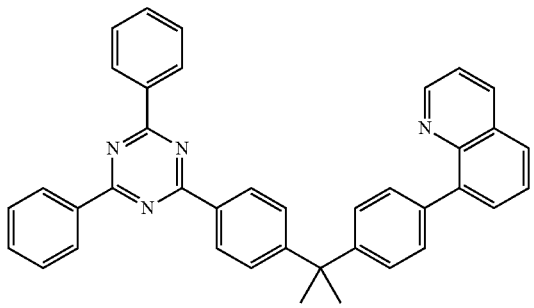
Compound 177
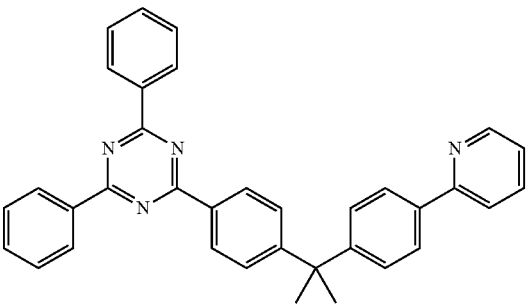

Compound 178
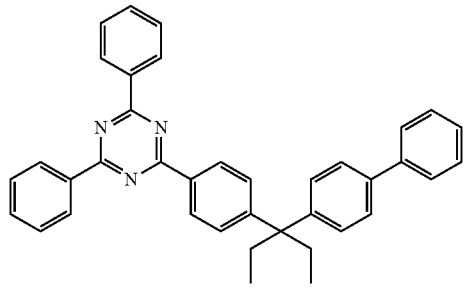
Compound 179
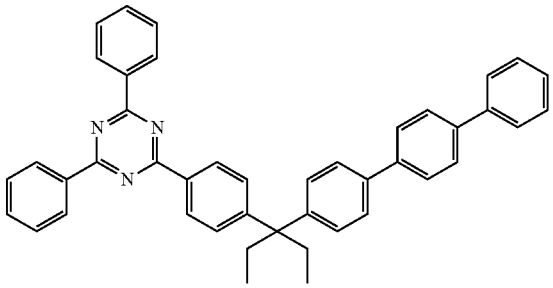
Compound 180
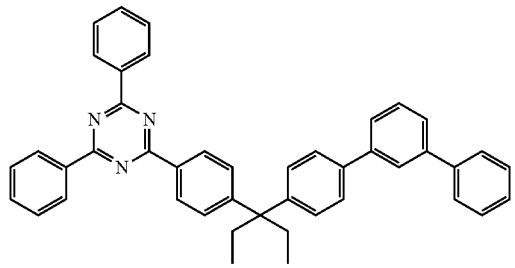
Compound 181
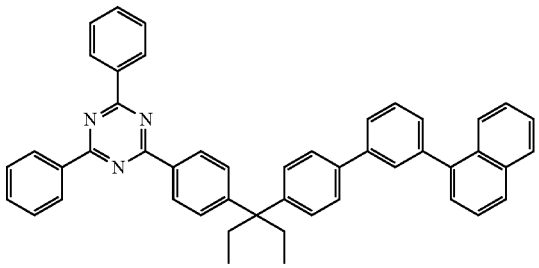
Compound 182
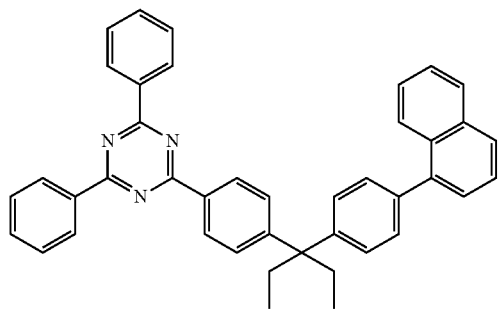
Compound 183
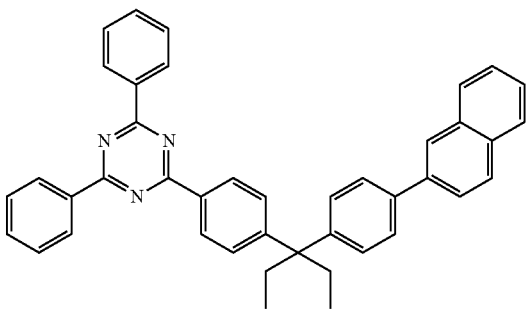
Compound 184
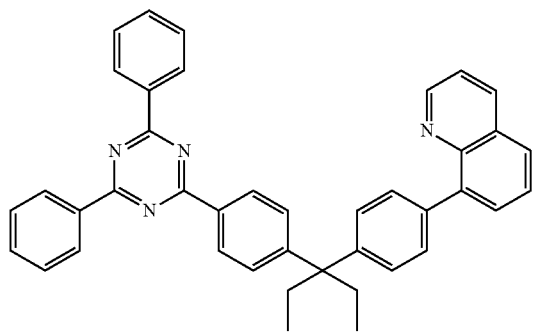
Compound 185
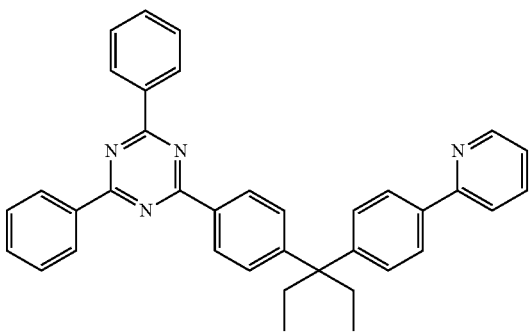

-continued
Compound 186
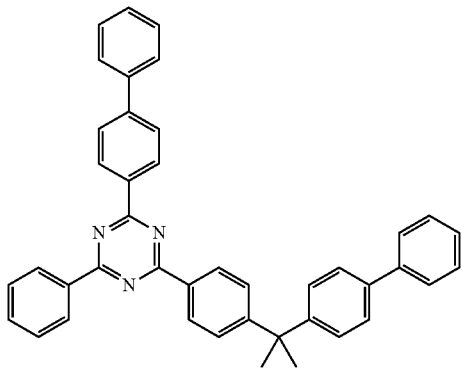
Compound 187
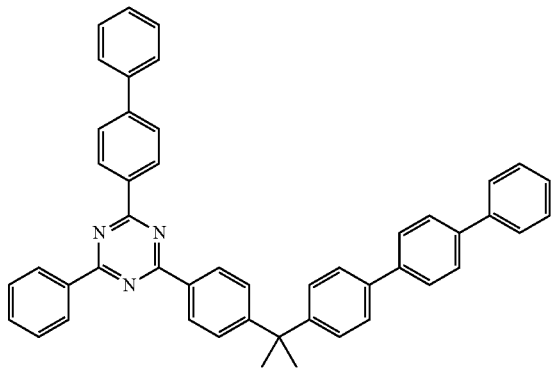
Compound 188
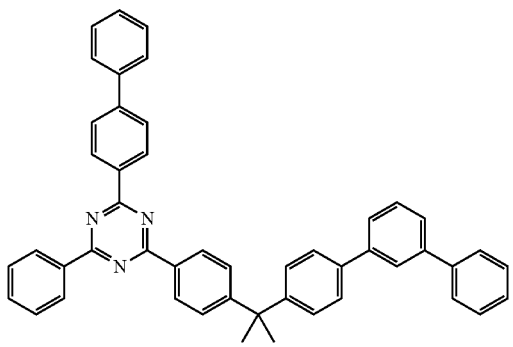
Compound 189
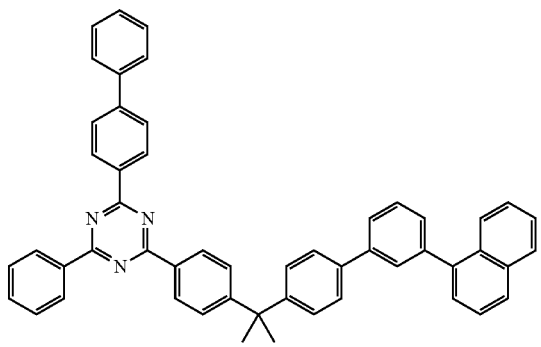
Compound 190
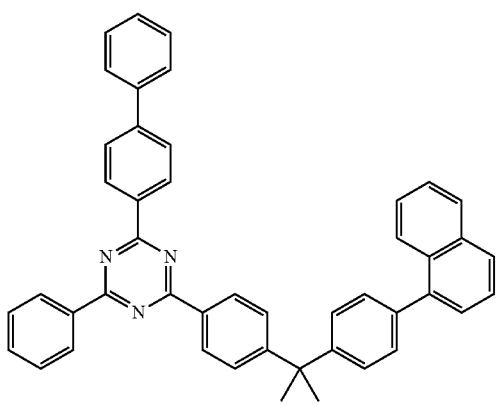
Compound 191
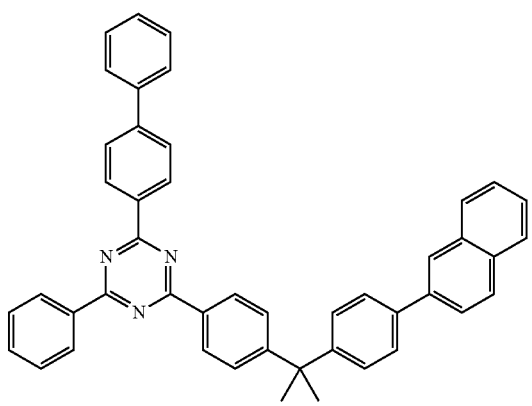
Compound 192
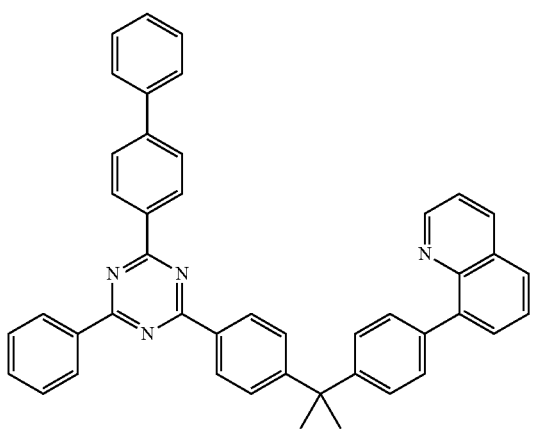
Compound 193
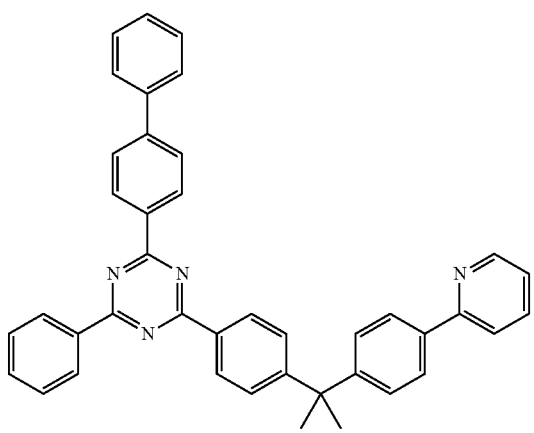

-continued
Compound 194
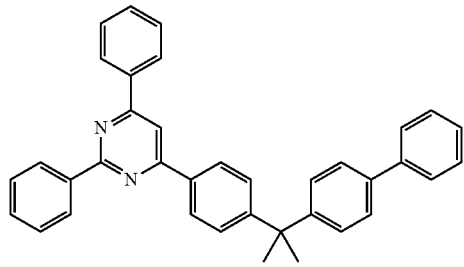
Compound 195
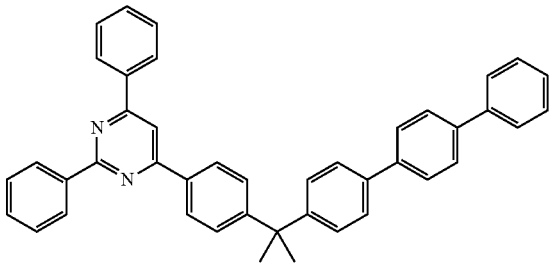
Compound 196
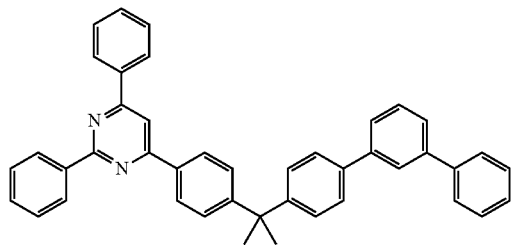
Compound 197
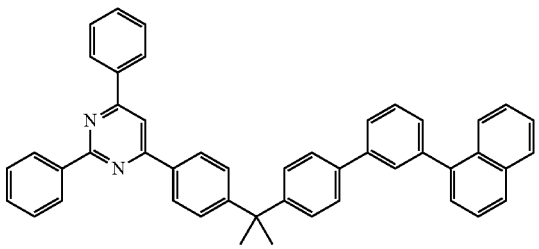
Compound 198
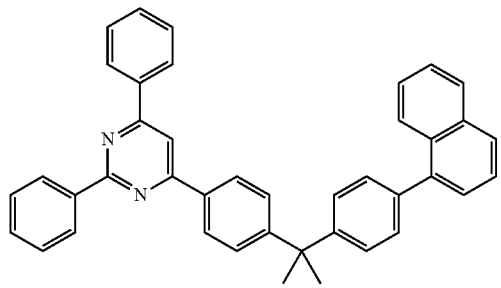
Compound 199
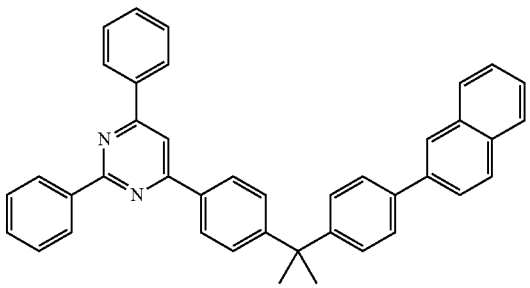
Compound 200
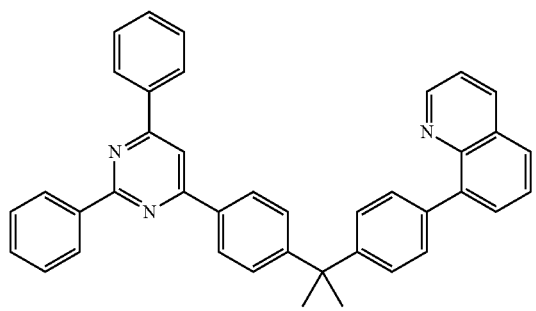
Compound 201
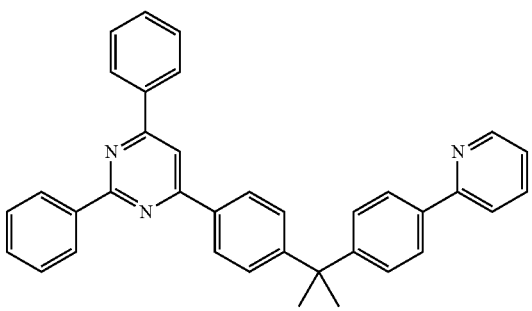
Compound 202
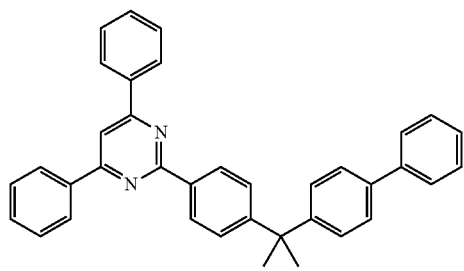
Compound 203
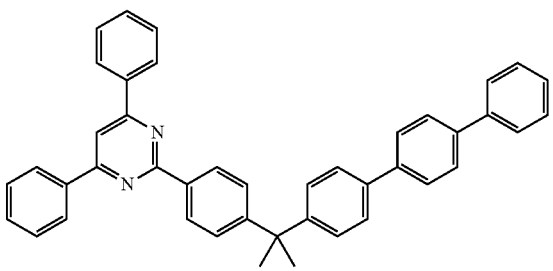

Compound 204

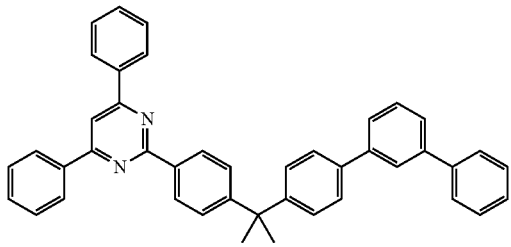

Compound 205

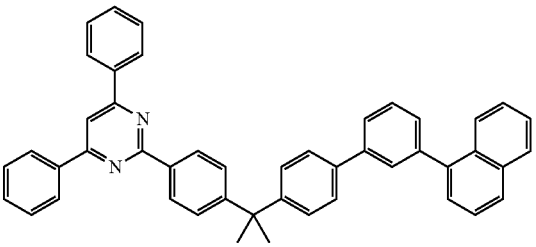

Compound 206

Compound 207

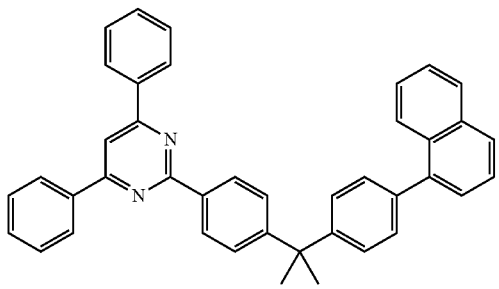

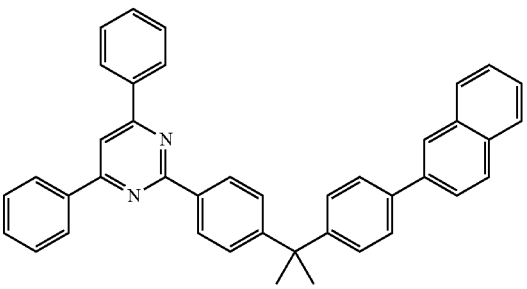

Compound 208

Compound 209

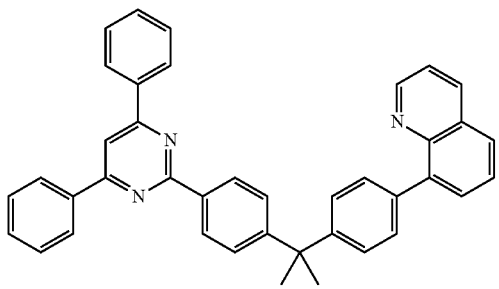

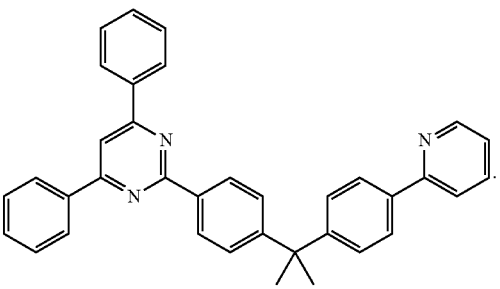

6. An organic light emitting device comprising:
a first electrode;
a second electrode provided opposite to the first electrode; and
one or two or more organic material layers provided between the first electrode and the second electrode,
wherein one or more layers of the organic material layers include the cyclic compound of claim 1.

7. The organic light emitting device of claim 6, wherein the organic material layer includes a light emitting layer, and the light emitting layer includes the cyclic compound.

8. The organic light emitting device of claim 6, wherein the organic material layer includes an electron transfer layer, an electron injection layer or a layer carrying out electron transfer and electron injection at the same time, and the electron transfer layer, the electron injection layer or the layer carrying out electron transfer and electron injection at the same time includes the cyclic compound.

9. The organic light emitting device of claim 6, wherein the organic material layer includes a hole blocking layer, and the hole blocking layer includes the cyclic compound.

\* \* \* \* \*